(12) United States Patent
Doudna et al.

(10) Patent No.: US 12,312,614 B2
(45) Date of Patent: May 27, 2025

(54) CRISPR-Cas EFFECTOR POLYPEPTIDES AND METHODS OF USE THEREOF

(71) Applicant: The Regents of the University of California, Oakland, CA (US)

(72) Inventors: Jennifer A. Doudna, Berkeley, CA (US); Jillian F. Banfield, Berkeley, CA (US); Basem Al-Shayeb, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 832 days.

(21) Appl. No.: 17/403,236

(22) Filed: Aug. 16, 2021

(65) Prior Publication Data

US 2021/0380957 A1 Dec. 9, 2021

Related U.S. Application Data

(63) Continuation of application No. PCT/US2020/021214, filed on Mar. 5, 2020.

(60) Provisional application No. 62/815,179, filed on Mar. 7, 2019.

(51) Int. Cl.
*C12N 9/22* (2006.01)
*C12N 15/10* (2006.01)

(52) U.S. Cl.
CPC .............. *C12N 9/22* (2013.01); *C12N 15/102* (2013.01); *C07K 2319/09* (2013.01); *C12N 2310/20* (2017.05)

(58) Field of Classification Search
CPC .... C12N 9/22; C12N 15/102; C12N 2310/20; C07K 2319/09
See application file for complete search history.

(56) References Cited

U.S. PATENT DOCUMENTS

| 6,605,709 | B1 | 8/2003 | Breton et al. |
| 9,328,346 | B2* | 5/2016 | Lee .................. A61P 29/00 |
| 2004/0029129 | A1 | 2/2004 | Wang et al. |
| 2016/0208243 | A1* | 7/2016 | Zhang .............. C12N 15/111 |

FOREIGN PATENT DOCUMENTS

| WO | 2015089427 A1 | 6/2015 |
| WO | 2017117395 A1 | 7/2017 |

(Continued)

OTHER PUBLICATIONS

NCBI Reference Sequence: WP_058893454.1 (Jan. 5, 2016) (Year: 2016).*

(Continued)

*Primary Examiner* — Thomas J. Visone
*Assistant Examiner* — Georgiana C Reglas
(74) *Attorney, Agent, or Firm* — Shweta Chandra; Bozicevic, Field & Francis LLP

(57) ABSTRACT

The present disclosure provides RNA-guided CRISPR-Cas effector proteins, nucleic acids encoding same, and compositions comprising same. The present disclosure provides ribonucleoprotein complexes comprising: an RNA-guided CRISPR-Cas effector protein of the present disclosure; and a guide RNA. The present disclosure provides methods of modifying a target nucleic acid, using an RNA-guided CRISPR-Cas effector protein of the present disclosure and a guide RNA.

16 Claims, 29 Drawing Sheets

Specification includes a Sequence Listing.

(56) References Cited

FOREIGN PATENT DOCUMENTS

| WO | WO 2017/189308 | 11/2017 |
| WO | WO2018213351 | 11/2018 |

OTHER PUBLICATIONS

HMM accession No. NF040570.1 RNA-guided endonuclease TnpB family protein; last updated Oct. 16, 2021; accessed Jul. 18, 2024 from https://www.ncbi.nlm.nih.gov/genome/annotation_prok/evidence/NF040570/ (Year: 2021).*
Chen et al (Science. Apr. 27, 2018;360(6387):436-439) (Year: 2018).*
Abudayyeh et al (Science. Aug. 5, 2016;353(6299):aaf5573) (Year: 2016).*
Chen et al Supplementary material (Science. Apr. 27, 2018;360(6387):436-439) (Year: 2018).*
Harrington et al., (2018) "Programmed DNA Destruction by Miniature CRISPR-Cas14 Enzymes." Science, vol. 362, No. 6416, pp. 839-842.

\* cited by examiner

| | | | |
|---|---|---|---|
| HUMAN | Adult fecal samples, Bangladesh | 393-209 kbp | ① |
| | Hadza fecal samples, Tanzania | 255-216 kbp | ② |
| | Human fecal, Peru | 280-201 kbp | ③ |
| | Premature infant gut, Pittsburgh, PA | 266 kbp | ④ |
| | Saliva from pregnant woman, preterm, CA | 371-206 kbp | ⑤ |
| | Saliva from pregnant woman, term, CA | 341-201 kbp | ⑥ |
| | Stool from pregnant woman, CA | 225-206 kbp | ⑦ |
| OTHER ANIMAL | Baboon fecal samples, Kenya | 396-200 kbp | ⑧ |
| | Moose | 420-207 kbp | ⑨ |
| | Pig fecal material, Denmark | 286-206 kbp | ⑩ |
| SOIL | Riparian zone soil, East River, CO | 213 kbp | ⑪ |
| | Grassland soil, Northern CA | 636 kbp | ⑫ |
| | Prairie Potholes | 223 kbp | ⑬ |
| | Soil, East River, Colorado | 404-251 kbp | ⑭ |
| | Vernal pool mud, Lake County, CA | 595-210 kbp | ⑮ |
| SUB-SOIL | Sapolite, East River, CO | 350-299 kbp | ⑯ |
| RIVER | Eel River mats, CA | 356-209 kbp | ⑰ |
| | River, Wrighton | 383 kbp | ⑱ |
| | Amazon River | 203 kbp | ⑲ |
| LAKE | Anderson Lake, Canada | 368-209 kbp | ⑳ |
| | Moose Lake, Ontario | 207-227 kbp | ㉑ |
| | Mining impact water, Newfoundland | 339 kbp | ㉒ |
| | Mining-associated Lake, Manitoba | 271-204 kbp | ㉓ |

FIG. 5

| | | | |
|---|---|---|---|
| GROUNDWATER | Stratified Lake, Alberta | 395-206 kbp | ㉔ |
| | Lac Pavin, France | 716-210 kbp | ㉕ |
| | Sewerage pond, Modesto, CA | 349 kbp | ㉖ |
| | Groundwater enrichment, Modesto, CA | 438-215 kbp | ㉗ |
| | Groundwater, Modesto, CA | 402-208 kbp | ㉘ |
| | Groundwater, Rifle, CO | 485-206 kbp | ㉙ |
| | Crystal Geyser, UT | 415-235 kbp | ㉚ |
| | Sulfide Spring, OK | 214 kbp | ㉛ |
| SUBSURFACE | Deep subsurface, Horonobe, Japan | 635-231 kbp | ㉜ |
| | Giant Mine, Canada | 343 kbp | ㉝ |
| | Sediment, Rifle, CO | 503-420 kbp | ㉞ |
| | Hydraulically Fractured Shale | 299-232 kbp | ㉟ |
| MARINE | Landsort Deep, Baltic Sea | 444-437 kbp | ㊱ |
| | Marine, global ocean virome | 318 kbp | ㊲ |
| | Marine, Tara ocean study | 499 kbp | ㊳ |
| | Bay mud, Berkeley, CA | 438-401 kbp | ㊴ |
| | Oil Seep, Santa Barbara, CA | 347 kbp | ㊵ |
| HYPERSALINE | Atacama salt, Chile | 484-322 kbp | ㊶ |
| | Salt Pond, CA | 322-201 kbp | ㊷ |
| HOT SPRINGS | Tibet/Yunan Hot Springs | 326-213 kbp | ㊸ |
| BIOTECHNOLOGY | Thiocyanate bioreactor, Sount Africa | 338-209 kbp | ㊹ |
| ROOM | NICU, Pittsburgh, PA | 1235-234 kbp | ㊺ |

FIG. 5 (Cont.)

Cas14J

>PhageCas14J_k87_9374247_16
MIESKAFKFRVYPTDKQKELIHNSVRASNFIFNFSLRQQIDISDKMNEMGIIEKGERKKYMKDNDLYFNKYTM
SRQLTVMGNTEEFSFLKEIDATSKSYALRRIDNAFKNMVKMGAGFPKFKNINKSTYSFTGQIQYQNDRIKNLR
VIKTKNPKIVHLNLSKLKNLKCVCHIPMFIENWSNMDTIKINSYTISRKGNNYYISFQVEHNQPLISEPIKREIKYE
TTIGIDMGVERPITTSDEADFNLKLFNERFNILKKHRKELHKLSAILNKKRDYHKKNESEIKFYETATYKRILKKM
RGLYHKITNIRENLQHNITSNLVNKENIDTFILEELNLKNMTKRSGKGKSNNKSNLNRVLLDVGMHGIKSKLEY
KAEKMGKNVETINPRFTSQKCSDCGHINKLNRKSQAVFKCVKCGYTLNADLNAAINIKNNFFGKNT*
Guide: GTTGAAGGGTATTGTTATTTGAAAGGTACTCACAAC

FIG. 6A

>PhageCas14J_LacPavin_0818_WC40_scaffold_407201_205
MEDIIEISEKKKKTKISGTGKGFSIRIYPDKKQIEYIRDSFRVNNFIYNYFLSKQEKIVSELKEMGLEGKALKSHMK
LNNLYFDYNSSRDLLYEMKKTPEYSFLGNASALSYHYALMRLKNAFDNMWKMNTGFPNYRKRHINKSFSGQ
ILFNTKADKYSPFEIQTINDKWCEITLTKITELKCVVHNNELLDFWNDRSYMHLKSYTITETPSGEFYLAITADIIS
KPMLEKRIVNEETSIGIDMGVARPITTSDEELFNDKQLSDKFNLIKEYKSEVERLSQILAKKREGNKNWKESKKY
ERIKKRLAKLHSKIANIRKYLQHNITSKLINSKYDTIIIEDLDVKNMMKKSAKGKSNNKRGLNRVLSDTGLGEIKR
QLVYKSNWCGKNIVTVDPKYTSQMCSNCGHTHRDNRKKQDEFICVSCGHNENADLNAAKNIKNKFFKKLAE
LKN*
Guide: AGGTGTGACATCCTTTAATTTGAAGTGTTCCTCCACC

FIG. 6B

>PhageCas14J_BML_08042016_6_5m_scaffold_18_prodigal-single_54
MITKAYKFRIYPTKVQEETINNCFRVNDFIYNFFLGLEQETYDVLYMYGLRNGEKKEDKHLNKWRTENKLWF
NRFDASRLLTKMAKLEKYKFLKTYPSTSRTYSLKSLESGMKSFMKGGGFPKFKNKKSNKSFTIQTQKDLKIIHKN
GKWHSINLPSALDFPIKKLDIKIHNELFLSPNIKTNSCTVSKRGNQYFISFQVELPGELPRKREIKKETSVGVDFG
VKKIITISSDEENPYSCETRFLKNSMNELKRLQKALSQKKKGSVKYNNIKEKINKLHIKISNQRKNLQHNISSFLV
NLNADTIIMEDLNLKGMTKTPNPIESNGTFLPNGKSRKSGLNASILDVGIGEIKTQVQYKSDFCGKNVVLVNP
QYTSQKCNNCGFTHKENRISQSEFECKNCGHKDNADKNASKNIKQKYFDN*
Guide: ACTATTAATGATAGTTAAATGAAAGGTGGTCACAAC

FIG. 6C

\>Ga0194119_1000113823
VKQNKAYKYRIYPTEKQIEYFEGAFKAGRYVYNVSLDCEKQIYQLGGKSNLSHFGLNYHIKNYRVKAPFLNEYD
VNIYCNEMKALSKAYKNFFKNKGGYPKFKKESDTTQSFTTRPSTKQNSKNLYITYDGYLKIPKVEKLIKIKYHRPI
EGKIKTVTISKKHNKYYVSIMVEYTNNFKKVEVKKSVGIDLGVKAFVVTSDNEVIENPKHLTKNQEHLTVLQRK
LARAKKGSNNYKKIKKNISKIHENVANTRENFLHNESKKLVDNYDLICMEDLNVKGMTKSSKGTKENPGKNV
KQKSGLNRSIIDVGFGKFKTMIGYKTKNSGKYLVEIGRFEPTSKKCNCCGTINKNLELKDRIWKCENCGEILNRD
LNAALNIRDLGTKKFFDSLKK
Guide: ATTGTGAATCATCCTTAAATGAAAGGTAATCACAAC

FIG. 6D

\>Ga0116197_10005458
MLKAYKYRIYPTKEQITLIEKHFGSTRFLYNYFLEYRQKAYAKGNQKVGYMVTQAELTKLKKLKEYEWLNECGS
QSLQMALRDLDSAYSRFFKKQGGYPKFKSKKHTSQSFTAPQNIKLASNRVYLPKFTKDGIKVKLHREIPQDAVL
KQATVSRQNNQYFVSILIDDNNAIPKPIKAKNAVGLDMGLTDLIITSDFTKYPNNKYFVKSQQKLKKLQRRHSK
KQKGSNNRQKAKLRVQKLHTKVSNQRKDTLHKISNEITNQYDIICLETLNVRGMQKNRRLAKGIADVAWSEF
MRQLAYKAQWKGKTVLKIDQWFPSSQICSNCGASSKKKELHVRKWECPECHAKHDRDINASINIKNYGLGQ
IDNRNTVGTIGI*

FIG. 6E

\>Ga0116179_10426881
MKIINKTYRFRLFPTKEQEVLLNKHFGCCRWVYNHFLNERKEQYQANKKSDNYYKQAATLAKLKNEEDTKWL
KEVNSQSLQFALRSLDTAFLNFFRGKAQFPKFKSKKHKNTFTIPQFGKLEDGKIVIPKFKEGIKVKLHREVKGKI
GKMSITKTPTGKYYVSIFTEQEVEELPKTNKQVGIDLGLKDFVITSDNKKFKNNRYVKKYEKQLKKAQQHLSRK
QKGSKGFEKQKLKVAKIHEKIANCRLDILHKVSTELVKNYDLIAVEDLNVKGMTKNHKLSKHIADASWGKFVT
LLQYKCDWYGKKLVKVNRFYPSSKTCSECGWINQELKLSDREWTCNSCGAIHDRDLNASKNILKEGLKIISAG
AVDYTDGDLNDASVKKRKSVKSEAQPIAFGVGG*

FIG. 6F

>Ga0268285_10062095
MIKAFKYRIYPTQDQKELLSNIFGQVRFVYNLGLETKISAYTGNKKHLSCFDLNKQITQLKNECPWLKESPSQA
LQQSIRNLDVAYTNFFRGAGFPKFKNKYTKQSFQLPQGVFLSDDKKQIFIPKLKFTDIDLHKEFKGEVKTVTVSK
TTTNKYYISILVDDKKPIPEKRQIKLESTVGIDLGIKDFAITSDGKKFKNHDFFKSAMNELRIQQRSLARKQKGSN
HYIKQKMKVSLLHEHIKNQREDYLHKISKYLVYNYDTICIENLGVSNMMKNHKLSRVIGDMGWHKFKSMLEY
KCEWYGKNLSVIGRFDPSSKTCSSCGSINKELTLNDREWTCKCGTKHDRDINAAINIRNFGLRNQPSVTQSE
WLHCACDVETHQSLADV

FIG. 6G

Cas14i
>Ga0066868_100162752
MTRNYPYKFRLEPTEEQKTRLKHYGFTCRFIYNLALDQRNLSRDPKPLPTLLEMWEKRVADKLAGVKPERKER
NFEEERKQEVVHKNINYGFQSPQMTVLRREVEWMQDVPFSCLQETLRSLQTAFKNFFDRVKKGQRVSDGR
NPYGYPVYRSRYRLSIPFKPANVSIKKVSERAGGEEGAYFSELKVPLMGSLIRFRQDRPVLGTPKTPTLKLEGDG
KWYVVILTEQEVEDPQTPEAEVGIDLGVAKMITLSDGTIYPLTKKQQQTFTNIDTTEKRIRKLQAACDRRKTKF
SKNWIKVKRQVVKLKHRQKRSRESLHHEITHLITSGFGRVAVENLNIKGMTPSASGTEEEPGTNVAQKSGLN
REILKRGWGLLVSQLEYKAKWRGGEVIKVDPKYTSQTCSKCGHVEKANRATQATFLCQKCGHKENADVNAA
KNILTRAEKQ*
Guide: GTGTTCTCCATGCACGCGGGGGAGTTTGG

FIG. 6H

>PhageCas14_SR-VP_2-4_scaffold_141_2548329_92
MAKQAPGKRTDESKERKAFSFRLYPTPEQERYLARVVGSCRYIYNALVREHERRMKYMRTFGAWPKPIGFKT
SKKKQSLAEDYKLEASLYEIQTALHEPGGPAPWLEDVAGNIRNHAVAMFGAAQTNWMSGRTGPPNFKQRR
PAGSFRFQDTRVASITGGPDRQPGFDFIRIPLPHGIEIDSWICFRRHRRLRGQPKTATIRRAAGIWYVSILCEW
DKPAKLPVHRAPNAKVGVDLNVRNLCALSDGTIIDGRSADLARLEKSINRLKHRESKLRLREKAASAPRSKRHF
RLQCRIARLQDRQANLRNEVTNQVAHAVALKHAFVGLEGLDIKGMTASAKGTVDAPGLNVRAKAGLNRAIL
NRGWGKLREKIESKVKIYGGQTVRVPPQYTSQTCAKCGHIAAENRDGVIFHCVKCGFTAHADVNAATNILEK
ALRLSAQESPGSGSLDGERPTELGSTTRQRVRKQKDTKTLGAPKATSRKGATAPRSTIPSLHVDMQVTSARVV
PAPQEALATEIAQQMKALAKSEVDAAPRQKINRRRRSQTEVEVPTGSVE*
Guide: GTTGCGACGTGCAAAGAACGGATTGGCGATCGACAC

FIG. 6I

>PhageCas14_SR-VP_4-6_scaffold_141_3640689_5
MAKQAPGKRTDESKERKAFSFRLYPTPEQERYLARVVGSCRYIYNALVREHERRMKYMRTFGAWPKPIGFKT
SKKKQSLAEDYKLEASLYEIQTALHEPGGPAPWLEDVAGNIRNHAVALFGAAQTNWMSGRTGPPNFKQRR
PAGSFRFQDTRVASITGGPDRQPGFDFIRIPLPHGIEIDSWICFRRHRRLRGQPKTATIRRAAGIWYVSILCEW
DKPAKLPVHRAPNAKVGVDLNVRYLCALSDGTIIDGRSADLARLEKSINRLKHRESKLRLREKAASAPRSKRHF
RLQCRIARLQDRQANLRNEVTNQVAHAVALKHAFVGLEGLDIKGMTASAKGTVDAPGLNVRAKAGLNRAIL
NRGWGKLREKIESKVKIYGGQTVRVPPQYTSQTCAKCGHIAAENRDGVIFHCVKCGFTAHADVNAATNILEK
ALRLSAQESPGSGSLDGERPTELGSTTRQRVRKQKDTKTLGAPKATSRKGATAPRSTIRSLHVDMQVTSARVV
PAPQEALATEIAQQMKALAKSEVDAAPRQKINRRRRSQTEVEVPTGSVE*
Guide: GTTGCGACGTGCAAAGAACGGATTGGCGATCGACAC

FIG. 6J

Cas14K
>PhageCas14_RifSed
MTTQKTYNFCFYDQRFFELSKEAGEVYSRSLEEFWKIYDETGVWLSKFDLQKHMRNKLERKLLHSDSFLGAM
QQVHANLASWKQAKKVVPDACPPRKPKFLQAILFKKSQIKYKNGFLRLTLGTEKEFLYLKWDINIPLPIYGSVT
YSKTRGWKINLCLETEVEQKNLSENKYLSIDLGVKRVATIFDGENTITLSGKKFMGLMHYRNKLNGKTQSRLS
HKKKGSNNYKKIQRAKRKTTDRLLNIQKEMLHKYSSFIVNYAIRNDIGNIIIGDNSSTHDSPNMRGKTNQKISQ
NPEQKLKNYIKYKFESISGRVDIVPEPYTSRKCPHCKNIKKSSPKGRTYKCKKCGFIFDRDGVGAINIYNENVSFG
QIISPGRIRSLTEPIGMKFHNEIYFKSYVAA
Guide: GTTTTATACCCTTTAGAATTTAAACTGTCTAAAAG

FIG. 6K

>PhageCas14_16ft_4_scaffold_2_465_16ft_4_Phage_29_13
VITKKTYNFSLYDPRFFELAKEAGDVYSRSLEEFWKVYDETGVWLSKFDLQKHMRNKLERKLLHSDSFIGAMQ
QVHANLASWKQAKKVVKDACPPRKPKFLQAILFKKSQIKYKNGFLKLTLGIGNEYLNLKWNQEIPLPIYGSVTY
SKTRGWKINLCLETDVEQKNLDNNKFLSIDLGVKRIATIFDGENTITLSGKKFMGLMHYRNKLNGKTQSRLSH
KKKGSNNYKKIQRAKRRTTDKILNIQKDMLHKYSSFVVNYAIKNNIGNIIIGDNSSTHDSPNMRGKTNQKISQ
NPEQKLKNYIKYKFEGISGQVNIVPEPYTSRKCPCCKNIKKSSPRGRTYKCKKCDFVFDRDGVGAINIYNENVSF
GTCLNLDSGRIRFLTEPIGMKFHNEVYFKSYVAVA*
Guide: GTTTTATACCCTTGTAATTTTAGGAGCTCATCAAAG

FIG. 6L

>Ga0116179_10109322
LKELYKTYILPVKQQELARKLSRESGRIYSKVVSKVFDIYKRKGFWLNEFDMKKYIRLYAKNIGLHSQTKQGIVE
QYYIALDSFFKAYKNHRNPKPPYKRRKYNVVMYKDSAIKLKNGILKLSNGKGNEPLMVKANKLGKKPKYAELV
YHHNKRKYFLHITVEMKGVQRVYEKDRAIAVDLGQIHPMVTYDSKRSIIFNGGVLNSFIRFRNKQLSKLQQK
MSMCKKYSKRWKKLNGAKKKLLNKSKNKVNDVLQKYTSYLVGYCIEQGIGTIVIGDIKSIRENINYGVKTNQKL
HNSWLFRKMTNIIEHKANNVGIKVEYINEAYTSQTCPVCNKKHPGNRNFTCKCGFKYHRDAVGAINIHKKY
TSSLSARLEGDLTPPVGYRYRYNQRCLAGWNTSIFDAGYFSDLPTKKVA*

FIG. 6M

>Ga0116179_10465782
MSRYVVRTYKVAVPKELYPLCAELNKTAARIYNKTMSLVKKIKYKKGFWLSPNNTQKYILRWACSINVHTHSK
QAIIQQYFQALDSYFNAVKTKPDLNPPYKRKRFMPFIWKDTAIKLLPDGKLKLSMGSNREPIVIQTTLLADTKIR
QAKLVYEEGKYYLHLVIEGKNVARKPQNGKIMAVDLGILRPITCFDGTEVISYHGGILNSLIRYRNKELAKFQQ
MLSRCKKGSKRYRKLVKAKKKMLRRTRHQIKDILHKITSNFLKMCLQKGIGTIALGDVTNIRERVEGNDSANQ
KLHQWCFRKMVDMITYKAELLGMDVKLVPEEYTSQTCPMCGSRNHSNNRNYKCQNCGFKYHRDGVGAIN
IYVRYLGKKSQVVAGLAPVRGVRYKPHLCGHGVRNAPWKAA*

FIG. 6N

>Ga0134101_10165752
MPGYVVRTYKVPVPEELYPLCAELNKTAARIYNKTMSLVKKIKRKKGIWLSSNNAQKYILRWACGINVHTHSK
QAMVQQYFQALDSYFNAVKAKPDLRPPYKKKRFMPFIWKDAAIKLLPDGKLRLSMGNNQKPVVIQTTLPAD
TKIRQAKLVYEDGKYYLHLATEVKNEVQKQQGKKVMAVDLGILRPITCFDGIEVISYHGGILNSLIRYRNKELAK
FQQMLSRCKKGSKRYRKLVKAKKKMLRRIRHQIKDILHKITSNFLKMCLQKGIKTIAVGDITNIRERVQGNDN
ANQKLHQWCFRKMIDMLTYKVHPLGIDVKLVPENYTSQTCPACGSRNHPTDRNYECQNCGFKYHRDGVG
AINIYARYLGKKSQVVAGLAPVRGVRYKPHLCGHGV

FIG. 6O

>Ga0066665_100815632
MYQVRRVNIGKTAQLDELARECGRLYSQTLASFWRTVRHKGIWLKPKHLMRWHTSEKLHAHTADACVQAF
FASLKSWRERRKLGDPDAHPPRKRKWYFRIEYKSTAMHHKDSVLTLSNGKGNTPLVLEWPWETPKTVVIHW
TGTQYEAIATYKIEAQGQPQGNKVAGIDLGEIHMAVSHDGTETHILNGRLLRSKRQYQNKLKAELSTMIDVK
KKGSLRRKKLIRSKQKQLKKLQHQVNDIEHKQSSRLISTLHAKGVQTVVIGDVRDIRQDLDVGSKNNQKLHQ
WSHGSIRHKLTYKAEWLGMEVALQDEHYTSRTCPMCQHVRKSKVQGRVFRCPTCHWTYHRDGVGAINIR
QKYLGSLPVIGDMAPPIGMRFRPHTSVARWEKTYQ*

FIG. 6P

>Ga0224523_10070512
MYNVRKLKIDQTEQLDVLATASGELYSRTLVSFWRTVRKHGLWLKPSSMMRWQNSGELHAHSADAVVQS
FYASLKSWRALRKVDPDAKPPKRRKHFFKVQWKNSAIRLKDGCLVLSNGKGNEPLIIPWNWTLPTLVELGW
NGTGYELRVIYSTTPTGVPLGVKVAGVDMGEIHLAVTHDGDDCHIYNGRYLRSVKRYQNKKKAEISARLDRM
KKGSRRSKYLKHNKARTLKKLDNQINDILHKQTTKLVSTLHEAGVKTVVIGDVRDIRKGLDYGAKANQKIHQW
HLGKTRWLVSYKAERLGMEVVLQDEAYTSQTCPACGKRHKPKDRNYRCSCGFQYHRDGIGAYNIRAKYLGE
LETPHVVGAMMSPTGVRVLQRCSHLARKNPLPLGMG

FIG. 6Q

>Ga0247839_10583994
MNIAHQDAIWEASKESASIYNDAIKLNQDGIPKAQAMKSLSIQSKHTKYLQSQSSQAPYQNFFIDLSSYFASLK
RYQKSKRGYKNEPKPPHKIKTLHAITFKKSAIRVQNGYLLLSLRKPNKPIKLKWSLSKPIWVLINFDIRTGWKMN
CVMEQEVQQHQLDKTKILAIDLGNKRIAASFDGKRCVTYSGKILKSLTRLQNKCSARSKASTSSLIKNSKKYKRV
MRARRKITARINNQKRDILHKTSRAIVNYAIENNIDKIVFGDCSSIHDGTTLGKENTQQVQQGCEQKLRKYVE
YKFRNVGGTTELVSERYSSQECPICDHRYEPRGRTYKCSACGYVYDRDGVGSINIYTNVSSGLTLDVVGGLMP
PRGWKFHSQLPCTTLRNSYFSMLYCGEPNDL

FIG. 6R

>Cas14u9|PhageCas14|LacPavin_0818_WC55_scaffold_56344_prodigal-single_16
VRKIAESKGYFTKAVSVELVGHSKEDTVWLLDILNRGYPLANKMYLLYRWYYEGLFPT
EIELNKLETYVYHKAREDSRFTDIPSNIIACTNRTILQKIKYDIKSGAKSGKRSWSQFKKG
QPLYFVQHNYLEKTDDGYNYNFIFGHKFKLKFGRHNEGEQLIEKLMDSESQFKLNANA
AFKVIKRRLFLLLSYEIPDKIENKPNPDNIMGIDFGMANFATCYLANDRKFKIVRDHKYLK
KRLLLQRKIKNLQSELSMHHAGLGRARKTRKIEDYRNKEKNLTKTEISQILSSIVRLAQA
NNIGTIKIEYLTIDQKTQLEDKYVYRNWAVMMTIDMLREKAKYVGINVVTIDPYHTSQKC
STCGTIGTRDGRIFSCENPSCKSFHKVVNADKNAAINIANSTQFVDDVKDTEYYKQKQE
FFKTLREKKETNIT*
Guide: TGTGTATACCATTCAAATTGTAT

FIG. 6S

\>Cas14u10|Ga0153798_100522201
MAKKNIDDTKKVTLCEKVKLTQIYSPVVDWKEFHKIFKILQKETILASNKIISICNIFNSFNN
KEEQKDWLIKKYQSEKLRNVLYDVARKYCYYSYSRNANAISNDIYYKYFKGPNSYKVKI
QKGIGNPPMTFTESIPLYITVQRHKIECTNNVRHYYTIEVPLLSNNCKSGIQITDTEQTQV
NNNALRFGINAAGNKRLIEILDNIIYGKYEFCDSKLKRVKSKKRSHRYDYYFLLSYKKPVI
EIKSLKPENVLGVDLGMTVPAYCAVNYCDYKKKAVGDSRIIRFNLIQEKINKRIQRNIKYN
LRDGHGRKYKLDGYDGASNKIAKRNSTFNFNLASEIIQLAIKWQCGTIHLEDLTKIHEINP
QNRFLKNWTYYDLQKKIENKAKEYGIVVKYINPYYTSQICSNCGHFESGQRISQSQFQC
KSCGYSANADYNAARNIALYKF*
Guide: CTTTCAATCTGCACATGCGTACGGATTGTATC

FIG. 6T

\>Cas14u_VU_u11|rifcsplowo2_12_scaffold_23_prodigal-single_23
MSTMVFEYYLRSPEKEQEQIVIQQLRASYEYYNTLIRIEQNRRNQFRAIQSQDPKIAQLE
LEISSLDTEIDLHLTSIQNTRSTNRKNVLDKKDVDRVKSLKADRKLKRDELKIAKKSFCD
NLIFQKACEDINLFAKNESKAARKATPSYWGSYLLIENAIDAAKKSKTDPKRKYWDWTG
RLGVQVQGGMSVSELFGNDTRIQIDPVSLDAWYHPIRGKRKYAQRQPKLRFRINSDDK
GKPIFVEFPMIMHRPLPQNACIKQANVIVTNRDRKLCYVLQLTVNIPEPVASPCTNGVGI
DLGWRLMDSGDIRVAYGYDQKGTKIDLRLPKSITSLFQKAESIRAIRDKEFEDHRKIMIP
LIQGVTFPNINTTNIGLSKSFRRFHSLYLGWKANRQDGDQIAFDALETWHRKDRHLEQ
YEVGCRKRAMNYRREEYRKFAKQMTSTYGYLALENWNISKVALRPEIEDGTREQSEP
QHQRVMACVSMLRQILINTAKREGVSIISVPAAYTTLECAACHKINTWDTSKNVCQTCE
NCDTVWDQDENAARNLLASGTVLKNTAPLPEEANIANTEKKSRWSKRKAEVVIDEKVD
RSQIAS*
Guide: CTTGTAATGGTTGCTCAACACCTTGAAAGTTGAGAC

FIG. 6U

\>Cas14u_VU_u12|SR-VP_4-6_scaffold_141_2630357_509
MKVYKYGLLPPIKNQTLVFEQLNKAYQYKKQLIDLVNQEKALLKKEEDNIFQRLNPALIS
KKETTQQTVEELLALMKQQRSKNRSKQDNIELKQQFKIAKENAKQAKKDYFTELSRIKT
LEEVKTSKEKIKTNFKQLHKEARKKCGVYWGTYLLIEEAVEQSKKTSFKKDFIFYGRRD
NERLGNQIQTSKDDSGSKIMGMLSSHLFNEKNSQIYIEPVADTAWIGVYRKDRRRTAKT
ILHWRIASDEKLKPIWAEFPMIMHRPLPKDSKIKSATISRRFYGPHQEWTLEITIDDNLSP
TKELGNGVVALDIGWRKLNDKIRVATLYDGEFHKELVISTYQLDKANELKSLRDDLFNQ
VKNQITEWNKEKFPEWILKELEFVSKWKSQARLVRLVKNWKKERWQDDNIYFELVEA
WRYKDQHLWQWECGSRRSGLRERIIIATLPPNLERNITVLYWKTLIFQRWQNYQNFRQ
KKI*
Guide: ATAGTAATGGCAGCTCAATGCCCTATAAATTGAGAC

FIG. 6V

\>Cas14u_VU_u13|gwd1_scaffold_1554_3
MPVKAVKFQIIKPLNATWDVLGKTLRDLNYHTTLMCNRAIQLYWEYGNFRSQYKAEHG
KYPIDKDIYGCSYRNHVYRQLRLMYPLMASSNTSQTNQFALKRWQTDVPDIRKLAKSIP
SFKLGTPIQVANQNFDLRFNDDTFSVDVTLLGRESEVGRFSILLDTGDKSKRVIFQRILD
RTYKQGSMQIVYSKKKGKWFCVIAYDSPIKVNELDIDKVMGIDLGIVNAVYWAFNSGHN
RGCISGGEIDTFRKQIEVRRRQILRTPRKDGHGRKRNMQAADILGEKISNFRDTVNHKY
SKKIIDIAIANKCGVIQMEDLTGISKDSFFLRNWTYRDLQDKIVYKALQEGIIVKLIDPRNT
SKTCSVCGHLDAENREDQATFICKNPECGSNMNADHNAAKNISVWSKVSKEFGL*
Guide: ACTCCAACCCCACATAGTTACCATGGAAAC

FIG. 6W

\>Cas14u_VU_u14|pig_F100_scaffold_13388_4
MNKVMRYQIIKPIDIDWKTFGDILNKLRQEVRFTKNKTIALYNDWLTYCFQYKNEHNEY
PKLVDYCGYKVFSGYAYDKFKTEVVFSNTANYTTSVREACSAYDAHKTDILKGNCSIPS
MGANQPIDLHNKSLSVDINEFGDYIATISLLSNRGKKEFGLKSGQIKIVLKAGDKSSRDIL
QRCVSKEYKICGSKIIYKDKKTFINLCYGFEPVTSELDKSKVMGIDLGVSVPAYMAFNFD
KYKRDSIKDNRIMATKWMMDRQLSIAKQSCKYLSDGNCGHGRKKKMVCYDKYSNKS
RNLSQTINHGWSKYIVDVAFRNGCGTIQMEDLSGVTSEKDKFLKNWTFYDLQQKIEYK
AKERGINVVKINPKYTSQRCCECGCICKRNRPDQKTFKCISCGYSANADFNAAKNIATI
GIEDIIANTEVIE*
Guide: CGAAGCAACTCGCGCATTCGCGCGAGGTGAGAG

FIG. 6X

\>Cas14u_VU_u15|pig_ID_3640_F65_scaffold_73762_2
MRIEIMVKKKGINMNKIMKYQILKPTNIGWEDFGNILYNLRSEVRKIKNRTIALYHEWTGY
TLECHDRTGEWPKPKDVYNYGTIGGYIYDRLKGEVKYSNSVNFSSSVRDAMSKYDTH
KKDILAGKASVPSMGDGQPIDIYNKNIVLHHLDNEKKDYAATLSLLNNGAKTELGLLSG
RVDVILTIKNETQTAILDRCLSGEYRVCGSQLVYEAAGKEKKGKKDKPKVWLYLCYGFE
PEAPELDDSRIMGIDLGMKLPAVMAFNFNDKKYEVIDDNRILDRKIRLDKMLSISKHQCQ
WRCDGNSGHGRKKKVDVYERYSHKSHNLSMHINHQWSKYIVDTAVKNKCGVIQMED
LSGIKASRQNFLGNWTYYDLQQKITYKAEEKGVKVIKVDPSYTSQMCPVCGYINKRNR
STQADFECLECGHIANADYNAARNIATPDIANIIKNRLAQQKKEGKPIE*
Guide: GTCTCATTCCATATATGTGCGTGAGA

FIG. 6Y

>Cas14u_VU_u16|pig_ID_1851_F40_2_scaffold_55126_1
MPMSSYRKTHYTNTCELREIYMRIEIMVKKGINMNKIMKYQILKPTNISWEDFGNILYN
LRSEVRKIKNRTIALYHEWTNYTLECHDKTGEWPKPKDVYNYGTMSGYIYDRLKGEVR
YSNSVNFNSSVRDAMSKYDTHKKDILAGKVSVPSMGDGQPIDIYNKNIVLHHLDNEKK
DYAATLSLLNNGAKAELGLLSGRVDVILTIKNETQTAILDRCLSGEYRICGSQLIYEGGK
EKKGKKDKPKVWLYLCYGFEPEAPELDDSRIMGIDLGMKLPAVMAFNFNDKKYEVIDD
NRILDRKIRLDKMLSMSKHQCQWRCDGNSGHGRNKKVDVYERYSHKSHNLSMDINH
QWSKYIVDTAVKNKCGVIQMEDLSGIKASRQNFLGNWTYYDLQQKITYKAEEKGIKVIK
VDPCYTSQMCPVCGYINKRNRSTQADFECLECGHIANADYNAARNIATPDIANIIKNRL
AQQKKEGKPIE*
Guide: CACGCGTGTGTGTGAAATGAGAC

FIG. 6Z

>Cas14u_VU_u17|pig_ID_3784_F96_scaffold_13509_10
MNKIMKYQIIKPLNIDWETFGNILFNLRKESRQVKNRAIAIYHEWVLYSMAYYDECGKW
PKIIDVYPPYKTADGYIYDKLKNEMGHMLSNNFNATIRNALSKYDTHKKDIMAGKVSVP
SMDAGQPIDVYAKGITLHHIDGDKGDYVATLSLLNSKAKATLNLPSGRIDMVLKMNDKT
QTAILDRCLSGEYRICGSQLVYEAAGKEKKGKKDKPKVWLYLCYGFEPEAPELDDSRI
MGIDLGMKLPAVMAFNFNDKKYEVIDDNRILDRKIRLDKMLSISKHQCQWRCDGNSGH
GRKKKVDVYERYSHKSHNLSMDINHQWSKYIVETAVKNKCGVIQVEDLSGIKASRQNF
LGNWTYYDLQQKITYKAEEKGIKVIKVDPSYTSQMCPVCGYINKRNRSTQADFECLEC
GHIANADYNAARNIATPDIANIIKNRLAQQKKEGKPIE*
Guide: CGCGTGTGTGTGAAATGAGAACG

FIG. 6AA

>Cas14u_VU_u18|SRR1747065_scaffold_28
MNKVMKYQIIKPLNIDWEDFGNILFNLRKESRQIKNRAIAIYHEWVQYSMSYYDEYGKW
PKVIDVYPPYKTVDGYIYDRLKNEMGHTSNNFNATIRNALSKYDTHKKDIMAGKVSVP
SMDAGQPIDVYAKGITLHHIDGDKDDYVATLSLLNSKAKATLNLPSGRIDMVLKMNDKT
QTAILDRCLSGEYRICGSQLIYEAAGKEKKGKKDKPKVWLYLCYGFEPEAPELDDSRIM
GIDLGMKLPAVMAFNFNDKKYEVIDDNRILGQKIRLDKMLSISKHQCQWRCDGNSGHG
RKKKVDVYEKCSHRSHNLSMDINHQWSKYIVETAIKNKCGVIQMEDLSGIKASRQNFL
GNWTYYDLQQKITYKAEGKGIKVIKIDPHYTSQMCPICGYINKRNRSTQADFECLECGH
IANADYNAARNIATPDIANIIKNRVKQQEKEGKSID
Guide: CCTCTCATTCCACATATGCGTGTGAGATGCGAC

FIG. 6BB

Cas14J

>PhageCas14J_k87_9374247_16
Guide: GTTGAAGGGTATTGTTATTTGAAAGGTACTCACAAC

>PhageCas14J_LacPavin_0818_WC40_scaffold_407201_205
Guide: AGGTGTGACATCCTTTAATTTGAAGTGTTCCTCCACC >PhageCas14J_BML_08042016_6_5m_scaffold_18_prodigal-single_54
Guide: ACTATTAATGATAGTTAAATGAAAGGTGGTCACAAC >Ga0194119_1000113823
Guide: ATTGTGAATCATCCTTAAATGAAAGGTAATCACAAC

FIG. 7A

>Ga0066868_100162752
Guide: GTGTTCTCCATGCACGCGGGGGAGTTTGG

>PhageCas14_SR-VP_2-4_scaffold_141_2548329_92
Guide: GTTGCGACGTGCAAAGAACGGATTGGCGATCGACAC >PhageCas14_SR-VP_4-6_scaffold_141_3640689_5
Guide: GTTGCGACGTGCAAAGAACGGATTGGCGATCGACAC

FIG. 7B

Cas14i

>Ga0066868_100162752
Guide: GTGTTCTCCATGCACGCGGGGGAGTTTGG

>PhageCas14_SR-VP_2-4_scaffold_141_2548329_92
Guide: GTTGCGACGTGCAAAGAACGGATTGGCGATCGACAC >PhageCas14_SR-VP_4-6_scaffold_141_3640689_5
Guide: GTTGCGACGTGCAAAGAACGGATTGGCGATCGACAC

FIG. 7C

\>Cas14u9|PhageCas14|LacPavin_0818_WC55_scaffold_56344_prodigal-single_16
Guide: TGTGTATACCATTCAAATTGTAT \>Cas14u10|Ga0153798_100522201
Guide: CTTTCAATCTGCACATGCGTACGGATTGTATC \>Cas14u_VU_u11|rifcsplowo2_12_scaffold_23_prodigal-single_23
Guide: CTTGTAATGGTTGCTCAACACCTTGAAAGTTGAGAC \>Cas14u_VU_u12|SR-VP_4-6_scaffold_141_2630357_509
Guide: ATAGTAATGGCAGCTCAATGCCCTATAAATTGAGAC \>Cas14u_VU_u13|gwd1_scaffold_1554_3
Guide: ACTCCAACCCCACATAGTTACCATGGAAAC \>Cas14u_VU_u14|pig_F100_scaffold_13388_4
Guide: CGAAGCAACTCGCGCATTCGCGCGAGGTGAGAG \>Cas14u_VU_u15|pig_ID_3640_F65_scaffold_73762_2
Guide: GTCTCATTCCATATATGTGCGTGAGA \>Cas14u_VU_u16|pig_ID_1851_F40_2_scaffold_55126_1
Guide: CACGCGTGTGTGTGAAATGAGAC \>Cas14u_VU_u17|pig_ID_3784_F96_scaffold_13509_10
Guide: CGCGTGTGTGTGAAATGAGAACG \>Cas14u_VU_u18|SRR1747065_scaffold_28
Guide: CCTCTCATTCCACATATGCGTGTGAGATGCGAC

```
  1         10         20         30         40         50         60
MAKKNIDDTKKVTLCEKVKLTQIYSPVVDWKEFHKIFKILQKETLLASNKIITSICNIFNSFNNKEE 70         80         90        100        110        120        130
QKDWLIKKYQSEKLRNVLYDVARKYCYYSYSRNANAISNDIYYKYFKGPNSYKVKIQKGIGNPPMT 140        150        160     165  170        180        190
FTESIPLYITVQRHKIECTNNVRHYYTIEVPLLSNNCKSGIQITDTEQTQVNNNALRFGINAAGNK 200        210        220        230        240        250        260
RLIEILDNIIYGKYEFCDSKLKRVKSKKRSHRYDYFLLSYKKPVIEIKSLKPENVLGVDLGMTVP
                                                                RuvC-I 270        280        290        300        310        320        330
AYCAVNYCDYKKKAVGDSRIIRFNLIQEKINKRIQRNIKYNLRDGHGRKYKLDGYDGASNKIAKRN 340        350        360        370        380        390
STFNFNLASEIIQLAIKWQCGTIHLEDLTKIHEINPQNRFLKNWTYDLQKKIENKAKEYGIVVKY
                        RuvC-II 400        410        420        430        440        448
INPYTSQICSNCGHFEESGQRISQSQFQCKSCGYSANADYNAARNIALYKF*
                                            RuvC-III
```

FIG. 9

SEQUENCE LISTING

<160> NUMBER OF SEQ ID NOS: 188

<210> SEQ ID NO 1
<211> LENGTH: 84
<212> TYPE: PRT
<213> ORGANISM: Artificial sequence

```
<220> FEATURE:
<223> OTHER INFORMATION: Synthetic sequence

<400> SEQUENCE: 1

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 2
<211> LENGTH: 57
<212> TYPE: PRT
<213> ORGANISM: Artificial sequence
<220> FEATURE:
<223> OTHER INFORMATION: Synthetic sequence

<400> SEQUENCE: 2

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 3
<211> LENGTH: 85
<212> TYPE: PRT
<213> ORGANISM: Artificial sequence
<220> FEATURE:
<223> OTHER INFORMATION: Synthetic sequence

<400> SEQUENCE: 3

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 4
<211> LENGTH: 76
<212> TYPE: PRT
<213> ORGANISM: Artificial sequence
<220> FEATURE:
<223> OTHER INFORMATION: Synthetic sequence
```

<400> SEQUENCE: 4

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Cys
65                  70                  75

<210> SEQ ID NO 5
<211> LENGTH: 76
<212> TYPE: PRT
<213> ORGANISM: Artificial sequence
<220> FEATURE:
<223> OTHER INFORMATION: Synthetic sequence

<400> SEQUENCE: 5

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60

Pro Leu Lys Val Met Ser Ser Val Ser Thr Ala Cys
65                  70                  75

<210> SEQ ID NO 6
<211> LENGTH: 72
<212> TYPE: PRT
<213> ORGANISM: Artificial sequence
<220> FEATURE:
<223> OTHER INFORMATION: Synthetic sequence

<400> SEQUENCE: 6

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
                20                  25                  30

Val Phe Gly Ser Lys Lys Leu Lys Asn Ser Ala Asn Ser Met Leu Val
            35                  40                  45

Leu Lys Lys Asp Ser Ile Phe Met Gln Leu Phe Cys Ser Phe Arg Ile
        50                  55                  60

Ser Ala Ser Val Ala Thr Ala Cys
65                  70

<210> SEQ ID NO 7
<211> LENGTH: 69
<212> TYPE: PRT
<213> ORGANISM: Artificial sequence
<220> FEATURE:
<223> OTHER INFORMATION: Synthetic sequence

<400> SEQUENCE: 7

Met Ala Ala Leu Val Thr Ser Gln Leu Ala Thr Ser Gly Thr Val Leu

```
                1               5                  10                  15
Ser Val Thr Asp Arg Phe Arg Arg Pro Gly Phe Gln Gly Leu Arg Pro
                    20                  25                  30

Arg Asn Pro Ala Asp Ala Ala Leu Gly Met Arg Thr Val Gly Ala Ser
                35                  40                  45

Ala Ala Pro Lys Gln Ser Arg Lys Pro His Arg Phe Asp Arg Arg Cys
            50                  55                  60

Leu Ser Met Val Val
65

<210> SEQ ID NO 8
<211> LENGTH: 77
<212> TYPE: PRT
<213> ORGANISM: Artificial sequence
<220> FEATURE:
<223> OTHER INFORMATION: Synthetic sequence

<400> SEQUENCE: 8

Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
                20                  25                  30

Gln Gly Leu Lys Pro Arg Ser Pro Ala Gly Gly Asp Ala Thr Ser Leu
            35                  40                  45

Ser Val Thr Thr Ser Ala Arg Ala Thr Pro Lys Gln Gln Arg Ser Val
        50                  55                  60

Gln Arg Gly Ser Arg Arg Phe Pro Ser Val Val Val Cys
65                  70                  75

<210> SEQ ID NO 9
<211> LENGTH: 57
<212> TYPE: PRT
<213> ORGANISM: Artificial sequence
<220> FEATURE:
<223> OTHER INFORMATION: Synthetic sequence

<400> SEQUENCE: 9

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
                20                  25                  30

Ala Ser Phe Pro Val Ser Arg Lys Gln Asn Leu Asp Ile Thr Ser Ile
            35                  40                  45

Ala Ser Asn Gly Gly Arg Val Gln Cys
        50                  55

<210> SEQ ID NO 10
<211> LENGTH: 65
<212> TYPE: PRT
<213> ORGANISM: Artificial sequence
<220> FEATURE:
<223> OTHER INFORMATION: Synthetic sequence

<400> SEQUENCE: 10

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
                20                  25                  30

Arg Arg Thr Ser Ser Thr Ser Gly Thr Ser Gly Val Lys Cys Ser Ala
            35                  40                  45
```

```
Ala Val Thr Pro Gln Ala Ser Pro Val Ile Ser Arg Ser Ala Ala Ala
    50                  55                  60

Ala
65

<210> SEQ ID NO 11
<211> LENGTH: 72
<212> TYPE: PRT
<213> ORGANISM: Artificial sequence
<220> FEATURE:
<223> OTHER INFORMATION: Synthetic sequence

<400> SEQUENCE: 11

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Thr Thr
    50                  55                  60

Asn Gly Ala Ser Ala Ala Ser Ser
65                  70

<210> SEQ ID NO 12
<211> LENGTH: 20
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: The amino acid at position 4 is selected from
      lysine, histidine and arginine.
<220> FEATURE:
<221> NAME/KEY: misc_feature
<222> LOCATION: (8)..(8)
<223> OTHER INFORMATION: The amino acid at position 8 is selected from
      lysine, histidine and arginine.
<220> FEATURE:
<221> NAME/KEY: misc_feature
<222> LOCATION: (11)..(11)
<223> OTHER INFORMATION: The amino acid at position 11 is selected from
      lysine, histidine and arginine.
<220> FEATURE:
<221> NAME/KEY: misc_feature
<222> LOCATION: (15)..(15)
<223> OTHER INFORMATION: The amino acid at position 15 is selected from
      lysine, histidine and arginine
<220> FEATURE:
<221> NAME/KEY: misc_feature
<222> LOCATION: (19)..(19)
<223> OTHER INFORMATION: The amino acid at position 19 is selected from
      lysine, histidine and arginine.

<400> SEQUENCE: 12

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 13
<211> LENGTH: 20
<212> TYPE: PRT
<213> ORGANISM: Artificial sequence
<220> FEATURE:
```

-continued

```
<223> OTHER INFORMATION: Synthetic sequence

<400> SEQUENCE: 13

Gly Leu Phe His Ala Leu Leu His Leu Leu His Ser Leu Trp His Leu
1               5                   10                  15

Leu Leu His Ala
            20

<210> SEQ ID NO 14
<211> LENGTH: 7
<212> TYPE: PRT
<213> ORGANISM: Artificial sequence
<220> FEATURE:
<223> OTHER INFORMATION: Synthetic sequence

<400> SEQUENCE: 14

Pro Lys Lys Lys Arg Lys Val
1               5

<210> SEQ ID NO 15
<211> LENGTH: 16
<212> TYPE: PRT
<213> ORGANISM: Artificial sequence
<220> FEATURE:
<223> OTHER INFORMATION: Synthetic sequence

<400> SEQUENCE: 15

Lys Arg Pro Ala Ala Thr Lys Lys Ala Gly Gln Ala Lys Lys Lys Lys
1               5                   10                  15

<210> SEQ ID NO 16
<211> LENGTH: 9
<212> TYPE: PRT
<213> ORGANISM: Artificial sequence
<220> FEATURE:
<223> OTHER INFORMATION: Synthetic sequence

<400> SEQUENCE: 16

Pro Ala Ala Lys Arg Val Lys Leu Asp
1               5

<210> SEQ ID NO 17
<211> LENGTH: 11
<212> TYPE: PRT
<213> ORGANISM: Artificial sequence
<220> FEATURE:
<223> OTHER INFORMATION: Synthetic sequence

<400> SEQUENCE: 17

Arg Gln Arg Arg Asn Glu Leu Lys Arg Ser Pro
1               5                   10

<210> SEQ ID NO 18
<211> LENGTH: 38
<212> TYPE: PRT
<213> ORGANISM: Artificial sequence
<220> FEATURE:
<223> OTHER INFORMATION: Synthetic sequence

<400> SEQUENCE: 18

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
```

```
<210> SEQ ID NO 19
<211> LENGTH: 42
<212> TYPE: PRT
<213> ORGANISM: Artificial sequence
<220> FEATURE:
<223> OTHER INFORMATION: Synthetic sequence

<400> SEQUENCE: 19

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 20
<211> LENGTH: 8
<212> TYPE: PRT
<213> ORGANISM: Artificial sequence
<220> FEATURE:
<223> OTHER INFORMATION: Synthetic sequence

<400> SEQUENCE: 20

Val Ser Arg Lys Arg Pro Arg Pro
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic sequence

<400> SEQUENCE: 21

Pro Pro Lys Lys Ala Arg Glu Asp
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic sequence

<400> SEQUENCE: 22

Pro Gln Pro Lys Lys Lys Pro Leu
1               5

<210> SEQ ID NO 23
<211> LENGTH: 12
<212> TYPE: PRT
<213> ORGANISM: Artificial sequence
<220> FEATURE:
<223> OTHER INFORMATION: Synthetic sequence

<400> SEQUENCE: 23

Ser Ala Leu Ile Lys Lys Lys Lys Lys Met Ala Pro
1               5                   10

<210> SEQ ID NO 24
<211> LENGTH: 5
<212> TYPE: PRT
<213> ORGANISM: Artificial sequence
<220> FEATURE:
```

```
<223> OTHER INFORMATION: Synthetic sequence

<400> SEQUENCE: 24

Asp Arg Leu Arg Arg
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic sequence

<400> SEQUENCE: 25

Pro Lys Gln Lys Lys Arg Lys
1               5

<210> SEQ ID NO 26
<211> LENGTH: 10
<212> TYPE: PRT
<213> ORGANISM: Artificial sequence
<220> FEATURE:
<223> OTHER INFORMATION: Synthetic sequence

<400> SEQUENCE: 26

Arg Lys Leu Lys Lys Lys Ile Lys Lys Leu
1               5                   10

<210> SEQ ID NO 27
<211> LENGTH: 10
<212> TYPE: PRT
<213> ORGANISM: Artificial sequence
<220> FEATURE:
<223> OTHER INFORMATION: Synthetic sequence

<400> SEQUENCE: 27

Arg Glu Lys Lys Lys Phe Leu Lys Arg Arg
1               5                   10

<210> SEQ ID NO 28
<211> LENGTH: 20
<212> TYPE: PRT
<213> ORGANISM: Artificial sequence
<220> FEATURE:
<223> OTHER INFORMATION: Synthetic sequence

<400> SEQUENCE: 28

Lys Arg Lys Gly Asp Glu Val Asp Gly Val Asp Glu Val Ala Lys Lys
1               5                   10                  15

Lys Ser Lys Lys
            20

<210> SEQ ID NO 29
<211> LENGTH: 17
<212> TYPE: PRT
<213> ORGANISM: Artificial sequence
<220> FEATURE:
<223> OTHER INFORMATION: Synthetic sequence

<400> SEQUENCE: 29

Arg Lys Cys Leu Gln Ala Gly Met Asn Leu Glu Ala Arg Lys Thr Lys
1               5                   10                  15

Lys

<210> SEQ ID NO 30
```

```
<211> LENGTH: 12
<212> TYPE: PRT
<213> ORGANISM: Artificial sequence
<220> FEATURE:
<223> OTHER INFORMATION: Synthetic sequence

<400> SEQUENCE: 30

Arg Arg Gln Arg Arg Thr Ser Lys Leu Met Lys Arg
1               5                   10

<210> SEQ ID NO 31
<211> LENGTH: 27
<212> TYPE: PRT
<213> ORGANISM: Artificial sequence
<220> FEATURE:
<223> OTHER INFORMATION: Synthetic sequence

<400> SEQUENCE: 31

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 32
<211> LENGTH: 33
<212> TYPE: PRT
<213> ORGANISM: Artificial sequence
<220> FEATURE:
<223> OTHER INFORMATION: Synthetic sequence

<400> SEQUENCE: 32

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 33
<211> LENGTH: 16
<212> TYPE: PRT
<213> ORGANISM: Artificial sequence
<220> FEATURE:
<223> OTHER INFORMATION: Synthetic sequence

<400> SEQUENCE: 33

Arg Gln Ile Lys Ile Trp Phe Gln Asn Arg Arg Met Lys Trp Lys Lys
1               5                   10                  15

<210> SEQ ID NO 34
<211> LENGTH: 11
<212> TYPE: PRT
<213> ORGANISM: Artificial sequence
<220> FEATURE:
<223> OTHER INFORMATION: Synthetic sequence

<400> SEQUENCE: 34

Tyr Gly Arg Lys Lys Arg Arg Gln Arg Arg Arg
1               5                   10

<210> SEQ ID NO 35
<211> LENGTH: 9
<212> TYPE: PRT
<213> ORGANISM: Artificial sequence
<220> FEATURE:
<223> OTHER INFORMATION: Synthetic sequence
```

```
<400> SEQUENCE: 35

Arg Lys Lys Arg Arg Gln Arg Arg
1               5

<210> SEQ ID NO 36
<211> LENGTH: 8
<212> TYPE: PRT
<213> ORGANISM: Artificial sequence
<220> FEATURE:
<223> OTHER INFORMATION: Synthetic sequence

<400> SEQUENCE: 36

Arg Lys Lys Arg Arg Gln Arg Arg
1               5

<210> SEQ ID NO 37
<211> LENGTH: 11
<212> TYPE: PRT
<213> ORGANISM: Artificial sequence
<220> FEATURE:
<223> OTHER INFORMATION: Synthetic sequence

<400> SEQUENCE: 37

Tyr Ala Arg Ala Ala Ala Arg Gln Ala Arg Ala
1               5                   10

<210> SEQ ID NO 38
<211> LENGTH: 11
<212> TYPE: PRT
<213> ORGANISM: Artificial sequence
<220> FEATURE:
<223> OTHER INFORMATION: Synthetic sequence

<400> SEQUENCE: 38

Thr His Arg Leu Pro Arg Arg Arg Arg Arg
1               5                   10

<210> SEQ ID NO 39
<211> LENGTH: 11
<212> TYPE: PRT
<213> ORGANISM: Artificial sequence
<220> FEATURE:
<223> OTHER INFORMATION: Synthetic sequence

<400> SEQUENCE: 39

Gly Gly Arg Arg Ala Arg Arg Arg Arg Arg
1               5                   10

<210> SEQ ID NO 40
<211> LENGTH: 5
<212> TYPE: PRT
<213> ORGANISM: Artificial sequence
<220> FEATURE:
<223> OTHER INFORMATION: Synthetic sequence

<400> SEQUENCE: 40

Gly Ser Gly Gly Ser
1               5

<210> SEQ ID NO 41
<211> LENGTH: 6
<212> TYPE: PRT
<213> ORGANISM: Artificial sequence
<220> FEATURE:
<223> OTHER INFORMATION: Synthetic sequence

<400> SEQUENCE: 41
```

```
Gly Gly Ser Gly Gly Ser
1               5

<210> SEQ ID NO 42
<211> LENGTH: 4
<212> TYPE: PRT
<213> ORGANISM: Artificial sequence
<220> FEATURE:
<223> OTHER INFORMATION: Synthetic sequence

<400> SEQUENCE: 42

Gly Gly Gly Ser
1

<210> SEQ ID NO 43
<211> LENGTH: 4
<212> TYPE: PRT
<213> ORGANISM: Artificial sequence
<220> FEATURE:
<223> OTHER INFORMATION: Synthetic sequence

<400> SEQUENCE: 43

Gly Gly Ser Gly
1

<210> SEQ ID NO 44
<211> LENGTH: 5
<212> TYPE: PRT
<213> ORGANISM: Artificial sequence
<220> FEATURE:
<223> OTHER INFORMATION: Synthetic sequence

<400> SEQUENCE: 44

Gly Gly Ser Gly Gly
1               5

<210> SEQ ID NO 45
<211> LENGTH: 5
<212> TYPE: PRT
<213> ORGANISM: Artificial sequence
<220> FEATURE:
<223> OTHER INFORMATION: Synthetic sequence

<400> SEQUENCE: 45

Gly Ser Gly Ser Gly
1               5

<210> SEQ ID NO 46
<211> LENGTH: 5
<212> TYPE: PRT
<213> ORGANISM: Artificial sequence
<220> FEATURE:
<223> OTHER INFORMATION: Synthetic sequence

<400> SEQUENCE: 46

Gly Ser Gly Gly Gly
1               5

<210> SEQ ID NO 47
<211> LENGTH: 5
<212> TYPE: PRT
<213> ORGANISM: Artificial sequence
<220> FEATURE:
<223> OTHER INFORMATION: Synthetic sequence

<400> SEQUENCE: 47
```

```
Gly Gly Gly Ser Gly
1               5

<210> SEQ ID NO 48
<211> LENGTH: 5
<212> TYPE: PRT
<213> ORGANISM: Artificial sequence
<220> FEATURE:
<223> OTHER INFORMATION: Synthetic sequence

<400> SEQUENCE: 48

Gly Ser Ser Ser Gly
1               5

<210> SEQ ID NO 49
<211> LENGTH: 28
<212> TYPE: DNA
<213> ORGANISM: Artificial sequence
<220> FEATURE:
<223> OTHER INFORMATION: Synthetic sequence

<400> SEQUENCE: 49
gttaactgcc gcataggcag cttagaaa                                          28

<210> SEQ ID NO 50
<211> LENGTH: 28
<212> TYPE: DNA
<213> ORGANISM: Artificial sequence
<220> FEATURE:
<223> OTHER INFORMATION: Synthetic sequence

<400> SEQUENCE: 50
gtgaaccgcc gtataggcag cttagaaa                                          28

<210> SEQ ID NO 51
<211> LENGTH: 439
<212> TYPE: PRT
<213> ORGANISM: Artificial sequence
<220> FEATURE:
<223> OTHER INFORMATION: Synthetic sequence

<400> SEQUENCE: 51

Met Ile Glu Ser Lys Ala Phe Lys Phe Arg Val Tyr Pro Thr Asp Lys
1               5                   10                  15

Gln Lys Glu Leu Ile His Asn Ser Val Arg Ala Ser Asn Phe Ile Phe
                20                  25                  30

Asn Phe Ser Leu Arg Gln Gln Ile Asp Ile Ser Asp Lys Met Asn Glu
            35                  40                  45

Met Gly Ile Ile Glu Lys Gly Glu Arg Lys Tyr Met Lys Asp Asn
        50                  55                  60

Asp Leu Tyr Phe Asn Lys Tyr Thr Met Ser Arg Gln Leu Thr Val Met
65                  70                  75                  80

Gly Asn Thr Glu Glu Phe Ser Phe Leu Lys Glu Ile Asp Ala Thr Ser
                85                  90                  95

Lys Ser Tyr Ala Leu Arg Arg Ile Asp Asn Ala Phe Lys Asn Met Val
                100                 105                 110

Lys Met Gly Ala Gly Phe Pro Lys Phe Lys Asn Ile Asn Lys Ser Thr
            115                 120                 125

Tyr Ser Phe Thr Gly Gln Ile Gln Tyr Gln Asn Asp Arg Ile Lys Asn
        130                 135                 140

Leu Arg Val Ile Lys Thr Lys Asn Pro Lys Ile Val His Leu Asn Leu
145                 150                 155                 160
```

```
Ser Lys Leu Lys Asn Leu Lys Cys Val Cys His Ile Pro Met Phe Ile
            165                 170                 175

Glu Asn Trp Ser Asn Met Asp Thr Ile Lys Ile Asn Ser Tyr Thr Ile
        180                 185                 190

Ser Arg Lys Gly Asn Asn Tyr Tyr Ile Ser Phe Gln Val Glu His Asn
    195                 200                 205

Gln Pro Leu Ile Ser Glu Pro Ile Lys Arg Glu Ile Lys Tyr Glu Thr
210                 215                 220

Thr Ile Gly Ile Asp Met Gly Val Glu Arg Pro Ile Thr Thr Ser Asp
225                 230                 235                 240

Glu Ala Asp Phe Asn Leu Lys Leu Phe Asn Glu Arg Phe Asn Ile Leu
                245                 250                 255

Lys Lys His Arg Lys Glu Leu His Lys Leu Ser Ala Ile Leu Asn Lys
            260                 265                 270

Lys Arg Asp Tyr His Lys Lys Asn Glu Ser Glu Ile Lys Phe Tyr Glu
        275                 280                 285

Thr Ala Thr Tyr Lys Arg Ile Leu Lys Lys Met Arg Gly Leu Tyr His
    290                 295                 300

Lys Ile Thr Asn Ile Arg Glu Asn Leu Gln His Asn Ile Thr Ser Asn
305                 310                 315                 320

Leu Val Asn Lys Glu Asn Ile Asp Thr Phe Ile Leu Glu Gly Leu Asn
                325                 330                 335

Leu Lys Asn Met Thr Lys Arg Ser Gly Lys Gly Lys Ser Asn Asn Lys
            340                 345                 350

Ser Asn Leu Asn Arg Val Leu Leu Asp Val Gly Met His Gly Ile Lys
        355                 360                 365

Ser Lys Leu Glu Tyr Lys Ala Glu Lys Met Gly Lys Asn Val Glu Thr
    370                 375                 380

Ile Asn Pro Arg Phe Thr Ser Gln Lys Cys Ser Asp Cys Gly His Ile
385                 390                 395                 400

Asn Lys Leu Asn Arg Lys Ser Gln Ala Val Phe Lys Cys Val Lys Cys
                405                 410                 415

Gly Tyr Thr Leu Asn Ala Asp Leu Asn Ala Ala Ile Asn Ile Lys Asn
            420                 425                 430

Asn Phe Phe Gly Lys Asn Thr
            435

<210> SEQ ID NO 52
<211> LENGTH: 36
<212> TYPE: DNA
<213> ORGANISM: Artificial sequence
<220> FEATURE:
<223> OTHER INFORMATION: Synthetic sequence

<400> SEQUENCE: 52
gttgaagggt attgttattt gaaaggtact cacaac                          36

<210> SEQ ID NO 53
<211> LENGTH: 450
<212> TYPE: PRT
<213> ORGANISM: Artificial sequence
<220> FEATURE:
<223> OTHER INFORMATION: Synthetic sequence

<400> SEQUENCE: 53

Met Glu Asp Ile Ile Glu Ile Ser Glu Lys Lys Lys Thr Lys Ile
1               5                   10                  15
```

```
Ser Gly Thr Gly Lys Gly Phe Ser Ile Arg Ile Tyr Pro Asp Lys Lys
         20                  25                  30

Gln Ile Glu Tyr Ile Arg Asp Ser Phe Arg Val Asn Phe Ile Tyr
         35                  40                  45

Asn Tyr Phe Leu Ser Lys Gln Glu Lys Ile Val Ser Glu Leu Lys Glu
 50                  55                  60

Met Gly Leu Glu Gly Lys Ala Leu Lys Ser His Met Lys Leu Asn Asn
 65                  70                  75                  80

Leu Tyr Phe Asp Tyr Asn Ser Ser Arg Asp Leu Leu Tyr Glu Met Lys
                 85                  90                  95

Lys Thr Pro Glu Tyr Ser Phe Leu Gly Asn Ala Ser Ala Leu Ser Tyr
                100                 105                 110

His Tyr Ala Leu Met Arg Leu Lys Asn Ala Phe Asp Asn Met Trp Lys
            115                 120                 125

Met Asn Thr Gly Phe Pro Asn Tyr Arg Lys Arg His Ile Asn Lys Ser
130                 135                 140

Phe Ser Gly Gln Ile Leu Phe Asn Thr Lys Ala Asp Lys Tyr Ser Pro
145                 150                 155                 160

Phe Glu Ile Gln Thr Ile Asn Asp Lys Trp Cys Glu Ile Thr Leu Thr
                165                 170                 175

Lys Ile Thr Glu Leu Lys Cys Val Val His Asn Asn Glu Leu Leu Asp
            180                 185                 190

Phe Trp Asn Asp Arg Ser Tyr Met His Leu Lys Ser Tyr Thr Ile Thr
        195                 200                 205

Glu Thr Pro Ser Gly Glu Phe Tyr Leu Ala Ile Thr Ala Asp Ile Ile
    210                 215                 220

Ser Lys Pro Met Leu Glu Lys Arg Ile Val Asn Glu Glu Thr Ser Ile
225                 230                 235                 240

Gly Ile Asp Met Gly Val Ala Arg Pro Ile Thr Thr Ser Asp Glu Glu
                245                 250                 255

Leu Phe Asn Asp Lys Gln Leu Ser Asp Lys Phe Asn Leu Ile Lys Glu
            260                 265                 270

Tyr Lys Ser Glu Val Glu Arg Leu Ser Gln Ile Leu Ala Lys Lys Arg
        275                 280                 285

Glu Gly Asn Lys Asn Trp Lys Glu Ser Lys Lys Tyr Glu Arg Ile Lys
    290                 295                 300

Lys Arg Leu Ala Lys Leu His Ser Lys Ile Ala Asn Ile Arg Lys Tyr
305                 310                 315                 320

Leu Gln His Asn Ile Thr Ser Lys Leu Ile Asn Ser Lys Tyr Asp Thr
                325                 330                 335

Ile Ile Ile Glu Asp Leu Asp Val Lys Asn Met Met Lys Lys Ser Ala
            340                 345                 350

Lys Gly Lys Ser Asn Asn Lys Arg Gly Leu Asn Arg Val Leu Ser Asp
        355                 360                 365

Thr Gly Leu Gly Glu Ile Lys Arg Gln Leu Val Tyr Lys Ser Asn Trp
    370                 375                 380

Cys Gly Lys Asn Ile Val Thr Val Asp Pro Lys Tyr Thr Ser Gln Met
385                 390                 395                 400

Cys Ser Asn Cys Gly His Thr His Arg Asp Asn Arg Lys Lys Gln Asp
                405                 410                 415

Glu Phe Ile Cys Val Ser Cys Gly His Asn Glu Asn Ala Asp Leu Asn
            420                 425                 430
```

-continued

```
Ala Ala Lys Asn Ile Lys Asn Lys Phe Phe Lys Lys Leu Ala Glu Leu
        435                 440                 445

Lys Asn
    450

<210> SEQ ID NO 54
<211> LENGTH: 37
<212> TYPE: DNA
<213> ORGANISM: Artificial sequence
<220> FEATURE:
<223> OTHER INFORMATION: Synthetic sequence

<400> SEQUENCE: 54
aggtgtgaca tcctttaatt tgaagtgttc ctccacc                                37

<210> SEQ ID NO 55
<211> LENGTH: 422
<212> TYPE: PRT
<213> ORGANISM: Artificial sequence
<220> FEATURE:
<223> OTHER INFORMATION: Synthetic sequence

<400> SEQUENCE: 55

Met Ile Thr Lys Ala Tyr Lys Phe Arg Ile Tyr Pro Thr Lys Val Gln
1               5                   10                  15

Glu Glu Thr Ile Asn Asn Cys Phe Arg Val Asn Asp Phe Ile Tyr Asn
            20                  25                  30

Phe Phe Leu Gly Leu Glu Gln Glu Thr Tyr Asp Val Leu Tyr Met Tyr
        35                  40                  45

Gly Leu Arg Asn Gly Glu Lys Lys Glu Asp Lys His Leu Asn Lys Trp
    50                  55                  60

Arg Thr Glu Asn Lys Leu Trp Phe Asn Arg Phe Asp Ala Ser Arg Leu
65                  70                  75                  80

Leu Thr Lys Met Ala Lys Leu Glu Lys Tyr Lys Phe Leu Lys Thr Tyr
                85                  90                  95

Pro Ser Thr Ser Arg Thr Tyr Ser Leu Lys Ser Leu Glu Ser Gly Met
            100                 105                 110

Lys Ser Phe Met Lys Gly Gly Phe Pro Lys Phe Lys Asn Lys Lys
        115                 120                 125

Ser Asn Lys Ser Phe Thr Ile Gln Thr Gln Lys Asp Leu Lys Ile Ile
130                 135                 140

His Lys Asn Gly Lys Trp His Ser Ile Asn Leu Pro Ser Ala Leu Asp
145                 150                 155                 160

Phe Pro Ile Lys Lys Leu Asp Ile Lys Ile His Asn Glu Leu Phe Leu
                165                 170                 175

Ser Pro Asn Ile Lys Thr Asn Ser Cys Thr Val Ser Lys Arg Gly Asn
            180                 185                 190

Gln Tyr Phe Ile Ser Phe Gln Val Glu Leu Pro Gly Glu Leu Pro Arg
        195                 200                 205

Lys Arg Glu Ile Lys Lys Glu Thr Ser Val Gly Val Asp Phe Gly Val
    210                 215                 220

Lys Lys Ile Ile Thr Ile Ser Ser Asp Glu Glu Asn Pro Tyr Ser Cys
225                 230                 235                 240

Glu Thr Arg Phe Leu Lys Asn Ser Met Asn Glu Leu Lys Arg Leu Gln
                245                 250                 255

Lys Ala Leu Ser Gln Lys Lys Gly Ser Val Lys Tyr Asn Asn Ile
            260                 265                 270
```

```
Lys Glu Lys Ile Asn Lys Leu His Ile Lys Ile Ser Asn Gln Arg Lys
            275                 280                 285

Asn Leu Gln His Asn Ile Ser Ser Phe Leu Val Asn Leu Asn Ala Asp
        290                 295                 300

Thr Ile Ile Met Glu Asp Leu Asn Leu Lys Gly Met Thr Lys Thr Pro
305                 310                 315                 320

Asn Pro Ile Glu Ser Asn Gly Thr Phe Leu Pro Asn Gly Lys Ser Arg
            325                 330                 335

Lys Ser Gly Leu Asn Ala Ser Ile Leu Asp Val Gly Ile Gly Glu Ile
        340                 345                 350

Lys Thr Gln Val Gln Tyr Lys Ser Asp Phe Cys Gly Lys Asn Val Val
        355                 360                 365

Leu Val Asn Pro Gln Tyr Thr Ser Gln Lys Cys Asn Asn Cys Gly Phe
370                 375                 380

Thr His Lys Glu Asn Arg Ile Ser Gln Ser Glu Phe Glu Cys Lys Asn
385                 390                 395                 400

Cys Gly His Lys Asp Asn Ala Asp Lys Asn Ala Ser Lys Asn Ile Lys
                405                 410                 415

Gln Lys Tyr Phe Asp Asn
            420

<210> SEQ ID NO 56
<211> LENGTH: 36
<212> TYPE: DNA
<213> ORGANISM: Artificial sequence
<220> FEATURE:
<223> OTHER INFORMATION: Synthetic sequence

<400> SEQUENCE: 56
actattaatg atagttaaat gaaaggtggt cacaac                              36

<210> SEQ ID NO 57
<211> LENGTH: 392
<212> TYPE: PRT
<213> ORGANISM: Artificial sequence
<220> FEATURE:
<223> OTHER INFORMATION: Synthetic sequence

<400> SEQUENCE: 57

Val Lys Gln Asn Lys Ala Tyr Lys Tyr Arg Ile Tyr Pro Thr Glu Lys
1               5                   10                  15

Gln Ile Glu Tyr Phe Glu Gly Ala Phe Lys Ala Gly Arg Tyr Val Tyr
            20                  25                  30

Asn Val Ser Leu Asp Cys Glu Lys Gln Ile Tyr Gln Leu Gly Gly Lys
        35                  40                  45

Ser Asn Leu Ser His Phe Gly Leu Asn Tyr His Ile Lys Asn Tyr Arg
    50                  55                  60

Val Lys Ala Pro Phe Leu Asn Glu Tyr Asp Val Asn Ile Tyr Cys Asn
65                  70                  75                  80

Glu Met Lys Ala Leu Ser Lys Ala Tyr Lys Asn Phe Phe Lys Asn Lys
                85                  90                  95

Gly Gly Tyr Pro Lys Phe Lys Lys Glu Ser Asp Thr Thr Gln Ser Phe
            100                 105                 110

Thr Thr Arg Pro Ser Thr Lys Gln Asn Ser Lys Asn Leu Tyr Ile Thr
        115                 120                 125

Tyr Asp Gly Tyr Leu Lys Ile Pro Lys Val Glu Lys Leu Ile Lys Ile
    130                 135                 140
```

```
Lys Tyr His Arg Pro Ile Glu Gly Lys Ile Lys Thr Val Thr Ile Ser
145                 150                 155                 160

Lys Lys His Asn Lys Tyr Tyr Val Ser Ile Met Val Glu Tyr Thr Asn
            165                 170                 175

Asn Phe Lys Lys Val Glu Val Lys Ser Val Gly Ile Asp Leu Gly
        180                 185                 190

Val Lys Ala Phe Val Val Thr Ser Asp Asn Glu Val Ile Glu Asn Pro
        195                 200                 205

Lys His Leu Thr Lys Asn Gln Glu His Leu Thr Val Leu Gln Arg Lys
    210                 215                 220

Leu Ala Arg Ala Lys Lys Gly Ser Asn Tyr Lys Ile Lys Lys
225                 230                 235                 240

Asn Ile Ser Lys Ile His Glu Asn Val Ala Asn Thr Arg Glu Asn Phe
                245                 250                 255

Leu His Asn Glu Ser Lys Lys Leu Val Asp Asn Tyr Asp Leu Ile Cys
                260                 265                 270

Met Glu Asp Leu Asn Val Lys Gly Met Thr Lys Ser Ser Lys Gly Thr
            275                 280                 285

Lys Glu Asn Pro Gly Lys Asn Val Lys Gln Lys Ser Gly Leu Asn Arg
    290                 295                 300

Ser Ile Ile Asp Val Gly Phe Gly Lys Phe Lys Thr Met Ile Gly Tyr
305                 310                 315                 320

Lys Thr Lys Asn Ser Gly Lys Tyr Leu Val Glu Ile Gly Arg Phe Glu
                325                 330                 335

Pro Thr Ser Lys Lys Cys Asn Cys Cys Gly Thr Ile Asn Lys Asn Leu
                340                 345                 350

Glu Leu Lys Asp Arg Ile Trp Lys Cys Glu Asn Cys Gly Glu Ile Leu
                355                 360                 365

Asn Arg Asp Leu Asn Ala Ala Leu Asn Ile Arg Asp Leu Gly Thr Lys
            370                 375                 380

Lys Phe Phe Asp Ser Leu Lys Lys
385                 390

<210> SEQ ID NO 58
<211> LENGTH: 36
<212> TYPE: DNA
<213> ORGANISM: Artificial sequence
<220> FEATURE:
<223> OTHER INFORMATION: Synthetic sequence

<400> SEQUENCE: 58
attgtgaatc atccttaaat gaaaggtaat cacaac                                    36

<210> SEQ ID NO 59
<211> LENGTH: 377
<212> TYPE: PRT
<213> ORGANISM: Artificial sequence
<220> FEATURE:
<223> OTHER INFORMATION: Synthetic sequence

<400> SEQUENCE: 59

Met Leu Lys Ala Tyr Lys Tyr Arg Ile Tyr Pro Thr Lys Glu Gln Ile
1               5                   10                  15

Thr Leu Ile Glu Lys His Phe Gly Ser Thr Arg Phe Leu Tyr Asn Tyr
            20                  25                  30

Phe Leu Glu Tyr Arg Gln Lys Ala Tyr Ala Lys Gly Asn Gln Lys Val
        35                  40                  45
```

```
Gly Tyr Met Val Thr Gln Ala Glu Leu Thr Lys Leu Lys Leu Lys
 50                  55                  60

Glu Tyr Glu Trp Leu Asn Glu Cys Gly Ser Gln Ser Leu Gln Met Ala
 65                  70                  75                  80

Leu Arg Asp Leu Asp Ser Ala Tyr Ser Arg Phe Phe Lys Lys Gln Gly
                 85                  90                  95

Gly Tyr Pro Lys Phe Lys Ser Lys Lys His Thr Ser Gln Ser Phe Thr
            100                 105                 110

Ala Pro Gln Asn Ile Lys Leu Ala Ser Asn Arg Val Tyr Leu Pro Lys
        115                 120                 125

Phe Thr Lys Asp Gly Ile Lys Val Lys Leu His Arg Glu Ile Pro Gln
130                 135                 140

Asp Ala Val Leu Lys Gln Ala Thr Val Ser Arg Gln Asn Asn Gln Tyr
145                 150                 155                 160

Phe Val Ser Ile Leu Ile Asp Asp Asn Ala Ile Pro Lys Pro Ile
                165                 170                 175

Lys Ala Lys Asn Ala Val Gly Leu Asp Met Gly Leu Thr Asp Leu Ile
            180                 185                 190

Ile Thr Ser Asp Phe Thr Lys Tyr Pro Asn Asn Lys Tyr Phe Val Lys
        195                 200                 205

Ser Gln Gln Lys Leu Lys Lys Leu Gln Arg Arg His Ser Lys Lys Gln
210                 215                 220

Lys Gly Ser Asn Asn Arg Gln Lys Ala Lys Leu Arg Val Gln Lys Leu
225                 230                 235                 240

His Thr Lys Val Ser Asn Gln Arg Lys Asp Thr Leu His Lys Ile Ser
                245                 250                 255

Asn Glu Ile Thr Asn Gln Tyr Asp Ile Ile Cys Leu Glu Thr Leu Asn
            260                 265                 270

Val Arg Gly Met Gln Lys Asn Arg Arg Leu Ala Lys Gly Ile Ala Asp
        275                 280                 285

Val Ala Trp Ser Glu Phe Met Arg Gln Leu Ala Tyr Lys Ala Gln Trp
290                 295                 300

Lys Gly Lys Thr Val Leu Lys Ile Asp Gln Trp Phe Pro Ser Ser Gln
305                 310                 315                 320

Ile Cys Ser Asn Cys Gly Ala Ser Ser Lys Lys Lys Glu Leu His Val
                325                 330                 335

Arg Lys Trp Glu Cys Pro Glu Cys His Ala Lys His Asp Arg Asp Ile
            340                 345                 350

Asn Ala Ser Ile Asn Ile Lys Asn Tyr Gly Leu Gly Gln Ile Asp Asn
        355                 360                 365

Arg Asn Thr Val Gly Thr Ile Gly Ile
370                 375

<210> SEQ ID NO 60
<211> LENGTH: 400
<212> TYPE: PRT
<213> ORGANISM: Artificial sequence
<220> FEATURE:
<223> OTHER INFORMATION: Synthetic sequence

<400> SEQUENCE: 60

Met Lys Ile Ile Asn Lys Thr Tyr Arg Phe Arg Leu Phe Pro Thr Lys
 1               5                  10                  15

Glu Gln Glu Val Leu Leu Asn Lys His Phe Gly Cys Cys Arg Trp Val
                20                  25                  30
```

Tyr Asn His Phe Leu Asn Glu Arg Lys Glu Gln Tyr Gln Ala Asn Lys
                 35                  40                  45

Lys Ser Asp Asn Tyr Tyr Lys Gln Ala Ala Thr Leu Ala Lys Leu Lys
 50                  55                  60

Asn Glu Glu Asp Thr Lys Trp Leu Lys Glu Val Asn Ser Gln Ser Leu
 65                  70                  75                  80

Gln Phe Ala Leu Arg Ser Leu Asp Thr Ala Phe Leu Asn Phe Phe Arg
                 85                  90                  95

Gly Lys Ala Gln Phe Pro Lys Phe Ser Lys Lys His Lys Asn Thr
                100                 105                 110

Phe Thr Ile Pro Gln Phe Gly Lys Leu Glu Asp Gly Lys Ile Val Ile
                115                 120                 125

Pro Lys Phe Lys Glu Gly Ile Lys Val Lys Leu His Arg Glu Val Lys
130                 135                 140

Gly Lys Ile Gly Lys Met Ser Ile Thr Lys Thr Pro Thr Gly Lys Tyr
145                 150                 155                 160

Tyr Val Ser Ile Phe Thr Glu Gln Glu Val Glu Glu Leu Pro Lys Thr
                165                 170                 175

Asn Lys Gln Val Gly Ile Asp Leu Gly Leu Lys Asp Phe Val Ile Thr
                180                 185                 190

Ser Asp Asn Lys Lys Phe Lys Asn Asn Arg Tyr Val Lys Lys Tyr Glu
195                 200                 205

Lys Gln Leu Lys Lys Ala Gln Gln His Leu Ser Arg Lys Gln Lys Gly
                210                 215                 220

Ser Lys Gly Phe Glu Lys Gln Lys Leu Lys Val Ala Lys Ile His Glu
225                 230                 235                 240

Lys Ile Ala Asn Cys Arg Leu Asp Ile Leu His Lys Val Ser Thr Glu
                245                 250                 255

Leu Val Lys Asn Tyr Asp Leu Ile Ala Val Glu Asp Leu Asn Val Lys
                260                 265                 270

Gly Met Thr Lys Asn His Lys Leu Ser Lys His Ile Ala Asp Ala Ser
                275                 280                 285

Trp Gly Lys Phe Val Thr Leu Leu Gln Tyr Lys Cys Asp Trp Tyr Gly
290                 295                 300

Lys Lys Leu Val Lys Val Asn Arg Phe Tyr Pro Ser Ser Lys Thr Cys
305                 310                 315                 320

Ser Glu Cys Gly Trp Ile Asn Gln Glu Leu Lys Leu Ser Asp Arg Glu
                325                 330                 335

Trp Thr Cys Asn Ser Cys Gly Ala Ile His Asp Arg Asp Leu Asn Ala
                340                 345                 350

Ser Lys Asn Ile Leu Lys Glu Gly Leu Lys Ile Ile Ser Ala Gly Ala
                355                 360                 365

Val Asp Tyr Thr Asp Gly Asp Leu Asn Asp Ala Ser Val Lys Lys Arg
                370                 375                 380

Lys Ser Val Lys Ser Glu Ala Gln Pro Ile Ala Phe Gly Val Gly Gly
385                 390                 395                 400

<210> SEQ ID NO 61
<211> LENGTH: 386
<212> TYPE: PRT
<213> ORGANISM: Artificial sequence
<220> FEATURE:
<223> OTHER INFORMATION: Synthetic sequence

<400> SEQUENCE: 61

```
Met Ile Lys Ala Phe Lys Tyr Arg Ile Tyr Pro Thr Gln Asp Gln Lys
1               5                   10                  15

Glu Leu Leu Ser Asn Ile Phe Gly Gln Val Arg Phe Val Tyr Asn Leu
            20                  25                  30

Gly Leu Glu Thr Lys Ile Ser Ala Tyr Thr Gly Asn Lys Lys His Leu
            35                  40                  45

Ser Cys Phe Asp Leu Asn Lys Gln Ile Thr Gln Leu Lys Asn Glu Cys
50                  55                  60

Pro Trp Leu Lys Glu Ser Pro Ser Gln Ala Leu Gln Gln Ser Ile Arg
65                  70                  75                  80

Asn Leu Asp Val Ala Tyr Thr Asn Phe Phe Arg Gly Ala Gly Phe Pro
                85                  90                  95

Lys Phe Lys Asn Lys Tyr Thr Lys Gln Ser Phe Gln Leu Pro Gln Gly
            100                 105                 110

Val Phe Leu Ser Asp Asp Lys Lys Gln Ile Phe Ile Pro Lys Leu Lys
            115                 120                 125

Phe Thr Asp Ile Asp Leu His Lys Glu Phe Lys Gly Glu Val Lys Thr
            130                 135                 140

Val Thr Val Ser Lys Thr Thr Asn Lys Tyr Tyr Ile Ser Ile Leu
145                 150                 155                 160

Val Asp Asp Lys Lys Pro Ile Pro Glu Lys Arg Gln Ile Lys Leu Glu
                165                 170                 175

Ser Thr Val Gly Ile Asp Leu Gly Ile Lys Asp Phe Ala Ile Thr Ser
            180                 185                 190

Asp Gly Lys Lys Phe Lys Asn His Asp Phe Phe Lys Ser Ala Met Asn
            195                 200                 205

Glu Leu Arg Ile Gln Gln Arg Ser Leu Ala Arg Lys Gln Lys Gly Ser
            210                 215                 220

Asn His Tyr Ile Lys Gln Lys Met Lys Val Ser Leu Leu His Glu His
225                 230                 235                 240

Ile Lys Asn Gln Arg Glu Asp Tyr Leu His Lys Ile Ser Lys Tyr Leu
                245                 250                 255

Val Tyr Asn Tyr Asp Thr Ile Cys Ile Glu Asn Leu Gly Val Ser Asn
            260                 265                 270

Met Met Lys Asn His Lys Leu Ser Arg Val Ile Gly Asp Met Gly Trp
            275                 280                 285

His Lys Phe Lys Ser Met Leu Glu Tyr Lys Cys Glu Trp Tyr Gly Lys
            290                 295                 300

Asn Leu Ser Val Ile Gly Arg Phe Asp Pro Ser Ser Lys Thr Cys Ser
305                 310                 315                 320

Ser Cys Gly Ser Ile Asn Lys Glu Leu Thr Leu Asn Asp Arg Glu Trp
                325                 330                 335

Thr Cys Lys Cys Gly Thr Lys His Asp Arg Asp Ile Asn Ala Ala Ile
            340                 345                 350

Asn Ile Arg Asn Phe Gly Leu Arg Asn Gln Pro Ser Val Thr Gln Ser
            355                 360                 365

Glu Trp Leu His Cys Ala Cys Asp Val Glu Thr His Gln Ser Leu Ala
370                 375                 380

Asp Val
385

<210> SEQ ID NO 62
<211> LENGTH: 445
<212> TYPE: PRT
```

<213> ORGANISM: Artificial sequence
<220> FEATURE:
<223> OTHER INFORMATION: Synthetic sequence

<400> SEQUENCE: 62

```
Met Thr Arg Asn Tyr Pro Tyr Lys Phe Arg Leu Glu Pro Thr Glu Glu
1               5                   10                  15

Gln Lys Thr Arg Leu Lys His Tyr Gly Phe Thr Cys Arg Phe Ile Tyr
            20                  25                  30

Asn Leu Ala Leu Asp Gln Arg Asn Leu Ser Arg Asp Pro Lys Pro Leu
        35                  40                  45

Pro Thr Leu Leu Glu Met Trp Glu Lys Arg Val Ala Asp Lys Leu Ala
    50                  55                  60

Gly Val Lys Pro Glu Arg Lys Glu Arg Asn Phe Glu Glu Arg Lys
65                  70                  75                  80

Gln Glu Val Val His Lys Asn Ile Asn Tyr Gly Phe Gln Ser Pro Gln
                85                  90                  95

Met Thr Val Leu Arg Arg Glu Val Glu Trp Met Gln Asp Val Pro Phe
            100                 105                 110

Ser Cys Leu Gln Glu Thr Leu Arg Ser Leu Gln Thr Ala Phe Lys Asn
        115                 120                 125

Phe Phe Asp Arg Val Lys Lys Gly Gln Arg Val Ser Asp Gly Arg Asn
    130                 135                 140

Pro Tyr Gly Tyr Pro Val Tyr Arg Ser Arg Tyr Arg Leu Ser Ile Pro
145                 150                 155                 160

Phe Lys Pro Ala Asn Val Ser Ile Lys Lys Val Ser Glu Arg Ala Gly
                165                 170                 175

Gly Glu Glu Gly Ala Tyr Phe Ser Glu Leu Lys Val Pro Leu Met Gly
            180                 185                 190

Ser Leu Ile Arg Phe Arg Gln Asp Arg Pro Val Leu Gly Thr Pro Lys
        195                 200                 205

Thr Pro Thr Leu Lys Leu Glu Gly Asp Gly Lys Trp Tyr Val Val Ile
    210                 215                 220

Leu Thr Glu Gln Glu Val Glu Asp Pro Gln Thr Pro Glu Ala Glu Val
225                 230                 235                 240

Gly Ile Asp Leu Gly Val Ala Lys Met Ile Thr Leu Ser Asp Gly Thr
                245                 250                 255

Ile Tyr Pro Leu Thr Lys Lys Gln Gln Thr Phe Thr Asn Ile Asp
            260                 265                 270

Thr Thr Glu Lys Arg Ile Arg Lys Leu Gln Ala Ala Cys Asp Arg Arg
        275                 280                 285

Lys Thr Lys Phe Ser Lys Asn Trp Ile Lys Val Lys Arg Gln Val Val
    290                 295                 300

Lys Leu Lys His Arg Gln Lys Arg Ser Arg Glu Ser Leu His His Glu
305                 310                 315                 320

Ile Thr His Leu Ile Thr Ser Gly Phe Gly Arg Val Ala Val Glu Asn
                325                 330                 335

Leu Asn Ile Lys Gly Met Thr Pro Ser Ala Ser Gly Thr Glu Glu Glu
            340                 345                 350

Pro Gly Thr Asn Val Ala Gln Lys Ser Gly Leu Asn Arg Glu Ile Leu
        355                 360                 365

Lys Arg Gly Trp Gly Leu Leu Val Ser Gln Leu Glu Tyr Lys Ala Lys
    370                 375                 380

Trp Arg Gly Gly Glu Val Ile Lys Val Asp Pro Lys Tyr Thr Ser Gln
```

```
385                 390                 395                 400
Thr Cys Ser Lys Cys Gly His Val Glu Lys Ala Asn Arg Ala Thr Gln
                405                 410                 415
Ala Thr Phe Leu Cys Gln Lys Cys Gly His Lys Glu Asn Ala Asp Val
                420                 425                 430
Asn Ala Ala Lys Asn Ile Leu Thr Arg Ala Glu Lys Gln
                435                 440                 445
```

<210> SEQ ID NO 63
<211> LENGTH: 29
<212> TYPE: DNA
<213> ORGANISM: Artificial sequence
<220> FEATURE:
<223> OTHER INFORMATION: Synthetic sequence

<400> SEQUENCE: 63
gtgttctcca tgcacgcggg ggagtttgg                                    29

<210> SEQ ID NO 64
<211> LENGTH: 555
<212> TYPE: PRT
<213> ORGANISM: Artificial sequence
<220> FEATURE:
<223> OTHER INFORMATION: Synthetic sequence

<400> SEQUENCE: 64

```
Met Ala Lys Gln Ala Pro Gly Lys Arg Thr Asp Glu Ser Lys Glu Arg
1               5                   10                  15
Lys Ala Phe Ser Phe Arg Leu Tyr Pro Thr Pro Glu Gln Glu Arg Tyr
                20                  25                  30
Leu Ala Arg Val Val Gly Ser Cys Arg Tyr Ile Tyr Asn Ala Leu Val
                35                  40                  45
Arg Glu His Glu Arg Arg Met Lys Tyr Met Arg Thr Phe Gly Ala Trp
            50                  55                  60
Pro Lys Pro Ile Gly Phe Lys Thr Ser Lys Lys Gln Ser Leu Ala
65                  70                  75                  80
Glu Asp Tyr Lys Leu Glu Ala Ser Leu Tyr Glu Ile Gln Thr Ala Leu
                85                  90                  95
His Glu Pro Gly Gly Pro Ala Pro Trp Leu Glu Asp Val Ala Gly Asn
                100                 105                 110
Ile Arg Asn His Ala Val Ala Met Phe Gly Ala Ala Gln Thr Asn Trp
            115                 120                 125
Met Ser Gly Arg Thr Gly Pro Pro Asn Phe Lys Gln Arg Arg Pro Ala
    130                 135                 140
Gly Ser Phe Arg Phe Gln Asp Thr Arg Val Ala Ser Ile Thr Gly Gly
145                 150                 155                 160
Pro Asp Arg Gln Pro Gly Phe Asp Phe Ile Arg Ile Pro Leu Pro His
                165                 170                 175
Gly Ile Glu Ile Asp Ser Trp Ile Cys Phe Arg Arg His Arg Arg Leu
                180                 185                 190
Arg Gly Gln Pro Lys Thr Ala Thr Ile Arg Arg Ala Ala Gly Ile Trp
            195                 200                 205
Tyr Val Ser Ile Leu Cys Glu Trp Asp Lys Pro Ala Lys Leu Pro Val
    210                 215                 220
His Arg Ala Pro Asn Ala Lys Val Gly Val Asp Leu Asn Val Arg Asn
225                 230                 235                 240
Leu Cys Ala Leu Ser Asp Gly Thr Ile Ile Asp Gly Arg Ser Ala Asp
```

```
                    245                 250                 255
Leu Ala Arg Leu Glu Lys Ser Ile Asn Arg Leu Lys His Arg Glu Ser
            260                 265                 270
Lys Leu Arg Leu Arg Glu Lys Ala Ala Ser Ala Pro Arg Ser Lys Arg
        275                 280                 285
His Phe Arg Leu Gln Cys Arg Ile Ala Arg Leu Gln Asp Arg Gln Ala
    290                 295                 300
Asn Leu Arg Asn Glu Val Thr Asn Gln Val Ala His Ala Val Ala Leu
305                 310                 315                 320
Lys His Ala Phe Val Gly Leu Glu Gly Leu Asp Ile Lys Gly Met Thr
                325                 330                 335
Ala Ser Ala Lys Gly Thr Val Asp Ala Pro Gly Leu Asn Val Arg Ala
            340                 345                 350
Lys Ala Gly Leu Asn Arg Ala Ile Leu Asn Arg Gly Trp Gly Lys Leu
        355                 360                 365
Arg Glu Lys Ile Glu Ser Lys Val Lys Ile Tyr Gly Gly Gln Thr Val
    370                 375                 380
Arg Val Pro Pro Gln Tyr Thr Ser Gln Thr Cys Ala Lys Cys Gly His
385                 390                 395                 400
Ile Ala Ala Glu Asn Arg Asp Gly Val Ile Phe His Cys Val Lys Cys
                405                 410                 415
Gly Phe Thr Ala His Ala Asp Val Asn Ala Ala Thr Asn Ile Leu Glu
            420                 425                 430
Lys Ala Leu Arg Leu Ser Ala Gln Glu Ser Pro Gly Ser Gly Ser Leu
        435                 440                 445
Asp Gly Glu Arg Pro Thr Glu Leu Gly Ser Thr Thr Arg Gln Arg Val
    450                 455                 460
Arg Lys Gln Lys Asp Thr Lys Thr Leu Gly Ala Pro Lys Ala Thr Ser
465                 470                 475                 480
Arg Lys Gly Ala Thr Ala Pro Arg Ser Thr Ile Pro Ser Leu His Val
                485                 490                 495
Asp Met Gln Val Thr Ser Ala Arg Val Val Pro Ala Pro Gln Glu Ala
            500                 505                 510
Leu Ala Thr Glu Ile Ala Gln Gln Met Lys Ala Leu Ala Lys Ser Glu
        515                 520                 525
Val Asp Ala Ala Pro Arg Gln Lys Ile Asn Arg Arg Arg Ser Gln
    530                 535                 540
Thr Glu Val Glu Val Pro Thr Gly Ser Val Glu
545                 550                 555

<210> SEQ ID NO 65
<211> LENGTH: 36
<212> TYPE: DNA
<213> ORGANISM: Artificial sequence
<220> FEATURE:
<223> OTHER INFORMATION: Synthetic sequence

<400> SEQUENCE: 65
gttgcgacgt gcaaagaacg gattggcgat cgacac                                 36

<210> SEQ ID NO 66
<211> LENGTH: 555
<212> TYPE: PRT
<213> ORGANISM: Artificial sequence
<220> FEATURE:
<223> OTHER INFORMATION: Synthetic sequence
```

```
<400> SEQUENCE: 66

Met Ala Lys Gln Ala Pro Gly Lys Arg Thr Asp Glu Ser Lys Glu Arg
1               5                   10                  15

Lys Ala Phe Ser Phe Arg Leu Tyr Pro Thr Pro Glu Gln Glu Arg Tyr
                20                  25                  30

Leu Ala Arg Val Val Gly Ser Cys Arg Tyr Ile Tyr Asn Ala Leu Val
            35                  40                  45

Arg Glu His Glu Arg Arg Met Lys Tyr Met Arg Thr Phe Gly Ala Trp
        50                  55                  60

Pro Lys Pro Ile Gly Phe Lys Thr Ser Lys Lys Gln Ser Leu Ala
65                  70                  75                  80

Glu Asp Tyr Lys Leu Glu Ala Ser Leu Tyr Glu Ile Gln Thr Ala Leu
                85                  90                  95

His Glu Pro Gly Gly Pro Ala Pro Trp Leu Glu Asp Val Ala Gly Asn
            100                 105                 110

Ile Arg Asn His Ala Val Ala Leu Phe Gly Ala Gln Thr Asn Trp
        115                 120                 125

Met Ser Gly Arg Thr Gly Pro Pro Asn Phe Lys Gln Arg Arg Pro Ala
130                 135                 140

Gly Ser Phe Arg Phe Gln Asp Thr Arg Val Ala Ser Ile Thr Gly Gly
145                 150                 155                 160

Pro Asp Arg Gln Pro Gly Phe Asp Phe Ile Arg Ile Pro Leu Pro His
                165                 170                 175

Gly Ile Glu Ile Asp Ser Trp Ile Cys Phe Arg Arg His Arg Arg Leu
            180                 185                 190

Arg Gly Gln Pro Lys Thr Ala Thr Ile Arg Arg Ala Ala Gly Ile Trp
        195                 200                 205

Tyr Val Ser Ile Leu Cys Glu Trp Asp Lys Pro Ala Lys Leu Pro Val
    210                 215                 220

His Arg Ala Pro Asn Ala Lys Val Gly Val Asp Leu Asn Val Arg Tyr
225                 230                 235                 240

Leu Cys Ala Leu Ser Asp Gly Thr Ile Ile Asp Gly Arg Ser Ala Asp
                245                 250                 255

Leu Ala Arg Leu Glu Lys Ser Ile Asn Arg Leu Lys His Arg Glu Ser
            260                 265                 270

Lys Leu Arg Leu Arg Glu Lys Ala Ala Ser Ala Pro Arg Ser Lys Arg
        275                 280                 285

His Phe Arg Leu Gln Cys Arg Ile Ala Arg Leu Gln Asp Arg Gln Ala
    290                 295                 300

Asn Leu Arg Asn Glu Val Thr Asn Gln Val Ala His Ala Val Ala Leu
305                 310                 315                 320

Lys His Ala Phe Val Gly Leu Glu Gly Leu Asp Ile Lys Gly Met Thr
                325                 330                 335

Ala Ser Ala Lys Gly Thr Val Asp Ala Pro Gly Leu Asn Val Arg Ala
            340                 345                 350

Lys Ala Gly Leu Asn Arg Ala Ile Leu Asn Arg Gly Trp Gly Lys Leu
        355                 360                 365

Arg Glu Lys Ile Glu Ser Lys Val Lys Ile Tyr Gly Gly Gln Thr Val
    370                 375                 380

Arg Val Pro Pro Gln Tyr Thr Ser Gln Thr Cys Ala Lys Cys Gly His
385                 390                 395                 400

Ile Ala Ala Glu Asn Arg Asp Gly Val Ile Phe His Cys Val Lys Cys
                405                 410                 415
```

```
Gly Phe Thr Ala His Ala Asp Val Asn Ala Ala Thr Asn Ile Leu Glu
            420                 425                 430

Lys Ala Leu Arg Leu Ser Ala Gln Glu Ser Pro Gly Ser Gly Ser Leu
            435                 440                 445

Asp Gly Glu Arg Pro Thr Glu Leu Gly Ser Thr Thr Arg Gln Arg Val
450                 455                 460

Arg Lys Gln Lys Asp Thr Lys Thr Leu Gly Ala Pro Lys Ala Thr Ser
465                 470                 475                 480

Arg Lys Gly Ala Thr Ala Pro Arg Ser Thr Ile Arg Ser Leu His Val
                485                 490                 495

Asp Met Gln Val Thr Ser Ala Arg Val Val Pro Ala Pro Gln Glu Ala
            500                 505                 510

Leu Ala Thr Glu Ile Ala Gln Gln Met Lys Ala Leu Ala Lys Ser Glu
            515                 520                 525

Val Asp Ala Ala Pro Arg Gln Lys Ile Asn Arg Arg Arg Ser Gln
530                 535                 540

Thr Glu Val Glu Val Pro Thr Gly Ser Val Glu
545                 550                 555

<210> SEQ ID NO 67
<211> LENGTH: 36
<212> TYPE: DNA
<213> ORGANISM: Artificial sequence
<220> FEATURE:
<223> OTHER INFORMATION: Synthetic sequence

<400> SEQUENCE: 67
gttgcgacgt gcaaagaacg gattggcgat cgacac                              36

<210> SEQ ID NO 68
<211> LENGTH: 400
<212> TYPE: PRT
<213> ORGANISM: Artificial sequence
<220> FEATURE:
<223> OTHER INFORMATION: Synthetic sequence

<400> SEQUENCE: 68

Met Thr Thr Gln Lys Thr Tyr Asn Phe Cys Phe Tyr Asp Gln Arg Phe
1               5                   10                  15

Phe Glu Leu Ser Lys Glu Ala Gly Glu Val Tyr Ser Arg Ser Leu Glu
            20                  25                  30

Glu Phe Trp Lys Ile Tyr Asp Glu Thr Gly Val Trp Leu Ser Lys Phe
        35                  40                  45

Asp Leu Gln Lys His Met Arg Asn Lys Leu Glu Arg Lys Leu Leu His
50                  55                  60

Ser Asp Ser Phe Leu Gly Ala Met Gln Gln Val His Ala Asn Leu Ala
65                  70                  75                  80

Ser Trp Lys Gln Ala Lys Lys Val Val Pro Asp Ala Cys Pro Pro Arg
                85                  90                  95

Lys Pro Lys Phe Leu Gln Ala Ile Leu Phe Lys Lys Ser Gln Ile Lys
            100                 105                 110

Tyr Lys Asn Gly Phe Leu Arg Leu Thr Leu Gly Thr Glu Lys Glu Phe
            115                 120                 125

Leu Tyr Leu Lys Trp Asp Ile Asn Ile Pro Leu Pro Ile Tyr Gly Ser
        130                 135                 140

Val Thr Tyr Ser Lys Thr Arg Gly Trp Lys Ile Asn Leu Cys Leu Glu
145                 150                 155                 160
```

```
Thr Glu Val Glu Gln Lys Asn Leu Ser Glu Asn Lys Tyr Leu Ser Ile
                165                 170                 175

Asp Leu Gly Val Lys Arg Val Ala Thr Ile Phe Asp Gly Glu Asn Thr
            180                 185                 190

Ile Thr Leu Ser Gly Lys Lys Phe Met Gly Leu Met His Tyr Arg Asn
        195                 200                 205

Lys Leu Asn Gly Lys Thr Gln Ser Arg Leu Ser His Lys Lys Lys Gly
    210                 215                 220

Ser Asn Asn Tyr Lys Lys Ile Gln Arg Ala Lys Arg Lys Thr Thr Asp
225                 230                 235                 240

Arg Leu Leu Asn Ile Gln Lys Glu Met Leu His Lys Tyr Ser Ser Phe
                245                 250                 255

Ile Val Asn Tyr Ala Ile Arg Asn Asp Ile Gly Asn Ile Ile Ile Gly
            260                 265                 270

Asp Asn Ser Ser Thr His Asp Ser Pro Asn Met Arg Gly Lys Thr Asn
        275                 280                 285

Gln Lys Ile Ser Gln Asn Pro Glu Gln Lys Leu Lys Asn Tyr Ile Lys
    290                 295                 300

Tyr Lys Phe Glu Ser Ile Ser Gly Arg Val Asp Ile Val Pro Glu Pro
305                 310                 315                 320

Tyr Thr Ser Arg Lys Cys Pro His Cys Lys Asn Ile Lys Lys Ser Ser
                325                 330                 335

Pro Lys Gly Arg Thr Tyr Lys Cys Lys Lys Cys Gly Phe Ile Phe Asp
            340                 345                 350

Arg Asp Gly Val Gly Ala Ile Asn Ile Tyr Asn Glu Asn Val Ser Phe
        355                 360                 365

Gly Gln Ile Ile Ser Pro Gly Arg Ile Arg Ser Leu Thr Glu Pro Ile
    370                 375                 380

Gly Met Lys Phe His Asn Glu Ile Tyr Phe Lys Ser Tyr Val Ala Ala
385                 390                 395                 400

<210> SEQ ID NO 69
<211> LENGTH: 35
<212> TYPE: DNA
<213> ORGANISM: Artificial sequence
<220> FEATURE:
<223> OTHER INFORMATION: Synthetic sequence

<400> SEQUENCE: 69
gttttatacc ctttagaatt taaactgtct aaaag                              35

<210> SEQ ID NO 70
<211> LENGTH: 403
<212> TYPE: PRT
<213> ORGANISM: Artificial sequence
<220> FEATURE:
<223> OTHER INFORMATION: Synthetic sequence

<400> SEQUENCE: 70

Val Ile Thr Lys Lys Thr Tyr Asn Phe Ser Leu Tyr Asp Pro Arg Phe
1               5                   10                  15

Phe Glu Leu Ala Lys Glu Ala Gly Asp Val Tyr Ser Arg Ser Leu Glu
            20                  25                  30

Glu Phe Trp Lys Val Tyr Asp Glu Thr Gly Val Trp Leu Ser Lys Phe
        35                  40                  45

Asp Leu Gln Lys His Met Arg Asn Lys Leu Glu Arg Lys Leu Leu His
    50                  55                  60
```

Ser Asp Ser Phe Ile Gly Ala Met Gln Gln Val His Ala Asn Leu Ala
 65                  70                  75                  80

Ser Trp Lys Gln Ala Lys Lys Val Val Lys Asp Ala Cys Pro Pro Arg
             85                  90                  95

Lys Pro Lys Phe Leu Gln Ala Ile Leu Phe Lys Ser Gln Ile Lys
         100                 105                 110

Tyr Lys Asn Gly Phe Leu Lys Leu Thr Leu Gly Ile Gly Asn Glu Tyr
             115                 120                 125

Leu Asn Leu Lys Trp Asn Gln Glu Ile Pro Leu Pro Ile Tyr Gly Ser
    130                 135                 140

Val Thr Tyr Ser Lys Thr Arg Gly Trp Lys Ile Asn Leu Cys Leu Glu
145                 150                 155                 160

Thr Asp Val Glu Gln Lys Asn Leu Asp Asn Asn Lys Phe Leu Ser Ile
                165                 170                 175

Asp Leu Gly Val Lys Arg Ile Ala Thr Ile Phe Asp Gly Glu Asn Thr
            180                 185                 190

Ile Thr Leu Ser Gly Lys Lys Phe Met Gly Leu Met His Tyr Arg Asn
        195                 200                 205

Lys Leu Asn Gly Lys Thr Gln Ser Arg Leu Ser His Lys Lys Gly
    210                 215                 220

Ser Asn Asn Tyr Lys Lys Ile Gln Arg Ala Lys Arg Thr Thr Asp
225                 230                 235                 240

Lys Ile Leu Asn Ile Gln Lys Asp Met Leu His Lys Tyr Ser Ser Phe
                245                 250                 255

Val Val Asn Tyr Ala Ile Lys Asn Asn Ile Gly Asn Ile Ile Gly
            260                 265                 270

Asp Asn Ser Ser Thr His Asp Ser Pro Asn Met Arg Gly Lys Thr Asn
                275                 280                 285

Gln Lys Ile Ser Gln Asn Pro Glu Gln Lys Leu Lys Asn Tyr Ile Lys
    290                 295                 300

Tyr Lys Phe Glu Gly Ile Ser Gly Gln Val Asn Ile Val Pro Glu Pro
305                 310                 315                 320

Tyr Thr Ser Arg Lys Cys Pro Cys Cys Lys Asn Ile Lys Ser Ser
            325                 330                 335

Pro Arg Gly Arg Thr Tyr Lys Cys Lys Lys Cys Asp Phe Val Phe Asp
            340                 345                 350

Arg Asp Gly Val Gly Ala Ile Asn Ile Tyr Asn Glu Asn Val Ser Phe
        355                 360                 365

Gly Thr Cys Leu Asn Leu Asp Ser Gly Arg Ile Arg Phe Leu Thr Glu
            370                 375                 380

Pro Ile Gly Met Lys Phe His Asn Glu Val Tyr Phe Lys Ser Tyr Val
385                 390                 395                 400

Ala Val Ala

<210> SEQ ID NO 71
<211> LENGTH: 36
<212> TYPE: DNA
<213> ORGANISM: Artificial sequence
<220> FEATURE:
<223> OTHER INFORMATION: Synthetic sequence

<400> SEQUENCE: 71
gttttatacc cttgtaattt taggagctca tcaaag                                    36

```
<210> SEQ ID NO 72
<211> LENGTH: 415
<212> TYPE: PRT
<213> ORGANISM: Artificial sequence
<220> FEATURE:
<223> OTHER INFORMATION: Synthetic sequence

<400> SEQUENCE: 72

Leu Lys Glu Leu Tyr Lys Thr Tyr Ile Leu Pro Val Lys Gln Gln Glu
1               5                   10                  15

Leu Ala Arg Lys Leu Ser Arg Glu Ser Gly Arg Ile Tyr Ser Lys Val
            20                  25                  30

Val Ser Lys Val Phe Asp Ile Tyr Lys Arg Lys Gly Phe Trp Leu Asn
        35                  40                  45

Glu Phe Asp Met Lys Lys Tyr Ile Arg Leu Tyr Ala Lys Asn Ile Gly
    50                  55                  60

Leu His Ser Gln Thr Lys Gln Gly Ile Val Glu Gln Tyr Tyr Ile Ala
65                  70                  75                  80

Leu Asp Ser Phe Phe Lys Ala Tyr Lys Asn His Arg Asn Pro Lys Pro
                85                  90                  95

Pro Tyr Lys Arg Arg Lys Tyr Asn Val Val Met Tyr Lys Asp Ser Ala
            100                 105                 110

Ile Lys Leu Lys Asn Gly Ile Leu Lys Leu Ser Asn Gly Lys Gly Asn
        115                 120                 125

Glu Pro Leu Met Val Lys Ala Asn Lys Leu Gly Lys Lys Pro Lys Tyr
    130                 135                 140

Ala Glu Leu Val Tyr His His Asn Lys Arg Lys Tyr Phe Leu His Ile
145                 150                 155                 160

Thr Val Glu Met Lys Gly Val Gln Arg Val Tyr Glu Lys Asp Arg Ala
                165                 170                 175

Ile Ala Val Asp Leu Gly Gln Ile His Pro Met Val Thr Tyr Asp Ser
            180                 185                 190

Lys Arg Ser Ile Ile Phe Asn Gly Gly Val Leu Asn Ser Phe Ile Arg
        195                 200                 205

Phe Arg Asn Lys Gln Leu Ser Lys Leu Gln Gln Lys Met Ser Met Cys
    210                 215                 220

Lys Lys Tyr Ser Lys Arg Trp Lys Lys Leu Asn Gly Ala Lys Lys Lys
225                 230                 235                 240

Leu Leu Asn Lys Ser Lys Asn Lys Val Asn Asp Val Leu Gln Lys Tyr
                245                 250                 255

Thr Ser Tyr Leu Val Gly Tyr Cys Ile Glu Gln Gly Ile Gly Thr Ile
            260                 265                 270

Val Ile Gly Asp Ile Lys Ser Ile Arg Glu Asn Ile Asn Tyr Gly Val
        275                 280                 285

Lys Thr Asn Gln Lys Leu His Asn Ser Trp Leu Phe Arg Lys Met Thr
    290                 295                 300

Asn Ile Ile Glu His Lys Ala Asn Asn Val Gly Ile Lys Val Glu Tyr
305                 310                 315                 320

Ile Asn Glu Ala Tyr Thr Ser Gln Thr Cys Pro Val Cys Asn Lys Lys
                325                 330                 335

His Lys Pro Gly Asn Arg Asn Phe Thr Cys Lys Cys Gly Phe Lys Tyr
            340                 345                 350

His Arg Asp Ala Val Gly Ala Ile Asn Ile His Lys Lys Tyr Thr Ser
        355                 360                 365

Ser Leu Ser Ala Arg Leu Glu Gly Asp Leu Thr Pro Pro Val Gly Tyr
```

```
                370              375              380
Arg Tyr Arg Tyr Asn Gln Arg Cys Leu Ala Gly Trp Asn Thr Ser Ile
385                      390              395                  400

Phe Asp Ala Gly Tyr Phe Ser Asp Leu Pro Thr Lys Lys Val Ala
                    405              410              415

<210> SEQ ID NO 73
<211> LENGTH: 405
<212> TYPE: PRT
<213> ORGANISM: Artificial sequence
<220> FEATURE:
<223> OTHER INFORMATION: Synthetic sequence

<400> SEQUENCE: 73

Met Ser Arg Tyr Val Arg Thr Tyr Lys Val Ala Val Pro Lys Glu
1               5                   10                  15

Leu Tyr Pro Leu Cys Ala Glu Leu Asn Lys Thr Ala Ala Arg Ile Tyr
                20                  25                  30

Asn Lys Thr Met Ser Leu Val Lys Lys Ile Lys Tyr Lys Lys Gly Phe
            35                  40                  45

Trp Leu Ser Pro Asn Asn Thr Gln Lys Tyr Ile Leu Arg Trp Ala Cys
50                  55                  60

Ser Ile Asn Val His Thr His Ser Lys Gln Ala Ile Ile Gln Gln Tyr
65                  70                  75                  80

Phe Gln Ala Leu Asp Ser Tyr Phe Asn Ala Val Lys Thr Lys Pro Asp
                85                  90                  95

Leu Asn Pro Pro Tyr Lys Arg Lys Arg Phe Met Pro Phe Ile Trp Lys
            100                 105                 110

Asp Thr Ala Ile Lys Leu Leu Pro Asp Gly Lys Leu Lys Leu Ser Met
        115                 120                 125

Gly Ser Asn Arg Glu Pro Ile Val Ile Gln Thr Thr Leu Leu Ala Asp
130                 135                 140

Thr Lys Ile Arg Gln Ala Lys Leu Val Tyr Glu Glu Gly Lys Tyr Tyr
145                 150                 155                 160

Leu His Leu Val Ile Glu Gly Lys Asn Val Ala Arg Lys Pro Gln Asn
                165                 170                 175

Gly Lys Ile Met Ala Val Asp Leu Gly Ile Leu Arg Pro Ile Thr Cys
            180                 185                 190

Phe Asp Gly Thr Glu Val Ile Ser Tyr His Gly Gly Ile Leu Asn Ser
        195                 200                 205

Leu Ile Arg Tyr Arg Asn Lys Glu Leu Ala Lys Phe Gln Gln Met Leu
210                 215                 220

Ser Arg Cys Lys Lys Gly Ser Lys Arg Tyr Arg Lys Leu Val Lys Ala
225                 230                 235                 240

Lys Lys Lys Met Leu Arg Arg Thr Arg His Gln Ile Lys Asp Ile Leu
                245                 250                 255

His Lys Ile Thr Ser Asn Phe Leu Lys Met Cys Leu Gln Lys Gly Ile
            260                 265                 270

Gly Thr Ile Ala Leu Gly Asp Val Thr Asn Ile Arg Glu Arg Val Glu
        275                 280                 285

Gly Asn Asp Ser Ala Asn Gln Lys Leu His Gln Trp Cys Phe Arg Lys
290                 295                 300

Met Val Asp Met Ile Thr Tyr Lys Ala Glu Leu Leu Gly Met Asp Val
305                 310                 315                 320

Lys Leu Val Pro Glu Glu Tyr Thr Ser Gln Thr Cys Pro Met Cys Gly
```

325                 330                 335
Ser Arg Asn His Ser Asn Asn Arg Asn Tyr Lys Cys Gln Asn Cys Gly
            340                 345                 350

Phe Lys Tyr His Arg Asp Gly Val Gly Ala Ile Asn Ile Tyr Val Arg
            355                 360                 365

Tyr Leu Gly Lys Lys Ser Gln Val Val Ala Gly Leu Ala Pro Val Arg
            370                 375                 380

Gly Val Arg Tyr Lys Pro His Leu Cys Gly His Gly Val Arg Asn Ala
385                 390                 395                 400

Pro Trp Lys Ala Ala
                405

<210> SEQ ID NO 74
<211> LENGTH: 397
<212> TYPE: PRT
<213> ORGANISM: Artificial sequence
<220> FEATURE:
<223> OTHER INFORMATION: Synthetic sequence

<400> SEQUENCE: 74

Met Pro Gly Tyr Val Val Arg Thr Tyr Lys Val Pro Val Pro Glu Glu
1               5                   10                  15

Leu Tyr Pro Leu Cys Ala Glu Leu Asn Lys Thr Ala Ala Arg Ile Tyr
                20                  25                  30

Asn Lys Thr Met Ser Leu Val Lys Ile Lys Arg Lys Lys Gly Ile
            35                  40                  45

Trp Leu Ser Ser Asn Asn Ala Gln Lys Tyr Ile Leu Arg Trp Ala Cys
    50                  55                  60

Gly Ile Asn Val His Thr His Ser Lys Gln Ala Met Val Gln Gln Tyr
65              70                  75                  80

Phe Gln Ala Leu Asp Ser Tyr Phe Asn Ala Val Lys Ala Lys Pro Asp
                85                  90                  95

Leu Arg Pro Pro Tyr Lys Lys Arg Phe Met Pro Phe Ile Trp Lys
                100                 105                 110

Asp Ala Ala Ile Lys Leu Leu Pro Asp Gly Lys Leu Arg Leu Ser Met
            115                 120                 125

Gly Asn Asn Gln Lys Pro Val Val Ile Gln Thr Thr Leu Pro Ala Asp
130                 135                 140

Thr Lys Ile Arg Gln Ala Lys Leu Val Tyr Glu Asp Gly Lys Tyr Tyr
145                 150                 155                 160

Leu His Leu Ala Thr Glu Val Lys Asn Glu Val Gln Lys Gln Gln Gly
                165                 170                 175

Lys Lys Val Met Ala Val Asp Leu Gly Ile Leu Arg Pro Ile Thr Cys
            180                 185                 190

Phe Asp Gly Ile Glu Val Ile Ser Tyr His Gly Gly Ile Leu Asn Ser
        195                 200                 205

Leu Ile Arg Tyr Arg Asn Lys Glu Leu Ala Lys Phe Gln Gln Met Leu
    210                 215                 220

Ser Arg Cys Lys Lys Gly Ser Lys Arg Tyr Arg Lys Leu Val Lys Ala
225                 230                 235                 240

Lys Lys Lys Met Leu Arg Arg Ile Arg His Gln Ile Lys Asp Ile Leu
                245                 250                 255

His Lys Ile Thr Ser Asn Phe Leu Lys Met Cys Leu Gln Lys Gly Ile
            260                 265                 270

Lys Thr Ile Ala Val Gly Asp Ile Thr Asn Ile Arg Glu Arg Val Gln

```
                    275                 280                 285
Gly Asn Asp Asn Ala Asn Gln Lys Leu His Gln Trp Cys Phe Arg Lys
290                 295                 300

Met Ile Asp Met Leu Thr Tyr Lys Val His Pro Leu Gly Ile Asp Val
305                 310                 315                 320

Lys Leu Val Pro Glu Asn Tyr Thr Ser Gln Thr Cys Pro Ala Cys Gly
                325                 330                 335

Ser Arg Asn His Pro Thr Asp Arg Asn Tyr Glu Cys Gln Asn Cys Gly
            340                 345                 350

Phe Lys Tyr His Arg Asp Gly Val Gly Ala Ile Asn Ile Tyr Ala Arg
                355                 360                 365

Tyr Leu Gly Lys Lys Ser Gln Val Val Ala Gly Leu Ala Pro Val Arg
            370                 375                 380

Gly Val Arg Tyr Lys Pro His Leu Cys Gly His Gly Val
385                 390                 395

<210> SEQ ID NO 75
<211> LENGTH: 389
<212> TYPE: PRT
<213> ORGANISM: Artificial sequence
<220> FEATURE:
<223> OTHER INFORMATION: Synthetic sequence

<400> SEQUENCE: 75

Met Tyr Gln Val Arg Arg Val Asn Ile Gly Lys Thr Ala Gln Leu Asp
1               5                  10                  15

Glu Leu Ala Arg Glu Cys Gly Arg Leu Tyr Ser Gln Thr Leu Ala Ser
                20                  25                  30

Phe Trp Arg Thr Val Arg His Lys Gly Ile Trp Leu Lys Pro Lys His
            35                  40                  45

Leu Met Arg Trp His Thr Ser Glu Lys Leu His Ala His Thr Ala Asp
        50                  55                  60

Ala Cys Val Gln Ala Phe Phe Ala Ser Leu Lys Ser Trp Arg Glu Arg
65                  70                  75                  80

Arg Lys Leu Gly Asp Pro Asp Ala His Pro Pro Arg Lys Arg Lys Trp
                85                  90                  95

Tyr Phe Arg Ile Glu Tyr Lys Ser Thr Ala Met His His Lys Asp Ser
            100                 105                 110

Val Leu Thr Leu Ser Asn Gly Lys Gly Asn Thr Pro Leu Val Leu Glu
        115                 120                 125

Trp Pro Trp Glu Thr Pro Lys Thr Val Val Ile His Trp Thr Gly Thr
130                 135                 140

Gln Tyr Glu Ala Ile Ala Thr Tyr Lys Ile Glu Ala Gln Gly Gln Pro
145                 150                 155                 160

Gln Gly Asn Lys Val Ala Gly Ile Asp Leu Gly Glu Ile His Met Ala
                165                 170                 175

Val Ser His Asp Gly Thr Glu Thr His Ile Leu Asn Gly Arg Leu Leu
            180                 185                 190

Arg Ser Lys Arg Gln Tyr Gln Asn Lys Leu Lys Ala Glu Leu Ser Thr
        195                 200                 205

Met Ile Asp Val Lys Lys Gly Ser Leu Arg Arg Lys Lys Leu Ile
        210                 215                 220

Arg Ser Lys Gln Lys Gln Leu Lys Lys Leu Gln His Gln Val Asn Asp
225                 230                 235                 240

Ile Glu His Lys Gln Ser Ser Arg Leu Ile Ser Thr Leu His Ala Lys
```

-continued

```
                    245                 250                 255
Gly Val Gln Thr Val Val Ile Gly Asp Val Arg Asp Ile Arg Gln Asp
                260                 265                 270
Leu Asp Val Gly Ser Lys Asn Asn Gln Lys Leu His Gln Trp Ser His
                275                 280                 285
Gly Ser Ile Arg His Lys Leu Thr Tyr Lys Ala Glu Trp Leu Gly Met
            290                 295                 300
Glu Val Ala Leu Gln Asp Glu His Tyr Thr Ser Arg Thr Cys Pro Met
305                 310                 315                 320
Cys Gln His Val Arg Lys Ser Lys Val Gln Gly Arg Val Phe Arg Cys
                325                 330                 335
Pro Thr Cys His Trp Thr Tyr His Arg Asp Gly Val Gly Ala Ile Asn
                340                 345                 350
Ile Arg Gln Lys Tyr Leu Gly Ser Leu Pro Val Ile Gly Asp Met Ala
                355                 360                 365
Pro Pro Ile Gly Met Arg Phe Arg Pro His Thr Ser Val Ala Arg Trp
            370                 375                 380
Glu Lys Thr Tyr Gln
385

<210> SEQ ID NO 76
<211> LENGTH: 392
<212> TYPE: PRT
<213> ORGANISM: Artificial sequence
<220> FEATURE:
<223> OTHER INFORMATION: Synthetic sequence

<400> SEQUENCE: 76

Met Tyr Asn Val Arg Lys Leu Lys Ile Asp Gln Thr Glu Gln Leu Asp
1               5                   10                  15
Val Leu Ala Thr Ala Ser Gly Glu Leu Tyr Ser Arg Thr Leu Val Ser
                20                  25                  30
Phe Trp Arg Thr Val Arg Lys His Gly Leu Trp Leu Lys Pro Ser Ser
                35                  40                  45
Met Met Arg Trp Gln Asn Ser Gly Glu Leu His Ala His Ser Ala Asp
            50                  55                  60
Ala Val Val Gln Ser Phe Tyr Ala Ser Leu Lys Ser Trp Arg Ala Leu
65                  70                  75                  80
Arg Lys Val Asp Pro Asp Ala Lys Pro Pro Lys Arg Arg Lys His Phe
                85                  90                  95
Phe Lys Val Gln Trp Lys Asn Ser Ala Ile Arg Leu Lys Asp Gly Cys
                100                 105                 110
Leu Val Leu Ser Asn Gly Lys Gly Asn Glu Pro Leu Ile Ile Pro Trp
            115                 120                 125
Asn Trp Thr Leu Pro Thr Leu Val Glu Leu Gly Trp Asn Gly Thr Gly
130                 135                 140
Tyr Glu Leu Arg Val Ile Tyr Ser Thr Thr Pro Thr Gly Val Pro Leu
145                 150                 155                 160
Gly Val Lys Val Ala Gly Val Asp Met Gly Glu Ile His Leu Ala Val
                165                 170                 175
Thr His Asp Gly Asp Asp Cys His Ile Tyr Asn Gly Arg Tyr Leu Arg
                180                 185                 190
Ser Val Lys Arg Tyr Gln Asn Lys Lys Ala Glu Ile Ser Ala Arg
                195                 200                 205
Leu Asp Arg Met Lys Lys Gly Ser Arg Arg Ser Lys Tyr Leu Lys His
```

Asn Lys Ala Arg Thr Leu Lys Lys Leu Asp Asn Gln Ile Asn Asp Ile
225                 230                 235                 240

Leu His Lys Gln Thr Thr Lys Leu Val Ser Thr Leu His Glu Ala Gly
            245                 250                 255

Val Lys Thr Val Val Ile Gly Asp Val Arg Asp Ile Arg Lys Gly Leu
                260                 265                 270

Asp Tyr Gly Ala Lys Ala Asn Gln Lys Ile His Gln Trp His Leu Gly
            275                 280                 285

Lys Thr Arg Trp Leu Val Ser Tyr Lys Ala Glu Arg Leu Gly Met Glu
        290                 295                 300

Val Val Leu Gln Asp Glu Ala Tyr Thr Ser Gln Thr Cys Pro Ala Cys
305                 310                 315                 320

Gly Lys Arg His Lys Pro Lys Asp Arg Asn Tyr Arg Cys Ser Cys Gly
                325                 330                 335

Phe Gln Tyr His Arg Asp Gly Ile Gly Ala Tyr Asn Ile Arg Ala Lys
            340                 345                 350

Tyr Leu Gly Glu Leu Glu Thr Pro His Val Val Gly Ala Met Met Ser
        355                 360                 365

Pro Thr Gly Val Arg Val Leu Gln Arg Cys Ser His Leu Ala Arg Lys
370                 375                 380

Asn Pro Leu Pro Leu Gly Met Gly
385                 390

<210> SEQ ID NO 77
<211> LENGTH: 401
<212> TYPE: PRT
<213> ORGANISM: Artificial sequence
<220> FEATURE:
<223> OTHER INFORMATION: Synthetic sequence

<400> SEQUENCE: 77

Met Asn Ile Ala His Gln Asp Ala Ile Trp Glu Ala Ser Lys Glu Ser
1               5                   10                  15

Ala Ser Ile Tyr Asn Asp Ala Ile Lys Leu Asn Gln Asp Gly Ile Pro
            20                  25                  30

Lys Ala Gln Ala Met Lys Ser Leu Ser Ile Gln Ser Lys His Thr Lys
        35                  40                  45

Tyr Leu Gln Ser Gln Ser Ser Gln Ala Pro Tyr Gln Asn Phe Phe Ile
    50                  55                  60

Asp Leu Ser Ser Tyr Phe Ala Ser Leu Lys Arg Tyr Gln Lys Ser Lys
65                  70                  75                  80

Arg Gly Tyr Lys Asn Glu Pro Lys Pro Pro His Lys Ile Lys Thr Leu
                85                  90                  95

His Ala Ile Thr Phe Lys Lys Ser Ala Ile Arg Val Gln Asn Gly Tyr
            100                 105                 110

Leu Leu Leu Ser Leu Arg Lys Pro Asn Lys Pro Ile Lys Leu Lys Trp
        115                 120                 125

Ser Leu Ser Lys Pro Ile Trp Val Leu Ile Asn Phe Asp Ile Arg Thr
    130                 135                 140

Gly Trp Lys Met Asn Cys Val Met Glu Gln Glu Val Gln Gln His Gln
145                 150                 155                 160

Leu Asp Lys Thr Lys Ile Leu Ala Ile Asp Leu Gly Asn Lys Arg Ile
                165                 170                 175

Ala Ala Ser Phe Asp Gly Lys Arg Cys Val Thr Tyr Ser Gly Lys Ile

```
                180                 185                 190
Leu Lys Ser Leu Thr Arg Leu Gln Asn Lys Cys Ser Ala Arg Ser Lys
        195                 200                 205

Ala Ser Thr Ser Ser Leu Ile Lys Asn Ser Lys Tyr Lys Arg Val
    210                 215                 220

Met Arg Ala Arg Arg Lys Ile Thr Ala Arg Ile Asn Asn Gln Lys Arg
225                 230                 235                 240

Asp Ile Leu His Lys Thr Ser Arg Ala Ile Val Asn Tyr Ala Ile Glu
                245                 250                 255

Asn Asn Ile Asp Lys Ile Val Phe Gly Asp Cys Ser Ser Ile His Asp
                260                 265                 270

Gly Thr Thr Leu Gly Lys Glu Asn Thr Gln Gln Val Gln Gln Gly Cys
                275                 280                 285

Glu Gln Lys Leu Arg Lys Tyr Val Glu Tyr Lys Phe Arg Asn Val Gly
    290                 295                 300

Gly Thr Thr Glu Leu Val Ser Glu Arg Tyr Ser Ser Gln Glu Cys Pro
305                 310                 315                 320

Ile Cys Asp His Arg Tyr Glu Pro Arg Gly Arg Thr Tyr Lys Cys Ser
                325                 330                 335

Ala Cys Gly Tyr Val Tyr Asp Arg Asp Gly Val Gly Ser Ile Asn Ile
                340                 345                 350

Tyr Thr Asn Val Ser Ser Gly Leu Thr Leu Asp Val Val Gly Gly Leu
                355                 360                 365

Met Pro Pro Arg Gly Trp Lys Phe His Ser Gln Leu Pro Cys Thr Thr
370                 375                 380

Leu Arg Asn Ser Tyr Phe Ser Met Leu Tyr Cys Gly Glu Pro Asn Asp
385                 390                 395                 400

Leu

<210> SEQ ID NO 78
<211> LENGTH: 431
<212> TYPE: PRT
<213> ORGANISM: Artificial sequence
<220> FEATURE:
<223> OTHER INFORMATION: Synthetic sequence

<400> SEQUENCE: 78

Val Arg Lys Ile Ala Glu Ser Lys Gly Tyr Phe Thr Lys Ala Val Ser
1               5                   10                  15

Val Glu Leu Val Gly His Ser Lys Glu Asp Thr Val Trp Leu Leu Asp
                20                  25                  30

Ile Leu Asn Arg Gly Tyr Pro Leu Ala Asn Lys Met Tyr Leu Leu Tyr
                35                  40                  45

Arg Trp Tyr Tyr Glu Gly Leu Phe Pro Thr Glu Ile Glu Leu Asn Lys
        50                  55                  60

Leu Glu Thr Tyr Val Tyr His Lys Ala Arg Glu Asp Ser Arg Phe Thr
65                  70                  75                  80

Asp Ile Pro Ser Asn Ile Ile Ala Cys Thr Asn Arg Thr Ile Leu Gln
                85                  90                  95

Lys Ile Lys Tyr Asp Ile Lys Ser Gly Ala Lys Ser Gly Lys Arg Ser
                100                 105                 110

Trp Ser Gln Phe Lys Lys Gly Gln Pro Leu Tyr Phe Val Gln His Asn
        115                 120                 125

Tyr Leu Glu Lys Thr Asp Asp Gly Tyr Asn Tyr Asn Phe Ile Phe Gly
        130                 135                 140
```

His Lys Phe Lys Leu Lys Phe Gly Arg His Asn Glu Gly Glu Gln Leu
145                 150                 155                 160

Ile Glu Lys Leu Met Asp Ser Glu Ser Gln Phe Lys Leu Asn Ala Asn
                165                 170                 175

Ala Ala Phe Lys Val Ile Lys Arg Arg Leu Phe Leu Leu Leu Ser Tyr
            180                 185                 190

Glu Ile Pro Asp Lys Ile Glu Asn Lys Pro Asn Pro Asp Asn Ile Met
        195                 200                 205

Gly Ile Asp Phe Gly Met Ala Asn Phe Ala Thr Cys Tyr Leu Ala Asn
    210                 215                 220

Asp Arg Lys Phe Lys Ile Val Arg Asp His Lys Tyr Leu Lys Lys Arg
225                 230                 235                 240

Leu Leu Leu Gln Arg Lys Ile Lys Asn Leu Gln Ser Glu Leu Ser Met
                245                 250                 255

His His Ala Gly Leu Gly Arg Ala Arg Lys Thr Arg Lys Ile Glu Asp
            260                 265                 270

Tyr Arg Asn Lys Glu Lys Asn Leu Thr Lys Thr Glu Ile Ser Gln Ile
        275                 280                 285

Leu Ser Ser Ile Val Arg Leu Ala Gln Ala Asn Asn Ile Gly Thr Ile
    290                 295                 300

Lys Ile Glu Tyr Leu Thr Ile Asp Gln Lys Thr Gln Leu Glu Asp Lys
305                 310                 315                 320

Tyr Val Tyr Arg Asn Trp Ala Val Met Met Thr Ile Asp Met Leu Arg
                325                 330                 335

Glu Lys Ala Lys Tyr Val Gly Ile Asn Val Val Thr Ile Asp Pro Tyr
            340                 345                 350

His Thr Ser Gln Lys Cys Ser Thr Cys Gly Thr Ile Gly Thr Arg Asp
        355                 360                 365

Gly Arg Ile Phe Ser Cys Glu Asn Pro Ser Cys Lys Ser Phe His Lys
    370                 375                 380

Val Val Asn Ala Asp Lys Asn Ala Ala Ile Asn Ile Ala Asn Ser Thr
385                 390                 395                 400

Gln Phe Val Asp Asp Val Lys Asp Thr Glu Tyr Tyr Lys Gln Lys Gln
                405                 410                 415

Glu Phe Phe Lys Thr Leu Arg Glu Lys Lys Glu Thr Asn Ile Thr
            420                 425                 430

<210> SEQ ID NO 79
<211> LENGTH: 23
<212> TYPE: DNA
<213> ORGANISM: Artificial sequence
<220> FEATURE:
<223> OTHER INFORMATION: Synthetic sequence

<400> SEQUENCE: 79
tgtgtatacc attcaaattg tat                                          23

<210> SEQ ID NO 80
<211> LENGTH: 447
<212> TYPE: PRT
<213> ORGANISM: Artificial sequence
<220> FEATURE:
<223> OTHER INFORMATION: Synthetic sequence

<400> SEQUENCE: 80

Met Ala Lys Lys Asn Ile Asp Asp Thr Lys Lys Val Thr Leu Cys Glu
1               5                   10                  15

```
Lys Val Lys Leu Thr Gln Ile Tyr Ser Pro Val Val Asp Trp Lys Glu
             20                  25                  30

Phe His Lys Ile Phe Lys Ile Leu Gln Lys Glu Thr Ile Leu Ala Ser
             35                  40                  45

Asn Lys Ile Ile Ser Ile Cys Asn Ile Phe Asn Ser Phe Asn Asn Lys
 50                  55                  60

Glu Gln Lys Asp Trp Leu Ile Lys Tyr Gln Ser Glu Lys Leu
65                   70                  75                  80

Arg Asn Val Leu Tyr Asp Val Ala Arg Lys Tyr Cys Tyr Tyr Ser Tyr
                 85                  90                  95

Ser Arg Asn Ala Asn Ala Ile Ser Asn Asp Ile Tyr Tyr Lys Tyr Phe
                100                 105                 110

Lys Gly Pro Asn Ser Tyr Lys Val Lys Ile Gln Lys Gly Ile Gly Asn
             115                 120                 125

Pro Pro Met Thr Phe Thr Glu Ser Ile Pro Leu Tyr Ile Thr Val Gln
130                 135                 140

Arg His Lys Ile Glu Cys Thr Asn Asn Val Arg His Tyr Tyr Thr Ile
145                 150                 155                 160

Glu Val Pro Leu Leu Ser Asn Asn Cys Lys Ser Gly Ile Gln Ile Thr
                165                 170                 175

Asp Thr Glu Gln Thr Gln Val Asn Asn Asn Ala Leu Arg Phe Gly Ile
             180                 185                 190

Asn Ala Ala Gly Asn Lys Arg Leu Ile Glu Ile Leu Asp Asn Ile Ile
         195                 200                 205

Tyr Gly Lys Tyr Glu Phe Cys Asp Ser Lys Leu Lys Arg Val Lys Ser
     210                 215                 220

Lys Lys Arg Ser His Arg Tyr Asp Tyr Tyr Phe Leu Leu Ser Tyr Lys
225                 230                 235                 240

Lys Pro Val Ile Glu Ile Lys Ser Leu Lys Pro Glu Asn Val Leu Gly
                245                 250                 255

Val Asp Leu Gly Met Thr Val Pro Ala Tyr Cys Ala Val Asn Tyr Cys
             260                 265                 270

Asp Tyr Lys Lys Lys Ala Val Gly Asp Ser Arg Ile Ile Arg Phe Asn
         275                 280                 285

Leu Ile Gln Glu Lys Ile Asn Lys Arg Ile Gln Arg Asn Ile Lys Tyr
     290                 295                 300

Asn Leu Arg Asp Gly His Gly Arg Lys Tyr Lys Leu Asp Gly Tyr Asp
305                 310                 315                 320

Gly Ala Ser Asn Lys Ile Ala Lys Arg Asn Ser Thr Phe Asn Phe Asn
                325                 330                 335

Leu Ala Ser Glu Ile Ile Gln Leu Ala Ile Lys Trp Gln Cys Gly Thr
             340                 345                 350

Ile His Leu Glu Asp Leu Thr Lys Ile His Glu Ile Asn Pro Gln Asn
         355                 360                 365

Arg Phe Leu Lys Asn Trp Thr Tyr Tyr Asp Leu Gln Lys Lys Ile Glu
     370                 375                 380

Asn Lys Ala Lys Glu Tyr Gly Ile Val Val Lys Tyr Ile Asn Pro Tyr
385                 390                 395                 400

Tyr Thr Ser Gln Ile Cys Ser Asn Cys Gly His Phe Glu Ser Gly Gln
                405                 410                 415

Arg Ile Ser Gln Ser Gln Phe Gln Cys Lys Ser Cys Gly Tyr Ser Ala
             420                 425                 430
```

Asn Ala Asp Tyr Asn Ala Ala Arg Asn Ile Ala Leu Tyr Lys Phe
            435                 440                 445

<210> SEQ ID NO 81
<211> LENGTH: 32
<212> TYPE: DNA
<213> ORGANISM: Artificial sequence
<220> FEATURE:
<223> OTHER INFORMATION: Synthetic sequence

<400> SEQUENCE: 81
ctttcaatct gcacatgcgt acggattgta tc                                    32

<210> SEQ ID NO 82
<211> LENGTH: 595
<212> TYPE: PRT
<213> ORGANISM: Artificial sequence
<220> FEATURE:
<223> OTHER INFORMATION: Synthetic sequence

<400> SEQUENCE: 82

Met Ser Thr Met Val Phe Glu Tyr Tyr Leu Arg Ser Pro Glu Lys Glu
1               5                   10                  15

Gln Glu Gln Ile Val Ile Gln Gln Leu Arg Ala Ser Tyr Glu Tyr Tyr
            20                  25                  30

Asn Thr Leu Ile Arg Ile Glu Gln Asn Arg Arg Asn Gln Phe Arg Ala
        35                  40                  45

Ile Gln Ser Gln Asp Pro Lys Ile Ala Gln Leu Glu Leu Glu Ile Ser
    50                  55                  60

Ser Leu Asp Thr Glu Ile Asp Leu His Leu Thr Ser Ile Gln Asn Thr
65                  70                  75                  80

Arg Ser Thr Asn Arg Lys Asn Val Leu Asp Lys Lys Asp Val Asp Arg
                85                  90                  95

Val Lys Ser Leu Lys Ala Asp Arg Lys Leu Lys Arg Asp Glu Leu Lys
            100                 105                 110

Ile Ala Lys Lys Ser Phe Cys Asp Asn Leu Ile Phe Gln Lys Ala Cys
        115                 120                 125

Glu Asp Ile Asn Leu Phe Ala Lys Asn Glu Ser Lys Ala Ala Arg Lys
    130                 135                 140

Ala Thr Pro Ser Tyr Trp Gly Ser Tyr Leu Leu Ile Glu Asn Ala Ile
145                 150                 155                 160

Asp Ala Ala Lys Lys Ser Lys Thr Asp Pro Lys Arg Lys Tyr Trp Asp
                165                 170                 175

Trp Thr Gly Arg Leu Gly Val Gln Val Gln Gly Gly Met Ser Val Ser
            180                 185                 190

Glu Leu Phe Gly Asn Asp Thr Arg Ile Gln Ile Asp Pro Val Ser Leu
        195                 200                 205

Asp Ala Trp Tyr His Pro Ile Arg Gly Lys Arg Lys Tyr Ala Gln Arg
    210                 215                 220

Gln Pro Lys Leu Arg Phe Arg Ile Asn Ser Asp Lys Gly Lys Pro
225                 230                 235                 240

Ile Phe Val Glu Phe Pro Met Ile Met His Arg Pro Leu Pro Gln Asn
                245                 250                 255

Ala Cys Ile Lys Gln Ala Asn Val Ile Val Thr Asn Arg Asp Arg Lys
            260                 265                 270

Leu Cys Tyr Val Leu Gln Leu Thr Val Asn Ile Pro Glu Pro Val Ala
        275                 280                 285

```
Ser Pro Cys Thr Asn Gly Val Gly Ile Asp Leu Gly Trp Arg Leu Met
    290             295                 300

Asp Ser Gly Asp Ile Arg Val Ala Tyr Gly Tyr Asp Gln Lys Gly Thr
305             310                 315                 320

Lys Ile Asp Leu Arg Leu Pro Lys Ser Ile Thr Ser Leu Phe Gln Lys
                325                 330                 335

Ala Glu Ser Ile Arg Ala Ile Arg Asp Lys Glu Phe Glu Asp His Arg
            340                 345                 350

Lys Ile Met Ile Pro Leu Ile Gln Gly Val Thr Phe Pro Asn Ile Asn
        355                 360                 365

Thr Thr Asn Ile Gly Leu Ser Lys Ser Phe Arg Phe His Ser Leu
370                 375                 380

Tyr Leu Gly Trp Lys Ala Asn Arg Gln Asp Gly Asp Gln Ile Ala Phe
385             390                 395                 400

Asp Ala Leu Glu Thr Trp His Arg Lys Asp Arg His Leu Glu Gln Tyr
                405                 410                 415

Glu Val Gly Cys Arg Lys Arg Ala Met Asn Tyr Arg Arg Glu Glu Tyr
            420                 425                 430

Arg Lys Phe Ala Lys Gln Met Thr Ser Thr Tyr Gly Tyr Leu Ala Leu
        435                 440                 445

Glu Asn Trp Asn Ile Ser Lys Val Ala Leu Arg Pro Glu Ile Glu Asp
450                 455                 460

Gly Thr Arg Glu Gln Ser Glu Pro Gln His Gln Arg Val Met Ala Cys
465                 470                 475                 480

Val Ser Met Leu Arg Gln Ile Leu Ile Asn Thr Ala Lys Arg Glu Gly
                485                 490                 495

Val Ser Ile Ile Ser Val Pro Ala Ala Tyr Thr Thr Leu Glu Cys Ala
            500                 505                 510

Ala Cys His Lys Ile Asn Thr Trp Asp Thr Ser Lys Asn Val Cys Gln
        515                 520                 525

Thr Cys Glu Asn Cys Asp Thr Val Trp Asp Gln Asp Glu Asn Ala Ala
    530                 535                 540

Arg Asn Leu Leu Ala Ser Gly Thr Val Leu Lys Asn Thr Ala Pro Leu
545                 550                 555                 560

Pro Glu Glu Ala Asn Ile Ala Asn Thr Glu Lys Lys Ser Arg Trp Ser
                565                 570                 575

Lys Arg Lys Ala Glu Val Val Ile Asp Glu Lys Val Asp Arg Ser Gln
            580                 585                 590

Ile Ala Ser
        595

<210> SEQ ID NO 83
<211> LENGTH: 36
<212> TYPE: DNA
<213> ORGANISM: Artificial sequence
<220> FEATURE:
<223> OTHER INFORMATION: Synthetic sequence

<400> SEQUENCE: 83
cttgtaatgg ttgctcaaca ccttgaaagt tgagac                            36

<210> SEQ ID NO 84
<211> LENGTH: 475
<212> TYPE: PRT
<213> ORGANISM: Artificial sequence
<220> FEATURE:
<223> OTHER INFORMATION: Synthetic sequence
```

-continued

<400> SEQUENCE: 84

```
Met Lys Val Tyr Lys Tyr Gly Leu Leu Pro Ile Lys Asn Gln Thr
1               5                   10                  15

Leu Val Phe Glu Gln Leu Asn Lys Ala Tyr Gln Tyr Lys Lys Gln Leu
            20                  25                  30

Ile Asp Leu Val Asn Gln Glu Lys Ala Leu Leu Lys Lys Glu Glu Asp
            35                  40                  45

Asn Ile Phe Gln Arg Leu Asn Pro Ala Leu Ile Ser Lys Lys Glu Thr
50                      55                      60

Thr Gln Gln Thr Val Glu Glu Leu Leu Ala Leu Met Lys Gln Gln Arg
65                  70                  75                  80

Ser Lys Asn Arg Ser Lys Gln Asp Asn Ile Glu Leu Lys Gln Gln Phe
                85                  90                  95

Lys Ile Ala Lys Glu Asn Ala Lys Gln Ala Lys Lys Asp Tyr Phe Thr
            100                 105                 110

Glu Leu Ser Arg Ile Lys Thr Leu Glu Glu Val Lys Thr Ser Lys Glu
            115                 120                 125

Lys Ile Lys Thr Asn Phe Lys Gln Leu His Lys Glu Ala Arg Lys Lys
130                 135                 140

Cys Gly Val Tyr Trp Gly Thr Tyr Leu Leu Ile Glu Glu Ala Val Glu
145                 150                 155                 160

Gln Ser Lys Lys Thr Ser Phe Lys Lys Asp Phe Ile Phe Tyr Gly Arg
                165                 170                 175

Arg Asp Asn Glu Arg Leu Gly Asn Gln Ile Gln Thr Ser Lys Asp Asp
            180                 185                 190

Ser Gly Ser Lys Ile Met Gly Met Leu Ser Ser His Leu Phe Asn Glu
            195                 200                 205

Lys Asn Ser Gln Ile Tyr Ile Glu Pro Val Ala Asp Thr Ala Trp Ile
210                 215                 220

Gly Val Tyr Arg Lys Asp Arg Arg Thr Ala Lys Thr Ile Leu His
225                 230                 235                 240

Trp Arg Ile Ala Ser Asp Glu Lys Leu Lys Pro Ile Trp Ala Glu Phe
                245                 250                 255

Pro Met Ile Met His Arg Pro Leu Pro Lys Asp Ser Lys Ile Lys Ser
            260                 265                 270

Ala Thr Ile Ser Arg Arg Phe Tyr Gly Pro His Gln Glu Trp Thr Leu
            275                 280                 285

Glu Ile Thr Ile Asp Asp Asn Leu Ser Pro Thr Lys Glu Leu Gly Asn
290                 295                 300

Gly Val Val Ala Leu Asp Ile Gly Trp Arg Lys Leu Asn Asp Lys Ile
305                 310                 315                 320

Arg Val Ala Thr Leu Tyr Asp Gly Glu Phe His Lys Glu Leu Val Ile
                325                 330                 335

Ser Thr Tyr Gln Leu Asp Lys Ala Asn Glu Leu Lys Ser Leu Arg Asp
            340                 345                 350

Asp Leu Phe Asn Gln Val Lys Asn Gln Ile Thr Glu Trp Asn Lys Glu
            355                 360                 365

Lys Phe Pro Glu Trp Ile Leu Lys Glu Leu Glu Phe Val Ser Lys Trp
370                 375                 380

Lys Ser Gln Ala Arg Leu Val Arg Leu Val Lys Asn Trp Lys Lys Glu
385                 390                 395                 400

Arg Trp Gln Asp Asp Asn Ile Tyr Phe Glu Leu Val Glu Ala Trp Arg
```

```
              405                 410                 415
Tyr Lys Asp Gln His Leu Trp Gln Trp Glu Cys Gly Ser Arg Arg Ser
            420                 425                 430

Gly Leu Arg Glu Arg Ile Ile Ile Ala Thr Leu Pro Pro Asn Leu Glu
        435                 440                 445

Arg Asn Ile Thr Val Leu Tyr Trp Lys Thr Leu Ile Phe Gln Arg Trp
450                 455                 460

Gln Asn Tyr Gln Asn Phe Arg Gln Lys Ile
465                 470                 475

<210> SEQ ID NO 85
<211> LENGTH: 36
<212> TYPE: DNA
<213> ORGANISM: Artificial sequence
<220> FEATURE:
<223> OTHER INFORMATION: Synthetic sequence

<400> SEQUENCE: 85
atagtaatgg cagctcaatg ccctataaat tgagac                              36

<210> SEQ ID NO 86
<211> LENGTH: 411
<212> TYPE: PRT
<213> ORGANISM: Artificial sequence
<220> FEATURE:
<223> OTHER INFORMATION: Synthetic sequence

<400> SEQUENCE: 86

Met Pro Val Lys Ala Val Lys Phe Gln Ile Ile Lys Pro Leu Asn Ala
1               5                   10                  15

Thr Trp Asp Val Leu Gly Lys Thr Leu Arg Asp Leu Asn Tyr His Thr
            20                  25                  30

Thr Leu Met Cys Asn Arg Ala Ile Gln Leu Tyr Trp Glu Tyr Gly Asn
        35                  40                  45

Phe Arg Ser Gln Tyr Lys Ala Glu His Gly Lys Tyr Pro Ile Asp Lys
    50                  55                  60

Asp Ile Tyr Gly Cys Ser Tyr Arg Asn His Val Tyr Arg Gln Leu Arg
65                  70                  75                  80

Leu Met Tyr Pro Leu Met Ala Ser Ser Asn Thr Ser Gln Thr Asn Gln
                85                  90                  95

Phe Ala Leu Lys Arg Trp Gln Thr Asp Val Pro Asp Ile Arg Lys Leu
            100                 105                 110

Ala Lys Ser Ile Pro Ser Phe Lys Leu Gly Thr Pro Ile Gln Val Ala
        115                 120                 125

Asn Gln Asn Phe Asp Leu Arg Phe Asn Asp Asp Thr Phe Ser Val Asp
    130                 135                 140

Val Thr Leu Leu Gly Arg Glu Ser Glu Val Gly Arg Phe Ser Ile Leu
145                 150                 155                 160

Leu Asp Thr Gly Asp Lys Ser Lys Arg Val Ile Phe Gln Arg Ile Leu
                165                 170                 175

Asp Arg Thr Tyr Lys Gln Gly Ser Met Gln Ile Val Tyr Ser Lys Lys
            180                 185                 190

Lys Gly Lys Trp Phe Cys Val Ile Ala Tyr Asp Ser Pro Ile Lys Val
        195                 200                 205

Asn Glu Leu Asp Ile Asp Lys Val Met Gly Ile Asp Leu Gly Ile Val
    210                 215                 220

Asn Ala Val Tyr Trp Ala Phe Asn Ser Gly His Asn Arg Gly Cys Ile
```

```
225                 230                 235                 240
Ser Gly Gly Glu Ile Asp Thr Phe Arg Lys Gln Ile Glu Val Arg Arg
            245                 250                 255

Arg Gln Ile Leu Arg Thr Pro Arg Lys Asp Gly His Gly Arg Lys Arg
            260                 265                 270

Asn Met Gln Ala Ala Asp Ile Leu Gly Glu Lys Ile Ser Asn Phe Arg
            275                 280                 285

Asp Thr Val Asn His Lys Tyr Ser Lys Ile Ile Asp Ile Ala Ile
        290                 295                 300

Ala Asn Lys Cys Gly Val Ile Gln Met Glu Asp Leu Thr Gly Ile Ser
305                 310                 315                 320

Lys Asp Ser Phe Phe Leu Arg Asn Trp Thr Tyr Arg Asp Leu Gln Asp
                325                 330                 335

Lys Ile Val Tyr Lys Ala Leu Gln Glu Gly Ile Val Lys Leu Ile
            340                 345                 350

Asp Pro Arg Asn Thr Ser Lys Thr Cys Ser Val Cys Gly His Leu Asp
            355                 360                 365

Ala Glu Asn Arg Glu Asp Gln Ala Thr Phe Ile Cys Lys Asn Pro Glu
        370                 375                 380

Cys Gly Ser Asn Met Asn Ala Asp His Asn Ala Ala Lys Asn Ile Ser
385                 390                 395                 400

Val Trp Ser Lys Val Ser Lys Glu Phe Gly Leu
                405                 410

<210> SEQ ID NO 87
<211> LENGTH: 30
<212> TYPE: DNA
<213> ORGANISM: Artificial sequence
<220> FEATURE:
<223> OTHER INFORMATION: Synthetic sequence

<400> SEQUENCE: 87
actccaaccc cacatagtta ccatggaaac                                    30

<210> SEQ ID NO 88
<211> LENGTH: 425
<212> TYPE: PRT
<213> ORGANISM: Artificial sequence
<220> FEATURE:
<223> OTHER INFORMATION: Synthetic sequence

<400> SEQUENCE: 88

Met Asn Lys Val Met Arg Tyr Gln Ile Ile Lys Pro Ile Asp Ile Asp
1               5                   10                  15

Trp Lys Thr Phe Gly Asp Ile Leu Asn Lys Leu Arg Gln Glu Val Arg
            20                  25                  30

Phe Thr Lys Asn Lys Thr Ile Ala Leu Tyr Asn Asp Trp Leu Thr Tyr
        35                  40                  45

Cys Phe Gln Tyr Lys Asn Glu His Asn Glu Tyr Pro Lys Leu Val Asp
    50                  55                  60

Tyr Cys Gly Tyr Lys Val Phe Ser Gly Tyr Ala Tyr Asp Lys Phe Lys
65                  70                  75                  80

Thr Glu Val Val Phe Ser Asn Thr Ala Asn Tyr Thr Ser Val Arg
                85                  90                  95

Glu Ala Cys Ser Ala Tyr Asp Ala His Lys Thr Asp Ile Leu Lys Gly
            100                 105                 110

Asn Cys Ser Ile Pro Ser Met Gly Ala Asn Gln Pro Ile Asp Leu His
```

```
            115                 120                 125
Asn Lys Ser Leu Ser Val Asp Ile Asn Glu Phe Gly Asp Tyr Ile Ala
        130                 135                 140
Thr Ile Ser Leu Leu Ser Asn Arg Gly Lys Lys Glu Phe Gly Leu Lys
145                 150                 155                 160
Ser Gly Gln Ile Lys Ile Val Leu Lys Ala Gly Asp Lys Ser Ser Arg
                165                 170                 175
Asp Ile Leu Gln Arg Cys Val Ser Lys Glu Tyr Lys Ile Cys Gly Ser
            180                 185                 190
Lys Ile Ile Tyr Lys Asp Lys Lys Thr Phe Ile Asn Leu Cys Tyr Gly
        195                 200                 205
Phe Glu Pro Val Thr Ser Glu Leu Asp Lys Ser Lys Val Met Gly Ile
    210                 215                 220
Asp Leu Gly Val Ser Val Pro Ala Tyr Met Ala Phe Asn Phe Asp Lys
225                 230                 235                 240
Tyr Lys Arg Asp Ser Ile Lys Asp Asn Arg Ile Met Ala Thr Lys Trp
                245                 250                 255
Met Met Asp Arg Gln Leu Ser Ile Ala Lys Gln Ser Cys Lys Tyr Leu
            260                 265                 270
Ser Asp Gly Asn Cys Gly His Gly Arg Lys Lys Met Val Cys Tyr
        275                 280                 285
Asp Lys Tyr Ser Asn Lys Ser Arg Asn Leu Ser Gln Thr Ile Asn His
    290                 295                 300
Gly Trp Ser Lys Tyr Ile Val Asp Val Ala Phe Arg Asn Gly Cys Gly
305                 310                 315                 320
Thr Ile Gln Met Glu Asp Leu Ser Gly Val Thr Ser Glu Lys Asp Lys
                325                 330                 335
Phe Leu Lys Asn Trp Thr Phe Tyr Asp Leu Gln Gln Lys Ile Glu Tyr
            340                 345                 350
Lys Ala Lys Glu Arg Gly Ile Asn Val Val Lys Ile Asn Pro Lys Tyr
        355                 360                 365
Thr Ser Gln Arg Cys Cys Glu Cys Gly Cys Ile Cys Lys Arg Asn Arg
    370                 375                 380
Pro Asp Gln Lys Thr Phe Lys Cys Ile Ser Cys Gly Tyr Ser Ala Asn
385                 390                 395                 400
Ala Asp Phe Asn Ala Ala Lys Asn Ile Ala Thr Ile Gly Ile Glu Asp
                405                 410                 415
Ile Ile Ala Asn Thr Glu Val Ile Glu
            420                 425

<210> SEQ ID NO 89
<211> LENGTH: 33
<212> TYPE: DNA
<213> ORGANISM: Artificial sequence
<220> FEATURE:
<223> OTHER INFORMATION: Synthetic sequence

<400> SEQUENCE: 89
cgaagcaact cgcgcattcg cgcgaggtga gag                              33

<210> SEQ ID NO 90
<211> LENGTH: 459
<212> TYPE: PRT
<213> ORGANISM: Artificial sequence
<220> FEATURE:
<223> OTHER INFORMATION: Synthetic sequence
```

<400> SEQUENCE: 90

Met Arg Ile Glu Ile Met Val Lys Lys Gly Ile Asn Met Asn Lys
1               5                   10                  15

Ile Met Lys Tyr Gln Ile Leu Lys Pro Thr Asn Ile Gly Trp Glu Asp
                20                  25                  30

Phe Gly Asn Ile Leu Tyr Asn Leu Arg Ser Glu Val Arg Lys Ile Lys
            35                  40                  45

Asn Arg Thr Ile Ala Leu Tyr His Glu Trp Thr Gly Tyr Thr Leu Glu
    50                  55                  60

Cys His Asp Arg Thr Gly Glu Trp Pro Lys Pro Lys Asp Val Tyr Asn
65                  70                  75                  80

Tyr Gly Thr Ile Gly Gly Tyr Ile Tyr Asp Arg Leu Lys Gly Glu Val
                85                  90                  95

Lys Tyr Ser Asn Ser Val Asn Phe Ser Ser Val Arg Asp Ala Met
                100                 105                 110

Ser Lys Tyr Asp Thr His Lys Lys Asp Ile Leu Ala Gly Lys Ala Ser
            115                 120                 125

Val Pro Ser Met Gly Asp Gly Gln Pro Ile Asp Ile Tyr Asn Lys Asn
    130                 135                 140

Ile Val Leu His His Leu Asp Asn Glu Lys Lys Asp Tyr Ala Ala Thr
145                 150                 155                 160

Leu Ser Leu Leu Asn Asn Gly Ala Lys Thr Glu Leu Gly Leu Leu Ser
                165                 170                 175

Gly Arg Val Asp Val Ile Leu Thr Ile Lys Asn Glu Thr Gln Thr Ala
            180                 185                 190

Ile Leu Asp Arg Cys Leu Ser Gly Glu Tyr Arg Val Cys Gly Ser Gln
    195                 200                 205

Leu Val Tyr Glu Ala Ala Gly Lys Glu Lys Gly Lys Lys Asp Lys
210                 215                 220

Pro Lys Val Trp Leu Tyr Leu Cys Tyr Gly Phe Glu Pro Glu Ala Pro
225                 230                 235                 240

Glu Leu Asp Asp Ser Arg Ile Met Gly Ile Asp Leu Gly Met Lys Leu
                245                 250                 255

Pro Ala Val Met Ala Phe Asn Phe Asn Asp Lys Lys Tyr Glu Val Ile
            260                 265                 270

Asp Asp Asn Arg Ile Leu Asp Arg Lys Ile Arg Leu Asp Lys Met Leu
    275                 280                 285

Ser Ile Ser Lys His Gln Cys Gln Trp Arg Cys Asp Gly Asn Ser Gly
290                 295                 300

His Gly Arg Lys Lys Lys Val Asp Val Tyr Glu Arg Tyr Ser His Lys
305                 310                 315                 320

Ser His Asn Leu Ser Met His Ile Asn His Gln Trp Ser Lys Tyr Ile
                325                 330                 335

Val Asp Thr Ala Val Lys Asn Lys Cys Gly Val Ile Gln Met Glu Asp
            340                 345                 350

Leu Ser Gly Ile Lys Ala Ser Arg Gln Asn Phe Leu Gly Asn Trp Thr
    355                 360                 365

Tyr Tyr Asp Leu Gln Gln Lys Ile Thr Tyr Lys Ala Glu Glu Lys Gly
370                 375                 380

Val Lys Val Ile Lys Val Asp Pro Ser Tyr Thr Ser Gln Met Cys Pro
385                 390                 395                 400

Val Cys Gly Tyr Ile Asn Lys Arg Asn Arg Ser Thr Gln Ala Asp Phe
            405                 410                 415

-continued

Glu Cys Leu Glu Cys Gly His Ile Ala Asn Ala Asp Tyr Asn Ala Ala
            420                 425                 430

Arg Asn Ile Ala Thr Pro Asp Ile Ala Asn Ile Ile Lys Asn Arg Leu
            435                 440                 445

Ala Gln Gln Lys Lys Glu Gly Lys Pro Ile Glu
            450                 455

<210> SEQ ID NO 91
<211> LENGTH: 26
<212> TYPE: DNA
<213> ORGANISM: Artificial sequence
<220> FEATURE:
<223> OTHER INFORMATION: Synthetic sequence

<400> SEQUENCE: 91
gtctcattcc atatatgtgc gtgaga                                    26

<210> SEQ ID NO 92
<211> LENGTH: 479
<212> TYPE: PRT
<213> ORGANISM: Artificial sequence
<220> FEATURE:
<223> OTHER INFORMATION: Synthetic sequence

<400> SEQUENCE: 92

Met Pro Met Ser Ser Tyr Arg Lys Thr His Tyr Thr Asn Thr Cys Glu
1               5                   10                  15

Leu Arg Glu Ile Tyr Met Arg Ile Glu Ile Met Val Lys Lys Lys Gly
            20                  25                  30

Ile Asn Met Asn Lys Ile Met Lys Tyr Gln Ile Leu Lys Pro Thr Asn
            35                  40                  45

Ile Ser Trp Glu Asp Phe Gly Asn Ile Leu Tyr Asn Leu Arg Ser Glu
        50                  55                  60

Val Arg Lys Ile Lys Asn Arg Thr Ile Ala Leu Tyr His Glu Trp Thr
65                  70                  75                  80

Asn Tyr Thr Leu Glu Cys His Asp Lys Thr Gly Glu Trp Pro Lys Pro
                85                  90                  95

Lys Asp Val Tyr Asn Tyr Gly Thr Met Ser Gly Tyr Ile Tyr Asp Arg
            100                 105                 110

Leu Lys Gly Glu Val Arg Tyr Ser Asn Ser Val Asn Phe Asn Ser Ser
            115                 120                 125

Val Arg Asp Ala Met Ser Lys Tyr Asp Thr His Lys Lys Asp Ile Leu
        130                 135                 140

Ala Gly Lys Val Ser Val Pro Ser Met Gly Asp Gly Gln Pro Ile Asp
145                 150                 155                 160

Ile Tyr Asn Lys Asn Ile Val Leu His His Leu Asp Asn Glu Lys Lys
                165                 170                 175

Asp Tyr Ala Ala Thr Leu Ser Leu Leu Asn Asn Gly Ala Lys Ala Glu
            180                 185                 190

Leu Gly Leu Leu Ser Gly Arg Val Asp Val Ile Leu Thr Ile Lys Asn
            195                 200                 205

Glu Thr Gln Thr Ala Ile Leu Asp Arg Cys Leu Ser Gly Glu Tyr Arg
        210                 215                 220

Ile Cys Gly Ser Gln Leu Ile Tyr Glu Gly Gly Lys Glu Lys Lys Gly
225                 230                 235                 240

Lys Lys Asp Lys Pro Lys Val Trp Leu Tyr Leu Cys Tyr Gly Phe Glu
                245                 250                 255

```
Pro Glu Ala Pro Glu Leu Asp Asp Ser Arg Ile Met Gly Ile Asp Leu
            260                 265                 270

Gly Met Lys Leu Pro Ala Val Met Ala Phe Asn Phe Asn Asp Lys Lys
            275                 280                 285

Tyr Glu Val Ile Asp Asp Asn Arg Ile Leu Asp Arg Lys Ile Arg Leu
            290                 295                 300

Asp Lys Met Leu Ser Met Ser Lys His Gln Cys Gln Trp Arg Cys Asp
305                 310                 315                 320

Gly Asn Ser Gly His Gly Arg Asn Lys Lys Val Asp Val Tyr Glu Arg
                325                 330                 335

Tyr Ser His Lys Ser His Asn Leu Ser Met Asp Ile Asn His Gln Trp
            340                 345                 350

Ser Lys Tyr Ile Val Asp Thr Ala Val Lys Asn Lys Cys Gly Val Ile
            355                 360                 365

Gln Met Glu Asp Leu Ser Gly Ile Lys Ala Ser Arg Gln Asn Phe Leu
    370                 375                 380

Gly Asn Trp Thr Tyr Tyr Asp Leu Gln Gln Lys Ile Thr Tyr Lys Ala
385                 390                 395                 400

Glu Glu Lys Gly Ile Lys Val Ile Lys Val Asp Pro Cys Tyr Thr Ser
                405                 410                 415

Gln Met Cys Pro Val Cys Gly Tyr Ile Asn Lys Arg Asn Arg Ser Thr
            420                 425                 430

Gln Ala Asp Phe Glu Cys Leu Glu Cys Gly His Ile Ala Asn Ala Asp
    435                 440                 445

Tyr Asn Ala Ala Arg Asn Ile Ala Thr Pro Asp Ile Ala Asn Ile Ile
            450                 455                 460

Lys Asn Arg Leu Ala Gln Gln Lys Lys Glu Gly Lys Pro Ile Glu
465                 470                 475

<210> SEQ ID NO 93
<211> LENGTH: 23
<212> TYPE: DNA
<213> ORGANISM: Artificial sequence
<220> FEATURE:
<223> OTHER INFORMATION: Synthetic sequence

<400> SEQUENCE: 93
cacgcgtgtg tgtgaaatga gac                                          23

<210> SEQ ID NO 94
<211> LENGTH: 447
<212> TYPE: PRT
<213> ORGANISM: Artificial sequence
<220> FEATURE:
<223> OTHER INFORMATION: Synthetic sequence

<400> SEQUENCE: 94

Met Asn Lys Ile Met Lys Tyr Gln Ile Ile Lys Pro Leu Asn Ile Asp
1               5                   10                  15

Trp Glu Thr Phe Gly Asn Ile Leu Phe Asn Leu Arg Lys Glu Ser Arg
            20                  25                  30

Gln Val Lys Asn Arg Ala Ile Ala Ile Tyr His Glu Trp Val Leu Tyr
        35                  40                  45

Ser Met Ala Tyr Tyr Asp Glu Cys Gly Lys Trp Pro Lys Ile Ile Asp
    50                  55                  60

Val Tyr Pro Pro Tyr Lys Thr Ala Asp Gly Tyr Ile Tyr Asp Lys Leu
65                  70                  75                  80
```

```
Lys Asn Glu Met Gly His Met Leu Ser Asn Asn Phe Asn Ala Thr Ile
                85                  90                  95

Arg Asn Ala Leu Ser Lys Tyr Asp Thr His Lys Lys Asp Ile Met Ala
            100                 105                 110

Gly Lys Val Ser Val Pro Ser Met Asp Ala Gly Gln Pro Ile Asp Val
        115                 120                 125

Tyr Ala Lys Gly Ile Thr Leu His His Ile Asp Gly Asp Lys Gly Asp
    130                 135                 140

Tyr Val Ala Thr Leu Ser Leu Leu Asn Ser Lys Ala Lys Ala Thr Leu
145                 150                 155                 160

Asn Leu Pro Ser Gly Arg Ile Asp Met Val Leu Lys Met Asn Asp Lys
                165                 170                 175

Thr Gln Thr Ala Ile Leu Asp Arg Cys Leu Ser Gly Glu Tyr Arg Ile
            180                 185                 190

Cys Gly Ser Gln Leu Val Tyr Glu Ala Ala Gly Lys Glu Lys Lys Gly
        195                 200                 205

Lys Lys Asp Lys Pro Lys Val Trp Leu Tyr Leu Cys Tyr Gly Phe Glu
    210                 215                 220

Pro Glu Ala Pro Glu Leu Asp Asp Ser Arg Ile Met Gly Ile Asp Leu
225                 230                 235                 240

Gly Met Lys Leu Pro Ala Val Met Ala Phe Asn Phe Asn Asp Lys Lys
                245                 250                 255

Tyr Glu Val Ile Asp Asp Asn Arg Ile Leu Asp Arg Lys Ile Arg Leu
            260                 265                 270

Asp Lys Met Leu Ser Ile Ser Lys His Gln Cys Gln Trp Arg Cys Asp
        275                 280                 285

Gly Asn Ser Gly His Gly Arg Lys Lys Val Asp Val Tyr Glu Arg
    290                 295                 300

Tyr Ser His Lys Ser His Asn Leu Ser Met Asp Ile Asn His Gln Trp
305                 310                 315                 320

Ser Lys Tyr Ile Val Glu Thr Ala Val Lys Asn Lys Cys Gly Val Ile
                325                 330                 335

Gln Val Glu Asp Leu Ser Gly Ile Lys Ala Ser Arg Gln Asn Phe Leu
            340                 345                 350

Gly Asn Trp Thr Tyr Tyr Asp Leu Gln Gln Lys Ile Thr Tyr Lys Ala
        355                 360                 365

Glu Glu Lys Gly Ile Lys Val Ile Lys Val Asp Pro Ser Tyr Thr Ser
    370                 375                 380

Gln Met Cys Pro Val Cys Gly Tyr Ile Asn Lys Arg Asn Arg Ser Thr
385                 390                 395                 400

Gln Ala Asp Phe Glu Cys Leu Glu Cys Gly His Ile Ala Asn Ala Asp
                405                 410                 415

Tyr Asn Ala Ala Arg Asn Ile Ala Thr Pro Asp Ile Ala Asn Ile Ile
            420                 425                 430

Lys Asn Arg Leu Ala Gln Gln Lys Lys Glu Gly Lys Pro Ile Glu
        435                 440                 445

<210> SEQ ID NO 95
<211> LENGTH: 23
<212> TYPE: DNA
<213> ORGANISM: Artificial sequence
<220> FEATURE:
<223> OTHER INFORMATION: Synthetic sequence

<400> SEQUENCE: 95
```
cgcgtgtgtg tgaaatgaga acg                                                    23

<210> SEQ ID NO 96
<211> LENGTH: 447
<212> TYPE: PRT
<213> ORGANISM: Artificial sequence
<220> FEATURE:
<223> OTHER INFORMATION: Synthetic sequence

<400> SEQUENCE: 96

Met Asn Lys Val Met Lys Tyr Gln Ile Ile Lys Pro Leu Asn Ile Asp
1               5                   10                  15

Trp Glu Asp Phe Gly Asn Ile Leu Phe Asn Leu Arg Lys Glu Ser Arg
            20                  25                  30

Gln Ile Lys Asn Arg Ala Ile Ala Ile Tyr His Glu Trp Val Gln Tyr
        35                  40                  45

Ser Met Ser Tyr Tyr Asp Glu Tyr Gly Lys Trp Pro Lys Val Ile Asp
    50                  55                  60

Val Tyr Pro Pro Tyr Lys Thr Val Asp Gly Tyr Ile Tyr Asp Arg Leu
65                  70                  75                  80

Lys Asn Glu Met Gly His Thr Ser Ser Asn Phe Asn Ala Thr Ile
            85                  90                  95

Arg Asn Ala Leu Ser Lys Tyr Asp Thr His Lys Lys Asp Ile Met Ala
            100                 105                 110

Gly Lys Val Ser Val Pro Ser Met Asp Ala Gly Gln Pro Ile Asp Val
        115                 120                 125

Tyr Ala Lys Gly Ile Thr Leu His His Ile Asp Gly Asp Lys Asp Asp
    130                 135                 140

Tyr Val Ala Thr Leu Ser Leu Leu Asn Ser Lys Ala Lys Ala Thr Leu
145                 150                 155                 160

Asn Leu Pro Ser Gly Arg Ile Asp Met Val Leu Lys Met Asn Asp Lys
                165                 170                 175

Thr Gln Thr Ala Ile Leu Asp Arg Cys Leu Ser Gly Glu Tyr Arg Ile
            180                 185                 190

Cys Gly Ser Gln Leu Ile Tyr Glu Ala Ala Gly Lys Glu Lys Lys Gly
        195                 200                 205

Lys Lys Asp Lys Pro Lys Val Trp Leu Tyr Leu Cys Tyr Gly Phe Glu
    210                 215                 220

Pro Glu Ala Pro Glu Leu Asp Asp Ser Arg Ile Met Gly Ile Asp Leu
225                 230                 235                 240

Gly Met Lys Leu Pro Ala Val Met Ala Phe Asn Phe Asn Asp Lys Lys
                245                 250                 255

Tyr Glu Val Ile Asp Asp Asn Arg Ile Leu Gly Gln Lys Ile Arg Leu
            260                 265                 270

Asp Lys Met Leu Ser Ile Ser Lys His Gln Cys Gln Trp Arg Cys Asp
        275                 280                 285

Gly Asn Ser Gly His Gly Arg Lys Lys Val Asp Val Tyr Glu Lys
    290                 295                 300

Cys Ser His Arg Ser His Asn Leu Ser Met Asp Ile Asn His Gln Trp
305                 310                 315                 320

Ser Lys Tyr Ile Val Glu Thr Ala Ile Lys Asn Lys Cys Gly Val Ile
                325                 330                 335

Gln Met Glu Asp Leu Ser Gly Ile Lys Ala Ser Arg Gly Asn Phe Leu
            340                 345                 350

```
Gly Asn Trp Thr Tyr Tyr Asp Leu Gln Gln Lys Ile Thr Tyr Lys Ala
            355                 360                 365
Glu Gly Lys Gly Ile Lys Val Ile Lys Ile Asp Pro His Tyr Thr Ser
        370                 375                 380
Gln Met Cys Pro Ile Cys Gly Tyr Ile Asn Lys Arg Asn Arg Ser Thr
385                 390                 395                 400
Gln Ala Asp Phe Glu Cys Leu Glu Cys Gly His Ile Ala Asn Ala Asp
            405                 410                 415
Tyr Asn Ala Ala Arg Asn Ile Ala Thr Pro Asp Ile Ala Asn Ile Ile
            420                 425                 430
Lys Asn Arg Val Lys Gln Gln Glu Lys Glu Gly Lys Ser Ile Asp
            435                 440                 445
```

<210> SEQ ID NO 97
<211> LENGTH: 33
<212> TYPE: DNA
<213> ORGANISM: Artificial sequence
<220> FEATURE:
<223> OTHER INFORMATION: Synthetic sequence

<400> SEQUENCE: 97
cctctcattc cacatatgcg tgtgagatgc gac         33

<210> SEQ ID NO 98
<211> LENGTH: 36
<212> TYPE: DNA
<213> ORGANISM: Artificial sequence
<220> FEATURE:
<223> OTHER INFORMATION: Synthetic sequence

<400> SEQUENCE: 98
gttgaagggt attgttattt gaaaggtact cacaac      36

<210> SEQ ID NO 99
<211> LENGTH: 37
<212> TYPE: DNA
<213> ORGANISM: Artificial sequence
<220> FEATURE:
<223> OTHER INFORMATION: Synthetic sequence

<400> SEQUENCE: 99
aggtgtgaca tcctttaatt tgaagtgttc ctccacc     37

<210> SEQ ID NO 100
<211> LENGTH: 36
<212> TYPE: DNA
<213> ORGANISM: Artificial sequence
<220> FEATURE:
<223> OTHER INFORMATION: Synthetic sequence

<400> SEQUENCE: 100
actattaatg atagttaaat gaaaggtggt cacaac      36

<210> SEQ ID NO 101
<211> LENGTH: 36
<212> TYPE: DNA
<213> ORGANISM: Artificial sequence
<220> FEATURE:
<223> OTHER INFORMATION: Synthetic sequence

<400> SEQUENCE: 101
attgtgaatc atccttaaat gaaaggtaat cacaac      36

```
<210> SEQ ID NO 102
<211> LENGTH: 29
<212> TYPE: DNA
<213> ORGANISM: Artificial sequence
<220> FEATURE:
<223> OTHER INFORMATION: Synthetic sequence

<400> SEQUENCE: 102
gtgttctcca tgcacgcggg ggagtttgg                                29

<210> SEQ ID NO 103
<211> LENGTH: 36
<212> TYPE: DNA
<213> ORGANISM: Artificial sequence
<220> FEATURE:
<223> OTHER INFORMATION: Synthetic sequence

<400> SEQUENCE: 103
gttgcgacgt gcaaagaacg gattggcgat cgacac                        36

<210> SEQ ID NO 104
<211> LENGTH: 36
<212> TYPE: DNA
<213> ORGANISM: Artificial sequence
<220> FEATURE:
<223> OTHER INFORMATION: Synthetic sequence

<400> SEQUENCE: 104
gttgcgacgt gcaaagaacg gattggcgat cgacac                        36

<210> SEQ ID NO 105
<211> LENGTH: 35
<212> TYPE: DNA
<213> ORGANISM: Artificial sequence
<220> FEATURE:
<223> OTHER INFORMATION: Synthetic sequence

<400> SEQUENCE: 105
gttttatacc ctttagaatt taaactgtct aaaag                         35

<210> SEQ ID NO 106
<211> LENGTH: 36
<212> TYPE: DNA
<213> ORGANISM: Artificial sequence
<220> FEATURE:
<223> OTHER INFORMATION: Synthetic sequence

<400> SEQUENCE: 106
gttttatacc cttgtaattt taggagctca tcaaag                        36

<210> SEQ ID NO 107
<211> LENGTH: 23
<212> TYPE: DNA
<213> ORGANISM: Artificial sequence
<220> FEATURE:
<223> OTHER INFORMATION: Synthetic sequence

<400> SEQUENCE: 107
tgtgtatacc attcaaattg tat                                      23

<210> SEQ ID NO 108
<211> LENGTH: 32
<212> TYPE: DNA
<213> ORGANISM: Artificial sequence
<220> FEATURE:
<223> OTHER INFORMATION: Synthetic sequence
```

```
<400> SEQUENCE: 108
ctttcaatct gcacatgcgt acggattgta tc                           32

<210> SEQ ID NO 109
<211> LENGTH: 36
<212> TYPE: DNA
<213> ORGANISM: Artificial sequence
<220> FEATURE:
<223> OTHER INFORMATION: Synthetic sequence

<400> SEQUENCE: 109
cttgtaatgg ttgctcaaca ccttgaaagt tgagac                       36

<210> SEQ ID NO 110
<211> LENGTH: 36
<212> TYPE: DNA
<213> ORGANISM: Artificial sequence
<220> FEATURE:
<223> OTHER INFORMATION: Synthetic sequence

<400> SEQUENCE: 110
atagtaatgg cagctcaatg ccctataaat tgagac                       36

<210> SEQ ID NO 111
<211> LENGTH: 30
<212> TYPE: DNA
<213> ORGANISM: Artificial sequence
<220> FEATURE:
<223> OTHER INFORMATION: Synthetic sequence

<400> SEQUENCE: 111
actccaaccc cacatagtta ccatggaaac                              30

<210> SEQ ID NO 112
<211> LENGTH: 33
<212> TYPE: DNA
<213> ORGANISM: Artificial sequence
<220> FEATURE:
<223> OTHER INFORMATION: Synthetic sequence

<400> SEQUENCE: 112
cgaagcaact cgcgcattcg cgcgaggtga gag                          33

<210> SEQ ID NO 113
<211> LENGTH: 26
<212> TYPE: DNA
<213> ORGANISM: Artificial sequence
<220> FEATURE:
<223> OTHER INFORMATION: Synthetic sequence

<400> SEQUENCE: 113
gtctcattcc atatatgtgc gtgaga                                  26

<210> SEQ ID NO 114
<211> LENGTH: 23
<212> TYPE: DNA
<213> ORGANISM: Artificial sequence
<220> FEATURE:
<223> OTHER INFORMATION: Synthetic sequence

<400> SEQUENCE: 114
cacgcgtgtg tgtgaaatga gac                                     23

<210> SEQ ID NO 115
<211> LENGTH: 23
```

```
<212> TYPE: DNA
<213> ORGANISM: Artificial sequence
<220> FEATURE:
<223> OTHER INFORMATION: Synthetic sequence

<400> SEQUENCE: 115
cgcgtgtgtg tgaaatgaga acg                                         23

<210> SEQ ID NO 116
<211> LENGTH: 33
<212> TYPE: DNA
<213> ORGANISM: Artificial sequence
<220> FEATURE:
<223> OTHER INFORMATION: Synthetic sequence

<400> SEQUENCE: 116
cctctcattc acatatgcg tgtgagatgc gac                               33

<210> SEQ ID NO 117
<211> LENGTH: 143
<212> TYPE: PRT
<213> ORGANISM: Artificial sequence
<220> FEATURE:
<223> OTHER INFORMATION: Synthetic sequence

<400> SEQUENCE: 117
```

Lys Lys Leu Gly Glu His Gln Lys Trp Phe Ala Asn Phe Ser Ile Glu
1               5                   10                  15

Gln Pro Ile Tyr Glu Arg Lys Pro Asn Arg Ser Ile Val Gly Gly Leu
            20                  25                  30

Asp Val Gly Ile Arg Ser Ala His Lys Leu Glu Pro Ile Thr Glu Met
        35                  40                  45

Thr Glu Lys Asn Asp Lys Phe Arg Lys Ile Ile Glu Arg Trp Ala
    50                  55                  60

Lys Glu Val Thr Asn Phe Phe Val Lys Asn Gln Val Gly Ile Val Gln
65                  70                  75                  80

Ile Glu Asp Leu Ser Thr Met Lys Asp Arg Tyr Thr Ser Gln Leu Cys
                85                  90                  95

Ser Asn Cys Arg Tyr Trp Asn Asn Glu Tyr Arg Lys Val Asn Lys Phe
            100                 105                 110

Pro Lys Phe Lys Cys Glu Lys Cys Asn Leu Glu Ile Ser Ala Asp Tyr
        115                 120                 125

Asn Ala Ala Arg Asn Leu Ser Thr Pro Asp Ile Glu Lys Phe Val
    130                 135                 140

```
<210> SEQ ID NO 118
<211> LENGTH: 143
<212> TYPE: PRT
<213> ORGANISM: Artificial sequence
<220> FEATURE:
<223> OTHER INFORMATION: Synthetic sequence

<400> SEQUENCE: 118
```

Lys Lys Leu Gly Asp His Gln Lys Trp Phe Val Asn Phe Thr Ile Glu
1               5                   10                  15

Gln Pro Ile Tyr Glu Arg Lys Leu Asp Lys Asn Ile Ile Gly Gly Ile
            20                  25                  30

Asp Val Gly Ile Lys Ser Lys Asn Lys Leu Asp Pro Ile Thr Arg Met
        35                  40                  45

Thr Glu Lys Asn Asp Arg Phe Arg Lys Ile Ile Glu Arg Trp Ala
    50                  55                  60

```
Lys Glu Val Thr Asn Phe Phe Ile Lys Asn Gln Val Gly Thr Val Gln
 65                  70                  75                  80

Ile Glu Asp Leu Ser Thr Met Lys Asp Arg Tyr Thr Ser Gln Leu Cys
                 85                  90                  95

Ser Ser Cys Arg His Trp Asn Ser Asp His Arg Lys Thr Asn Asn Phe
            100                 105                 110

Pro Lys Phe Lys Cys Glu Lys Cys Ala Leu Glu Ile Ser Ala Asp Tyr
            115                 120                 125

Asn Ala Ala Arg Asn Ile Ser Thr Pro Asp Ile Glu Lys Phe Val
            130                 135                 140

<210> SEQ ID NO 119
<211> LENGTH: 144
<212> TYPE: PRT
<213> ORGANISM: Artificial sequence
<220> FEATURE:
<223> OTHER INFORMATION: Synthetic sequence

<400> SEQUENCE: 119

Ser Lys Ile Gly Glu Lys Ser Ala Trp Met Leu Asn Leu Ser Ile Asp
 1                5                  10                  15

Val Pro Lys Ile Asp Lys Gly Val Asp Pro Ser Ile Ile Gly Gly Ile
                 20                  25                  30

Asp Val Gly Val Lys Ser Lys Asn Lys Leu Lys Pro Ile Thr Ile Leu
             35                  40                  45

Thr Glu Lys Ser Glu Arg Phe Arg Lys Lys Leu Ile Glu Arg Trp Ala
         50                  55                  60

Cys Glu Ile Ala Asp Phe Phe Ile Lys Asn Lys Val Gly Thr Val Gln
 65                  70                  75                  80

Met Glu Asn Leu Glu Ser Met Lys Arg Lys Asn Thr Ser Lys Thr Cys
                 85                  90                  95

Ser Lys Cys Gly His Leu Asn Asn Glu Tyr Arg Lys Lys Asn Lys Phe
            100                 105                 110

Pro His Phe Lys Cys Glu Lys Cys Asn Phe Lys Glu Asn Ala Asp Tyr
            115                 120                 125

Asn Ala Ala Leu Asn Ile Ser Asn Pro Lys Leu Lys Ser Thr Lys Glu
            130                 135                 140

<210> SEQ ID NO 120
<211> LENGTH: 146
<212> TYPE: PRT
<213> ORGANISM: Artificial sequence
<220> FEATURE:
<223> OTHER INFORMATION: Synthetic sequence

<400> SEQUENCE: 120

Ser Phe Leu Ile Pro Glu Asn Tyr Lys Trp Lys Leu His Phe Ser Ile
 1                5                  10                  15

Glu Ile Pro Pro Met Val Asn Asp Ile Asp Ser Asn Leu Tyr Gly Gly
                 20                  25                  30

Ile Asp Phe Gly Glu Gln Asn Ser Arg Lys Thr Lys Ala Gln Glu Asp
             35                  40                  45

Tyr Ser Glu Arg Met Gln Lys Leu Arg Gln Lys Ile Thr Glu Arg Leu
         50                  55                  60

Val Lys Gln Ile Ser Asp Phe Phe Leu His Met Ala Val Cys Ser Leu
 65                  70                  75                  80

Arg Tyr Glu Asp Leu Asn Thr Leu Tyr Lys Tyr Thr Ser Arg Leu Cys
```

```
                85                  90                  95
Ser Lys Cys Gly Lys Leu Asn Leu Lys Phe Arg Thr Lys Asn Glu Ile
            100                 105                 110

Lys Tyr Met Pro Phe Phe Ile Cys Glu Phe Cys Gly Trp Lys Gln Ala
            115                 120                 125

Gly Asp Lys Asn Ala Ser Ala Asn Ile Ala Asp Lys Asp Tyr Gln Asp
        130                 135                 140

Lys Leu
145

<210> SEQ ID NO 121
<211> LENGTH: 94
<212> TYPE: PRT
<213> ORGANISM: Artificial sequence
<220> FEATURE:
<223> OTHER INFORMATION: Synthetic sequence

<400> SEQUENCE: 121

Lys Arg Gln Arg Asp Arg Asn Lys Trp Phe Val Asn Ile Thr Ile Thr
1               5                   10                  15

Arg Pro Pro Phe Ile Asn Lys Glu Leu Asp Asp Thr Lys Phe Gly Gly
            20                  25                  30

Ile Asp Leu Gly Val Lys Val Lys Asn Lys Phe Ile Lys Lys Glu Ile
        35                  40                  45

Phe Asn Glu Arg Asn Glu Leu Phe Arg Lys Lys Ile Ile Glu Arg Trp
    50                  55                  60

Ala Asn Gln Ile Val Lys Phe Phe Glu Asp Gln Lys Cys Ala Thr Val
65                  70                  75                  80

Gln Ile Glu Asn Leu Glu Ser Phe Asp Arg Thr Ser Tyr Lys
                85                  90

<210> SEQ ID NO 122
<211> LENGTH: 141
<212> TYPE: PRT
<213> ORGANISM: Artificial sequence
<220> FEATURE:
<223> OTHER INFORMATION: Synthetic sequence

<400> SEQUENCE: 122

Leu Gln Arg Asp Asp Ser Trp Phe Val Asn Phe Asn Ile Ala Tyr Asp
1               5                   10                  15

Ser Leu Lys Lys Gln Pro Asp Arg Asp Lys Ile Ala Gly Ile His Met
            20                  25                  30

Gly Ile Thr Arg Asn Ala Lys Val Thr Gly Thr Asp Thr Leu Ser Glu
        35                  40                  45

Ala Tyr Arg Gln Arg Arg Lys Lys Ile Ile Glu Asp Trp Ile Ala Ser
    50                  55                  60

Ile Val Lys Phe Ala Ile Asn Asn Glu Ile Gly Thr Ile Tyr Leu Glu
65                  70                  75                  80

Asp Ile Ser Asn Thr Asn Ser Phe Tyr Val Asn Gln Ile Cys Ser Leu
                85                  90                  95

Cys Gly His Tyr Asn Lys Gln Phe Arg Arg Lys Asn Lys Phe Pro Lys
            100                 105                 110

Met Lys Cys Gln Gly Cys Leu Glu Ala Thr Ser Thr Glu Phe Asn Ala
            115                 120                 125

Ala Ala Asn Val Ala Asn Pro Asp Tyr Glu Lys Leu Leu
        130                 135                 140
```

<210> SEQ ID NO 123
<211> LENGTH: 127
<212> TYPE: PRT
<213> ORGANISM: Artificial sequence
<220> FEATURE:
<223> OTHER INFORMATION: Synthetic sequence

<400> SEQUENCE: 123

```
Asp Asp Asn Phe Tyr Leu Gln Tyr Thr Leu Glu Thr Glu Phe Asn Leu
1               5                   10                  15

Lys Glu Asp Tyr Ser Gly Ile Val Gly Ile Asp Arg Gly Val Ser His
                20                  25                  30

Lys Ser Asn Met Arg Asn Ile Glu Lys Ile Gln Leu Ile Leu His
                35                  40                  45

Asn Tyr Ser Lys Gln Ile Val Asp Phe Ala Lys Asn Lys Asn Ala Phe
        50                  55                  60

Ile Val Phe Glu Lys Leu Glu Lys Pro Lys Lys Asn Tyr Thr Ser Lys
65                  70                  75                  80

Glu Cys Ser His Cys Gly Glu Lys Asn Thr Gln Arg Pro Phe Asn Asn
                85                  90                  95

Ser Ser Leu Phe Lys Cys Asn Lys Cys Gly Val Glu Leu Asn Ala Asp
                100                 105                 110

Tyr Asn Ala Ser Ile Asn Ile Ala Lys Lys Gly Leu Asn Ile Leu
            115                 120                 125
```

<210> SEQ ID NO 124
<211> LENGTH: 131
<212> TYPE: PRT
<213> ORGANISM: Artificial sequence
<220> FEATURE:
<223> OTHER INFORMATION: Synthetic sequence

<400> SEQUENCE: 124

```
Ser Glu Lys Lys Asn Tyr Glu Tyr Tyr Leu Gln Tyr Thr Leu Glu Ile
1               5                   10                  15

Lys Pro Glu Leu Lys Asp Phe Tyr Asp Gly Ala Ile Gly Ile Asp Arg
                20                  25                  30

Gly Ile Asn His Lys Gly Asn Met Arg Val Ile Glu Asn Lys Ile Asn
                35                  40                  45

Leu Ile Leu His Arg Tyr Ser Lys Gln Ile Val Asp Met Ala Lys Lys
        50                  55                  60

Leu Asn Ala Ser Ile Val Phe Glu Glu Leu Gly Arg Ile Gly Lys Ser
65                  70                  75                  80

Tyr Thr Ser Lys Glu Cys Ser His Cys Gly Glu Lys Asn Thr Gln Arg
                85                  90                  95

Pro Phe Asn Asn Tyr Ser Leu Phe Lys Cys Asn Lys Cys Gly Ile Gln
                100                 105                 110

Leu Asn Ser Asp Tyr Asn Ala Ser Ile Asn Ile Ala Lys Lys Gly Leu
            115                 120                 125

Lys Ile Pro
        130
```

<210> SEQ ID NO 125
<211> LENGTH: 127
<212> TYPE: PRT
<213> ORGANISM: Artificial sequence
<220> FEATURE:
<223> OTHER INFORMATION: Synthetic sequence

<400> SEQUENCE: 125

Glu Gly Ser Phe Phe Ile Gln Tyr Thr Ile Glu Asn Val Pro Lys Thr
1               5                   10                  15

Phe Ser Asp Tyr Leu Gly Ala Ile Gly Ile Asp Arg Gly Ile Ser His
                20                  25                  30

Lys Ser Asn Met Arg Asn Ile Asp Asn Lys Ile Asn Leu Ile Leu His
            35                  40                  45

Lys Tyr Ser Arg Asn Ile Val Asn Leu Ala Lys Ser Glu Lys Ala Phe
50                      55                  60

Ile Val Phe Glu Lys Leu Glu Lys Ile Lys Ser Tyr Thr Ser Lys
65                  70                  75                  80

Glu Cys Ser His Cys Gly Glu Lys Asp Thr Gln Arg Pro Phe Asn Asn
                85                  90                  95

Ser Ser Leu Phe Lys Cys Asn Lys Cys Arg Val Gln Leu Asn Ala Asp
                100                 105                 110

Tyr Asn Ala Ser Ile Asn Ile Ala Lys Lys Ser Leu Asn Ile Ser
            115                 120                 125

<210> SEQ ID NO 126
<211> LENGTH: 134
<212> TYPE: PRT
<213> ORGANISM: Artificial sequence
<220> FEATURE:
<223> OTHER INFORMATION: Synthetic sequence

<400> SEQUENCE: 126

Ser Ser Asn Lys Tyr Glu Tyr Tyr Leu Gln Tyr Thr Tyr Glu Ala Glu
1               5                   10                  15

Val Glu Ala Asn Lys Glu Tyr Ala Gly Cys Leu Gly Val Asp Ile Gly
                20                  25                  30

Cys Ser Lys Arg Arg Lys Leu Met Gln Leu Ser Lys Thr Glu Pro Ile
            35                  40                  45

Ile Asp Tyr Thr Cys His Lys Thr Ala Arg Lys Ile Val Glu Met Ala
50                  55                      60

Asn Thr Ala Lys Ala Phe Ile Ser Met Glu Asn Leu Glu Thr Gly Ile
65                  70                  75                  80

Lys Gln Lys Gln Tyr Thr Ser Gln Thr Cys Ser Ser Cys Gly Ala Lys
                85                  90                  95

Glu Lys Thr Glu Arg Pro Ser Gln Ala Ile Phe Arg Cys Leu Asn Cys
                100                 105                 110

Gln Arg Asp Ile Asn Ala Asp Phe Asn Ala Ala Val Asn Ile Ala Lys
            115                 120                 125

Lys Ala Leu Asn Asn Thr
            130

<210> SEQ ID NO 127
<211> LENGTH: 128
<212> TYPE: PRT
<213> ORGANISM: Artificial sequence
<220> FEATURE:
<223> OTHER INFORMATION: Synthetic sequence

<400> SEQUENCE: 127

Glu Tyr Tyr Val Gln Trp Ser Ile Asp Thr Glu Thr Pro Ala Ile Thr
1               5                   10                  15

Ser Tyr Asp Asn Ile Leu Gly Ile Asp Ala Gly Ile Thr Asn Ile Lys
                20                  25                  30

Arg Ile Arg Pro Ile Glu Gln Lys Val Asp Gly Tyr Cys His Val Val
             35                  40                  45

Ser Lys Gln Ile Val Glu Met Ala Lys Glu Arg Asn Ser Cys Ile Ala
 50                  55                  60

Leu Glu Lys Leu Glu Lys Pro Lys Lys Ser Gly Thr Ser Tyr Thr Cys
 65                  70                  75                  80

Ser His Cys Lys Asn Ala Asn Asn Gln Arg Pro Tyr Phe Lys Lys Ser
                 85                  90                  95

Trp Thr Ser Met Phe Lys Cys Gly Lys Cys Gly Ile Glu Leu Asn Ser
                100                 105                 110

Asp Tyr Asn Ala Ala Phe Asn Ile Ala Gln Lys Ala Leu Asn Met Thr
                115                 120                 125

<210> SEQ ID NO 128
<211> LENGTH: 139
<212> TYPE: PRT
<213> ORGANISM: Artificial sequence
<220> FEATURE:
<223> OTHER INFORMATION: Synthetic sequence

<400> SEQUENCE: 128

Glu Asn Pro Asn Ala Asp Leu Cys Asp Phe Tyr Leu Gln Tyr Thr Ile
 1               5                  10                  15

Glu Thr Glu Ser Arg Asn Asn Glu Ile Asn Gly Ile Ile Gly Ile
                20                  25                  30

Asp Arg Gly Ile Thr Asn Gln Arg Gln Ile Arg Ala Ile Glu Pro Lys
                35                  40                  45

Ile Asn Leu Ile Leu His Gln Ile Ser Lys Asp Ile Val Lys Ile Ala
 50                  55                  60

Lys Glu Lys Asn Phe Ala Ile Ala Leu Glu Gln Leu Glu Lys Pro Lys
 65                  70                  75                  80

Lys Ala Lys Thr Ser Gln Met Cys Ser His Cys Ala Ile Asn Gly Asp
                 85                  90                  95

Thr Gln Arg Pro Tyr Lys Gln Lys Pro Ser Tyr Ser Leu Phe Lys Cys
                100                 105                 110

Asn Lys Cys Gly Ile Glu Leu Asn Ala Asp Tyr Asn Ala Ala Phe Asn
                115                 120                 125

Ile Ala Gln Lys Gly Leu Lys Thr Leu Met Leu
130                 135

<210> SEQ ID NO 129
<211> LENGTH: 130
<212> TYPE: PRT
<213> ORGANISM: Artificial sequence
<220> FEATURE:
<223> OTHER INFORMATION: Synthetic sequence

<400> SEQUENCE: 129

Ser Glu Asp Glu Thr Asp Phe Tyr Leu Gln Tyr Thr Trp Arg Pro Asp
 1               5                  10                  15

Ala His Pro Lys Lys Asp Tyr Thr Gly Cys Leu Gly Ile Asp Ile Gly
                20                  25                  30

Gly Ser Lys Leu Glu Ser Leu Arg Asn Ile Glu Pro Arg Ile Asp Val
                35                  40                  45

His Cys His Arg Ile Ala Arg Lys Ile Val Gly Met Ala Leu Ala Ala
 50                  55                  60

Asn Ala Phe Ile Ser Met Glu Asn Leu Glu Gly Gly Ile Arg Glu Lys
 65                  70                  75                  80

Gln Tyr Thr Ser Gln Leu Cys Ser Ser Cys Gly Thr Asn Asn Thr Lys
                85                  90                  95

Arg Pro Lys Gln Ala Ile Phe Met Cys Gln Asn Cys Gly Lys Asn Ile
            100                 105                 110

Asn Ala Asp Phe Asn Ala Ala Ile Asn Ile Ala Lys Lys Ala Leu Asn
        115                 120                 125

Arg Lys
    130

<210> SEQ ID NO 130
<211> LENGTH: 126
<212> TYPE: PRT
<213> ORGANISM: Artificial sequence
<220> FEATURE:
<223> OTHER INFORMATION: Synthetic sequence

<400> SEQUENCE: 130

Glu Asn Asn Ile Phe Leu Gln Tyr Thr Leu Asp Ser Ile Pro Glu Ile
1               5                   10                  15

His Ser Glu Tyr Ser Gly Ala Val Gly Ile Asp Arg Gly Val Ser His
            20                  25                  30

Lys Gly Asn Met Arg Asn Ile Glu Gln Lys Ile Asn Leu Ile Leu His
        35                  40                  45

Glu Tyr Ser Lys Gln Ile Val Asn Phe Ala Lys Asp Lys Asn Ala Phe
    50                  55                  60

Ile Val Phe Glu Leu Leu Glu Lys Pro Lys Lys Ser Tyr Thr Ser Lys
65                  70                  75                  80

Asp Cys Ser His Cys Gly Glu Arg Asn Thr Gln Arg Pro Phe Asn Asn
                85                  90                  95

Phe Ser Leu Phe Lys Cys Asn Lys Cys Gly Ile Val Leu Asn Ser Asp
            100                 105                 110

Tyr Asn Ala Ser Leu Asn Ile Ala Arg Lys Gly Leu Asn Ile
        115                 120                 125

<210> SEQ ID NO 131
<211> LENGTH: 126
<212> TYPE: PRT
<213> ORGANISM: Artificial sequence
<220> FEATURE:
<223> OTHER INFORMATION: Synthetic sequence

<400> SEQUENCE: 131

Asp Tyr Tyr Leu Gln Tyr Thr Val Glu Phe Leu Pro Asn Ile Ile Thr
1               5                   10                  15

Asn Tyr Asn Gly Ile Leu Gly Ile Asp Arg Gly Ile Asn Thr Gln Gln
            20                  25                  30

Lys Ile Arg Pro Ile Glu Pro Arg Ile Asp Gln Ile Leu His Asp Ile
        35                  40                  45

Ser Lys Gln Ile Ile Asp Leu Ala Lys Glu Lys Arg Val Ala Ile Ser
    50                  55                  60

Leu Glu Gln Leu Glu Lys Pro Gln Lys Pro Met Thr Ser Gln Asn Cys
65                  70                  75                  80

Ser Arg Cys Ala Met Lys Asn Asn Thr Gln Arg Pro Tyr Lys Thr Ser
                85                  90                  95

Ser Leu Phe Lys Cys Asn Lys Cys Gly Val Glu Leu Asn Ala Asp Tyr
            100                 105                 110

Asn Ala Ala Phe Asn Ile Ala Gln Lys Gly Leu Lys Ile Leu

<210> SEQ ID NO 132
<211> LENGTH: 145
<212> TYPE: PRT
<213> ORGANISM: Artificial sequence
<220> FEATURE:
<223> OTHER INFORMATION: Synthetic sequence

<400> SEQUENCE: 132

Asn Leu Ser Pro Ser Glu Trp Lys Tyr Tyr Leu Gln Phe Gly Val Lys
1               5                   10                  15

Pro Leu Leu Lys Gln Lys Ser Arg Arg Lys Ser Arg Asn Val Leu Gly
            20                  25                  30

Ile Asp Arg Gly Leu Lys His Thr Ile His Glu Asn Gln Thr Arg Lys
        35                  40                  45

Lys Leu Lys Ser Leu Gln Gly Arg Ile Asp Asp Leu Leu His Asn Ile
    50                  55                  60

Ser Arg Lys Ile Val Glu Thr Ala Lys Glu Tyr Asp Ala Val Ile Val
65                  70                  75                  80

Val Glu Asp Leu Arg Gln His Gly Arg Ser Gly Thr Ser Gln Asn Cys
                85                  90                  95

Ala Tyr Cys Leu Leu Ala Gln Glu Tyr Lys Arg Ser Gln Glu Asn Ser
            100                 105                 110

Lys Ile Gly Asn Cys Gln Asn His Lys Lys Gln Ile Asp Ala Asp Leu
        115                 120                 125

Asn Ala Ala Arg Val Ile Ala Ala Leu Lys Ile Asn Asp Ser Gln Pro
    130                 135                 140

Phe
145

<210> SEQ ID NO 133
<211> LENGTH: 146
<212> TYPE: PRT
<213> ORGANISM: Artificial sequence
<220> FEATURE:
<223> OTHER INFORMATION: Synthetic sequence

<400> SEQUENCE: 133

Asn Leu Lys Pro Glu Asp Trp Thr Tyr Tyr Ile Gln Phe Gly Phe Gln
1               5                   10                  15

Pro Leu Leu Asp Thr Pro Lys Pro Ile Lys Thr Lys Thr Val Leu Gly
            20                  25                  30

Ile Asp Arg Gly Val Arg His His Leu His Glu Asn Gln Phe Lys Ala
        35                  40                  45

Lys Leu Arg Ser Leu Glu Gly Arg Ile Glu Asp His Phe His Asn Leu
    50                  55                  60

Ser Lys Glu Ile Val Asp Leu Ala Lys Glu Asn Asn Ser Val Ile Val
65                  70                  75                  80

Val Glu Asn Leu Arg Gln His Gly Arg Gly Thr Ser Ile Asn Cys
                85                  90                  95

Ala Tyr Cys Leu Leu Asn Asp Asn Tyr Thr Arg Gly Gly Lys Lys Asn
            100                 105                 110

Thr Lys Ile Gly Glu Cys Lys Thr Cys Lys Lys Glu Phe Asp Ala Asp
        115                 120                 125

Leu Asn Ala Ala Arg Val Ile Ala Glu Lys Arg Leu Asn Asp Pro Gln
    130                 135                 140

Pro Phe
145

<210> SEQ ID NO 134
<211> LENGTH: 148
<212> TYPE: PRT
<213> ORGANISM: Artificial sequence
<220> FEATURE:
<223> OTHER INFORMATION: Synthetic sequence

<400> SEQUENCE: 134

```
Asn Leu Lys Pro Asp Glu Trp Ser Tyr Tyr Ile Gln Phe Gly Tyr Asp
1               5                   10                  15

Ser Ile Asn Pro Val Gln Leu Met Ser Thr Asp Lys Phe Leu Gly Ile
            20                  25                  30

Asp Arg Gly Leu Thr His Lys Leu Pro Glu Asn Gln Met Lys Lys Lys
        35                  40                  45

Leu Lys Ser Ile Glu Pro Lys Ile Glu Val His Tyr His Asn Ile Ser
    50                  55                  60

Arg Lys Ile Val Asn Leu Ala Lys Asp Tyr Asn Ala Ser Ile Val Val
65                  70                  75                  80

Glu Ser Leu Glu Gly Lys Gln His Gly Arg Lys Tyr Thr Ser Gln Gln
                85                  90                  95

Cys Ala Lys Cys Val Leu Glu Lys Asp Tyr Lys Arg Gly Lys Glu Tyr
            100                 105                 110

Thr Gly Asn Lys Lys Val Gly Tyr Cys Ser Lys His Gly Gln Val Asp
        115                 120                 125

Ala Asp Leu Asn Ala Ser Arg Val Ile Ala Tyr Leu Asp Ile Asn Asp
    130                 135                 140

Pro Ile Leu Phe
145
```

<210> SEQ ID NO 135
<211> LENGTH: 148
<212> TYPE: PRT
<213> ORGANISM: Artificial sequence
<220> FEATURE:
<223> OTHER INFORMATION: Synthetic sequence

<400> SEQUENCE: 135

```
Asn Leu Lys Pro Glu Glu Trp Asp Tyr Tyr Ile Gln Phe Gly Tyr Gly
1               5                   10                  15

Leu Ile Asn Ser Pro Met Lys Ile Glu Thr Lys Asn Phe Met Gly Ile
            20                  25                  30

Asp Arg Gly Leu Thr His Lys Leu Pro Glu Asn Gln Met Lys Lys Arg
        35                  40                  45

Leu Lys Ser Ile Glu Pro Lys Ile Glu Ser Tyr Tyr His Asn Leu Ser
    50                  55                  60

Arg Lys Ile Val Asn Leu Ala Lys Ala Asn Asn Ala Ser Ile Val Val
65                  70                  75                  80

Glu Ser Leu Glu Gly Lys Gln His Gly Arg Lys Tyr Thr Ser Gln Gln
                85                  90                  95

Cys Ala Lys Cys Val Leu Lys Lys Glu Tyr Lys Arg Gly Lys Glu Tyr
            100                 105                 110

Thr Gly Asn Lys Lys Val Gly Tyr Cys Ser Val His Gly Gln Val Asp
        115                 120                 125

Ala Asp Leu Asn Ala Ser Arg Val Ile Ala Tyr Leu Gly Ile Asn Glu
    130                 135                 140
```

```
Pro Ile Val Phe
145

<210> SEQ ID NO 136
<211> LENGTH: 147
<212> TYPE: PRT
<213> ORGANISM: Artificial sequence
<220> FEATURE:
<223> OTHER INFORMATION: Synthetic sequence

<400> SEQUENCE: 136

Asn Leu Glu Pro Asp Glu Trp Lys Tyr Tyr Ile Gln Phe Gly Tyr Glu
1               5                   10                  15

Gln Ile Asn Asn Pro Lys Leu Glu Thr Glu Asn Ile Leu Gly Ile Asp
            20                  25                  30

Arg Gly Leu Thr His Lys Leu Pro Glu Asn Gln Met Lys Lys Asn Leu
        35                  40                  45

Arg Ser Ile Glu Asp Lys Val Glu Asn Leu Tyr His Asn Leu Ser Arg
    50                  55                  60

Lys Ile Val Asp Leu Ala Lys Glu Lys Asn Ala Cys Ile Val Phe Glu
65                  70                  75                  80

Lys Leu Glu Gly Lys Gln His Gly Arg Lys Tyr Thr Ser Gln Asn Cys
                85                  90                  95

Ala Lys Cys Val Leu Glu Ser Gln Tyr Thr Arg Arg Lys Glu Tyr Thr
            100                 105                 110

Gly Asn Thr Lys Ile Gly Tyr Cys Met Lys His Gly Gln Val Asp Ala
        115                 120                 125

Asp Leu Asn Ala Ser Arg Thr Ile Ala Asn Phe Asp Ile Asn Asn Pro
    130                 135                 140

Glu Ile Trp
145

<210> SEQ ID NO 137
<211> LENGTH: 147
<212> TYPE: PRT
<213> ORGANISM: Artificial sequence
<220> FEATURE:
<223> OTHER INFORMATION: Synthetic sequence

<400> SEQUENCE: 137

Asn Leu Lys Pro Asn Met Trp Lys Tyr Tyr Ile Gln Phe Gly Tyr Glu
1               5                   10                  15

Pro Ile Phe Glu Arg Lys Ala Ser Gly Lys Pro Lys Asn Ile Met Gly
            20                  25                  30

Ile Asp Arg Gly Leu Thr His His Ile His Glu Ala Gln Leu Lys Lys
        35                  40                  45

Arg Leu Gly Ser Ile Glu Glu Lys Thr Glu Gln His Tyr His Ile Val
    50                  55                  60

Ser Ser Lys Ile Ile Asn Trp Ala Ile Glu Tyr Glu Ala Ala Ile Val
65                  70                  75                  80

Leu Glu Ser Leu Lys Gln Arg Gly Gly Lys Met Thr Ser Lys Thr Cys
                85                  90                  95

Ala Thr Cys Leu Leu Asn Gly Tyr Val Arg Gly Leu Glu Lys Arg Lys
            100                 105                 110

Asn Met Lys Ile Gly Lys Cys Met Val Cys Asn Ser Ser Ile Asp Ala
        115                 120                 125

Asp Leu Asn Ala Ala Arg Val Ile Ala Tyr Lys Asn Leu Asn Asp Pro
```

130             135             140

Gln Pro Ala
145

<210> SEQ ID NO 138
<211> LENGTH: 142
<212> TYPE: PRT
<213> ORGANISM: Artificial sequence
<220> FEATURE:
<223> OTHER INFORMATION: Synthetic sequence

<400> SEQUENCE: 138

Asn Leu Lys Pro Thr Asp Tyr Lys Tyr Tyr Leu Gln Leu Ser Tyr Glu
1               5                   10                  15

Pro Phe Ser Lys Gln Leu Ile Ala Thr Lys Thr Ile Leu Gly Ile Asp
            20                  25                  30

Arg Gly Leu Lys His His Ile His Glu Asn Gln Leu Ile Lys Lys Leu
        35                  40                  45

Lys Ser Met Lys Asn Lys Ile Asn Val Leu Tyr His Asn Val Ser Lys
    50                  55                  60

Asn Ile Val Asp Leu Ala Lys Lys Tyr Glu Ser Thr Ile Val Leu Glu
65                  70                  75                  80

Arg Leu Lys Gln His Gly Arg Ser Tyr Thr Ser Lys Thr Cys Ala Lys
                85                  90                  95

Cys Leu Leu Glu Val Glu Leu Lys Asn Glu Tyr Asp Ser Lys Asn Ser
            100                 105                 110

Lys Ile Gly Ile Cys Asn Ile His Gly Gln Ile Asp Ala Asp Leu Asn
        115                 120                 125

Ala Ala Arg Val Ile Ala Ser Lys Asn Leu Asn Glu Pro His
    130                 135                 140

<210> SEQ ID NO 139
<211> LENGTH: 131
<212> TYPE: PRT
<213> ORGANISM: Artificial sequence
<220> FEATURE:
<223> OTHER INFORMATION: Synthetic sequence

<400> SEQUENCE: 139

Arg Thr Thr Asp Arg Trp Thr Ile Ser Phe Ser Thr Glu Tyr Asp Asp
1               5                   10                  15

Ser Asn Met Arg Lys Asn Asp Gly Gln Val Gly Ile Asp Val Gly
            20                  25                  30

Leu Lys Thr Thr Arg Leu Arg Leu Ser Arg Leu Trp Glu Lys
        35                  40                  45

Ile Arg Asn Ser Arg Ala Asp Leu Ile Gln Asn Glu Thr Tyr Glu Ile
    50                  55                  60

Leu Ser Glu Asn Lys Leu Ile Ala Ile Glu Asp Leu Asn Val Lys Gly
65                  70                  75                  80

Met Gln Glu Lys Ile Asp Ser Ser Lys Glu Cys His Asn Cys Gly Asn
                85                  90                  95

Lys Lys Gly Met Pro Leu Glu Ser Arg Ile Tyr Glu Cys Pro Lys Cys
            100                 105                 110

Gly Leu Lys Ile Asp Arg Asp Leu Asn Ser Ala Lys Val Ile Leu Ala
        115                 120                 125

Arg Ala Thr
    130

```
<210> SEQ ID NO 140
<211> LENGTH: 133
<212> TYPE: PRT
<213> ORGANISM: Artificial sequence
<220> FEATURE:
<223> OTHER INFORMATION: Synthetic sequence

<400> SEQUENCE: 140

Arg Arg Ala Asp Gly Tyr Tyr Val Gln Phe Cys Ile Ser Val Asp Val
1               5                   10                  15

Lys Val Glu Thr Glu Pro Thr Gly Lys Ala Ile Gly Leu Asp Val Gly
            20                  25                  30

Ile Lys Tyr His Lys Ala Arg Cys Arg Tyr Ala Arg Lys His Leu Arg
        35                  40                  45

Val Ser Arg Gln Arg Lys Glu Tyr Cys Lys Arg Val Ala Tyr Cys Val
    50                  55                  60

Ile His Ser Asn Asp Val Val Ala Tyr Glu Asp Leu Asn Val Lys Gly
65                  70                  75                  80

Met Val Lys Asn His Asn Thr Ser Gln Asn Cys Ser Asn Cys Asp Lys
                85                  90                  95

Lys Val Pro Lys Ser Leu Ser Thr Arg Thr His Ile Cys His His Cys
            100                 105                 110

Gly Tyr Ser Glu Asp Arg Asp Val Asn Ala Ala Lys Asn Ile Leu Lys
        115                 120                 125

Lys Ala Leu Ser Thr
        130

<210> SEQ ID NO 141
<211> LENGTH: 101
<212> TYPE: PRT
<213> ORGANISM: Artificial sequence
<220> FEATURE:
<223> OTHER INFORMATION: Synthetic sequence

<400> SEQUENCE: 141

Arg Arg Pro Thr His Arg Lys Trp Phe Ala Gln Leu Thr Ile Gly Tyr
1               5                   10                  15

Thr Asn Pro Ser Ser Leu Pro Glu Met Ala Leu Gly Ile His Phe Gly
            20                  25                  30

Met Lys Asp Lys Ser Leu Leu Asn Ala Thr Tyr Arg Val Val Asn Gly
        35                  40                  45

Val Leu Glu Phe Ser Lys Gly Ile Ser Ala Glu His Ala Ser Gln Pro
    50                  55                  60

Ile Gly Leu Gly Leu Glu Thr Ile Arg Phe Val Asp Lys Ala Gln Arg
65                  70                  75                  80

Asp Leu Ser Asp Ala Glu Gln Ala Arg Val Leu Ala Ile Glu Ala Thr
                85                  90                  95

Lys Arg Phe Ala Ser
            100

<210> SEQ ID NO 142
<211> LENGTH: 130
<212> TYPE: PRT
<213> ORGANISM: Artificial sequence
<220> FEATURE:
<223> OTHER INFORMATION: Synthetic sequence

<400> SEQUENCE: 142

Glu Val Met Arg Arg Thr Lys Ser Gln Pro Trp Gln Glu Phe Ile Leu
```

```
                1               5                  10                  15
            Arg Leu Val Leu Ala His Lys Ala Pro Lys Leu Lys Pro Arg Cys Phe
                            20                  25                  30

Ala Gly Ile Ser Leu Gly Pro Lys Thr Ala Tyr Arg Lys Gln Leu Lys
                            35                  40                  45

Ser Leu Ile Asn Thr Gln Val Phe Thr Ile Val Thr Phe Leu Arg Ala
                            50                  55                  60

Ala Val Arg Leu Glu Ser Ile Ala Arg Val Arg Lys Ser Tyr Gly Val
            65                  70                  75                  80

Arg Thr Cys Ser Gln Cys Gly Ala Thr Asn Gln Gly Ile Lys Asp Pro
                            85                  90                  95

Thr Val Asp Ile Glu Ser Glu Thr Phe Leu Cys Ser Cys Ser His Arg
                            100                 105                 110

Glu Ile Ala Ala Val Asn Thr Ala Thr Asn Leu Ala Lys Gln Leu Leu
                            115                 120                 125

Asp Glu
                130

<210> SEQ ID NO 143
<211> LENGTH: 120
<212> TYPE: PRT
<213> ORGANISM: Artificial sequence
<220> FEATURE:
<223> OTHER INFORMATION: Synthetic sequence

<400> SEQUENCE: 143

Gln Leu Ala Lys Ser Gly Arg Phe Trp Ile Ser Val Val Tyr Glu Leu
            1               5                   10                  15

Pro Lys Pro Glu Ala Thr Thr Cys Gln Ser Glu Gln Val Ala Phe Val
                            20                  25                  30

Ala Leu Gly Ala Ser Ser Leu Arg Leu Leu Asn Ser Gly Lys Arg Arg
                            35                  40                  45

Met His Met Ile Ser Ser Arg Gln His Val Gln Asp Glu Arg Ile Val
                            50                  55                  60

Asp Tyr Leu Val Arg Asn His Gly Ser His Phe Val Val Thr Glu Leu
            65                  70                  75                  80

Val Val Arg Ser Lys Glu Gly Lys Leu Ala Leu Thr Leu Thr Glu Ala
                            85                  90                  95

Pro Pro Ala Arg Gly Ala Glu Asn Lys Leu Trp Met Ala Arg Lys Leu
                            100                 105                 110

Arg Glu Ser Phe Leu Lys Glu Val
                            115                 120

<210> SEQ ID NO 144
<211> LENGTH: 118
<212> TYPE: PRT
<213> ORGANISM: Artificial sequence
<220> FEATURE:
<223> OTHER INFORMATION: Synthetic sequence

<400> SEQUENCE: 144

Ser Arg Asp Arg Arg Phe Trp Ile Ser Ile Ala Tyr Glu Ile Glu Leu
            1               5                   10                  15

Pro Asp Gln Arg Pro Phe Asn Pro Glu Glu Val Ile Tyr Ile Ala Phe
                            20                  25                  30

Gly Ala Ser Ser Lys Lys Arg Ala Ala Ala Arg Arg Lys Met Tyr Ala
                            35                  40                  45
```

```
Met Thr Gln Arg Gln Gln Lys Leu Asn His Arg Ile Val Ala Ser Leu
    50                  55                  60

Leu Arg Leu Gly Phe His Phe Val Val Thr Glu Tyr Thr Val Arg Ser
65                  70                  75                  80

Lys Pro Gly Lys Leu Ala Leu Gly Gln Ser Glu Arg Pro Glu Lys Arg
                85                  90                  95

Gly Arg Asp Asn Lys Ile Glu Met Val Arg Leu Leu Arg Glu Lys Tyr
                100                 105                 110

Leu Glu Ser Gln Thr Ile
            115

<210> SEQ ID NO 145
<211> LENGTH: 120
<212> TYPE: PRT
<213> ORGANISM: Artificial sequence
<220> FEATURE:
<223> OTHER INFORMATION: Synthetic sequence

<400> SEQUENCE: 145

Glu Met Ala Lys Pro Gly Arg Phe Trp Ile Ser Val Ala Tyr Glu Ile
1               5                   10                  15

Pro Lys Pro Glu Lys Val Pro Val Ser Lys Gln Ile Thr Tyr Leu
                20                  25                  30

Ala Ile Gly Ala Ser Arg Lys Lys Arg Met Ala Ala Cys Thr Arg Met
            35                  40                  45

Phe Ala Lys Leu Gly His Gln Gln Lys Gln His Gly Gln Tyr Val Val
    50                  55                  60

Lys Lys Leu Leu Arg His Gly Val His Phe Val Thr Glu Leu Lys
65                  70                  75                  80

Val Arg Ser Lys Pro Gly Ala Leu Ala Leu Leu Ser Leu Glu Glu Arg
                85                  90                  95

Gln Leu Pro Asp Ala Gln Arg Lys Ile Phe Ile Ala Lys Lys Leu Arg
                100                 105                 110

Glu Glu Phe Leu Ala Asp Gln Lys
            115                 120

<210> SEQ ID NO 146
<211> LENGTH: 132
<212> TYPE: PRT
<213> ORGANISM: Artificial sequence
<220> FEATURE:
<223> OTHER INFORMATION: Synthetic sequence

<400> SEQUENCE: 146

Arg Gln Gly Asp Arg Trp Tyr Leu Ser Cys Gln Trp Glu Arg Pro Gln
1               5                   10                  15

Pro Thr Leu Leu Pro Lys Thr Gly Arg Thr Ala Gly Val Lys Ile Ala
                20                  25                  30

Ala Ser Ile Tyr Lys Ser Ala Ala Arg Leu Ala Ala Cys Glu Ala Ile
            35                  40                  45

Glu Arg Asp Arg Arg Asp Gly Phe Leu His Arg Val Thr Asn Glu Ile
    50                  55                  60

Val His Lys Phe Asp Ala Val Ser Val Gln Lys Met Ser Val Ala Pro
65                  70                  75                  80

Met Met Arg Arg Gln Glu Pro Glu Val Gln Glu Cys Ser Arg Cys Gly
                85                  90                  95

Thr Lys Asn Pro Gln Met Lys Asp Gly Arg Arg Leu Leu Arg Cys Thr
                100                 105                 110
```

```
Asp Cys Asp Ala Val Leu Pro Arg Asn Arg Asn Ala Ala Arg Asn Ala
            115                 120                 125

Glu Lys Arg Leu
    130

<210> SEQ ID NO 147
<211> LENGTH: 135
<212> TYPE: PRT
<213> ORGANISM: Artificial sequence
<220> FEATURE:
<223> OTHER INFORMATION: Synthetic sequence

<400> SEQUENCE: 147

Arg Gln Gly Glu Asn Trp Tyr Leu Ser Cys Gln Trp Lys Met Pro Lys
1               5                   10                  15

Pro Ala Pro Leu Pro Arg Ala Gly Arg Thr Ala Ala Ile Lys Ile Ala
            20                  25                  30

Ala Ala Ile Tyr Ala Ala Ala Ala Lys Leu Ala Lys Leu Glu Ala Glu
        35                  40                  45

Asp Ala Asn Ala Arg Glu Ala Trp Leu His Glu Ile Thr Thr Gln Ile
    50                  55                  60

Val Arg Asn Phe Asp Val Ile Ala Val Pro Arg Met Glu Val Ala Lys
65                  70                  75                  80

Leu Met Lys Lys Pro Asp Val Thr Ala Ala Cys Ser Gly Cys Gly
                85                  90                  95

Val Leu Lys Pro Glu Trp Lys Met Ala Arg Lys Gly Arg Glu Ile Met
            100                 105                 110

Arg Cys Lys Thr Cys Asn Thr Val Leu Thr Tyr Thr Arg Asn Ser Ala
        115                 120                 125

Arg Val Ile Gly Arg Glu Leu
    130                 135

<210> SEQ ID NO 148
<211> LENGTH: 145
<212> TYPE: PRT
<213> ORGANISM: Artificial sequence
<220> FEATURE:
<223> OTHER INFORMATION: Synthetic sequence

<400> SEQUENCE: 148

Asp Lys Lys Ala Ala Tyr Leu Tyr Phe Thr Cys Asp Ile Pro Asp Glu
1               5                   10                  15

Pro Leu Thr Glu Thr Ala Lys Lys Ile Gln Trp Glu Thr Gly Asp Val
            20                  25                  30

Cys Ala Val Asp Leu Ser Met Arg Arg Gly Thr Gly Ile Asp Leu Gln
        35                  40                  45

Lys His Ile Asp Tyr Met Gly Glu Asp Arg Phe Lys Lys Ala Ala Arg
    50                  55                  60

Thr Ile Val Asn Phe Ala Leu Tyr Pro Arg Ala Asp Val Leu Leu
65                  70                  75                  80

Glu Asn Leu Glu Gly Leu Ile Pro Asp Gly Thr Ser Gln Val Cys Ser
                85                  90                  95

Lys Cys Gly Ala Leu Gly Arg Asn Asn Arg Arg Glu Phe Gly Tyr Val
            100                 105                 110

Glu Lys Leu Phe Ala Cys Pro Asn Cys Gly Tyr Cys Ala Asn Ala Asp
        115                 120                 125

His Asn Ala Ser Val Asn Leu Asn Arg Arg Phe Ile Glu Asp Ser Phe
```

```
            130                 135                 140

Lys
145

<210> SEQ ID NO 149
<211> LENGTH: 152
<212> TYPE: PRT
<213> ORGANISM: Artificial sequence
<220> FEATURE:
<223> OTHER INFORMATION: Synthetic sequence

<400> SEQUENCE: 149

Asp Ile Ala Asp Lys Pro Ser Ala Thr Tyr Leu Val Phe Ala Val Glu
1               5                   10                  15

Ile Lys Asp Glu Ala Arg Thr Glu Arg Ala Lys Ala Ile Arg Phe Glu
            20                  25                  30

Thr Ser Glu Leu Val Ala Val Asp Leu Asp Thr Arg Phe Leu Thr Arg
        35                  40                  45

Ala Ile Gly Val Arg Leu Gln Ala His Ile Asp Arg Met Gly Glu Asp
    50                  55                  60

Arg Phe Lys Lys Ala Ala Arg Lys Ile Val Asn Glu Ala Leu Tyr Thr
65                  70                  75                  80

Arg Ala Asp Val Leu Leu Tyr Glu Ser Leu Glu Thr Leu Leu Pro Asp
                85                  90                  95

Gly Thr Ser Gln Val Cys Ser Lys Cys Gly Ala Leu Gly Arg Asn Gly
            100                 105                 110

Arg Ala Val Phe Gly Trp Val Glu Arg Leu Phe Ala Cys Pro Asn Cys
        115                 120                 125

Pro Phe Thr Cys Asn Ser Asp His Asn Ala Ser Val Asn Leu His Arg
    130                 135                 140

Val Phe Leu Gly Asp Gln Ala Val
145                 150

<210> SEQ ID NO 150
<211> LENGTH: 134
<212> TYPE: PRT
<213> ORGANISM: Artificial sequence
<220> FEATURE:
<223> OTHER INFORMATION: Synthetic sequence

<400> SEQUENCE: 150

Arg Asp Val Asp Glu Trp Tyr Ala Val Phe Pro Leu Thr Phe Thr Lys
1               5                   10                  15

Glu Ile Glu Lys Pro Lys Gly Gly Ala Val Gly Ile Asn Arg Gly Ala
            20                  25                  30

Val His Glu Arg Ala Arg Arg Phe Leu Ala Leu Ala His Gln Arg Val
        35                  40                  45

Arg Arg Gln Arg Glu Trp Phe Leu His Asn Glu Ser Ala His Tyr Ala
    50                  55                  60

Gln Ser Tyr Thr Lys Ile Ala Ile Glu Asp Trp Ser Thr Lys Glu Met
65                  70                  75                  80

Thr Ser Ser Glu Leu Arg Ile Ser Gly Thr Cys Ser Arg Cys Gly Gly
                85                  90                  95

Leu Leu Arg Ala Ser Ala Ser Gly His Ala Asp Ala Glu Cys Glu Val
            100                 105                 110

Cys Leu His Val Glu Val Gly Asp Val Asn Ala Val Asn Val Leu
        115                 120                 125
```

```
Lys Arg Ala Met Phe Pro
    130

<210> SEQ ID NO 151
<211> LENGTH: 134
<212> TYPE: PRT
<213> ORGANISM: Artificial sequence
<220> FEATURE:
<223> OTHER INFORMATION: Synthetic sequence

<400> SEQUENCE: 151

Arg Asp Val Asp Glu Trp Tyr Ala Val Phe Pro Leu Thr Phe Val Ala
1               5                   10                  15

Glu Val Ala Arg Pro Lys Gly Gly Ala Val Gly Ile Asn Arg Gly Ala
            20                  25                  30

Val His Glu Lys Ala Arg Lys Phe Leu Ala Leu Ala His Gln Arg Val
        35                  40                  45

Arg Arg Gln Arg Glu Trp Phe Leu His Asn Glu Ser Ala His Tyr Ala
    50                  55                  60

Arg Thr Tyr Ser Lys Ile Ala Ile Glu Asp Trp Ser Thr Lys Glu Met
65                  70                  75                  80

Thr Ala Ser Glu Leu Lys Ile Ser Gly Thr Cys Ser Lys Cys Gly Gly
                85                  90                  95

Leu Leu Arg Ala Pro Ala Ser Gly His Ala Asp Ala Glu Cys Glu Ile
            100                 105                 110

Cys Leu Asn Val Glu Val Gly Asp Val Asn Ala Ala Val Asn Val Leu
        115                 120                 125

Lys Arg Ala Met Phe Pro
    130

<210> SEQ ID NO 152
<211> LENGTH: 136
<212> TYPE: PRT
<213> ORGANISM: Artificial sequence
<220> FEATURE:
<223> OTHER INFORMATION: Synthetic sequence

<400> SEQUENCE: 152

Arg Asp Val Asp Glu Trp Tyr Ala Cys Leu Pro Leu Thr Phe Thr Gln
1               5                   10                  15

Pro Ile Glu Ala Pro His Arg Ser Val Gly Leu Asn Arg Gly Val Val
            20                  25                  30

His His Lys Ala Arg Ile Lys Leu Ala Lys Ala His Gln Arg Val Arg
        35                  40                  45

Arg Gln Arg Ala Ala Phe Leu His Gln Glu Ser Ala Tyr Tyr Ser Lys
    50                  55                  60

Gly Phe Asp Leu Val Ala Leu Glu Asp Met Ser Val Arg Lys Met Thr
65                  70                  75                  80

Ala Thr Ala Gln Thr Ile Ser Ser Ala Cys Ala Val Cys Gly Ile Pro
                85                  90                  95

Leu Ala Arg Pro Ala Ser Gly Asn Ala Arg Met Arg Cys Thr Ala Cys
            100                 105                 110

Gly Ser Ser Gln Val Gly Asp Val Asn Ala Ala Glu Asn Val Leu Thr
        115                 120                 125

Arg Ala Leu Ser Ser Ala Pro Ser
    130                 135

<210> SEQ ID NO 153
```

```
<211> LENGTH: 134
<212> TYPE: PRT
<213> ORGANISM: Artificial sequence
<220> FEATURE:
<223> OTHER INFORMATION: Synthetic sequence

<400> SEQUENCE: 153

Lys Lys Arg Gly Lys Trp Ile Ala Asp Leu Thr Val Thr Gln Glu Asp
1               5                   10                  15

Ala Pro Glu Ser Ser Gly Ser Ala Ile Met Gly Val Asp Leu Gly Ile
            20                  25                  30

Lys Val Ala Lys Lys Leu Arg Ala Val Arg Lys Ser Lys Gly Lys Glu
        35                  40                  45

Ala Arg Trp Met Lys Thr Ile Asn His Gln Leu Ser Arg Gln Ile Val
    50                  55                  60

Asn His Ala His Ala Leu Gly Val Gly Thr Ile Lys Ile Glu Ala Leu
65                  70                  75                  80

Gln Gly Ile Arg Lys Gly Tyr Thr Ser Gln Asp Cys Pro Ala Cys Arg
                85                  90                  95

Ala Arg Asn Gly Ala Gln Asp Arg Thr Tyr Val Cys Ser Glu Cys Gly
            100                 105                 110

Trp Arg Gly His Arg Asp Thr Val Gly Ala Ile Asn Ile Ser Arg Arg
        115                 120                 125

Ala Leu Ser Gly His Arg
    130

<210> SEQ ID NO 154
<211> LENGTH: 136
<212> TYPE: PRT
<213> ORGANISM: Artificial sequence
<220> FEATURE:
<223> OTHER INFORMATION: Synthetic sequence

<400> SEQUENCE: 154

Lys Gly Val Phe Tyr Leu Cys Val Val Glu Val Ser Glu Glu Ser
1               5                   10                  15

Pro Asp Pro Lys Gly Val Leu Gly Val Asp Leu Gly Ile Lys Asn Lys
            20                  25                  30

Ser Ala Lys Arg His Leu Lys Lys Leu Ser Gly Arg Met Ala Lys Phe
        35                  40                  45

Ser Lys Asp Val Asn His Cys Ile Ser Lys Lys Leu Val Ala Lys Ala
    50                  55                  60

Lys Gly Thr Leu Met Ser Ile Ala Leu Glu Asp Leu Gln Gly Ile Arg
65                  70                  75                  80

Asp Arg Asn Thr Ser Arg Thr Cys Pro Ser Cys Gly His Val Ala Lys
                85                  90                  95

Ala Asn Arg Pro Thr Arg Asp Glu Phe Arg Cys Val Ser Cys Gly Phe
            100                 105                 110

Ala Gly Ala Ala Asp His Ile Ala Ala Met Asn Ile Ala Phe Arg Ala
        115                 120                 125

Val Ser Gln Pro Ile Val Phe Phe
    130                 135

<210> SEQ ID NO 155
<211> LENGTH: 136
<212> TYPE: PRT
<213> ORGANISM: Artificial sequence
<220> FEATURE:
<223> OTHER INFORMATION: Synthetic sequence
```

```
<400> SEQUENCE: 155

Arg Asn Gly Arg Ile Phe Val Asn Val Ala Cys Glu Ile Pro Thr Lys
1               5                   10                  15

Pro Leu Glu Val Glu Asn Phe Met Gly Val Ser Phe Gly Leu Glu His
            20                  25                  30

Lys Thr Tyr Phe Ala Arg Leu Glu Arg Leu Arg Arg Pro Phe Ser Gln
        35                  40                  45

Glu Leu Glu Thr Phe His Tyr Arg Gln Val Ala Gln Ile Val Glu Glu
    50                  55                  60

Ala Leu Ser Val Pro Ala Val Glu Gln Val Gly Asn Ile Pro Lys Gly
65                  70                  75                  80

Ala Thr Ala Lys Leu Cys Ser Thr Cys Gly Ala Ala Asn Lys Glu Gly
                85                  90                  95

Asp Gln Pro Ile Ser Leu Lys Gly Pro Thr Val Tyr Cys Gly Asn Cys
            100                 105                 110

Gly Thr Arg His Asn Thr Gly Phe Asn Thr Ala Leu Asn Leu Ala Arg
        115                 120                 125

Arg Ala Gln Glu Leu Phe Val Lys
    130                 135

<210> SEQ ID NO 156
<211> LENGTH: 136
<212> TYPE: PRT
<213> ORGANISM: Artificial sequence
<220> FEATURE:
<223> OTHER INFORMATION: Synthetic sequence

<400> SEQUENCE: 156

Lys Thr Arg Gly Trp Lys Ile Asn Leu Cys Leu Glu Thr Glu Val Glu
1               5                   10                  15

Gln Lys Asn Leu Ser Glu Asn Lys Tyr Leu Ser Ile Asp Leu Gly Val
            20                  25                  30

Lys Arg Lys Lys Ile Gln Arg Ala Lys Arg Lys Thr Thr Asp Arg Leu
        35                  40                  45

Leu Asn Ile Gln Lys Glu Met Leu His Lys Tyr Ser Ser Phe Ile Val
    50                  55                  60

Asn Tyr Ala Ile Arg Asn Asp Ile Gly Asn Ile Ile Ile Gly Asp Ser
65                  70                  75                  80

Ser Thr His Asp Ser Tyr Thr Ser Arg Lys Cys Pro His Cys Lys Asn
                85                  90                  95

Ile Lys Lys Ser Ser Pro Lys Gly Arg Thr Tyr Lys Cys Lys Lys Cys
            100                 105                 110

Gly Phe Ile Phe Asp Arg Asp Gly Val Gly Ala Ile Asn Ile Tyr Asn
        115                 120                 125

Glu Asn Val Ser Phe Gly Gln Ile
    130                 135

<210> SEQ ID NO 157
<211> LENGTH: 148
<212> TYPE: PRT
<213> ORGANISM: Artificial sequence
<220> FEATURE:
<223> OTHER INFORMATION: Synthetic sequence

<400> SEQUENCE: 157

Val Arg Val Gly Gly Arg His Arg Met Ser Val Ala Leu Thr Ala Lys
1               5                   10                  15
```

Leu Pro Asp Pro Pro Gln Val Gln Gly Leu Pro Val Ala Leu His
            20                  25                  30

Leu Gly Trp Arg Gln Arg Pro Asp Gly Leu Arg Arg Ile Gln Asp Lys
 35                  40                  45

Leu Leu Trp Glu Arg Glu Ser His Leu Arg Arg Leu Ala Ala Arg
 50                  55                  60

Arg Asp Asp Ala Trp Arg Arg Val Ala Ser Trp Leu Ala Arg His Ala
 65                  70                  75                  80

Gly Val Leu Val Val Asp Ala Asp Ile Ala Glu Leu Arg Arg Arg
            85                  90                  95

Asp Gly Leu Thr Arg Leu His Arg Lys Cys Gly His Gln Ala Gln Pro
            100                 105                 110

Asp Pro Arg Tyr Ala Ala Ser Ala Val Val Thr Cys Pro Gly Cys Gly
            115                 120                 125

Asn Gly Tyr Asp Gln Asp Tyr Asn Ala Ala Met Leu Met Leu Asp Arg
 130                 135                 140

Gln Gln Gln Pro
145

<210> SEQ ID NO 158
<211> LENGTH: 139
<212> TYPE: PRT
<213> ORGANISM: Artificial sequence
<220> FEATURE:
<223> OTHER INFORMATION: Synthetic sequence

<400> SEQUENCE: 158

Arg Ser Gly Lys Arg Trp Phe Val Ser Ile Ala Met Glu Met Pro Ser
1               5                   10                  15

Val Glu Pro Ala Ala Ser Gly Arg Pro Ala Val Gly Leu Asp Met Gly
            20                  25                  30

Val Arg Ala Thr Asp Pro Ser Arg Glu Lys Lys Ala Val Gln Ala Tyr
 35                  40                  45

Ala Arg Ala Lys Glu Arg Glu Arg Ser Ala Arg Gly Asp His Arg His
 50                  55                  60

Lys Val Ser Arg Ala Leu Val Arg Gln Phe Glu Glu Ile Ser Val Glu
65                  70                  75                  80

Ala Leu Asp Ile Lys Gln Leu Thr Val Ala Pro His Thr Thr Gln Glu
            85                  90                  95

Cys Ala Arg Cys Gly Thr Leu Val Pro Lys Pro Ile Ser Leu Arg Val
            100                 105                 110

His Arg Cys Pro Ala Cys Gly Tyr Thr Ala Pro Arg Thr Val Asn Ser
            115                 120                 125

Ala Arg Asn Val Leu Gln Arg Pro Leu Glu Glu
 130                 135

<210> SEQ ID NO 159
<211> LENGTH: 134
<212> TYPE: PRT
<213> ORGANISM: Artificial sequence
<220> FEATURE:
<223> OTHER INFORMATION: Synthetic sequence

<400> SEQUENCE: 159

Lys Asp Ala Gly Gln Tyr Phe Leu Ser Phe Val Val Glu Val Lys Pro
1               5                   10                  15

Glu Ile Lys Pro Pro Lys Asn Pro Ser Ile Gly Ile Asp Leu Gly Leu

```
            20                  25                  30
Lys Thr Glu Arg Met Arg Val Lys Val Ala Lys Leu Asn Ala Gln Ile
        35                  40                  45

Arg Asp Lys Arg Lys Asp Phe Leu His Lys Leu Ser Thr Lys Val Val
    50                  55                  60

Asn Glu Asn Gln Val Ile Ala Leu Glu Asp Leu Asn Val Gly Gly Met
65                  70                  75                  80

Leu Lys Asn Arg Glu Pro Thr Ser Gln Val Cys Ser Glu Cys Gly Tyr
                85                  90                  95

Arg Trp Gly Lys Ile Asp Leu Ser Val Arg Ser Ile Val Cys Ile Asn
                100                 105                 110

Cys Gly Val Glu His Asp Arg Asp Asn Ala Ser Val Asn Ile Glu
            115                 120                 125

Gln Ala Gly Leu Lys Val
        130

<210> SEQ ID NO 160
<211> LENGTH: 136
<212> TYPE: PRT
<213> ORGANISM: Artificial sequence
<220> FEATURE:
<223> OTHER INFORMATION: Synthetic sequence

<400> SEQUENCE: 160

Arg Thr Ser Gly Lys Tyr Phe Val Ser Leu Val Val Glu Thr Gln Pro
1               5                   10                  15

Ala Pro Met Pro Glu Thr Gly Glu Ser Val Gly Val Asp Phe Gly Val
            20                  25                  30

Ala Arg Met Arg Ile Lys Arg His Val Ala Arg Ile His Glu Lys Ile
        35                  40                  45

Gly Asn Ser Arg Ser Asp Thr Leu His Lys Leu Ser Thr Asp Leu Val
    50                  55                  60

Thr Arg Phe Asp Leu Ile Cys Val Glu Asp Leu Asn Leu Arg Gly Met
65                  70                  75                  80

Val Lys Asn His Phe Pro Ser Ser Lys Thr Cys Ser Asp Cys Gly His
                85                  90                  95

Ile Val Glu Gln Leu Pro Leu Asn Val Arg Glu Trp Thr Cys Pro Glu
                100                 105                 110

Cys Gly Thr Thr His Asp Arg Asp Ala Asn Ala Ala Asn Ile Leu
            115                 120                 125

Ala Val Gly Gln Thr Val Ser Ala
        130                 135

<210> SEQ ID NO 161
<211> LENGTH: 132
<212> TYPE: PRT
<213> ORGANISM: Artificial sequence
<220> FEATURE:
<223> OTHER INFORMATION: Synthetic sequence

<400> SEQUENCE: 161

Glu Gly Asp Gly Lys Trp Tyr Val Val Ile Leu Thr Glu Gln Glu Glu
1               5                   10                  15

Asp Pro Gln Thr Pro Glu Ala Glu Val Gly Ile Asp Leu Gly Val Ala
            20                  25                  30

Lys Ile Lys Val Lys Arg Gln Val Val Lys Leu Lys His Arg Gln Lys
        35                  40                  45
```

```
Arg Ser Arg Glu Ser Leu His His Glu Ile Thr His Leu Ile Thr Ser
    50                  55                  60

Gly Phe Gly Arg Val Ala Val Glu Asn Leu Asn Ile Lys Gly Met Thr
 65                  70                  75                  80

Pro Ser Ala Tyr Thr Ser Gln Thr Cys Ser Lys Cys Gly His Val Glu
                 85                  90                  95

Lys Ala Asn Arg Ala Thr Gln Ala Thr Phe Leu Cys Gln Lys Cys Gly
                100                 105                 110

His Lys Glu Asn Ala Asp Val Asn Ala Lys Asn Ile Leu Thr Arg
            115                 120                 125

Ala Glu Lys Gln
        130

<210> SEQ ID NO 162
<211> LENGTH: 135
<212> TYPE: PRT
<213> ORGANISM: Artificial sequence
<220> FEATURE:
<223> OTHER INFORMATION: Synthetic sequence

<400> SEQUENCE: 162

Arg Ala Ala Gly Ile Trp Tyr Val Ser Ile Leu Cys Glu Trp Asp Lys
 1               5                  10                  15

Pro Ala Lys Pro Val His Arg Ala Pro Asn Ala Lys Val Gly Val Asp
                 20                  25                  30

Leu Asn Val Arg Asn Phe Arg Leu Gln Cys Arg Ile Ala Arg Leu Gln
             35                  40                  45

Asp Arg Gln Ala Asn Leu Arg Asn Glu Val Thr Asn Gln Val Ala His
     50                  55                  60

Ala Val Ala Leu Lys His Ala Phe Val Gly Leu Glu Gly Leu Asp Ile
 65                  70                  75                  80

Lys Gly Met Thr Ala Ser Ala Tyr Thr Ser Gln Thr Cys Ala Lys Cys
                 85                  90                  95

Gly His Ile Ala Ala Glu Asn Arg Asp Gly Val Ile Phe His Cys Val
                100                 105                 110

Lys Cys Gly Phe Thr Ala His Ala Asp Val Asn Ala Ala Thr Asn Ile
            115                 120                 125

Leu Glu Lys Ala Leu Arg Leu
        130                 135

<210> SEQ ID NO 163
<211> LENGTH: 135
<212> TYPE: PRT
<213> ORGANISM: Artificial sequence
<220> FEATURE:
<223> OTHER INFORMATION: Synthetic sequence

<400> SEQUENCE: 163

Arg Ala Ala Gly Ile Trp Tyr Val Ser Ile Leu Cys Glu Trp Asp Lys
 1               5                  10                  15

Pro Ala Lys Pro Val His Arg Ala Pro Asn Ala Lys Val Gly Val Asp
                 20                  25                  30

Leu Asn Val Arg Tyr Phe Arg Leu Gln Cys Arg Ile Ala Arg Leu Gln
             35                  40                  45

Asp Arg Gln Ala Asn Leu Arg Asn Glu Val Thr Asn Gln Val Ala His
     50                  55                  60

Ala Val Ala Leu Lys His Ala Phe Val Gly Leu Glu Gly Leu Asp Ile
 65                  70                  75                  80
```

```
Lys Gly Met Thr Ala Ser Ala Tyr Thr Ser Gln Thr Cys Ala Lys Cys
                85                  90                  95

Gly His Ile Ala Ala Glu Asn Arg Asp Gly Val Ile Phe His Cys Val
            100                 105                 110

Lys Cys Gly Phe Thr Ala His Ala Asp Val Asn Ala Ala Thr Asn Ile
            115                 120                 125

Leu Glu Lys Ala Leu Arg Leu
    130             135

<210> SEQ ID NO 164
<211> LENGTH: 135
<212> TYPE: PRT
<213> ORGANISM: Artificial sequence
<220> FEATURE:
<223> OTHER INFORMATION: Synthetic sequence

<400> SEQUENCE: 164

Thr Gly Thr Gln Tyr Glu Ala Ile Ala Thr Tyr Lys Ile Glu Ala Gln
1               5                   10                  15

Gly Pro Gln Gly Asn Lys Val Ala Gly Ile Asp Leu Gly Glu Ile His
            20                  25                  30

Lys Lys Leu Ile Arg Ser Lys Gln Lys Gln Leu Lys Lys Leu Gln His
            35                  40                  45

Gln Val Asn Asp Ile Glu His Lys Gln Ser Ser Arg Leu Ile Ser Thr
50                  55                  60

Leu His Ala Lys Gly Val Gln Thr Val Val Ile Gly Asp Val Arg Asp
65                  70                  75                  80

Ile Arg Gln Asp Tyr Thr Ser Arg Thr Cys Pro Met Cys Gln His Val
                85                  90                  95

Arg Lys Ser Lys Val Gln Gly Arg Val Phe Arg Cys Pro Thr Cys His
            100                 105                 110

Trp Thr Tyr His Arg Asp Gly Val Gly Ala Ile Asn Ile Arg Gln Lys
            115                 120                 125

Tyr Leu Gly Ser Leu Pro Val
    130             135

<210> SEQ ID NO 165
<211> LENGTH: 136
<212> TYPE: PRT
<213> ORGANISM: Artificial sequence
<220> FEATURE:
<223> OTHER INFORMATION: Synthetic sequence

<400> SEQUENCE: 165

His His Asn Lys Arg Lys Tyr Phe Leu His Ile Thr Val Glu Met Lys
1               5                   10                  15

Gly Val Gln Arg Val Tyr Glu Lys Asp Arg Ala Ile Ala Val Asp Leu
            20                  25                  30

Gly Gln Ile His Lys Lys Leu Asn Gly Ala Lys Lys Leu Leu Asn
            35                  40                  45

Lys Ser Lys Asn Lys Val Asn Asp Val Leu Gln Lys Tyr Thr Ser Tyr
50                  55                  60

Leu Val Gly Tyr Cys Ile Glu Gln Gly Ile Gly Thr Ile Val Ile Gly
65                  70                  75                  80

Asp Ile Lys Ser Ile Arg Glu Asn Tyr Thr Ser Gln Thr Cys Pro Val
                85                  90                  95

Cys Asn Lys Lys His Lys Pro Gly Asn Arg Asn Phe Thr Cys Lys Cys
```

```
              100                 105                 110

Gly Phe Lys Tyr His Arg Asp Ala Val Gly Ala Ile Asn Ile His Lys
            115                 120                 125

Lys Tyr Thr Ser Ser Leu Ser Ala
            130                 135

<210> SEQ ID NO 166
<211> LENGTH: 135
<212> TYPE: PRT
<213> ORGANISM: Artificial sequence
<220> FEATURE:
<223> OTHER INFORMATION: Synthetic sequence

<400> SEQUENCE: 166

Glu Glu Gly Lys Tyr Tyr Leu His Leu Val Ile Glu Gly Lys Asn Val
1               5                   10                  15

Ala Arg Lys Pro Gln Asn Gly Lys Ile Met Ala Val Asp Leu Gly Ile
            20                  25                  30

Leu Arg Arg Lys Leu Val Lys Ala Lys Lys Met Leu Arg Arg Thr
            35                  40                  45

Arg His Gln Ile Lys Asp Ile Leu His Lys Ile Thr Ser Asn Phe Leu
50                  55                  60

Lys Met Cys Leu Gln Lys Gly Ile Gly Thr Ile Ala Leu Gly Asp Val
65                  70                  75                  80

Thr Asn Ile Arg Glu Arg Tyr Thr Ser Gln Thr Cys Pro Met Cys Gly
                85                  90                  95

Ser Arg Asn His Ser Asn Asn Arg Asn Tyr Lys Cys Gln Asn Cys Gly
            100                 105                 110

Phe Lys Tyr His Arg Asp Gly Val Gly Ala Ile Asn Ile Tyr Val Arg
            115                 120                 125

Tyr Leu Gly Lys Lys Ser Gln
            130                 135

<210> SEQ ID NO 167
<211> LENGTH: 135
<212> TYPE: PRT
<213> ORGANISM: Artificial sequence
<220> FEATURE:
<223> OTHER INFORMATION: Synthetic sequence

<400> SEQUENCE: 167

Glu Asp Gly Lys Tyr Tyr Leu His Leu Ala Thr Glu Val Lys Asn Glu
1               5                   10                  15

Val Gln Lys Gln Gln Gly Lys Lys Val Met Ala Val Asp Leu Gly Ile
            20                  25                  30

Leu Arg Arg Lys Leu Val Lys Ala Lys Lys Met Leu Arg Arg Ile
            35                  40                  45

Arg His Gln Ile Lys Asp Ile Leu His Lys Ile Thr Ser Asn Phe Leu
50                  55                  60

Lys Met Cys Leu Gln Lys Gly Ile Lys Thr Ile Ala Val Gly Asp Ile
65                  70                  75                  80

Thr Asn Ile Arg Glu Arg Tyr Thr Ser Gln Thr Cys Pro Ala Cys Gly
                85                  90                  95

Ser Arg Asn His Pro Thr Asp Arg Asn Tyr Glu Cys Gln Asn Cys Gly
            100                 105                 110

Phe Lys Tyr His Arg Asp Gly Val Gly Ala Ile Asn Ile Tyr Ala Arg
            115                 120                 125
```

Tyr Leu Gly Lys Lys Ser Gln
    130             135

<210> SEQ ID NO 168
<211> LENGTH: 132
<212> TYPE: PRT
<213> ORGANISM: Artificial sequence
<220> FEATURE:
<223> OTHER INFORMATION: Synthetic sequence

<400> SEQUENCE: 168

Asn Gly Thr Gly Tyr Glu Leu Arg Val Ile Tyr Ser Thr Thr Pro Thr
1               5                   10                  15

Gly Pro Leu Gly Val Lys Val Ala Gly Val Asp Met Gly Glu Ile His
            20                  25                  30

Lys Tyr Leu Lys His Asn Lys Ala Arg Thr Leu Lys Lys Leu Asp Asn
        35                  40                  45

Gln Ile Asn Asp Ile Leu His Lys Gln Thr Thr Lys Leu Val Ser Thr
    50                  55                  60

Leu His Glu Ala Gly Val Lys Thr Val Val Ile Gly Asp Val Arg Asp
65                  70                  75                  80

Ile Arg Lys Gly Tyr Thr Ser Gln Thr Cys Pro Ala Cys Gly Lys Arg
                85                  90                  95

His Lys Pro Lys Asp Arg Asn Tyr Arg Cys Ser Cys Gly Phe Gln Tyr
            100                 105                 110

His Arg Asp Gly Ile Gly Ala Tyr Asn Ile Arg Ala Lys Tyr Leu Gly
        115                 120                 125

Glu Leu Glu Thr
    130

<210> SEQ ID NO 169
<211> LENGTH: 135
<212> TYPE: PRT
<213> ORGANISM: Artificial sequence
<220> FEATURE:
<223> OTHER INFORMATION: Synthetic sequence

<400> SEQUENCE: 169

Asp Arg Thr Gly Trp Lys Met Asn Cys Val Met Glu Gln Glu Val Gln
1               5                   10                  15

Gln His Gln Leu Asp Lys Thr Lys Ile Leu Ala Ile Asp Leu Gly Asn
            20                  25                  30

Lys Arg Lys Arg Val Met Arg Ala Arg Arg Lys Ile Thr Ala Arg Ile
        35                  40                  45

Asn Asn Gln Lys Arg Asp Ile Leu His Lys Thr Ser Arg Ala Ile Val
    50                  55                  60

Asn Tyr Ala Ile Glu Asn Asn Ile Asp Lys Ile Val Phe Gly Asp Cys
65                  70                  75                  80

Ser Ser Ile His Asp Gly Tyr Ser Ser Gln Glu Cys Pro Ile Cys Asp
                85                  90                  95

His Arg Tyr Glu Pro Arg Gly Arg Thr Tyr Lys Cys Ser Ala Cys Gly
            100                 105                 110

Tyr Val Tyr Asp Arg Asp Gly Val Gly Ser Ile Asn Ile Tyr Thr Asn
        115                 120                 125

Val Ser Ser Gly Leu Thr Leu
    130             135

<210> SEQ ID NO 170

<211> LENGTH: 136
<212> TYPE: PRT
<213> ORGANISM: Artificial sequence
<220> FEATURE:
<223> OTHER INFORMATION: Synthetic sequence

<400> SEQUENCE: 170

Lys Thr Arg Gly Trp Lys Ile Asn Leu Cys Leu Glu Thr Asp Val Glu
1               5                   10                  15

Gln Lys Asn Leu Asp Asn Asn Lys Phe Leu Ser Ile Asp Leu Gly Val
            20                  25                  30

Lys Arg Lys Lys Ile Gln Arg Ala Lys Arg Arg Thr Thr Asp Lys Ile
        35                  40                  45

Leu Asn Ile Gln Lys Asp Met Leu His Lys Tyr Ser Ser Phe Val Val
    50                  55                  60

Asn Tyr Ala Ile Lys Asn Asn Ile Gly Asn Ile Ile Gly Asp Ser
65                  70                  75                  80

Ser Thr His Asp Ser Tyr Thr Ser Arg Lys Cys Pro Cys Cys Lys Asn
                85                  90                  95

Ile Lys Lys Ser Ser Pro Arg Gly Arg Thr Tyr Lys Cys Lys Lys Cys
            100                 105                 110

Asp Phe Val Phe Asp Arg Asp Gly Val Gly Ala Ile Asn Ile Tyr Asn
        115                 120                 125

Glu Asn Val Ser Phe Gly Thr Cys
    130                 135

<210> SEQ ID NO 171
<211> LENGTH: 136
<212> TYPE: PRT
<213> ORGANISM: Artificial sequence
<220> FEATURE:
<223> OTHER INFORMATION: Synthetic sequence

<400> SEQUENCE: 171

Lys Thr Arg Gly Trp Lys Ile Asn Leu Cys Leu Glu Thr Glu Val Glu
1               5                   10                  15

Gln Lys Asn Leu Ser Glu Asn Lys Tyr Leu Ser Ile Asp Leu Gly Val
            20                  25                  30

Lys Arg Lys Lys Ile Gln Arg Ala Lys Arg Lys Thr Thr Asp Arg Leu
        35                  40                  45

Leu Asn Ile Gln Lys Glu Met Leu His Lys Tyr Ser Ser Phe Ile Val
    50                  55                  60

Asn Tyr Ala Ile Arg Asn Asp Ile Gly Asn Ile Ile Gly Asp Ser
65                  70                  75                  80

Ser Thr His Asp Ser Tyr Thr Ser Arg Lys Cys Pro His Cys Lys Asn
                85                  90                  95

Ile Lys Lys Ser Ser Pro Lys Gly Arg Thr Tyr Lys Cys Lys Lys Cys
            100                 105                 110

Gly Phe Ile Phe Asp Arg Asp Gly Val Gly Ala Ile Asn Ile Tyr Asn
        115                 120                 125

Glu Asn Val Ser Phe Gly Gln Ile
    130                 135

<210> SEQ ID NO 172
<211> LENGTH: 134
<212> TYPE: PRT
<213> ORGANISM: Artificial sequence
<220> FEATURE:
<223> OTHER INFORMATION: Synthetic sequence

<400> SEQUENCE: 172

Lys Thr Thr Gly Lys Tyr Tyr Val Ser Ile Phe Thr Glu Gln Glu Val
1               5                   10                  15

Glu Glu Pro Lys Thr Asn Lys Gln Val Gly Ile Asp Leu Gly Leu Lys
            20                  25                  30

Asp Glu Lys Gln Lys Leu Lys Val Ala Lys Ile His Glu Lys Ile Ala
        35                  40                  45

Asn Cys Arg Leu Asp Ile Leu His Lys Val Ser Thr Glu Leu Val Lys
50                  55                  60

Asn Tyr Asp Leu Ile Ala Val Glu Asp Leu Asn Val Lys Gly Met Thr
65                  70                  75                  80

Lys Asn Tyr Pro Ser Ser Lys Thr Cys Ser Glu Cys Gly Trp Ile Asn
            85                  90                  95

Gln Glu Leu Lys Leu Ser Asp Arg Glu Trp Thr Cys Asn Ser Cys Gly
            100                 105                 110

Ala Ile His Asp Arg Asp Leu Asn Ala Ser Lys Asn Ile Leu Lys Glu
            115                 120                 125

Gly Leu Lys Ile Ile Ser
        130

<210> SEQ ID NO 173
<211> LENGTH: 137
<212> TYPE: PRT
<213> ORGANISM: Artificial sequence
<220> FEATURE:
<223> OTHER INFORMATION: Synthetic sequence

<400> SEQUENCE: 173

Arg Gln Asn Asn Gln Tyr Phe Val Ser Ile Leu Ile Asp Asp Asn Asn
1               5                   10                  15

Ala Ile Pro Lys Pro Ile Lys Ala Lys Asn Ala Val Gly Leu Asp Met
            20                  25                  30

Gly Leu Thr Asp Gln Lys Ala Lys Leu Arg Val Gln Lys Leu His Thr
        35                  40                  45

Lys Val Ser Asn Gln Arg Lys Asp Thr Leu His Lys Ile Ser Asn Glu
50                  55                  60

Ile Thr Asn Gln Tyr Asp Ile Ile Cys Leu Glu Thr Leu Asn Val Arg
65                  70                  75                  80

Gly Met Gln Lys Asn Phe Pro Ser Ser Gln Ile Cys Ser Asn Cys Gly
            85                  90                  95

Ala Ser Ser Lys Lys Glu Leu His Val Arg Lys Trp Glu Cys Pro
            100                 105                 110

Glu Cys His Ala Lys His Asp Arg Asp Ile Asn Ala Ser Ile Asn Ile
            115                 120                 125

Lys Asn Tyr Gly Leu Gly Gln Ile Asp
        130                 135

<210> SEQ ID NO 174
<211> LENGTH: 137
<212> TYPE: PRT
<213> ORGANISM: Artificial sequence
<220> FEATURE:
<223> OTHER INFORMATION: Synthetic sequence

<400> SEQUENCE: 174

Lys Lys His Asn Lys Tyr Tyr Val Ser Ile Met Val Glu Tyr Thr Asn
1               5                   10                  15

```
Asn Phe Lys Lys Val Glu Val Lys Ser Val Gly Ile Asp Leu Gly
            20                  25                  30

Val Lys Ala Lys Ile Lys Lys Asn Ile Ser Lys Ile His Glu Asn
            35                  40                  45

Val Ala Asn Thr Arg Glu Asn Phe Leu His Asn Glu Ser Lys Leu
 50                  55                  60

Val Asp Asn Tyr Asp Leu Ile Cys Met Glu Asp Leu Asn Val Lys Gly
 65                  70                  75                  80

Met Thr Lys Ser Ser Glu Pro Thr Ser Lys Lys Cys Asn Cys Cys Gly
                 85                  90                  95

Thr Ile Asn Lys Asn Leu Glu Leu Lys Asp Arg Ile Trp Lys Cys Glu
             100                 105                 110

Asn Cys Gly Glu Ile Leu Asn Arg Asp Leu Asn Ala Ala Leu Asn Ile
             115                 120                 125

Arg Asp Leu Gly Thr Lys Lys Phe Phe
             130                 135

<210> SEQ ID NO 175
<211> LENGTH: 137
<212> TYPE: PRT
<213> ORGANISM: Artificial sequence
<220> FEATURE:
<223> OTHER INFORMATION: Synthetic sequence

<400> SEQUENCE: 175

Lys Thr Thr Asn Lys Tyr Tyr Ile Ser Ile Leu Val Asp Asp Lys Lys
 1               5                  10                  15

Pro Ile Pro Lys Arg Gln Ile Lys Leu Glu Ser Thr Val Gly Ile Asp
             20                  25                  30

Leu Gly Ile Lys Asp Ile Lys Gln Lys Met Lys Val Ser Leu Leu His
             35                  40                  45

Glu His Ile Lys Asn Gln Arg Glu Asp Tyr Leu His Lys Ile Ser Lys
 50                  55                  60

Tyr Leu Val Tyr Asn Tyr Asp Thr Ile Cys Ile Glu Asn Leu Gly Val
 65                  70                  75                  80

Ser Asn Met Met Lys Asn Asp Pro Ser Ser Lys Thr Cys Ser Ser Cys
                 85                  90                  95

Gly Ser Ile Asn Lys Glu Leu Thr Leu Asn Asp Arg Glu Trp Thr Cys
             100                 105                 110

Lys Cys Gly Thr Lys His Asp Arg Asp Ile Asn Ala Ala Ile Asn Ile
             115                 120                 125

Arg Asn Phe Gly Leu Arg Asn Gln Pro
             130                 135

<210> SEQ ID NO 176
<211> LENGTH: 144
<212> TYPE: PRT
<213> ORGANISM: Artificial sequence
<220> FEATURE:
<223> OTHER INFORMATION: Synthetic sequence

<400> SEQUENCE: 176

Arg Lys Gly Asn Asn Tyr Tyr Ile Ser Phe Gln Val Glu His Asn Gln
 1               5                  10                  15

Pro Leu Ile Ser Glu Pro Ile Lys Arg Glu Ile Lys Tyr Glu Thr Thr
             20                  25                  30

Ile Gly Ile Asp Met Gly Val Glu Arg Lys Arg Ile Leu Lys Lys Met
```

```
                    35                  40                  45
Arg Gly Leu Tyr His Lys Ile Thr Asn Ile Arg Glu Asn Leu Gln His
    50                  55                  60

Asn Ile Thr Ser Asn Leu Val Asn Lys Glu Asn Ile Asp Thr Phe Ile
65                  70                  75                  80

Leu Glu Glu Leu Asn Leu Lys Asn Met Thr Lys Arg Ser Phe Thr Ser
                85                  90                  95

Gln Lys Cys Ser Asp Cys Gly His Ile Asn Lys Leu Asn Arg Lys Ser
            100                 105                 110

Gln Ala Val Phe Lys Cys Val Lys Cys Gly Tyr Thr Leu Asn Ala Asp
                115                 120                 125

Leu Asn Ala Ala Ile Asn Ile Lys Asn Asn Phe Phe Gly Lys Asn Thr
            130                 135                 140

<210> SEQ ID NO 177
<211> LENGTH: 139
<212> TYPE: PRT
<213> ORGANISM: Artificial sequence
<220> FEATURE:
<223> OTHER INFORMATION: Synthetic sequence

<400> SEQUENCE: 177

Glu Thr Ser Gly Glu Phe Tyr Leu Ala Ile Thr Ala Asp Ile Ile Ser
1               5                   10                  15

Lys Pro Met Lys Arg Ile Val Asn Glu Glu Thr Ser Ile Gly Ile Asp
                20                  25                  30

Met Gly Val Ala Arg Glu Arg Ile Lys Lys Arg Leu Ala Lys Leu His
            35                  40                  45

Ser Lys Ile Ala Asn Ile Arg Lys Tyr Leu Gln His Asn Ile Thr Ser
        50                  55                  60

Lys Leu Ile Asn Ser Lys Tyr Asp Thr Ile Ile Glu Asp Leu Asp
65                  70                  75                  80

Val Lys Asn Met Met Lys Lys Ser Tyr Thr Ser Gln Met Cys Ser Asn
                85                  90                  95

Cys Gly His Thr His Arg Asp Asn Arg Lys Lys Gln Asp Glu Phe Ile
            100                 105                 110

Cys Val Ser Cys Gly His Asn Glu Asn Ala Asp Leu Asn Ala Ala Lys
        115                 120                 125

Asn Ile Lys Asn Lys Phe Phe Lys Lys Leu Ala
            130                 135

<210> SEQ ID NO 178
<211> LENGTH: 138
<212> TYPE: PRT
<213> ORGANISM: Artificial sequence
<220> FEATURE:
<223> OTHER INFORMATION: Synthetic sequence

<400> SEQUENCE: 178

Lys Arg Gly Asn Gln Tyr Phe Ile Ser Phe Gln Val Glu Leu Pro Gly
1               5                   10                  15

Glu Leu Pro Arg Lys Arg Glu Ile Lys Lys Glu Thr Ser Val Gly Val
                20                  25                  30

Asp Phe Gly Val Lys Lys Asn Asn Ile Lys Glu Lys Ile Asn Lys Leu
            35                  40                  45

His Ile Lys Ile Ser Asn Gln Arg Lys Asn Leu Gln His Asn Ile Ser
        50                  55                  60
```

```
Ser Phe Leu Val Asn Leu Asn Ala Asp Thr Ile Ile Met Glu Asp Leu
 65                  70                  75                  80

Asn Leu Lys Gly Met Thr Lys Thr Pro Tyr Thr Ser Gln Lys Cys Asn
                 85                  90                  95

Asn Cys Gly Phe Thr His Lys Glu Asn Arg Ile Ser Gln Ser Glu Phe
            100                 105                 110

Glu Cys Lys Asn Cys Gly His Lys Asp Asn Ala Asp Lys Asn Ala Ser
        115                 120                 125

Lys Asn Ile Lys Gln Lys Tyr Phe Asp Asn
    130                 135
```

<210> SEQ ID NO 179
<211> LENGTH: 135
<212> TYPE: PRT
<213> ORGANISM: Artificial sequence
<220> FEATURE:
<223> OTHER INFORMATION: Synthetic sequence

<400> SEQUENCE: 179

```
Lys Val Ile Lys Arg Arg Leu Phe Leu Leu Leu Ser Tyr Glu Ile Pro
  1               5                  10                  15

Asp Lys Ile Glu Asn Lys Pro Asn Pro Asp Asn Ile Met Gly Ile Asp
                 20                  25                  30

Phe Gly Met Ala Asn Ala Arg Lys Thr Arg Lys Ile Glu Asp Tyr Arg
             35                  40                  45

Asn Lys Glu Lys Asn Leu Thr Lys Thr Glu Ile Ser Gln Ile Leu Ser
 50                  55                  60

Ser Ile Val Arg Leu Ala Gln Ala Asn Asn Ile Gly Thr Ile Lys Ile
 65                  70                  75                  80

Glu Tyr Leu Thr Ile Asp Gln Lys Thr His Thr Ser Gln Lys Cys Ser
                 85                  90                  95

Thr Cys Gly Thr Ile Gly Thr Arg Asp Gly Arg Ile Phe Ser Cys Glu
            100                 105                 110

Asn Cys Ser Phe Lys Val Asn Ala Asp Lys Asn Ala Ala Ile Asn Ile
        115                 120                 125

Ala Asn Ser Thr Gln Phe Val
    130                 135
```

<210> SEQ ID NO 180
<211> LENGTH: 148
<212> TYPE: PRT
<213> ORGANISM: Artificial sequence
<220> FEATURE:
<223> OTHER INFORMATION: Synthetic sequence

<400> SEQUENCE: 180

```
Thr Asn Arg Asp Arg Lys Leu Cys Tyr Val Leu Gln Leu Thr Val Asn
  1               5                  10                  15

Ile Pro Glu Pro Val Ala Ser Pro Cys Thr Asn Gly Val Gly Ile Asp
                 20                  25                  30

Leu Gly Trp Arg Leu Met Asp Ser Gly Ile Arg His Arg Lys Asp Arg
             35                  40                  45

His Leu Glu Gln Tyr Glu Val Gly Cys Arg Lys Arg Ala Met Asn Tyr
 50                  55                  60

Arg Arg Glu Glu Tyr Lys Phe Ala Lys Gln Met Thr Ser Thr Tyr
 65                  70                  75                  80

Gly Tyr Leu Ala Leu Glu Asn Trp Asn Ile Ser Lys Val Ala Leu Arg
                 85                  90                  95
```

Tyr Thr Thr Leu Glu Cys Ala Ala Cys His Lys Ile Asn Thr Trp Asp
            100                 105                 110

Thr Ser Lys Asn Val Cys Gln Thr Cys Glu Asn Cys Asp Thr Val Trp
            115                 120                 125

Asp Gln Asp Glu Asn Ala Ala Arg Asn Leu Leu Ala Ser Gly Thr Val
130                 135                 140

Leu Lys Asn Thr
145

<210> SEQ ID NO 181
<211> LENGTH: 89
<212> TYPE: PRT
<213> ORGANISM: Artificial sequence
<220> FEATURE:
<223> OTHER INFORMATION: Synthetic sequence

<400> SEQUENCE: 181

Arg Phe Tyr Gly Pro His Gln Glu Trp Thr Leu Glu Ile Thr Ile Asp
1               5                   10                  15

Asn Leu Ser Pro Thr Lys Glu Leu Gly Asn Gly Val Val Ala Leu Asp
            20                  25                  30

Ile Gly Trp Arg Lys Leu Asn Asp Lys Ile Arg Arg Tyr Lys Asp Gln
        35                  40                  45

His Leu Trp Gln Trp Glu Cys Gly Ser Arg Arg Ser Gly Leu Arg Glu
    50                  55                  60

Arg Ile Ile Ile Ala Thr Leu Leu Glu Arg Asn Ile Thr Val Leu Tyr
65                  70                  75                  80

Lys Thr Leu Ile Phe Gln Arg Trp Gln
                85

<210> SEQ ID NO 182
<211> LENGTH: 138
<212> TYPE: PRT
<213> ORGANISM: Artificial sequence
<220> FEATURE:
<223> OTHER INFORMATION: Synthetic sequence

<400> SEQUENCE: 182

Ser Lys Lys Lys Gly Lys Trp Phe Cys Val Ile Ala Tyr Asp Ser Pro
1               5                   10                  15

Ile Lys Val Asn Glu Leu Asp Ile Asp Lys Val Met Gly Ile Asp Leu
            20                  25                  30

Gly Ile Val Asn Lys Arg Asn Met Gln Ala Ala Asp Ile Leu Gly Glu
        35                  40                  45

Lys Ile Ser Asn Phe Arg Asp Thr Val Asn His Lys Tyr Ser Lys Lys
    50                  55                  60

Ile Ile Asp Ile Ala Ile Ala Asn Lys Cys Gly Val Ile Gln Met Glu
65                  70                  75                  80

Asp Leu Thr Gly Ile Ser Lys Asn Thr Ser Lys Thr Cys Ser Val Cys
                85                  90                  95

Gly His Leu Asp Ala Glu Asn Arg Glu Asp Gln Ala Thr Phe Ile Cys
            100                 105                 110

Lys Glu Cys Gly Ser Asn Met Asn Ala Asp His Asn Ala Ala Lys Asn
            115                 120                 125

Ile Ser Val Trp Ser Val Ser Lys Glu Phe
            130                 135

-continued

<210> SEQ ID NO 183
<211> LENGTH: 136
<212> TYPE: PRT
<213> ORGANISM: Artificial sequence
<220> FEATURE:
<223> OTHER INFORMATION: Synthetic sequence

<400> SEQUENCE: 183

Lys Asp Lys Lys Thr Phe Ile Asn Leu Cys Tyr Gly Phe Glu Pro Val
1               5                   10                  15

Thr Ser Glu Leu Asp Lys Ser Lys Val Met Gly Ile Asp Leu Gly Val
            20                  25                  30

Ser Val Lys Lys Met Val Cys Tyr Asp Lys Tyr Ser Asn Lys Ser
        35                  40                  45

Arg Asn Leu Ser Gln Thr Ile Asn His Gly Trp Ser Lys Tyr Ile Val
    50                  55                  60

Asp Val Ala Phe Arg Asn Gly Cys Gly Thr Ile Gln Met Glu Asp Leu
65                  70                  75                  80

Ser Gly Val Thr Ser Tyr Thr Ser Gln Arg Cys Cys Glu Cys Gly Cys
                85                  90                  95

Ile Cys Lys Arg Asn Arg Pro Asp Gln Lys Thr Phe Lys Cys Ile Ser
            100                 105                 110

Cys Gly Tyr Ser Ala Asn Ala Asp Phe Asn Ala Ala Lys Asn Ile Ala
        115                 120                 125

Thr Ile Gly Ile Glu Asp Ile Ile
    130                 135

<210> SEQ ID NO 184
<211> LENGTH: 141
<212> TYPE: PRT
<213> ORGANISM: Artificial sequence
<220> FEATURE:
<223> OTHER INFORMATION: Synthetic sequence

<400> SEQUENCE: 184

Ala Ala Gly Lys Lys Asp Lys Pro Lys Val Trp Leu Tyr Leu Cys Tyr
1               5                   10                  15

Gly Phe Glu Pro Glu Ala Pro Glu Leu Asp Asp Ser Arg Ile Met Gly
            20                  25                  30

Ile Asp Leu Gly Met Lys Leu Lys Lys Val Asp Val Tyr Glu Arg
        35                  40                  45

Tyr Ser His Lys Ser His Asn Leu Ser Met His Ile Asn His Gln Trp
50                  55                  60

Ser Lys Tyr Ile Val Asp Thr Ala Val Lys Asn Cys Gly Val Ile
65                  70                  75                  80

Gln Met Glu Asp Leu Ser Gly Ile Lys Ala Tyr Thr Ser Gln Met Cys
                85                  90                  95

Pro Val Cys Gly Tyr Ile Asn Lys Arg Asn Arg Ser Thr Gln Ala Asp
            100                 105                 110

Phe Glu Cys Leu Glu Cys Gly His Ile Ala Asn Ala Asp Tyr Asn Ala
        115                 120                 125

Ala Arg Asn Ile Ala Thr Pro Asp Ile Ala Asn Ile Ile
    130                 135                 140

<210> SEQ ID NO 185
<211> LENGTH: 140
<212> TYPE: PRT
<213> ORGANISM: Artificial sequence
<220> FEATURE:

<223> OTHER INFORMATION: Synthetic sequence

<400> SEQUENCE: 185

Gly Gly Lys Lys Asp Lys Pro Lys Val Trp Leu Tyr Leu Cys Tyr Gly
1               5                   10                  15
Phe Glu Pro Glu Ala Pro Glu Leu Asp Asp Ser Arg Ile Met Gly Ile
            20                  25                  30
Asp Leu Gly Met Lys Leu Asn Lys Lys Val Asp Val Tyr Glu Arg Tyr
        35                  40                  45
Ser His Lys Ser His Asn Leu Ser Met Asp Ile Asn His Gln Trp Ser
    50                  55                  60
Lys Tyr Ile Val Asp Thr Ala Val Lys Asn Lys Cys Gly Val Ile Gln
65                  70                  75                  80
Met Glu Asp Leu Ser Gly Ile Lys Ala Tyr Thr Ser Gln Met Cys Pro
                85                  90                  95
Val Cys Gly Tyr Ile Asn Lys Arg Asn Arg Ser Thr Gln Ala Asp Phe
            100                 105                 110
Glu Cys Leu Glu Cys Gly His Ile Ala Asn Ala Asp Tyr Asn Ala Ala
        115                 120                 125
Arg Asn Ile Ala Thr Pro Asp Ile Ala Asn Ile Ile
    130                 135                 140

<210> SEQ ID NO 186
<211> LENGTH: 141
<212> TYPE: PRT
<213> ORGANISM: Artificial sequence
<220> FEATURE:
<223> OTHER INFORMATION: Synthetic sequence

<400> SEQUENCE: 186

Ala Ala Gly Lys Lys Asp Lys Pro Lys Val Trp Leu Tyr Leu Cys Tyr
1               5                   10                  15
Gly Phe Glu Pro Glu Ala Pro Glu Leu Asp Asp Ser Arg Ile Met Gly
            20                  25                  30
Ile Asp Leu Gly Met Lys Leu Lys Lys Val Asp Val Tyr Glu Arg
        35                  40                  45
Tyr Ser His Lys Ser His Asn Leu Ser Met Asp Ile Asn His Gln Trp
    50                  55                  60
Ser Lys Tyr Ile Val Glu Thr Ala Val Lys Asn Lys Cys Gly Val Ile
65                  70                  75                  80
Gln Val Glu Asp Leu Ser Gly Ile Lys Ala Tyr Thr Ser Gln Met Cys
                85                  90                  95
Pro Val Cys Gly Tyr Ile Asn Lys Arg Asn Arg Ser Thr Gln Ala Asp
            100                 105                 110
Phe Glu Cys Leu Glu Cys Gly His Ile Ala Asn Ala Asp Tyr Asn Ala
        115                 120                 125
Ala Arg Asn Ile Ala Thr Pro Asp Ile Ala Asn Ile Ile
    130                 135                 140

<210> SEQ ID NO 187
<211> LENGTH: 141
<212> TYPE: PRT
<213> ORGANISM: Artificial sequence
<220> FEATURE:
<223> OTHER INFORMATION: Synthetic sequence

<400> SEQUENCE: 187

Ala Ala Gly Lys Lys Asp Lys Pro Lys Val Trp Leu Tyr Leu Cys Tyr

```
                1               5                      10                      15
            Gly Phe Glu Pro Glu Ala Pro Glu Leu Asp Asp Ser Arg Ile Met Gly
                            20                      25                      30
            Ile Asp Leu Gly Met Lys Leu Lys Lys Val Asp Val Tyr Glu Lys
                            35                      40                      45
            Cys Ser His Arg Ser His Asn Leu Ser Met Asp Ile Asn His Gln Trp
                50                      55                      60
            Ser Lys Tyr Ile Val Glu Thr Ala Ile Lys Asn Lys Cys Gly Val Ile
            65                      70                      75                      80
            Gln Met Glu Asp Leu Ser Gly Ile Lys Ala Tyr Thr Ser Gln Met Cys
                            85                      90                      95
            Pro Ile Cys Gly Tyr Ile Asn Lys Arg Asn Arg Ser Thr Gln Ala Asp
                            100                     105                     110
            Phe Glu Cys Leu Glu Cys Gly His Ile Ala Asn Ala Asp Tyr Asn Ala
                            115                     120                     125
            Ala Arg Asn Ile Ala Thr Pro Asp Ile Ala Asn Ile Ile
                            130                     135                     140

<210> SEQ ID NO 188
<211> LENGTH: 446
<212> TYPE: PRT
<213> ORGANISM: Artificial sequence
<220> FEATURE:
<223> OTHER INFORMATION: Synthetic sequence

<400> SEQUENCE: 188

Met Ala Lys Lys Asn Ile Asp Asp Thr Lys Lys Val Thr Leu Cys Glu
            1               5                      10                      15
            Lys Val Lys Leu Thr Gln Ile Tyr Ser Pro Val Val Asp Trp Lys Glu
                            20                      25                      30
            Phe His Lys Ile Phe Lys Ile Leu Gln Lys Glu Thr Ile Leu Ala Ser
                            35                      40                      45
            Asn Lys Ile Ile Ser Ile Cys Asn Ile Phe Asn Ser Phe Asn Asn Lys
                50                      55                      60
            Glu Glu Gln Lys Asp Trp Leu Ile Lys Tyr Gln Ser Glu Lys Leu
            65                      70                      75                      80
            Arg Asn Val Leu Tyr Asp Val Ala Arg Lys Tyr Cys Tyr Tyr Ser Tyr
                            85                      90                      95
            Ser Arg Asn Ala Asn Ala Ile Ser Asn Asp Ile Tyr Tyr Lys Tyr Phe
                            100                     105                     110
            Lys Gly Pro Asn Ser Tyr Lys Val Lys Ile Gln Lys Gly Ile Gly Asn
                            115                     120                     125
            Pro Pro Met Thr Phe Thr Glu Ser Ile Pro Leu Tyr Ile Thr Val Gln
                            130                     135                     140
            Arg His Lys Ile Glu Cys Thr Asn Asn Val Arg His Tyr Tyr Thr Ile
            145                     150                     155                     160
            Glu Val Pro Leu Leu Ser Asn Asn Cys Lys Ser Gly Ile Gln Ile Thr
                            165                     170                     175
            Asp Thr Glu Gln Thr Gln Val Asn Asn Asn Ala Leu Arg Phe Gly Ile
                            180                     185                     190
            Asn Ala Ala Gly Asn Lys Arg Leu Ile Glu Ile Leu Asp Asn Ile Ile
                            195                     200                     205
            Tyr Gly Lys Tyr Glu Phe Cys Asp Ser Lys Leu Lys Arg Val Lys Ser
                            210                     215                     220
            Lys Lys Arg Ser His Arg Tyr Asp Tyr Tyr Phe Leu Leu Ser Tyr Lys
```

```
225                 230                 235                 240
Lys Pro Val Ile Glu Ile Lys Ser Leu Lys Pro Glu Asn Val Leu Gly
                245                 250                 255

Val Asp Leu Gly Met Thr Val Pro Ala Tyr Cys Ala Val Asn Tyr Cys
                260                 265                 270

Asp Tyr Lys Ala Val Gly Asp Ser Arg Ile Ile Arg Phe Asn Leu
            275                 280                 285

Ile Gln Glu Lys Ile Asn Lys Arg Ile Gln Arg Asn Ile Lys Tyr Asn
                290                 295                 300

Leu Arg Asp Gly His Gly Arg Lys Tyr Lys Leu Asp Gly Tyr Asp Gly
305                 310                 315                 320

Ala Ser Asn Lys Ile Ala Lys Arg Asn Ser Thr Phe Asn Phe Asn Leu
                325                 330                 335

Ala Ser Glu Ile Ile Gln Leu Ala Ile Lys Trp Gln Cys Gly Thr Ile
                340                 345                 350

His Leu Glu Asp Leu Thr Lys Ile His Glu Ile Asn Pro Gln Asn Arg
                355                 360                 365

Phe Leu Lys Asn Trp Thr Tyr Tyr Asp Leu Gln Lys Lys Ile Glu Asn
            370                 375                 380

Lys Ala Lys Glu Tyr Gly Ile Val Val Lys Tyr Ile Asn Pro Tyr Tyr
385                 390                 395                 400

Thr Ser Gln Ile Cys Ser Asn Cys Gly His Phe Glu Ser Gly Gln Arg
                405                 410                 415

Ile Ser Gln Ser Gln Phe Gln Cys Lys Ser Cys Gly Tyr Ser Ala Asn
                420                 425                 430

Ala Asp Tyr Asn Ala Ala Arg Asn Ile Ala Leu Tyr Lys Phe
            435                 440                 445
```

CRISPR-Cas EFFECTOR POLYPEPTIDES AND METHODS OF USE THEREOF

CROSS-REFERENCE

This application is a continuation of PCT Application No. US2020/021214, filed Mar. 5, 2020, which claims the benefit of U.S. Provisional Patent Application No. 62/815,179, filed Mar. 7, 2019, which application is incorporated herein by reference in its entirety.

INCORPORATION BY REFERENCE OF SEQUENCE LISTING PROVIDED AS A TEXT FILE

A Sequence Listing is provided herewith as a text file, "05_BERK-404CON_SeqList_ST25" created on Aug. 16, 2021 and having a size of 226,130 bytes. The contents of the text file are incorporated by reference herein in their entirety.

INTRODUCTION

CRISPR-Cas systems include Cas proteins, which are involved in acquisition, targeting and cleavage of foreign DNA or RNA, and a guide RNA(s), which includes a segment that binds Cas proteins and a segment that binds to a target nucleic acid. For example, Class 2 CRISPR-Cas systems comprise a single Cas protein bound to a guide RNA, where the Cas protein binds to and cleaves a targeted nucleic acid. The programmable nature of these systems has facilitated their use as a versatile technology for use in modification of target nucleic acid.

SUMMARY

The present disclosure provides RNA-guided CRISPR-Cas effector proteins, nucleic acids encoding same, and compositions comprising same. The present disclosure provides ribonucleoprotein complexes comprising: an RNA-guided CRISPR-Cas effector protein of the present disclosure; and a guide RNA. The present disclosure provides methods of modifying a target nucleic acid, using an RNA-guided CRISPR-Cas effector protein of the present disclosure and a guide RNA.

BRIEF DESCRIPTION OF THE DRAWINGS

FIG. 6A-6BB provide amino acid sequences of examples of CRISPR-Cas effector polypeptides of the present disclosure (from top to bottom: SEQ ID NOs: 51-97).

FIG. 7A-7D provides nucleotide sequences of constant region portions of CRISPR-Cas effector guide RNAs (from top to bottom: SEQ ID NOs: 98-116).

FIG. 8 provides an amino acid sequence alignment of CRISPR-Cas effector polypeptides (from top to bottom: SEQ ID NOs: 117-187).

FIG. 9 provides the amino acid sequence of a CRISPR-Cas effector polypeptide (SEQ ID NO: 188).

DEFINITIONS

Figure 1A:
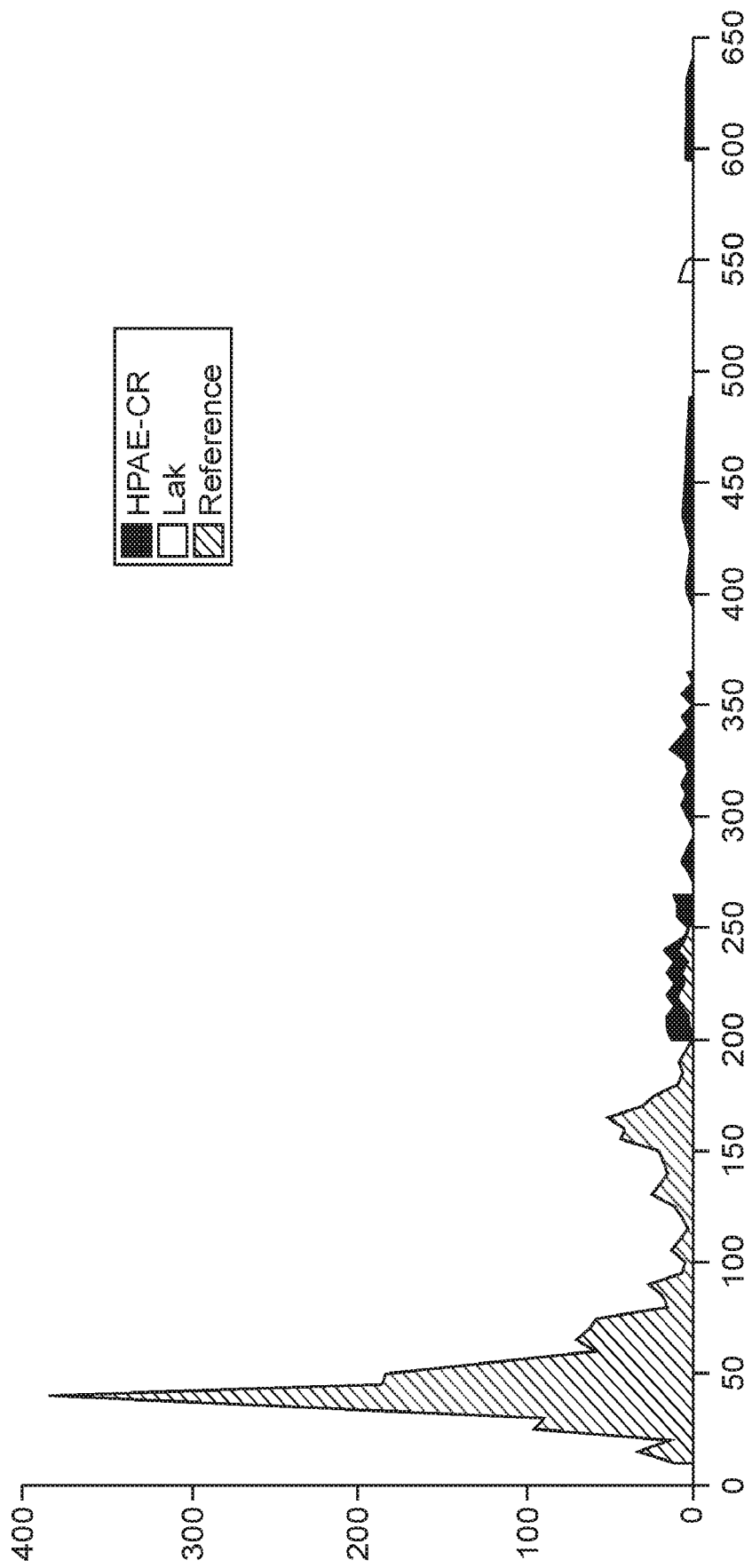
FIG. 1A shows the size distribution of complete bacteriophage genomes from this study, Lak phage reported recently from a subset of the same samples and reference sources (all dsDNA genomes from RefSeq v92 and non-artifactual assemblies>200 kb from (Paez-Espino et al. (2016) *Nature* 536: 425).

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is at least partially responsible for the degeneracy (i.e., redundancy) of the genetic code in the context of tRNA anti-codon base-pairing with codons in mRNA. Thus, in the context of this disclosure, a guanine (G) (e.g., of dsRNA duplex of a guide RNA molecule; of a guide RNA base pairing with a target nucleic acid, etc.) is considered complementary to both a uracil (U) and to an adenine (A). For example, when a G/U base-pair can be made at a given nucleotide position of a dsRNA duplex of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). Temperature, wash solution salt concentration, and other conditions may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a bulge, a loop structure or hairpin structure, etc.). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656), the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489), and the like.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a CRISPR-Cas effector polypeptide/guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleotide sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

A "protein coding sequence" or a sequence that encodes a particular protein or polypeptide, is a nucleotide sequence that is transcribed into mRNA (in the case of DNA) and is translated (in the case of mRNA) into a polypeptide in vitro or in vivo when placed under the control of appropriate regulatory sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., RNA-guided endonuclease, GeoCas9 polypeptide, GeoCas9 fusion polypeptide, and the like) and/or regulate translation of an encoded polypeptide.

As used herein, a "promoter" or a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive expression by the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism that can be isolated from a source in nature is naturally occurring.

The term "fusion" as used herein as applied to a nucleic acid or polypeptide refers to two components that are defined by structures derived from different sources. For example, where "fusion" is used in the context of a fusion polypeptide (e.g., a fusion CRISPR-Cas effector protein), the fusion polypeptide includes amino acid sequences that are derived from different polypeptides. A fusion polypeptide may comprise either modified or naturally-occurring polypeptide sequences (e.g., a first amino acid sequence from a modified or unmodified CRISPR-Cas effector protein; and a second amino acid sequence from a modified or unmodified protein other than a CRISPR-Cas effector protein, etc.). Similarly, "fusion" in the context of a polynucleotide encoding a fusion polypeptide includes nucleotide sequences derived from different coding regions (e.g., a first nucleotide sequence encoding a modified or unmodified CRISPR-Cas effector protein; and a second nucleotide sequence encoding a polypeptide other than a CRISPR-Cas effector protein).

The term "fusion polypeptide" refers to a polypeptide which is made by the combination (i.e., "fusion") of two otherwise separated segments of amino acid sequence, usually through human intervention.

"Heterologous," as used herein, means a nucleotide or polypeptide sequence that is not found in the native nucleic acid or protein, respectively. For example, in some cases, in a variant CRISPR-Cas effector protein of the present disclosure, a portion of naturally-occurring CRISPR-Cas effector polypeptide (or a variant thereof) may be fused to a heterologous polypeptide (i.e. an amino acid sequence from a protein other than a CRISPR-Cas effector polypeptide or an amino acid sequence from another organism). As another example, a fusion CRISPR-Cas effector polypeptide can comprise all or a portion of a naturally-occurring CRISPR-Cas effector polypeptide (or variant thereof) fused to a heterologous polypeptide, i.e., a polypeptide from a protein other than a CRISPR-Cas effector polypeptide, or a polypeptide from another organism. The heterologous polypeptide may exhibit an activity (e.g., enzymatic activity) that will also be exhibited by the variant CRISPR-Cas effector protein or the fusion CRISPR-Cas effector protein (e.g., biotin ligase activity; nuclear localization; etc.). A heterologous nucleic acid sequence may be linked to a naturally-occurring nucleic acid sequence (or a variant thereof) (e.g., by genetic engineering) to generate a nucleotide sequence encoding a fusion polypeptide (a fusion protein).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences"). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. An example of such a case is a DNA (a recombinant) encoding a wild-type protein where the DNA sequence is codon optimized for expression of the protein in a cell (e.g., a eukaryotic cell) in which the protein is not naturally found (e.g., expression of a CRISPR/Cas RNA-guided polypeptide such as CRISPR-Cas effector (e.g., wild-type CRISPR-Cas effector; variant CRISPR-Cas effector; fusion CRISPR-Cas effector; etc.) in a eukaryotic cell). A codon-optimized DNA can therefore be recombinant and non-naturally occurring while the protein encoded by the DNA may have a wild type amino acid sequence.

Thus, the term "recombinant" polypeptide does not necessarily refer to a polypeptide whose amino acid sequence does not naturally occur. Instead, a "recombinant" polypeptide is encoded by a recombinant non-naturally occurring DNA sequence, but the amino acid sequence of the polypeptide can be naturally occurring ("wild type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as plasmid, phage, virus, artificial chromosome, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression.

The terms "recombinant expression vector," or "DNA construct" are used interchangeably herein to refer to a DNA molecule comprising a vector and an insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA or exogenous RNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., DNA such as genomic DNA) that includes a site ("target site" or "target sequence") targeted by an RNA-guided endonuclease polypeptide (e.g., wild-type CRISPR-Cas effector; variant CRISPR-Cas effector; fusion CRISPR-Cas effector; etc.). The target sequence is the sequence to which the guide sequence of a subject CRISPR-Cas effector guide RNA (e.g., a dual CRISPR-Cas effector guide RNA or a single-molecule CRISPR-Cas effector guide RNA) will hybridize. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non-complementary strand."

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events.

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26al, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

In some instances, a component (e.g., a nucleic acid component (e.g., a CRISPR-Cas effector guide RNA); a protein component (e.g., wild-type CRISPR-Cas effector polypeptide; variant CRISPR-Cas effector polypeptide; fusion CRISPR-Cas effector polypeptide; etc.); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels; e.g., a fluorescent label) and indirectly detectable labels (indirect labels; e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3H$, $^{125}I$, $^{35}S$, $^{14}C$, or $^{32}P$); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, non-human primates, ungulates, felines, canines, bovines, ovines, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CRISPR-Cas effector CRISPR-Cas effector polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides RNA-guided CRISPR-Cas effector proteins (referred to herein variously as "Cas14i" polypeptides, "Cas14j" polypeptides, "Cas 14k" polypeptides, etc.), nucleic acids encoding same, and compositions comprising same. The present disclosure provides ribonucleoprotein complexes comprising: a CRISPR-Cas effector polypeptide of the present disclosure; and a guide RNA. The present disclosure provides methods of modifying a target nucleic acid, using a CRISPR-Cas effector polypeptide of the present disclosure and a guide RNA.

The present disclosure provides guide RNAs (referred to herein as "CRISPR-Cas effector guide RNAs") that bind to and provide sequence specificity to the CRISPR-Cas effector proteins of the present disclosure; nucleic acids encoding the CRISPR-Cas effector guide RNAs; and modified host cells comprising the CRISPR-Cas effector guide RNAs and/or nucleic acids encoding same. CRISPR-Cas effector guide RNAs are useful in a variety of applications, which are provided.

Compositions

Crispr/Cas Effector Proteins and Guide RNAs

A CRISPR-Cas effector polypeptide of the present disclosure (e.g., a Cas14i polypeptide of the present disclosure; a Cas14j polypeptide of the present disclosure; etc.) interacts with (binds to) a corresponding guide RNA (e.g., a CRISPR-Cas effector guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CRISPR-Cas effector protein of the present disclosure forms a complex with a CRISPR-Cas effector guide RNA and the guide RNA provides sequence specificity to the RNP complex via the guide sequence. The CRISPR-Cas effector protein of the complex provides the site-specific activity. In other words, the CRISPR-Cas effector protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a CRISPR-Cas effector polypeptide (and/or a nucleic acid comprising a nucleotide sequence encoding the CRISPR-Cas effector polypeptide) (e.g., where the CRISPR-Cas effector polypeptide can be a naturally existing protein, a nickase CRISPR-Cas effector protein, a catalytically inactive ("dead" CRISPR-Cas effector; also referred to herein as a "dCRISPR-Cas effector protein"), a fusion CRISPR-Cas effector protein, etc.). The present disclosure provides compositions comprising a CRISPR-Cas effector guide RNA (and/or a nucleic acid comprising a nucleotide sequence encoding the CRISPR-Cas effector guide RNA). The present disclosure provides compositions comprising (a) a CRISPR-Cas effector polypeptide (and/or a nucleic acid encoding the CRISPR-Cas effector polypeptide) (e.g., where the CRISPR-Cas effector polypeptide can be a naturally existing protein, a nickase CRISPR-Cas effector protein, a dCRISPR-Cas effector protein, a fusion CRISPR-Cas effector protein, etc.) and (b) a CRISPR-Cas effector guide RNA (and/or a nucleic acid encoding the CRISPR-Cas effector guide RNA). The present disclosure provides a nucleic acid/protein complex (RNP complex) comprising: (a) a CRISPR-Cas effector polypeptide of the present disclosure (e.g., where the CRISPR-Cas effector polypeptide can be a naturally existing protein, a nickase CRISPR-Cas effector protein, a Cdas12J protein, a fusion CRISPR-Cas effector protein, etc.); and (b) a CRISPR-Cas effector guide RNA.

CRISPR-Cas Effector Protein

A CRISPR-Cas effector polypeptide (this term is used interchangeably with the term "CRISPR-Cas effector protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases, the CRISPR-Cas effector protein includes a fusion partner with an activity, and in some cases, the CRISPR-Cas effector protein provides nuclease activity). In some cases, the CRISPR-Cas effector protein is a naturally-occurring protein (e.g., naturally occurs in bacteriophage). In other cases, the CRISPR-Cas effector protein is not a naturally-occurring polypeptide (e.g., the CRISPR-Cas effector protein is a variant CRISPR-Cas effector protein, a fusion CRISPR-Cas effector protein, and the like).

Assays to determine whether given protein interacts with a CRISPR-Cas effector guide RNA can be any convenient binding assay that tests for binding between a protein and a nucleic acid. Suitable binding assays (e.g., gel shift assays) will be known to one of ordinary skill in the art (e.g., assays that include adding a CRISPR-Cas effector guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring CRISPR-Cas effector protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring CRISPR-Cas effector guide RNA is a crRNA, where the crRNA includes (i) a guide sequence that hybridizes to a target sequence in the target DNA and (ii) a protein binding segment which includes a stem-loop (hairpin—dsRNA duplex) that binds to the CRISPR-Cas effector protein.

In some embodiments, the CRISPR-Cas effector protein of the subject methods and/or compositions is (or is derived from) a naturally occurring (wild type) protein. Examples of naturally occurring CRISPR-Cas effector proteins are depicted in FIG. 6A-6BB.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6A and designated "PhageCas14J_k87_9374247_16." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6A. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6A. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6A. In some cases, a CRISPR-Cas effector protein includes an amino acid sequence having the CRISPR-Cas effector protein sequence depicted in FIG. 6A. In some cases, a CRISPR-Cas effector protein includes an amino acid sequence having the CRISPR-Cas effector protein sequence depicted in FIG. 6A, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6A (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6B and designated "PhageCas14J_LaacPavin_0818_WC40_scaffold_407201_205." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6B. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6B. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6B. In some cases, a CRISPR-Cas effector protein includes an amino acid sequence having the CRISPR-Cas effector protein sequence depicted in FIG. 6B. In some cases, a CRISPR-Cas effector protein includes an amino acid sequence having the CRISPR-Cas effector protein sequence depicted in FIG. 6B, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6B (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6C and designated "PhageCas14J_BML_08042016_6_5m_scaffod__prodigal-single_54." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6C. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6C. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6C. In some cases, a CRISPR-Cas effector protein includes an amino acid sequence having the CRISPR-Cas effector protein sequence depicted in FIG. 6C. In some cases, a CRISPR-Cas effector protein includes an amino acid sequence having the CRISPR-Cas effector protein sequence depicted in FIG. 6C, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6C (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6D and designated "Ga0194119_1000113823." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6D. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6D. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6D. In some cases, a CRISPR-Cas effector protein includes an amino acid sequence having the CRISPR-Cas effector protein sequence depicted in FIG. 6D. In some cases, a CRISPR-Cas effector protein includes an amino acid sequence having the CRISPR-Cas effector protein sequence depicted in FIG. 6D, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6D (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6E and designated "Ga0116197_100054.58." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6E. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6E. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6E. In some cases, a CRISPR-Cas effector protein includes an amino acid sequence having the CRISPR-Cas effector protein sequence depicted in FIG. 6E. In some cases, a CRISPR-Cas effector protein includes an amino acid sequence having the CRISPR-Cas effector protein sequence depicted in FIG. 6E, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6E (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6F and designated "Ga0116179__10426881." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6F. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6F. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6F. In some cases, a CRISPR-Cas effector protein includes an amino acid sequence having the CRISPR-Cas effector protein sequence depicted in FIG. 6F. In some cases, a CRISPR-Cas effector protein includes an amino acid sequence having the CRISPR-Cas effector protein sequence depicted in FIG. 6F, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6F (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6G and designated "Ga0268285_10062095." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6G. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6G. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6G. In some cases, a CRISPR-Cas effector protein includes an amino acid sequence having the CRISPR-Cas effector protein sequence depicted in FIG. 6G. In some cases, a CRISPR-Cas effector protein includes an amino acid sequence having the CRISPR-Cas effector protein sequence depicted in FIG. 6G, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6G (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6H and designated "Ga0066868_100162752." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6H. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6H. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6H. In some cases, a CRISPR-Cas effector protein includes an amino acid sequence having the CRISPR-Cas effector protein sequence depicted in FIG. 6H. In some cases, a CRISPR-Cas effector protein includes an amino acid sequence having the CRISPR-Cas effector protein sequence depicted in FIG. 6H, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6H (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6I and designated "PhageCas14SR-VP2-4_scaffold_141_2548329_92." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6I. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6I. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6I. In some cases, a CRISPR-Cas effector protein includes an amino acid sequence having the CRISPR-Cas effector protein sequence depicted in FIG. 6I. In some cases, a CRISPR-Cas effector protein includes an amino acid sequence having the CRISPR-Cas effector protein sequence depicted in FIG. 6I, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6I (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6J and designated "PhageCas14_SR-VP_4-6_scaffold_141_3640689_5." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6J. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6J. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6J. In some cases, a CRISPR-Cas effector protein includes an amino acid sequence having the CRISPR-Cas effector protein sequence depicted in FIG. 6J. In some cases, a CRISPR-Cas effector protein includes an amino acid sequence having the CRISPR-Cas effector protein sequence depicted in FIG. 6J, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6J (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6K and designated "PhageCas14_RifSed." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6K. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6K. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6K. In some cases, a CRISPR-Cas effector protein includes an amino acid sequence having the CRISPR-Cas effector protein sequence depicted in FIG. 6K. In some cases, a CRISPR-Cas effector protein includes an amino acid sequence having the CRISPR-Cas effector protein sequence depicted in FIG. 6K, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6K (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6L and designated "PhageCas14_16 ft_4_scaffold_2_465_16 ft_4_Phage_29_13." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6L. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6L. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6L. In some cases, a CRISPR-Cas effector protein includes an amino acid sequence having the CRISPR-Cas effector protein sequence depicted in FIG. 6L. In some cases, a CRISPR-Cas effector protein includes an amino acid sequence having the CRISPR-Cas effector protein sequence depicted in FIG. 6L, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6L (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6M and designated "Ga0116179_10109322." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6M. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6M. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6M. In some cases, a CRISPR-Cas effector protein includes an amino acid sequence having the CRISPR-Cas effector protein sequence depicted in FIG. 6M. In some cases, a CRISPR-Cas effector protein includes an amino acid sequence having the CRISPR-Cas effector protein sequence depicted in FIG. 6M, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6M (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6N and designated "Ga0116179_10465782." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6N. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6N. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6N. In some cases, a CRISPR-Cas effector protein includes an amino acid sequence having the CRISPR-Cas effector protein sequence depicted in FIG. 6N. In some cases, a CRISPR-Cas effector protein includes an amino acid sequence having the CRISPR-Cas effector protein sequence depicted in FIG. 6N, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6N (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6O and designated "Ga0134101_10165752." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6O. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6O. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6O. In some cases, a CRISPR-Cas effector protein includes an amino acid sequence having the CRISPR-Cas effector protein sequence depicted in FIG. 6O. In some cases, a CRISPR-Cas effector protein includes an amino acid sequence having the CRISPR-Cas effector protein sequence depicted in FIG. 6O, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6O (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6P and designated "Ga0066665__100815632." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6P. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6P. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6P. In some cases, a CRISPR-Cas effector protein includes an amino acid sequence having the CRISPR-Cas effector protein sequence depicted in FIG. 6P. In some cases, a CRISPR-Cas effector protein includes an amino acid sequence having the CRISPR-Cas effector protein sequence depicted in FIG. 6P, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6P (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6Q and designated "Ga0224523_10070512." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6Q. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6Q. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6Q. In some cases, a CRISPR-Cas effector protein includes an amino acid sequence having the CRISPR-Cas effector protein sequence depicted in FIG. 6Q. In some cases, a CRISPR-Cas effector protein includes an amino acid sequence having the CRISPR-Cas effector protein sequence depicted in FIG. 6Q, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6Q (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6R and designated "Ga0247839_10583994." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6R. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6R. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6R. In some cases, a CRISPR-Cas effector protein includes an amino acid sequence having the CRISPR-Cas effector protein sequence depicted in FIG. 6R. In some cases, a CRISPR-Cas effector protein includes an amino acid sequence having the CRISPR-Cas effector protein sequence depicted in FIG. 6R, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6R (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6S and designated "Cas14u9|PhageCas14|LacPavin_0818_WC55_scaffold_56344_prodigal-single_16." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6S. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6S. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6S. In some cases, a CRISPR-Cas effector protein includes an amino acid sequence having the CRISPR-Cas effector protein sequence depicted in FIG. 6S. In some cases, a CRISPR-Cas effector protein includes an amino acid sequence having the CRISPR-Cas effector protein sequence depicted in FIG. 6S, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6S (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6T and designated "Cas14u10|Ga0153798_100522201." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6T. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6T. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6T. In some cases, a CRISPR-Cas effector protein includes an amino acid sequence having the CRISPR-Cas effector protein sequence depicted in FIG. 6T. In some cases, a CRISPR-Cas effector protein includes an amino acid sequence having the CRISPR-Cas effector protein sequence depicted in FIG. 6T, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6T (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6U and designated "Cas14u_VU_u11|rifcsplowo2_12_scaffold_23_prodigal-single_23." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6U. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6U. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6U. In some cases, a CRISPR-Cas effector protein includes an amino acid sequence having the CRISPR-Cas effector protein sequence depicted in FIG. 6U. In some cases, a CRISPR-Cas effector protein includes an amino acid sequence having the CRISPR-Cas effector protein sequence depicted in FIG. 6U, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6U (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6V and designated "Cas14u_VU_u12|SR-VP_4-6_scaffold_141_2630357_509." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6V. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6V. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6V. In some cases, a CRISPR-Cas effector protein includes an amino acid sequence having the CRISPR-Cas effector protein sequence depicted in FIG. 6V. In some cases, a CRISPR-Cas effector protein includes an amino acid sequence having the CRISPR-Cas effector protein sequence depicted in FIG. 6V, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6V (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6W and designated "Cas14u_VU_u13|gwd1_scaffold_1554_3." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6W. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6W. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6W. In some cases, a CRISPR-Cas effector protein includes an amino acid sequence having the CRISPR-Cas effector protein sequence depicted in FIG. 6W. In some cases, a CRISPR-Cas effector protein includes an amino acid sequence having the CRISPR-Cas effector protein sequence depicted in FIG. 6W, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6W (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6X and designated "Cas14u_VU_u14|pig_F100_scaffold_13388_4." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6X. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6X. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6X. In some cases, a CRISPR-Cas effector protein includes an amino acid sequence having the CRISPR-Cas effector protein sequence depicted in FIG. 6X. In some cases, a CRISPR-Cas effector protein includes an amino acid sequence having the CRISPR-Cas effector protein sequence depicted in FIG. 6X, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6X (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6Y and designated "Cas14u_VU_u15|pig_ID_3640_F65_scaffold_73762_2." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6Y. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6Y. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6Y. In some cases, a CRISPR-Cas effector protein includes an amino acid sequence having the CRISPR-Cas effector protein sequence depicted in FIG. 6Y. In some cases, a CRISPR-Cas effector protein includes an amino acid sequence having the CRISPR-Cas effector protein sequence depicted in FIG. 6Y, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6Y (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6Z and designated "Cas14u_VU_u16|pig_ID_1851_F40_2_scaffold_55126_1." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6Z. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6Z. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6Z. In some cases, a CRISPR-Cas effector protein includes an amino acid sequence having the CRISPR-Cas effector protein sequence depicted in FIG. 6Z. In some cases, a CRISPR-Cas effector protein includes an amino acid sequence having the CRISPR-Cas effector protein sequence depicted in FIG. 6Z, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6Z (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6AA and designated "Cas14u_VU_u17|pig_ID_3784_F96_scaffold_13509_10." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6AA. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6AA. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6AA. In some cases, a CRISPR-Cas effector protein includes an amino acid sequence having the CRISPR-Cas effector protein sequence depicted in FIG. 6AA. In some cases, a CRISPR-Cas effector protein includes an amino acid sequence having the CRISPR-Cas effector protein sequence depicted in FIG. 6AA, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6AA (with Ts substituted with Us), or the reverse complement thereof, where the guide RNA can include a target binding sequence as desired, depending on the target nucleic acid.

In some cases, a CRISPR-Cas effector protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6BB and designated "Cas14u_VU_u18|SRR1747065_scaffold_28." For example, in some cases, a CRISPR-Cas effector protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CRISPR-Cas effector amino acid sequence depicted in FIG. 6BB. In some cases, a CRISPR-Cas effector protein includes an amino acid sequence having 80% or more sequence identity (e.g., 85% or more, 90% or more, 95% or more, 97% or more, 98% or more, 99% or more, or 100% sequence identity) with the CRISPR-Cas effector amino acid sequence depicted in FIG. 6BB. In some cases, a CRISPR-Cas effector protein includes an amino acid sequence having 90% or more sequence identity (e.g., 95% or more, 97% or more, 98% or more, 99% or more, or 100% sequence identity) with the CRISPR-Cas effector amino acid sequence depicted in FIG. 6BB. In some cases, a CRISPR-Cas effector protein includes an amino acid sequence having the CRISPR-Cas effector protein sequence depicted in FIG. 6BB. In some cases, a CRISPR-Cas effector protein includes an amino acid sequence having the CRISPR-Cas effector protein sequence depicted in FIG. 6BB, with the exception that the sequence includes an amino acid substitution (e.g., 1, 2, or 3 amino acid substitutions) that reduces the naturally occurring catalytic activity of the protein. The CRISPR-Cas effector protein may bind a guide RNA comprising a constant region comprising the nucleotide sequence depicted in FIG. 6BB (with Ts substituted with Us), or the reverse complement thereof, where the guide RNA can include a target binding sequence as desired, depending on the target nucleic acid.

In some cases, a CRISPR-Cas effector protein of the present disclosure has a length of from about 350 amino acids (aa) to about 550 aa. In some cases, a CRISPR-Cas effector protein of the present disclosure has a length of from about 350 aa to about 375 aa. In some cases, a CRISPR-Cas effector protein of the present disclosure has a length of from about 375 aa to about 400 aa. In some cases, a CRISPR-Cas effector protein of the present disclosure has a length of from about 390 aa to about 410 aa. In some cases, a CRISPR-Cas effector protein of the present disclosure has a length of from about 400 aa to about 410 aa. In some cases, a CRISPR-Cas effector protein of the present disclosure has a length of from about 400 aa to about 450 aa. In some cases, a CRISPR-Cas effector protein of the present disclosure has a length of from about 410 aa to about 425 aa. In some cases, a CRISPR-Cas effector protein of the present disclosure has a length of from about 425 aa to about 450 aa. In some cases, a CRISPR-Cas effector protein of the present disclosure has a length of from about 450 aa to about 500 aa. In some cases, a CRISPR-Cas effector protein of the present disclosure has a length of from about 450 aa to about 475 aa.

CRISPR-Cas Effector Variants

A variant CRISPR-Cas effector protein has an amino acid sequence that is different by at least one amino acid (e.g., has a deletion, insertion, substitution, fusion) when compared to the amino acid sequence of the corresponding wild type CRISPR-Cas effector protein, e.g., when compared to the CRISPR-Cas effector amino acid sequence depicted in any one of FIG. 6A-6BB. In some cases, a CRISPR-Cas effector variant comprises from 1 amino acid substitution to 10 amino acid substitutions compared to the CRISPR-Cas effector amino acid sequence depicted in any one of FIG. 6A-6BB. In some cases, a CRISPR-Cas effector variant comprises from 1 amino acid substitution to 10 amino acid substitutions in the RuvC domain, compared to the CRISPR-Cas effector amino acid sequence depicted in any one of FIG. 6A-6BB.

Variants—Catalytic Activity

In some cases, the CRISPR-Cas effector protein is a variant CRISPR-Cas effector protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CRISPR-Cas effector protein is a catalytically 'dead' protein (has substantially no cleavage activity) and can be referred to as a 'dCRISPR-Cas effector.' In some cases, the variant CRISPR-Cas effector protein is a nickase (cleaves only one strand of a double stranded target nucleic acid, e.g., a double stranded target DNA). As described in more detail herein, in some cases, a CRISPR-Cas effector protein (in some case a CRISPR-Cas effector protein with wild type cleavage activity and in some cases a variant CRISPR-Cas effector with reduced cleavage activity, e.g., a dCRISPR-Cas effector or a nickase CRISPR-Cas effector) is fused (conjugated) to a heterologous polypeptide that has an activity of interest (e.g., a catalytic activity of interest) to form a fusion protein (a fusion CRISPR-Cas effector protein).

Figure 8:
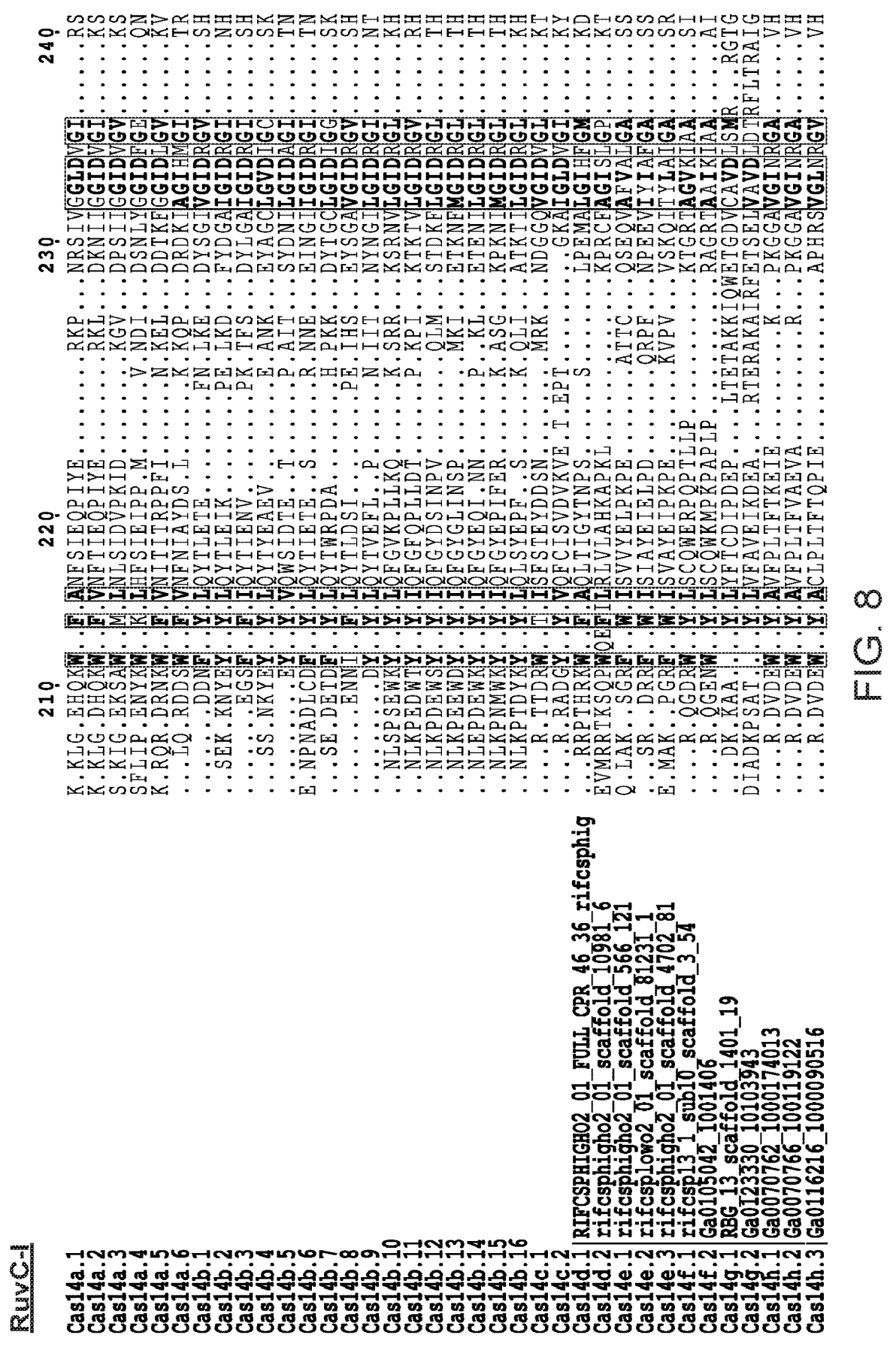
Figure 8:
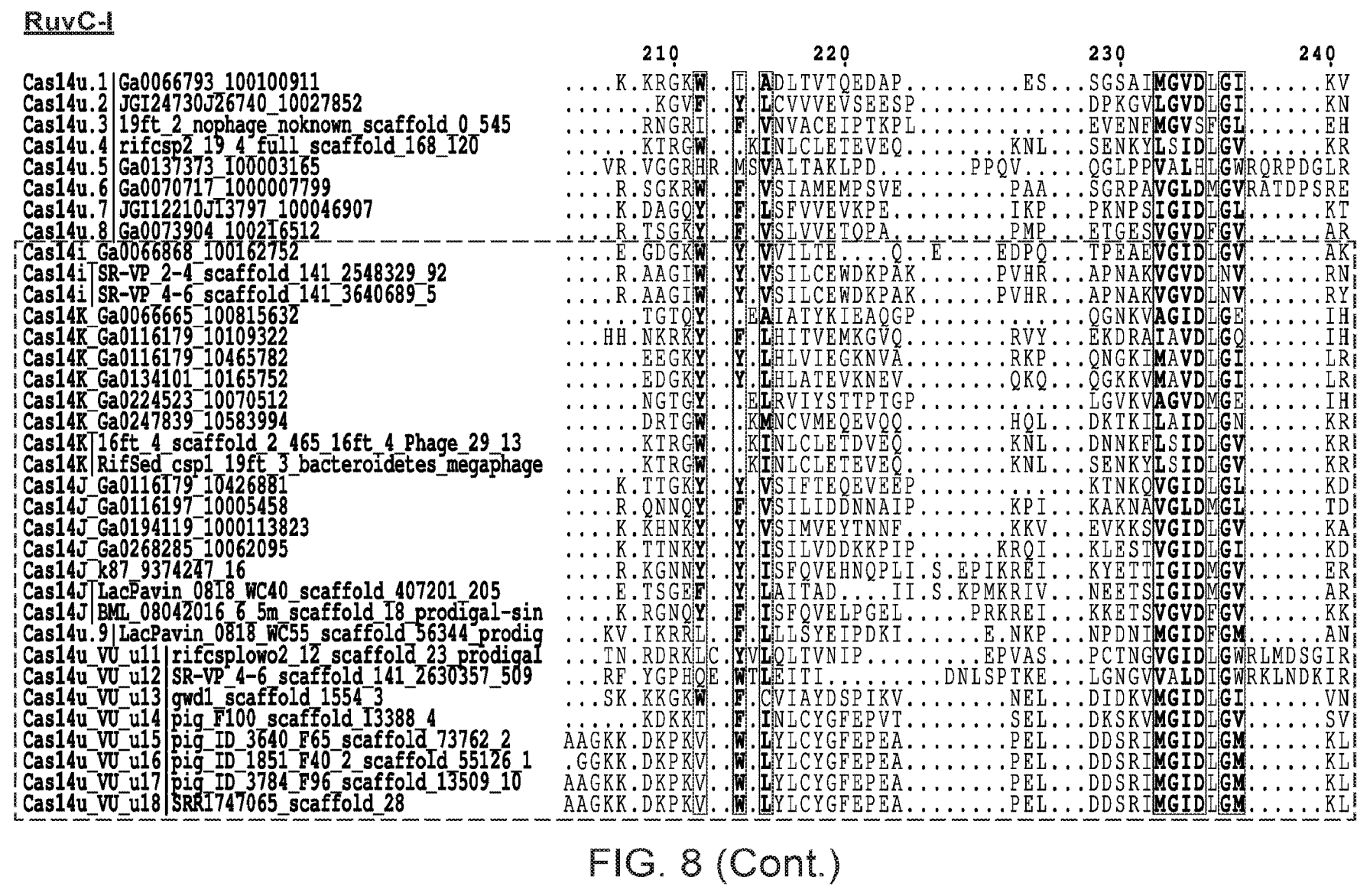
Figure 8:
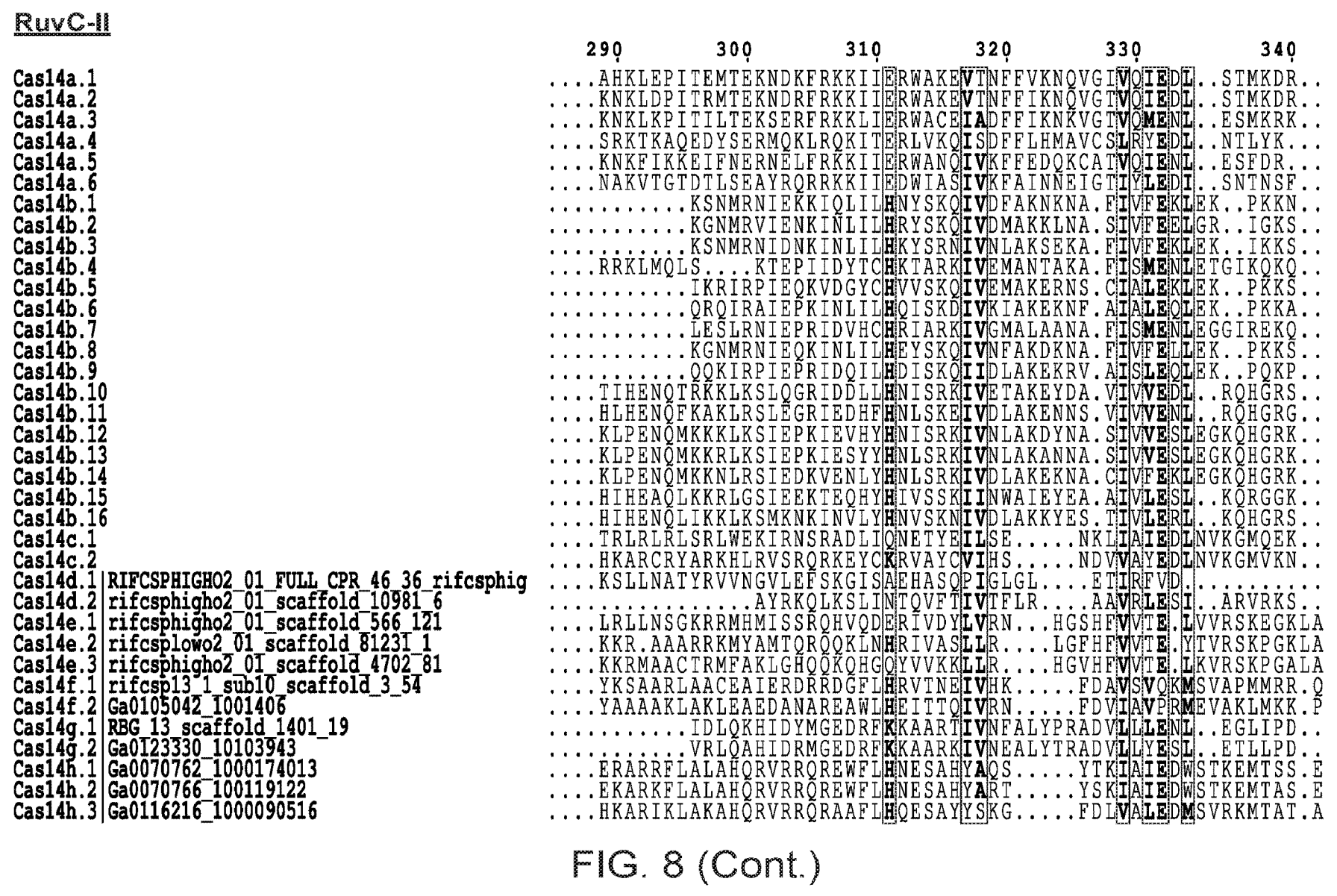
Figure 8:
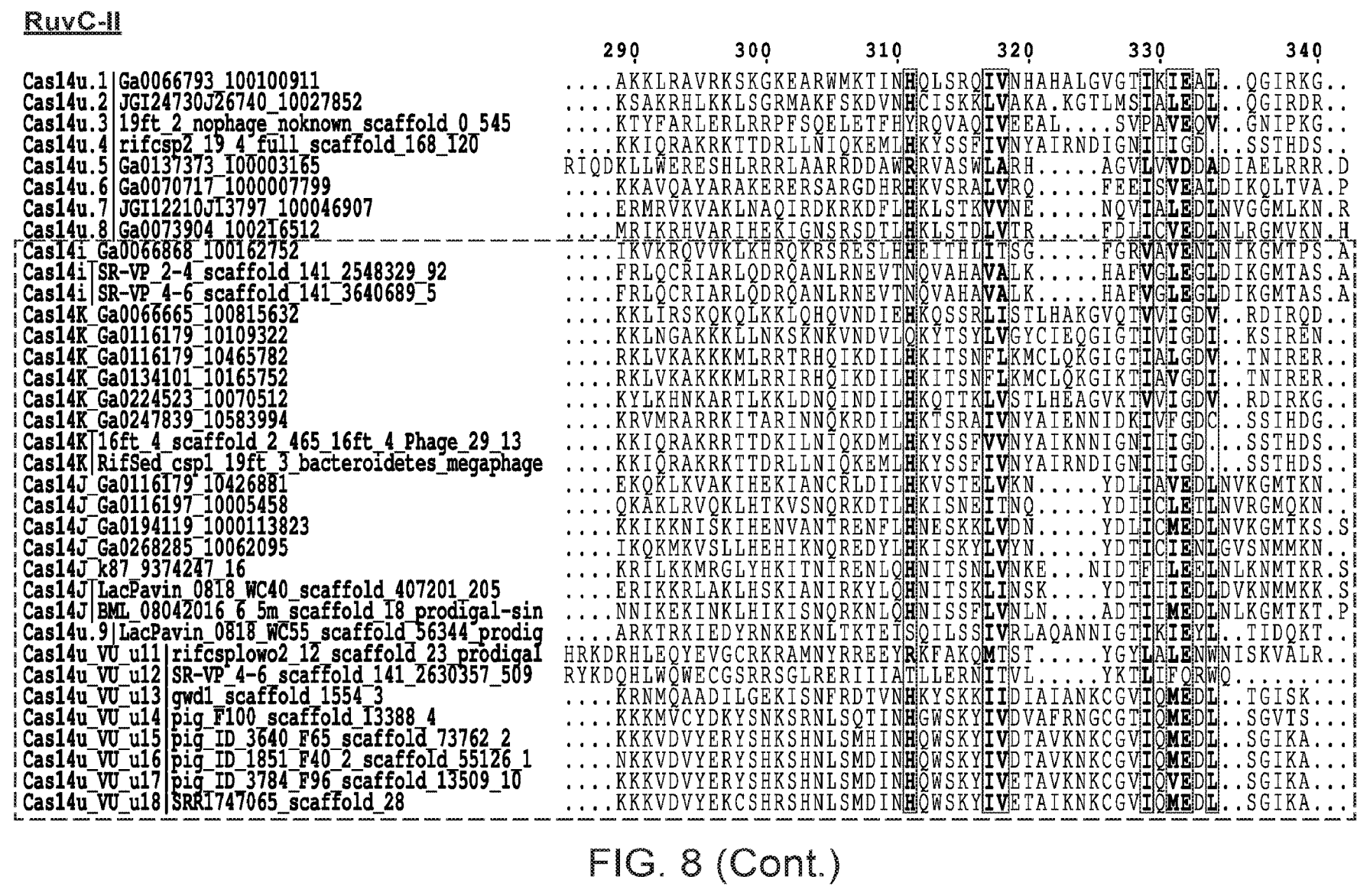
Figure 8:
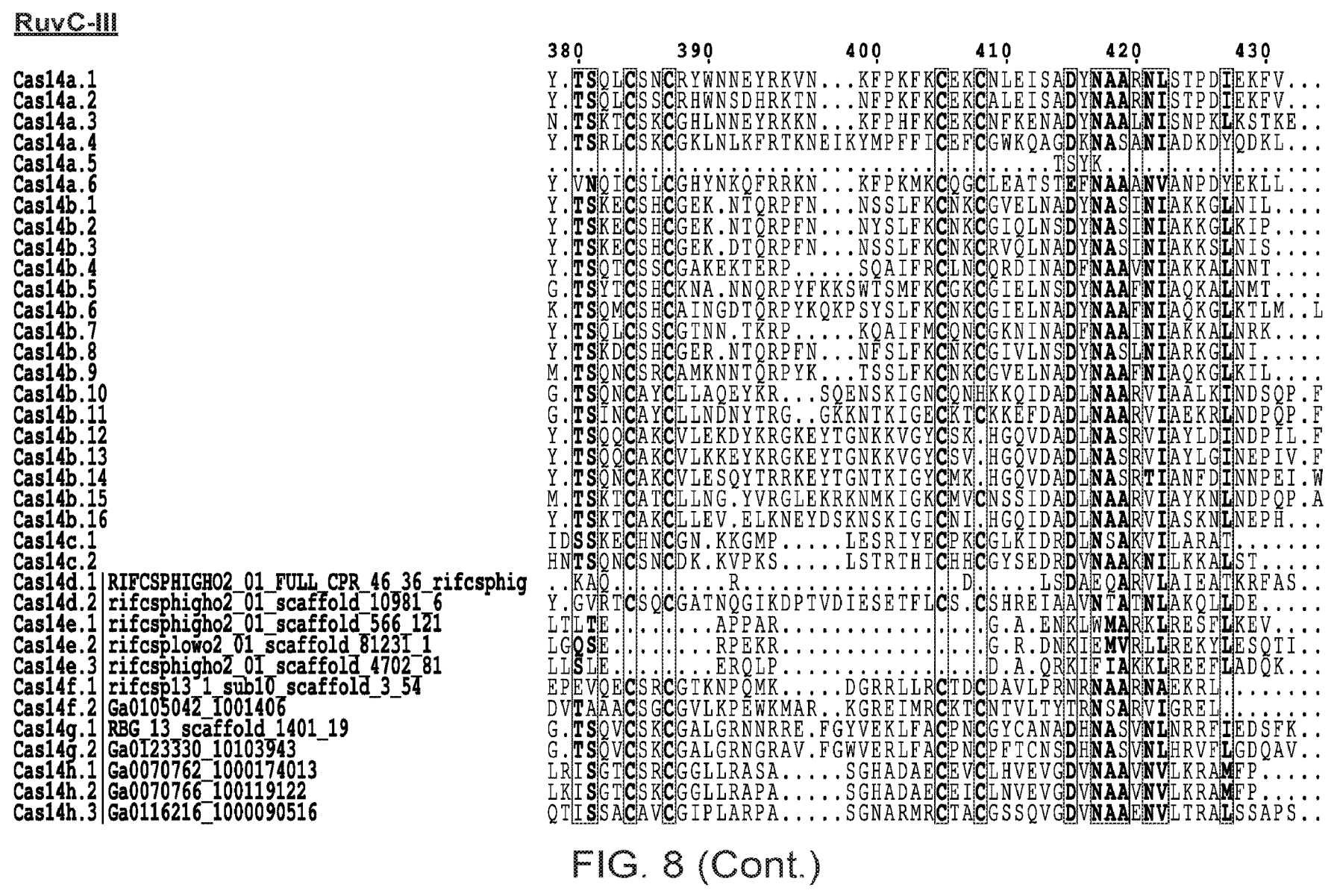
Figure 8:
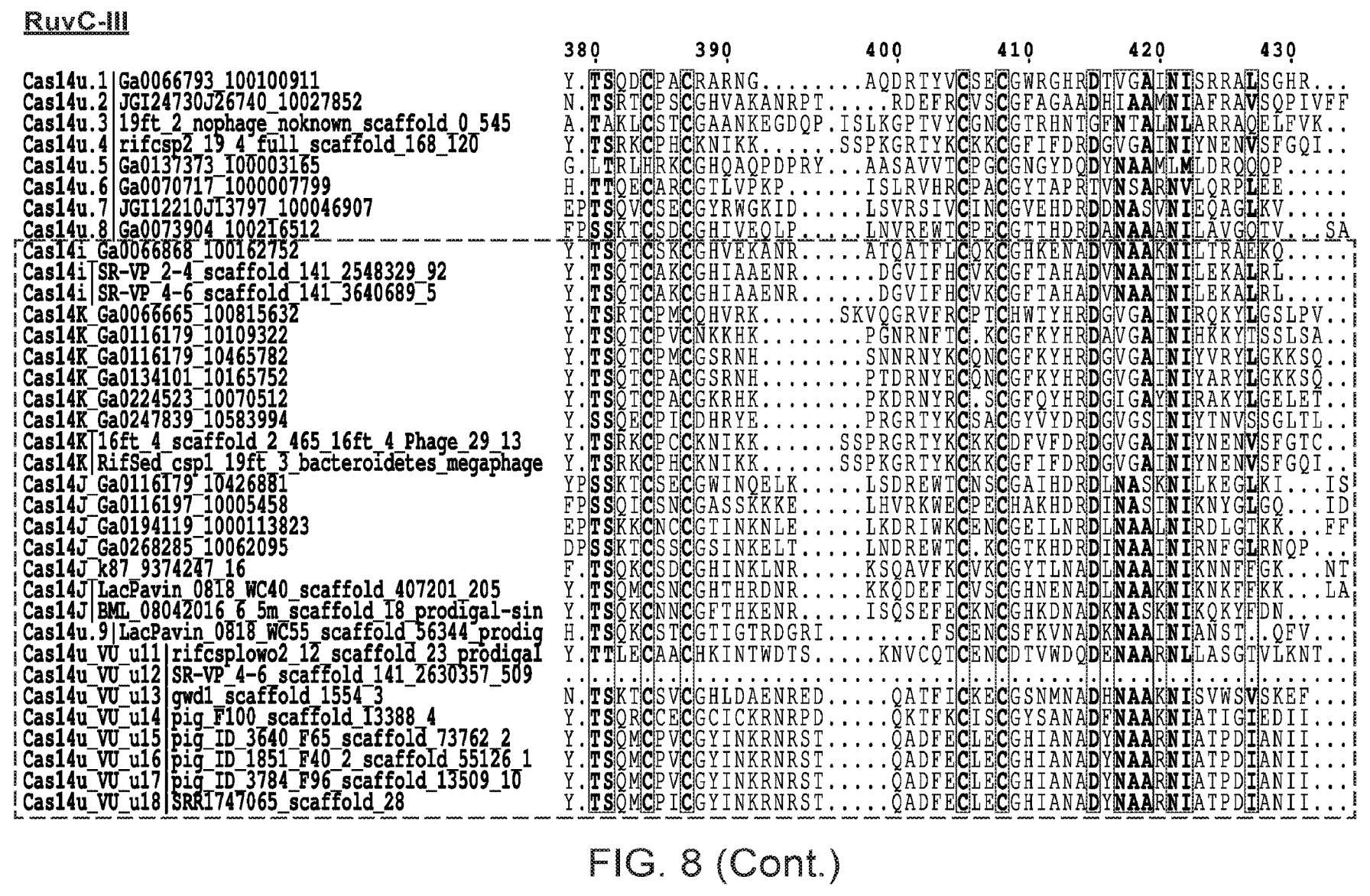

Amino acid substitutions that result in a CRISPR-Cas effector polypeptide that binds, but does not cleave, a target nucleic acid include, e.g., substitutions of amino acids that are conserved among Cas14i, among Cas14K, Cas14J, or Cas14u RuvC-I domains and/or RuvC-II domains and/or RuvC-III domains. FIG. 8 provides an amino acid sequence alignment of Cas14i, Cas14K, Cas14J, and Cas14u amino acid sequences. Conserved amino acids are shown. In some cases, a CRISPR-Cas effector polypeptide of the present disclosure comprises an amino acid substitution of one or more of: i) an Asp corresponding to the Asp at position 258 of the amino acid sequence depicted in FIG. 9; ii) a Glu corresponding to the Glu at position 356 of the amino acid sequence depicted in FIG. 9; and iii) an Asp corresponding to the Asp at position 435 of the amino acid sequence depicted in FIG. 9. Examples include: i) the Asp at position 236 of the sequences depicted in FIG. 8 (e.g., the Asp in the VGID sequence of Cas14i_ga0066868-100162752 in FIG. 8, or a corresponding position in another CRISPR-Cas effector polypeptide; ii) the Glu at position 332 of the sequences depicted in FIG. 8 (e.g., the Glu in the VAVENL sequence of Cas14i_ga0066868-100162752 in FIG. 8, or a corresponding position in another CRISPR-Cas effector polypeptide; and iii) the Asp at position 415 of the sequences depicted in FIG. 8 (e.g., the Asp in the NADVNAA sequence of Cas14i_ga0066868-100162752 in FIG. 8, or a corresponding position in another CRISPR-Cas effector polypeptide.

Variants—Fusion CRISPR-Cas Effector Polypeptides

As noted above, in some cases, a CRISPR-Cas effector protein (in some cases a CRISPR-Cas effector protein with wild type cleavage activity and in some cases a variant CRISPR-Cas effector with reduced cleavage activity, e.g., a dCRISPR-Cas effector or a nickase CRISPR-Cas effector) is fused (conjugated) to a heterologous polypeptide that has an activity of interest (e.g., a catalytic activity of interest) to form a fusion protein. A heterologous polypeptide to which a CRISPR-Cas effector protein can be fused is referred to herein as a 'fusion partner.'

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a fusion CRISPR-Cas effector protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a fusion CRISPR-Cas effector protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of a suitable fusion partners are dihydrofolate reductase (DHFR) destabilization domain (e.g., to generate a chemically controllable fusion CRISPR-Cas effector protein), and a chloroplast transit peptide. Suitable chloroplast transit peptides include, but are not limited to:

```
                                         (SEQ ID NO: 1)
MASMISSSAVTTVSRASRGQSAAMAPFGGLKSMTGFPVRKVNTDITSIT
SNGGRVKCMQVWPPIGKKKFETLSYLPPLTRDSRA;

(SEQ ID NO: 2)
MASMISSSAVTTVSRASRGQSAAMAPFGGLKSMTGFPVRKVNTDITSIT
SNGGRVKS;

(SEQ ID NO: 3)
MASSMLSSATMVASPAQATMVAPFNGLKSSAAFPATRKANNDITSITSN
GGRVNCMQVWPPIEKKKFETLSYLPDLTDSGGRVNC;

(SEQ ID NO: 4)
MAQVSRICNGVQNPSLISNLSKSSQRKSPLSVSLKTQQHPRAYPISSSW
GLKKSGMTLIGSELRPLKVMSSVSTAC;

(SEQ ID NO: 5)
MAQVSRICNGVWNPSLISNLSKSSQRKSPLSVSLKTQQHPRAYPISSSW
GLKKSGMTLIGSELRPLKVMSSVSTAC;

(SEQ ID NO: 6)
MAQINNMAQGIQTLNPNSNFHKPQVPKSSSFLVFGSKKLKNSANSMLVL
KKDSIFMQLFCSFRISASVATAC;

(SEQ ID NO: 7)
MAALVTSQLATSGTVLSVTDRFRRPGFQGLRPRNPADAALGMRTVGASA
APKQSRKPHRFDRRCLSMVV;

(SEQ ID NO: 8)
MAALTTSQLATSATGFGIADRSAPSSLLRHGFQGLKPRSPAGGDATSLS
VTTSARATPKQQRSVQRGSRRFPSVVVC;

(SEQ ID NO: 9)
MASSVLSSAAVATRSNVAQANMVAPFTGLKSAASFPVSRKQNLDITSIA
SNGGRVQC;

(SEQ ID NO: 10)
MESLAATSVFAPSRVAVPAARALVRAGTVVPTRRTSSTSGTSGVKCSAA
VTPQASPVISRSAAAA;
and (SEQ ID NO: 11)
MGAAATSMQSLKFSNRLVPPSRRLSPVPNNVTCNNLPKSAAPVRTVKCC
ASSWNSTINGAAATTNGASAASS.
```

In some case, a CRISPR-Cas effector fusion polypeptide of the present disclosure comprises: a) a CRISPR-Cas effector polypeptide of the present disclosure; and b) a chloroplast transit peptide. Thus, for example, a CRISPR-Cas effector polypeptide/guide RNA complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the amino terminus ($NH_2$ terminus) of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CRISPR-Cas effector fusion polypeptide of the present disclosure can comprise: a) a CRISPR-Cas effector polypeptide of the present disclosure; and b) an endosomal escape peptide. In some cases, an endosomal escape polypeptide comprises the amino acid sequence GLFXALLXLLXSLWXLLLXA (SEQ ID NO: 12), wherein each X is independently selected from lysine, histidine, and arginine. In some cases, an endosomal escape polypeptide comprises the amino acid sequence GLF-HALLHLLHSLWHLLLHA (SEQ ID NO: 13).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; *Nucleic Acids Res.* 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et., al., J Virol. 2006 February; 80(4):1939-48; Tan et al., Proc Natl Acad Sci USA. 2003 Oct. 14; 100(21): 11997-2002; Papworth et al., Proc Natl Acad Sci USA. 2003 Feb. 18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et.al., Xu et al., Cell Discov. 2016 May 3; 2:16009; Komor et al., *Nature.* 2016 Apr. 20; 533(7603):420-4; Chaikind et al., *Nucleic Acids Res.* 2016 Aug. 11; Choudhury at. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4):578-89; Hu et al., *Nucleic Acids Res.* 2014 April; 42(7):4375-90; Cheng et al., Cell Res. 2013 October; 23(10):1163-71; and Maeder et al., Nat Methods. 2013 October; 10(10):977-9.

Additional suitable heterologous polypeptides include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a fusion CRISPR-Cas effector polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject fusion CRISPR-Cas effector polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMPI, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a fusion CRISPR-Cas effector polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to, proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Aby1, etc.).

Examples of various additional suitable heterologous polypeptide (or fragments thereof) for a subject fusion CRISPR-Cas effector polypeptide include, but are not limited to, those described in the following applications (which publications are related to other CRISPR endonucleases such as Cas9, but the described fusion partners can also be used with CRISPR-Cas effector instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CRISPR-Cas effector fusion polypeptide does not include an NLS so that the protein is not targeted to the nucleus (which can be advantageous, e.g., when the target nucleic acid is an RNA that is present in the cytosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6XHis tag; a hemagglutinin (HA) tag; a FLAG tag; a Myc tag; and the like).

In some cases, a CRISPR-Cas effector protein (e.g., a wild type CRISPR-Cas effector protein, a variant CRISPR-Cas effector protein, a fusion CRISPR-Cas effector protein, a dCRISPR-Cas effector protein, and the like) includes (is fused to) a nuclear localization signal (NLS) (e.g., in some cases 2 or more, 3 or more, 4 or more, or 5 or more NLSs). Thus, in some cases, a CRISPR-Cas effector polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases, a CRISPR-Cas effector protein (e.g., a wild type CRISPR-Cas effector protein, a variant CRISPR-Cas effector protein, a fusion CRISPR-Cas effector protein, a dCRISPR-Cas effector protein, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a CRISPR-Cas effector protein (e.g., a wild type CRISPR-Cas effector protein, a variant CRISPR-Cas effector protein, a fusion CRISPR-Cas effector protein, a dCRISPR-Cas effector protein, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 14); the NLS from nucleoplasmin (e.g., the nucleoplasmin bipartite NLS with the sequence KRPAATKKAGQAKKKK (SEQ ID NO: 15)); the c-myc NLS having the amino acid sequence PAAKRVKLD (SEQ ID NO: 16) or RQRRNELKRSP (SEQ ID NO: 17); the hRNPA1 M9 NLS having the sequence NQSSNFGPMKGGNFGGRSSGPYGGGGQYFAKPRNQGGY (SEQ ID NO: 18); the sequence RMRIZFKNKGKDTAELRRRRVEVSVELRKAKKDEQILKRRNV (SEQ ID NO: 19) of the IBB domain from importin-alpha; the sequences VSRKRPRP (SEQ ID NO: 20) and PPKKARED (SEQ ID NO: 21) of the myoma T protein; the sequence PQPKKKPL (SEQ ID NO: 22) of human p53; the sequence SALIKKKKKMAP (SEQ ID NO: 23) of mouse c-abl IV; the sequences DRLRR (SEQ ID NO: 24) and PKQKKRK (SEQ ID NO: 25) of the influenza virus NS1; the sequence RKLKKKIKKL (SEQ ID NO: 26) of the Hepatitis virus delta antigen; the sequence REKKKFLKRR (SEQ ID NO: 27) of the mouse Mx1 protein; the sequence KRKGDEVDGVDEVAKKKSKK (SEQ ID NO: 28) of the human poly(ADP-ribose) polymerase; and the sequence RKCLQAGMNLEARKTKK (SEQ ID NO: 29) of the steroid hormone receptors (human) glucocorticoid. In general, NLS (or multiple NLSs) are of sufficient strength to drive accumulation of the CRISPR-Cas effector protein in a detectable amount in the nucleus of a eukaryotic cell. Detection of accumulation in the nucleus may be performed by any suitable technique. For example, a detectable marker may be fused to the CRISPR-Cas effector protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CRISPR-Cas effector fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CRISPR-Cas effector to generate a fusion protein, or linked to a variant CRISPR-Cas effector protein such as a dCRISPR-Cas effector, nickase CRISPR-Cas effector, or fusion CRISPR-Cas effector protein, to generate a fusion protein). In some embodiments, a PTD is covalently linked to the carboxyl terminus of a polypeptide (e.g., linked to a wild type CRISPR-Cas effector to generate a fusion protein, or linked to a variant CRISPR-Cas effector protein such as a dCRISPR-Cas effector, nickase CRISPR-Cas effector, or fusion CRISPR-Cas effector protein to generate a fusion protein). In some cases, the PTD is inserted internally in the CRISPR-Cas effector fusion polypeptide (i.e., is not at the N- or C-terminus of the CRISPR-Cas effector fusion polypeptide) at a suitable insertion site. In some cases, a subject CRISPR-Cas effector fusion polypeptide includes (is conjugated to, is fused to) one or more PTDs (e.g., two or more, three or more, four or more PTDs). In some cases, a PTD includes a nuclear localization signal (NLS) (e.g, in some cases 2 or more, 3 or more, 4 or more, or 5 or more NLSs). Thus, in some cases, a CRISPR-Cas effector fusion polypeptide includes one or more NLSs (e.g., 2 or more, 3 or more, 4 or more, or 5 or more NLSs). In some embodiments, a PTD is covalently linked to a nucleic acid (e.g., a CRISPR-Cas effector guide nucleic acid, a polynucleotide encoding a CRISPR-Cas effector guide nucleic acid, a polynucleotide encoding a CRISPR-Cas effector fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 30); Transportan GWTLNSAGYLLGKINLKA-LAALAKKIL (SEQ ID NO: 31); KALAWEAKLAKA-LAKALAKHLAKALAKALKCEA (SEQ ID NO: 32); and RQIKIWFQNRRMKWKK (SEQ ID NO: 33). Exemplary PTDs include but are not limited to, YGRKKRRQRRR (SEQ ID NO: 34), RKKRRQRRR (SEQ ID NO: 35); an arginine homopolymer of from 3 arginine residues to 50 arginine residues; Exemplary PTD domain amino acid sequences include, but are not limited to, any of the following: YGRKKRRQRRR (SEQ ID NO: 34); RKKRRQRR (SEQ ID NO: 36); YARAAARQARA (SEQ ID NO: 37); THRLPRRRRRR (SEQ ID NO: 38); and GGRRARRRRRR (SEQ ID NO: 39). In some embodiments, the PTD is an activatable CPP (ACPP) (Aguilera et al. (2009) *Integr Biol* (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some embodiments, a subject CRISPR-Cas effector protein can be fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 40), $GGSGGS_n$ (SEQ ID NO: 41), and $GGGS_n$(SEQ ID NO: 42), where n is an integer of at least one), glycine-alanine polymers, alanine-serine polymers. Exemplary linkers can comprise amino acid sequences including, but not limited to, GGSG (SEQ ID NO: 43), GGSGG (SEQ ID NO: 44), GSGSG (SEQ ID NO: 45), GSGGG (SEQ ID NO: 46), GGGSG (SEQ ID NO: 47), GSSSG (SEQ ID NO: 48), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CRISPR-Cas effector polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

CRISPR-Cas Effector Guide RNA

A nucleic acid that binds to a CRISPR-Cas effector protein, forming a ribonucleoprotein complex (RNP), and targets the complex to a specific location within a target nucleic acid (e.g., a target DNA) is referred to herein as a "CRISPR-Cas effector guide RNA" or simply as a "guide RNA." It is to be understood that in some cases, a hybrid DNA/RNA can be made such that a CRISPR-Cas effector guide RNA includes DNA bases in addition to RNA bases, but the term "CRISPR-Cas effector guide RNA" is still used to encompass such a molecule herein.

A CRISPR-Cas effector guide RNA can be said to include two segments, a targeting segment and a protein-binding segment. The protein-binding segment is also referred to herein as the "constant region" of the guide RNA. The targeting segment of a CRISPR-Cas effector guide RNA includes a nucleotide sequence (a guide sequence) that is complementary to (and therefore hybridizes with) a specific sequence (a target site) within a target nucleic acid (e.g., a target dsDNA, a target ssRNA, a target ssDNA, the complementary strand of a double stranded target DNA, etc.). The protein-binding segment (or "protein-binding sequence") interacts with (binds to) a CRISPR-Cas effector polypeptide. The protein-binding segment of a subject CRISPR-Cas effector guide RNA can include two complementary stretches of nucleotides that hybridize to one another to form a double stranded RNA duplex (dsRNA duplex). Site-specific binding and/or cleavage of a target nucleic acid (e.g., genomic DNA, ds DNA, RNA, etc.) can occur at locations (e.g., target sequence of a target locus) determined by base-pairing complementarity between the CRISPR-Cas effector guide RNA (the guide sequence of the CRISPR-Cas effector guide RNA) and the target nucleic acid.

A CRISPR-Cas effector guide RNA and a CRISPR-Cas effector protein (e.g., a wild-type CRISPR-Cas effector protein; a variant CRISPR-Cas effector protein; a fusion CRISPR-Cas effector polypeptide; etc.) form a complex (e.g., bind via non-covalent interactions). The CRISPR-Cas effector guide RNA provides target specificity to the complex by including a targeting segment, which includes a guide sequence (a nucleotide sequence that is complementary to a sequence of a target nucleic acid). The CRISPR-Cas effector protein of the complex provides the site-specific activity (e.g., cleavage activity provided by the CRISPR-Cas effector protein and/or an activity provided by the fusion partner in the case of a fusion CRISPR-Cas effector protein). In other words, the CRISPR-Cas effector protein is guided to a target nucleic acid sequence (e.g. a target sequence) by virtue of its association with the CRISPR-Cas effector guide RNA.

The "guide sequence" also referred to as the "targeting sequence" of a CRISPR-Cas effector guide RNA can be modified so that the CRISPR-Cas effector guide RNA can target a CRISPR-Cas effector protein (e.g., a naturally occurring CRISPR-Cas effector protein, a fusion CRISPR-Cas effector polypeptide, and the like) to any desired sequence of any desired target nucleic acid, with the exception (e.g., as described herein) that the PAM sequence can be taken into account. Thus, for example, a CRISPR-Cas effector guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

Guide Sequence of a CRISPR-Cas Effector Guide RNA

A subject CRISPR-Cas effector guide RNA includes a guide sequence (i.e., a targeting sequence), which is a nucleotide sequence that is complementary to a sequence (a target site) in a target nucleic acid. In other words, the guide sequence of a CRISPR-Cas effector guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CRISPR-Cas effector guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some cases, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 17 nt. In some cases, the guide sequence has a length of 18 nt. In some cases, the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

In some cases, the guide sequence (also referred to as a "spacer sequence") has a length of from 15 to 50 nucleotides (e.g., from 15 nucleotides (nt) to 20 nt, from 20 nt to 25 nt, from 25 nt to 30 nt, from 30 nt to 35 nt, from 35 nt to 40 nt, from 40 nt to 45 nt, or from 45 nt to 50 nt).

Protein-Binding Segment of a CRISPR-Cas Effector Guide RNA

The protein-binding segment (the "constant region") of a subject CRISPR-Cas effector guide RNA interacts with a CRISPR-Cas effector protein. The CRISPR-Cas effector guide RNA guides the bound CRISPR-Cas effector protein to a specific nucleotide sequence within target nucleic acid via the above-mentioned guide sequence. The protein-binding segment of a CRISPR-Cas effector guide RNA can include two stretches of nucleotides that are complementary to one another and hybridize to form a double stranded RNA duplex (dsRNA duplex). Thus, in some cases, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some embodiments, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a subject CRISPR-Cas effector guide RNA can include one or more (1, 2, 3, 4, 5, etc) mutations relative to a naturally occurring duplex region. For example, in some cases a base pair can be maintained while the nucleotides contributing to the base pair from each segment can be different. In some cases, the duplex region of a subject CRISPR-Cas effector guide RNA includes more paired bases, less paired bases, a smaller bulge, a larger bulge, fewer bulges, more bulges, or any convenient combination thereof, as compared to a naturally occurring duplex region (of a naturally occurring CRISPR-Cas effector guide RNA).

Examples of various Cas9 guide RNAs can be found in the art, and in some cases variations similar to those introduced into Cas9 guide RNAs can also be introduced into CRISPR-Cas effector guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4): 910-8; Auer et al., Genome Res. 2013 Oct. 31; Chen et al., *Nucleic Acids Res.* 2013 Nov. 1; 41(20):e19; Cheng et al., Cell Res. 2013 October; 23(10):1163-71; Cho et al., Genetics. 2013 November; 195(3):1177-80; DiCarlo et al., *Nucleic Acids Res.* 2013 April; 41(7):4336-43; Dickinson et al., Nat Methods. 2013 October; 10(10):1028-34; Ebina et al., Sci Rep. 2013; 3:2510; Fujii et. al, *Nucleic Acids Res.* 2013 Nov. 1; 41(20):e187; Hu et al., Cell Res. 2013 November; 23(11): 1322-5; Jiang et al., *Nucleic Acids Res.* 2013 Nov. 1; 41(20):e188; Larson et al., Nat Protoc. 2013 November; 8(11):2180-96; Mali et. at., Nat Methods. 2013 Oct; 10(10): 957-63; Nakayama et al., Genesis. 2013 December; 51(12): 835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Examples of constant regions suitable for inclusion in a CRISPR-Cas effector guide RNA are provided in FIG. 7 (e.g., where T is substituted with U). A CRISPR-Cas effector guide RNA can include a constant region having from 1 to 5 nucleotide substitutions compared to any one of the nucleotide sequences depicted in FIG. 7. A CRISPR-Cas effector guide RNA of the present disclosure can comprise a constant region having at least 85%, at least 85%, at least 90%, at least 95%, at least 98%, at least 99%, or 100%, nucleotide sequence identity with any one of the crRNA nucleotide sequences depicted in FIG. 7 (e.g., where Ts are substituted with Us).

The nucleotide sequences (with T substituted with U) can be combined with a spacer sequence (where the spacer sequence comprises a target nucleic acid-binding sequence ("guide sequence")) of choice that is from 15 to 50 nucleotides (e.g., from 15 nucleotides (nt) to 20 nt, from 20 nt to 25 nt, from 25 nt to 30 nt, from 30 nt to 35 nt, from 35 nt to 40 nt, from 40 nt to 45 nt, or from 45 nt to 50 nt in length). In some cases, the spacer sequence is 35-38 nucleotides in length. For example, any one of the nucleotide sequences (with T substituted with U) depicted in FIG. 7 can be included in a guide RNA comprising (N)n-constant region, where N is any nucleotide and n is an integer from 15 to 50 (e.g., from 15 to 20, from 20 to 25, from 25 to 30, from 30 to 35, from 35 to 38, from 35 to 40, from 40 to 45, or from 45 to 50).

Crispr-Cas Effector Systems

The present disclosure provides a CRISPR-Cas effector system. A CRISPR-Cas effector system of the present disclosure can comprise: a) a CRISPR-Cas effector polypeptide of the present disclosure and a CRISPR-Cas effector guide RNA; b) a CRISPR-Cas effector polypeptide of the present disclosure, a CRISPR-Cas effector guide RNA, and a donor template nucleic acid; c) a CRISPR-Cas effector fusion polypeptide of the present disclosure and a CRISPR-Cas effector guide RNA; d) a CRISPR-Cas effector fusion polypeptide of the present disclosure, a CRISPR-Cas effector guide RNA, and a donor template nucleic acid; e) an mRNA encoding a CRISPR-Cas effector polypeptide of the present disclosure; and a CRISPR-Cas effector guide RNA; f) an mRNA encoding a CRISPR-Cas effector polypeptide of the present disclosure, a CRISPR-Cas effector guide RNA, and a donor template nucleic acid; g) an mRNA encoding a CRISPR-Cas effector fusion polypeptide of the present disclosure; and a CRISPR-Cas effector guide RNA; h) an mRNA encoding a CRISPR-Cas effector fusion polypeptide of the present disclosure, a CRISPR-Cas effector guide RNA, and a donor template nucleic acid; i) a recombinant expression vector comprising a nucleotide sequence encoding a CRISPR-Cas effector polypeptide of the present disclosure and a nucleotide sequence encoding a CRISPR-Cas effector guide RNA; j) a recombinant expression vector comprising a nucleotide sequence encoding a CRISPR-Cas effector polypeptide of the present disclosure, a nucleotide sequence encoding a CRISPR-Cas effector guide RNA, and a nucleotide sequence encoding a donor template nucleic acid; k) a recombinant expression vector comprising a nucleotide sequence encoding a CRISPR-Cas effector fusion polypeptide of the present disclosure and a nucleotide sequence encoding a CRISPR-Cas effector guide RNA; l) a recombinant expression vector comprising a nucleotide sequence encoding a CRISPR-Cas effector fusion polypeptide of the present disclosure, a nucleotide sequence encoding a CRISPR-Cas effector guide RNA, and a nucleotide sequence encoding a donor template nucleic acid; m) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; n) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; and a donor template nucleic acid; o) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; p) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; and a donor template nucleic acid; q) a recombinant expression vector comprising a nucleotide sequence encoding a CRISPR-Cas effector polypeptide of the present disclosure, a nucleotide sequence encoding a first CRISPR-Cas effector guide RNA, and a nucleotide sequence encoding a second CRISPR-Cas effector guide RNA; or r) a recombinant expression vector comprising a nucleotide sequence encoding a CRISPR-Cas effector fusion polypeptide of the present disclosure, a nucleotide sequence encoding a first CRISPR-Cas effector guide RNA, and a nucleotide sequence encoding a second CRISPR-Cas effector guide RNA; or some variation of one of (a) through (r).

Nucleic Acids

The present disclosure provides one ore more nucleic acids comprising one or more of: a donor polynucleotide sequence, a nucleotide sequence encoding a CRISPR-Cas effector polypeptide (e.g., a wild type CRISPR-Cas effector protein, a nickase CRISPR-Cas effector protein, a dCRISPR-Cas effector protein, fusion CRISPR-Cas effector protein, and the like), a CRISPR-Cas effector guide RNA, and a nucleotide sequence encoding a CRISPR-Cas effector guide RNA. The present disclosure provides a nucleic acid comprising a nucleotide sequence encoding a CRISPR-Cas effector fusion polypeptide. The present disclosure provides a recombinant expression vector that comprises a nucleotide sequence encoding a CRISPR-Cas effector polypeptide. The present disclosure provides a recombinant expression vector that comprises a nucleotide sequence encoding a CRISPR-Cas effector fusion polypeptide. The present disclosure provides a recombinant expression vector that comprises: a) a nucleotide sequence encoding a CRISPR-Cas effector polypeptide; and b) a nucleotide sequence encoding a CRISPR-Cas effector guide RNA(s). The present disclosure provides a recombinant expression vector that comprises: a) a nucleotide sequence encoding a CRISPR-Cas effector fusion polypeptide; and b) a nucleotide sequence encoding a CRISPR-Cas effector guide RNA(s). In some cases, the nucleotide sequence encoding the CRISPR-Cas effector protein and/or the nucleotide sequence encoding the CRISPR-Cas effector guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a CRISPR-Cas effector polypeptide of the present disclosure is codon optimized. This type of optimization can entail a mutation of a CRISPR-Cas effector-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CRISPR-Cas effector-encoding nucleotide sequence could be used. As another non-limiting example, if the intended host cell were a mouse cell, then a mouse codon-optimized CRISPR-Cas effector-encoding nucleotide sequence could be generated. As another non-limiting example, if the intended host cell were a plant cell, then a plant codon-optimized CRISPR-Cas effector-encoding nucleotide sequence could be generated. As another non-limiting example, if the intended host cell were an insect cell, then an insect codon-optimized CRISPR-Cas effector-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a CRISPR-Cas effector guide RNA that hybridizes to a target sequence of the target locus of the targeted genome (e.g., operably linked to a promoter that is operable in a target cell such as a eukaryotic cell); and (iii) a nucleotide sequence encoding a CRISPR-Cas effector protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a CRISPR-Cas effector guide RNA that hybridizes to a target sequence of the target locus of the targeted genome (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a CRISPR-Cas effector guide RNA that hybridizes to a target sequence of the target locus of the targeted genome (e.g., operably linked to a promoter that is operable in a target cell such as a eukaryotic cell); and (ii) a nucleotide sequence encoding a CRISPR-Cas effector protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CRISPR-Cas effector guide RNA is operably linked to a control element, e.g., a transcriptional control element, such as a promoter. In some embodiments, a nucleotide sequence encoding a CRISPR-Cas effector protein or a CRISPR-Cas effector fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6xHis tag, hemagglutinin tag, fluorescent protein, etc.) that can be fused to the CRISPR-Cas effector protein, thus resulting in a fusion CRISPR-Cas effector polypeptide.

In some embodiments, a nucleotide sequence encoding a CRISPR-Cas effector guide RNA and/or a CRISPR-Cas effector fusion polypeptide is operably linked to an inducible promoter. In some embodiments, a nucleotide sequence encoding a CRISPR-Cas effector guide RNA and/or a CRISPR-Cas effector fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CRISPR-Cas effector guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding a CRISPR-Cas effector protein (e.g., a wild type CRISPR-Cas effector protein, a nickase CRISPR-Cas effector protein, a dCRISPR-Cas effector protein, a fusion CRISPR-Cas effector protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CRISPR-Cas effector protein and/or a CRISPR-Cas effector guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CRISPR-Cas effector protein can be provided as RNA. The RNA can be provided by direct chemical synthesis or may be transcribed in vitro from a DNA (e.g., encoding the CRISPR-Cas effector protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CRISPR-Cas effector guide RNA; recombinant expression vectors encoding the CRISPR-Cas effector protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CRISPR-Cas effector guide RNA and/or a CRISPR-Cas effector polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-3-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CRISPR-Cas effector guide RNA and/or a CRISPR-Cas effector protein to a cell may include nucleic acid sequences that encode for selectable markers in the target cells, so as to identify cells that have taken up the CRISPR-Cas effector guide RNA and/or CRISPR-Cas effector protein.

A nucleic acid comprising a nucleotide sequence encoding a CRISPR-Cas effector polypeptide, or a CRISPR-Cas effector fusion polypeptide, is in some cases an RNA. Thus, a CRISPR-Cas effector fusion protein can be introduced into cells as RNA. Methods of introducing RNA into cells are known in the art and may include, for example, direct injection, transfection, or any other method used for the introduction of DNA. A CRISPR-Cas effector protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a CRISPR-Cas effector polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 33). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CRISPR-Cas effector polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CRISPR-Cas effector guide RNA, encoding a CRISPR-Cas effector fusion protein, etc.) and proteins (e.g., a CRISPR-Cas effector fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CRISPR-Cas effector polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CRISPR-Cas effector polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CRISPR-Cas effector polypeptide, or a CRISPR-Cas effector fusion polypeptide, of the present disclosure is at least 80% pure, at least 85% pure, at least 90% pure, at least 95% pure, at least 98% pure, or at least 99% pure (e.g., free of contaminants, non-CRISPR-Cas effector proteins or other macromolecules, etc.).

To induce cleavage or any desired modification to a target nucleic acid (e.g., genomic DNA), or any desired modification to a polypeptide associated with target nucleic acid, the CRISPR-Cas effector guide RNA and/or the CRISPR-Cas effector polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CRISPR-Cas effector guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CRISPR-Cas effector guide RNA that does not change when the guide sequence is changed to hybridized to a desired target sequence (e.g., sequences that contribute to the CRISPR-Cas effector binding aspect of the guide RNA, e.g, the sequences that contribute to the dsRNA duplex(es) of the CRISPR-Cas effector guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CRISPR-Cas effector guide RNA, except that the portion encoding the guide sequence portion of the guide RNA is an insertion sequence (an insertion site). An insertion site is any nucleotide sequence used for the insertion of the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CRISPR-Cas effector guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2' Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CRISPR-Cas effector guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., Chem. Commun., 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., Tetrahedron, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_n ON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2$ $CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci.* USA, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N. Y Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO: 34); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci.* USA 97:13003-13008); RRQRRTSKLMKR SEQ ID NO: 30); Transportan GWTLNSAGYLLGKINLKALAALAKKIL SEQ ID NO: 31); KALAWEAKLAKALAKA-LAKHLAKALAKALKCEA SEQ ID NO: 32); and RQIKIWFQNRRMKWKK SEQ ID NO: 33). Exemplary PTDs include but are not limited to, YGRKKRRQRRR SEQ ID NO: 34), RKKRRQRRR SEQ ID NO: 35); an arginine homopolymer of from 3 arginine residues to 50 arginine residues; Exemplary PTD domain amino acid sequences include, but are not limited to, any of the following: YGRKKRRQRRR SEQ ID NO: 34); RKKRRQRR SEQ ID NO: 36); YARAAARQARA SEQ ID NO: 37); THRL-PRRRRRR SEQ ID NO: 38); and GGRRARRRRRR SEQ ID NO: 39). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A CRISPR-Cas effector guide RNA (or a nucleic acid comprising a nucleotide sequence encoding same) and/or a CRISPR-Cas effector polypeptide of the present disclosure (or a nucleic acid comprising a nucleotide sequence encoding same) and/or a CRISPR-Cas effector fusion polypeptide of the present disclosure (or a nucleic acid that includes a nucleotide sequence encoding a CRISPR-Cas effector fusion polypeptide of the present disclosure) and/or a donor polynucleotide (donor template) can be introduced into a host cell by any of a variety of well-known methods.

Any of a variety of compounds and methods can be used to deliver to a target cell a CRISPR-Cas effector system of the present disclosure (e.g., where a CRISPR-Cas effector system comprises: a) a CRISPR-Cas effector polypeptide of the present disclosure and a CRISPR-Cas effector guide RNA; b) a CRISPR-Cas effector polypeptide of the present disclosure, a CRISPR-Cas effector guide RNA, and a donor template nucleic acid; c) a CRISPR-Cas effector fusion polypeptide of the present disclosure and a CRISPR-Cas effector guide RNA; d) a CRISPR-Cas effector fusion polypeptide of the present disclosure, a CRISPR-Cas effector guide RNA, and a donor template nucleic acid; e) an mRNA encoding a CRISPR-Cas effector polypeptide of the present disclosure; and a CRISPR-Cas effector guide RNA; f) an mRNA encoding a CRISPR-Cas effector polypeptide of the present disclosure, a CRISPR-Cas effector guide RNA, and a donor template nucleic acid; g) an mRNA encoding a CRISPR-Cas effector fusion polypeptide of the present disclosure; and a CRISPR-Cas effector guide RNA; h) an mRNA encoding a CRISPR-Cas effector fusion polypeptide of the present disclosure, a CRISPR-Cas effector guide RNA, and a donor template nucleic acid; i) a recombinant expression vector comprising a nucleotide sequence encoding a CRISPR-Cas effector polypeptide of the present disclosure and a nucleotide sequence encoding a CRISPR-Cas effector guide RNA; j) a recombinant expression vector comprising a nucleotide sequence encoding a CRISPR-Cas effector polypeptide of the present disclosure, a nucleotide sequence encoding a CRISPR-Cas effector guide RNA, and a nucleotide sequence encoding a donor template nucleic acid; k) a recombinant expression vector comprising a nucleotide sequence encoding a CRISPR-Cas effector fusion polypeptide of the present disclosure and a nucleotide sequence encoding a CRISPR-Cas effector guide RNA; 1) a recombinant expression vector comprising a nucleotide sequence encoding a CRISPR-Cas effector fusion polypeptide of the present disclosure, a nucleotide sequence encoding a CRISPR-Cas effector guide RNA, and a nucleotide sequence encoding a donor template nucleic acid; m) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; n) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; and a donor template nucleic acid; o) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; p) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; and a donor template nucleic acid; q) a recombinant expression vector comprising a nucleotide sequence encoding a CRISPR-Cas effector polypeptide of the present disclosure, a nucleotide sequence encoding a first CRISPR-Cas effector guide RNA, and a nucleotide sequence encoding a second CRISPR-Cas effector guide RNA; or r) a recombinant expression vector comprising a nucleotide sequence encoding a CRISPR-Cas effector fusion polypeptide of the present disclosure, a nucleotide sequence encoding a first CRISPR-Cas effector guide RNA, and a nucleotide sequence encoding a second CRISPR-Cas effector guide RNA; or some variation of one of (a) through (r). As a non-limiting example, a CRISPR-Cas effector system of the present disclosure can be combined with a lipid. As another non-limiting example, a CRISPR-Cas effector system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a CRISPR-Cas effector polypeptide of the present disclosure is provided as a nucleic acid (e.g., an mRNA, a DNA, a plasmid, an expression vector, a viral vector, etc.) that encodes the CRISPR-Cas effector polypeptide. In some cases, the CRISPR-Cas effector polypeptide of the present disclosure is provided directly as a protein (e.g., without an associated guide RNA or with an associate guide RNA, i.e., as a ribonucleoprotein complex). A CRISPR-Cas effector polypeptide of the present disclosure can be introduced into a cell (provided to the cell) by any convenient method; such methods are known to those of ordinary skill in the art. As an illustrative example, a CRISPR-Cas effector polypeptide of the present disclosure can be injected directly into a cell (e.g., with or without a CRISPR-Cas effector guide RNA or nucleic acid encoding a CRISPR-Cas effector guide RNA, and with or without a donor polynucleotide). As another example, a preformed complex of a CRISPR-Cas effector polypeptide of the present disclosure and a CRISPR-Cas effector guide RNA (an RNP) can be introduced into a cell (e.g, eukaryotic cell) (e.g., via injection, via nucleofection; via a protein transduction domain (PTD) conjugated to one or more components, e.g., conjugated to the CRISPR-Cas effector protein, conjugated to a guide RNA, conjugated to a CRISPR-Cas effector polypeptide of the present disclosure and a guide RNA; etc.).

In some cases, a CRISPR-Cas effector fusion polypeptide (e.g., dCRISPR-Cas effector fused to a fusion partner, nickase CRISPR-Cas effector fused to a fusion partner, etc.) of the present disclosure is provided as a nucleic acid (e.g., an mRNA, a DNA, a plasmid, an expression vector, a viral vector, etc.) that encodes the CRISPR-Cas effector fusion polypeptide. In some cases, the CRISPR-Cas effector fusion polypeptide of the present disclosure is provided directly as a protein (e.g., without an associated guide RNA or with an associate guide RNA, i.e., as a ribonucleoprotein complex). A CRISPR-Cas effector fusion polypeptide of the present disclosure can be introduced into a cell (provided to the cell) by any convenient method; such methods are known to those of ordinary skill in the art. As an illustrative example, a CRISPR-Cas effector fusion polypeptide of the present disclosure can be injected directly into a cell (e.g., with or without nucleic acid encoding a CRISPR-Cas effector guide RNA and with or without a donor polynucleotide). As another example, a preformed complex of a CRISPR-Cas effector fusion polypeptide of the present disclosure and a CRISPR-Cas effector guide RNA (an RNP) can be introduced into a cell (e.g., via injection, via nucleofection; via a protein transduction domain (PTD) conjugated to one or more components, e.g., conjugated to the CRISPR-Cas effector fusion protein, conjugated to a guide RNA, conjugated to a CRISPR-Cas effector fusion polypeptide of the present disclosure and a guide RNA; etc.).

In some cases, a nucleic acid (e.g., a CRISPR-Cas effector guide RNA; a nucleic acid comprising a nucleotide sequence encoding a CRISPR-Cas effector polypeptide of the present disclosure; etc.) is delivered to a cell (e.g., a target host cell) and/or a polypeptide (e.g., a CRISPR-Cas effector polypeptide; a CRISPR-Cas effector fusion polypeptide) in a particle, or associated with a particle. In some cases, a CRISPR-Cas effector system of the present disclosure is delivered to a cell in a particle, or associated with a particle. The terms "particle" and nanoparticle" can be used interchangeable, as appropriate. A recombinant expression vector comprising a nucleotide sequence encoding a CRISPR-Cas effector polypeptide of the present disclosure and/or a CRISPR-Cas effector guide RNA, an mRNA comprising a nucleotide sequence encoding a CRISPR-Cas effector polypeptide of the present disclosure, and guide RNA may be delivered simultaneously using particles or lipid envelopes; for instance, a CRISPR-Cas effector polypeptide and a CRISPR-Cas effector guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CRISPR-Cas effector polypepide and a CRISPR-Cas effector guideRNA are mixed together, e.g., at a 1:1 molar ratio, e.g., at room temperature, e.g., for 30 minutes, e.g., in sterile, nuclease free 1×phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CRISPR-Cas effector polypeptide of the present disclosure (or an mRNA comprising a nucleotide sequence encoding a CRISPR-Cas effector polypeptide of the present disclosure; or a recombinant expression vector comprising a nucleotide sequence encoding a CRISPR-Cas effector polypeptide of the present disclosure) and/or CRISPR-Cas effector guide RNA (or a nucleic acid such as one or more expression vectors encoding the CRISPR-Cas effector guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure (e.g., where a CRISPR-Cas effector system comprises: a) a CRISPR-Cas effector polypeptide of the present disclosure and a CRISPR-Cas effector guide RNA; b) a CRISPR-Cas effector polypeptide of the present disclosure, a CRISPR-Cas effector guide RNA, and a donor template nucleic acid; c) a CRISPR-Cas effector fusion polypeptide of the present disclosure and a CRISPR-Cas effector guide RNA; d) a CRISPR-Cas effector fusion polypeptide of the present disclosure, a CRISPR-Cas effector guide RNA, and a donor template nucleic acid; e) an mRNA encoding a CRISPR-Cas effector polypeptide of the present disclosure; and a CRISPR-Cas effector guide RNA; f) an mRNA encoding a CRISPR-Cas effector polypeptide of the present disclosure, a CRISPR-Cas effector guide RNA, and a donor templat nucleic acid; g) an mRNA encoding a CRISPR-Cas effector fusion polypeptide of the present disclosure; and a CRISPR-Cas effector guide RNA; h) an mRNA encoding a CRISPR-Cas effector fusion polypeptide of the present disclosure, a CRISPR-Cas effector guide RNA, and a donor template nucleic acid; i) a recombinant expression vector comprising a nucleotide sequence encoding a CRISPR-Cas effector polypeptide of the present disclosure and a nucleotide sequence encoding a CRISPR-Cas effector guide RNA; j) a recombinant expression vector comprising a nucleotide sequence encoding a CRISPR-Cas effector polypeptide of the present disclosure, a nucleotide sequence encoding a CRISPR-Cas effector guide RNA, and a nucleotide sequence encoding a donor template nucleic acid; k) a recombinant expression vector comprising a nucleotide sequence encoding a CRISPR-Cas effector fusion polypeptide of the present disclosure and a nucleotide sequence encoding a CRISPR-Cas effector guide RNA; l) a recombinant expression vector comprising a nucleotide sequence encoding a CRISPR-Cas effector fusion polypeptide of the present disclosure, a nucleotide sequence encoding a CRISPR-Cas effector guide RNA, and a nucleotide sequence encoding a donor template nucleic acid; m) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; n) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; and a donor template nucleic acid; o) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; p) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; and a donor template nucleic acid; q) a recombinant expression vector comprising a nucleotide sequence encoding a CRISPR-Cas effector polypeptide of the present disclosure, a nucleotide sequence encoding a first CRISPR-Cas effector guide RNA, and a nucleotide sequence encoding a second CRISPR-Cas effector guide RNA; or r) a recombinant expression vector comprising a nucleotide sequence encoding a CRISPR-Cas effector fusion polypeptide of the present disclosure, a nucleotide sequence encoding a first CRISPR-Cas effector guide RNA, and a nucleotide sequence encoding a second CRISPR-Cas effector guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell.

In some cases, lipid nanoparticles (LNPs) are used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinKDMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a CRISPR-Cas effector guide RNA; a nucleic acid of the present disclosure; etc.) may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell have a diameter of from 25 nm to 200 nm. In some cases, nanoparticles suitable for use in delivering a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell have a diameter of 100 nm or less In some cases, nanoparticles suitable for use in delivering a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell have a diameter of from 35 nm to 60 nm.

Nanoparticles suitable for use in delivering a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. A prototype nanoparticle of semi-solid nature is the liposome.

In some cases, an exosome is used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. Exosomes are endogenous nano-vesicles that transport RNAs and proteins, and which can deliver RNA to the brain and other target organs.

In some cases, a liposome is used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. The SNALP formulation may contain the lipids 3-N-[(methoxy-poly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000)carbamoyl]-1, 2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl) aminopropane (DLinDMA).

Other cationic lipids, such as amino lipid 2,2-dilinoleyl-4-dimethylaminoethyl-[1,3]-dioxolane (DLin-KC2-DMA) can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. A preformed vesicle with the following lipid composition may be contemplated: amino lipid, distearoylphosphatidylcholine (DSPC), cholesterol and (R)-2, 3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CRISPR-Cas effector system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a CRISPR-Cas effector system, or component thereof, of the present disclosure, using a spontaneous vesicle formation procedure. The component molar ratio may be about 50/10/38.5/1.5 (DLin-KC2-DMA or C12-200/ disteroylphosphatidyl choline/cholesterol/PEG-DMG).

A CRISPR-Cas effector system of the present disclosure, or a component thereof, may be delivered encapsulated in PLGA microspheres such as that further described in US published applications 20130252281 and 20130245107 and 20130244279.

Supercharged proteins can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a CRISPR-Cas effector polypeptide of the present disclosure, a CRISPR-Cas effector fusion polypeptide of the present disclosure, an RNP of the present disclosure, a nucleic acid of the present disclosure (e.g., a CRISPR-Cas effector guide RNA, a nucleic acid encoding a CRISPR-Cas effector guide RNA, a nucleic acid encoding CRISPR-Cas effector polypeptide, a donor template, and the like), or a CRISPR-Cas effector system of the present disclosure, to a target cell (e.g., a target cell in vivo, where the target cell is a target cell in circulation, a target cell in a tissue, a target cell in an organ, etc.). An implantable device suitable for use in delivering a CRISPR-Cas effector polypeptide of the present disclosure, a CRISPR-Cas effector fusion polypeptide of the present disclosure, an RNP of the present disclosure, a nucleic acid of the present disclosure, or a CRISPR-Cas effector system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CRISPR-Cas effector polypeptide, the CRISPR-Cas effector fusion polypeptide, the RNP, or the CRISPR-Cas effector system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear—auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CRISPR-Cas effector polypeptide of the present disclosure and/or a nucleic acid comprising a nucleotide sequence encoding a CRISPR-Cas effector polypeptide of the present disclosure. The present disclosure provides a modified cell comprising a CRISPR-Cas effector polypeptide of the present disclosure, where the modified cell is a cell that does not normally comprise a CRISPR-Cas effector polypeptide of the present disclosure. The present disclosure provides a modified cell (e.g., a genetically modified cell) comprising nucleic acid comprising a nucleotide sequence encoding a CRISPR-Cas effector polypeptide of the present disclosure. The present disclosure provides a genetically modified cell that is genetically modified with an mRNA comprising a nucleotide sequence encoding a CRISPR-Cas effector polypeptide of the present disclosure. The present disclosure provides a genetically modified cell that is genetically modified with a recombinant expression vector comprising a nucleotide sequence encoding a CRISPR-Cas effector polypeptide of the present disclosure. The present disclosure provides a genetically modified cell that is genetically modified with a recombinant expression vector comprising: a) a nucleotide sequence encoding a CRISPR-Cas effector polypeptide of the present disclosure; and b) a nucleotide sequence encoding a CRISPR-Cas effector guide RNA of the present disclosure. The present disclosure provides a genetically modified cell that is genetically modified with a recombinant expression vector comprising: a) a nucleotide sequence encoding a CRISPR-Cas effector polypeptide of the present disclosure; b) a nucleotide sequence encoding a CRISPR-Cas effector guide RNA of the present disclosure; and c) a nucleotide sequence encoding a donor template.

A cell that serves as a recipient for a CRISPR-Cas effector polypeptide of the present disclosure and/or a nucleic acid comprising a nucleotide sequence encoding a CRISPR-Cas effector polypeptide of the present disclosure and/or a CRISPR-Cas effector guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a CRISPR-Cas effector polypeptide of the present disclosure and/or a nucleic acid comprising a nucleotide sequence encoding a CRISPR-Cas effector polypeptide of the present disclosure and/or a CRISPR-Cas effector guide RNA of the present disclosure is referred to as a "host cell" or a "target cell." A host cell or a target cell can be a recipient of a CRISPR-Cas effector system of the present disclosure. A host cell or a target cell can be a recipient of a CRISPR-Cas effector RNP of the present disclosure. A host cell or a target cell can be a recipient of a single component of a CRISPR-Cas effector system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens*, C. agardh, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, *salicornia* (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata*, Myriapodia, Hexipodia, Arachnida, *Insecta*, Archaeognatha, *Thysanura*, Palaeoptera, Ephemeroptera, *Odonata, Anisoptera, Zygoptera*, Neoptera, Exopterygota, *Plecoptera*, Embioptera, *Orthoptera, Zoraptera, Dermaptera, Dictyoptera, Notoptera*, Grylloblattidae, Mantophasmatidae, Phasmatodea, *Blattaria, Isoptera*, Mantodea, Parapneuroptera, Psocoptera, Thysanoptera, Phthiraptera, *Hemiptera*, Endopterygota or Holometabola, *Hymenoptera, Coleoptera*, Strepsiptera, Raphidioptera, *Megaloptera, Neuroptera*, Mecoptera, *Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CRISPR-Cas effector system of the present disclosure, or a component of a CRISPR-Cas effector system of the present disclosure.

A kit of the present disclosure can comprise: a) a CRISPR-Cas effector polypeptide of the present disclosure and a CRISPR-Cas effector guide RNA; b) a CRISPR-Cas effector polypeptide of the present disclosure, a CRISPR-Cas effector guide RNA, and a donor template nucleic acid; c) a CRISPR-Cas effector fusion polypeptide of the present disclosure and a CRISPR-Cas effector guide RNA; d) a CRISPR-Cas effector fusion polypeptide of the present disclosure, a CRISPR-Cas effector guide RNA, and a donor template nucleic acid; e) an mRNA encoding a CRISPR-Cas effector polypeptide of the present disclosure; and a CRISPR-Cas effector guide RNA; f) an mRNA encoding a CRISPR-Cas effector polypeptide of the present disclosure, a CRISPR-Cas effector guide RNA, and a donor templat nucleic acid; g) an mRNA encoding a CRISPR-Cas effector fusion polypeptide of the present disclosure; and a CRISPR- Cas effector guide RNA; h) an mRNA encoding a CRISPR-Cas effector fusion polypeptide of the present disclosure, a CRISPR-Cas effector guide RNA, and a donor template nucleic acid; i) a recombinant expression vector comprising a nucleotide sequence encoding a CRISPR-Cas effector polypeptide of the present disclosure and a nucleotide sequence encoding a CRISPR-Cas effector guide RNA; j) a recombinant expression vector comprising a nucleotide sequence encoding a CRISPR-Cas effector polypeptide of the present disclosure, a nucleotide sequence encoding a CRISPR-Cas effector guide RNA, and a nucleotide sequence encoding a donor template nucleic acid; k) a recombinant expression vector comprising a nucleotide sequence encoding a CRISPR-Cas effector fusion polypeptide of the present disclosure and a nucleotide sequence encoding a CRISPR-Cas effector guide RNA; l) a recombinant expression vector comprising a nucleotide sequence encoding a CRISPR-Cas effector fusion polypeptide of the present disclosure, a nucleotide sequence encoding a CRISPR-Cas effector guide RNA, and a nucleotide sequence encoding a donor template nucleic acid; m) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; n) a first recombinant expression vector comprising a nucleotide sequence encoding a CRISPR-Cas effector polypeptide of the present disclosure, and a second recombinant expression vector comprising a nucleotide sequence encoding a CRISPR-Cas effector guide RNA; and a donor template nucleic acid; o) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; p) a first recombinant expression vector comprising a nucleotide sequence encoding a CRISPR-Cas effector fusion polypeptide of the present disclosure, and a second recombinant expression vector comprising a nucleotide sequence encoding a CRISPR-Cas effector guide RNA; and a donor template nucleic acid; q) a recombinant expression vector comprising a nucleotide sequence encoding a CRISPR-Cas effector polypeptide of the present disclosure, a nucleotide sequence encoding a first CRISPR-Cas effector guide RNA, and a nucleotide sequence encoding a second CRISPR-Cas effector guide RNA; or r) a recombinant expression vector comprising a nucleotide sequence encoding a CRISPR-Cas effector fusion polypeptide of the present disclosure, a nucleotide sequence encoding a first CRISPR-Cas effector guide RNA, and a nucleotide sequence encoding a second CRISPR-Cas effector guide RNA; or some variation of one of (a) through (r).

A kit of the present disclosure can comprise: a) a component, as described above, of a CRISPR-Cas effector system of the present disclosure, or can comprise a CRISPR-Cas effector system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CRISPR-Cas effector guide RNA; and the like. A kit of the present disclosure can comprise: a) a component, as described above, of a CRISPR-Cas effector system of the present disclosure, or can comprise a CRISPR-Cas effector system of the present disclosure; and b) a therapeutic agent.

A kit of the present disclosure can comprise a recombinant expression vector comprising: a) an insertion site for inserting a nucleic acid comprising a nucleotide sequence encoding a portion of a CRISPR-Cas effector guide RNA that hybridizes to a target nucleotide sequence in a target nucleic acid; and b) a nucleotide sequence encoding the CRISPR-Cas effector-binding portion of a CRISPR-Cas effector guide RNA. A kit of the present disclosure can comprise a recombinant expression vector comprising: a) an insertion site for inserting a nucleic acid comprising a nucleotide sequence encoding a portion of a CRISPR-Cas effector guide RNA that hybridizes to a target nucleotide sequence in a target nucleic acid; b) a nucleotide sequence encoding the CRISPR-Cas effector-binding portion of a CRISPR-Cas effector guide RNA; and c) a nucleotide sequence encoding a CRISPR-Cas effector polypeptide of the present disclosure.

Utility

A CRISPR-Cas effector polypeptide of the present disclosure, or a CRISPR-Cas effector fusion polypeptide of the present disclosure, finds use in a variety of methods (e.g., in combination with a CRISPR-Cas effector guide RNA and in some cases further in combination with a donor template). For example, a CRISPR-Cas effector polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CRISPR-Cas effector polypeptide of the present disclosure; and b) one or more (e.g., two) CRISPR-Cas effector guide RNAs. In some cases, a method of the present disclosure for modifying a target nucleic acid comprises contacting the target nucleic acid with: a) a CRISPR-Cas effector polypeptide of the present disclosure; b) a CRISPR-Cas effector guide RNA; and c) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CRISPR-Cas effector polypeptide includes binding of the CRISPR-Cas effector polypeptide to a particular region in a target nucleic acid (by virtue of being targeted there by an associated CRISPR-Cas effector guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., *Nucleic Acids Res.* 2013 Nov. 1; 41(20):e19; Cheng et al., Cell Res. 2013 October; 23(10):1163-71; Cho et al., Genetics. 2013 November; 195(3):1177-80; DiCarlo et al., *Nucleic Acids Res.* 2013 Apr; 41(7):4336-43; Dickinson et al., Nat Methods. 2013 October; 10(10):1028-34; Ebina et al., Sci Rep. 2013; 3:2510; Fujii et al, *Nucleic Acids Res.* 2013 Nov. 1; 41(20):e187; Hu et al., Cell Res. 2013 November; 23(11): 1322-5; Jiang et al., *Nucleic Acids Res.* 2013 Nov. 1; 41(20):e188; Larson et al., Nat Protoc. 2013 Nov.; 8(11): 2180-96; Mali et. at., Nat Methods. 2013 October; 10(10): 957-63; Nakayama et al., Genesis. 2013 December; 51(12): 835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CRISPR-Cas effector polypeptide or with a CRISPR-Cas effector fusion polypeptide, etc., encompass all methods for contacting the target nucleic acid. For example, a CRISPR-Cas effector polypeptide can be provided to a cell as protein, RNA (encoding the CRISPR-Cas effector polypeptide), or DNA (encoding the CRISPR-Cas effector polypeptide); while a CRISPR-Cas effector guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CRISPR-Cas effector polypeptide; in the form of a protein for a CRISPR-Cas effector fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CRISPR-Cas effector polypeptide or a CRISPR-Cas effector fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises introducing into a target cell a CRISPR-Cas effector locus, e.g., a nucleic acid comprising a nucleotide sequence encoding a CRISPR-Cas effector polypeptide as well as nucleotide sequences of about 1 kilobase (kb) to 5 kb in length surrounding the CRISPR-Cas effector-encoding nucleotide sequence from a cell (e.g., in some cases a cell that in its natural state (the state in which it occurs in nature) comprises a CRISPR-Cas effector locus) comprising a CRISPR-Cas effector locus, where the target cell does not normally (in its natural state) comprise a CRISPR-Cas effector locus. However, one or more spacer sequences, encoding guide sequences for the encoded crRNA(s), can be modified such that one or more target sequences of interest are targeted. Thus, for example, in some cases, a method of the present disclosure for modifying a target nucleic acid comprises introducing into a target cell a CRISPR-Cas effector locus, e.g., a nucleic acid obtained from a source cell (e.g., in some cases a cell that in its natural state (the state in which it occurs in nature) comprises a CRISPR-Cas effector locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a CRISPR-Cas effector polypeptide. As noted above, in some such cases, one or more spacer sequences, encoding guide sequences for the encoded crRNA(s), can be modified such that one or more target sequences of interest are targeted. In some cases, the method comprises introducing into a target cell: i) a CRISPR-Cas effector locus; and ii) a donor DNA template. In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

In some cases, a method of the present disclosure for modifying a target nucleic acid comprises contacting a target nucleic acid with a CRISPR-Cas effector polypeptide of the present disclosure, or with a CRISPR-Cas effector fusion polypeptide of the present disclosure. In some cases, a method of the present disclosure for modifying a target nucleic acid comprises contacting a target nucleic acid with a CRISPR-Cas effector polypeptide and a CRISPR-Cas effector guide RNA. In some cases, a method of the present disclosure for modifying a target nucleic acid comprises contacting a target nucleic acid with a CRISPR-Cas effector polypeptide, a first CRISPR-Cas effector guide RNA, and a second CRISPR-Cas effector guide RNA In some cases, a method of the present disclosure for modifying a target nucleic acid comprises contacting a target nucleic acid with a CRISPR-Cas effector polypeptide of the present disclosure and a CRISPR-Cas effector guide RNA and a donor DNA template.

Target Nucleic Acids and Target Cells of Interest

A CRISPR-Cas effector polypeptide of the present disclosure, or a CRISPR-Cas effector fusion polypeptide of the present disclosure, when bound to a CRISPR-Cas effector guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CRISPR-Cas effector guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens*, C. agardh, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to geneically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens*, C. agardh, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CRISPR-Cas effector protein (and/or nucleic acid encoding the protein such as DNA and/or RNA), and/or CRISPR-Cas effector guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens*, C. agardh, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, *chrysanthemum* leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, *salicornia* (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams, yu choy, yuca (cassava), and the like.

A cell is in some cases an arthropod cell. For example, the cell can be a cell of a sub-order, a family, a sub-family, a group, a sub-group, or a species of, e.g., *Chelicerata*, Myriapodia, Hexipodia, Arachnida, *Insecta*, Archaeognatha, *Thysanura*, Palaeoptera, Ephemeroptera, *Odonata, Anisoptera, Zygoptera*, Neoptera, Exopterygota, *Plecoptera*, Embioptera, *Orthoptera, Zoraptera, Dermaptera, Dictyoptera, Notoptera*, Grylloblattidae, Mantophasmatidae, Phasmatodea, *Blattaria, Isoptera*, Mantodea, Parapneuroptera, Psocoptera, Thysanoptera, Phthiraptera, *Hemiptera*, Endopterygota or Holometabola, *Hymenoptera, Coleoptera*, Strepsiptera, Raphidioptera, *Megaloptera, Neuroptera*, Mecoptera, *Siphonaptera, Diptera, Trichoptera*, or *Lepidoptera*.

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A CRISPR-Cas effector guide RNA (or a nucleic acid comprising a nucleotide sequence encoding same), and/or a CRISPR-Cas effector fusion polypeptide (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a taret cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like. Any or all of the components can be introduced into a cell as a composition (e.g., including any convenient combination of: a CRISPR-Cas effector polypeptide, a CRISPR-Cas effector guide RNA, a donor polynucleotide, etc.) using known methods, e.g., such as nucleofection.

Donor Polynucleotide (Donor Template)

Guided by a CRISPR-Cas effector guide RNA, a CRISPR-Cas effector protein in some cases generates site-specific double strand breaks (DSBs) or single strand breaks (SSBs) (e.g., when the CRISPR-Cas effector protein is a nickase variant) within double-stranded DNA (dsDNA) target nucleic acids, which are repaired either by non-homologous end joining (NHEJ) or homology-directed recombination (HDR).

In some cases, contacting a target DNA (with a CRISPR-Cas effector protein and a CRISPR-Cas effector guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, CRISPR-Cas effector guide RNA (or DNA encoding same) and a CRISPR-Cas effector protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CRISPR-Cas effector guide RNA and CRISPR-Cas effector protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into the genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CRISPR-Cas effector protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair to a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CRISPR-Cas effector guide RNA and/or a CRISPR-Cas effector fusion polypeptide and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a CRISPR-Cas effector polypeptide of the present disclosure; a nucleic acid comprising a nucleotide sequence encoding a CRISPR-Cas effector fusion polypeptide of the present disclosure; etc.), is used as a transgene to generate a transgenic non-human organism that produces a CRISPR-Cas effector polypeptide, or a CRISPR-Cas effector fusion polypeptide, of the present disclosure. The present disclosure provides a transgenic-non-human organism comprising a nucleotide sequence encoding a CRISPR-Cas effector polypeptide, or a CRISPR-Cas effector fusion polypeptide, of the present disclosure.

Transgenic, Non-Human Animals

The present disclosure provides a transgenic non-human animal, which animal comprises a transgene comprising a nucleic acid comprising a nucleotide sequence encoding a CRISPR-Cas effector polypeptide or a CRISPR-Cas effector fusion polypeptide. In some embodiments, the genome of the transgenic non-human animal comprises a nucleotide sequence encoding a CRISPR-Cas effector polypeptide, or a CRISPR-Cas effector fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a CRISPR-Cas effector polypeptide, or a CRISPR-Cas effector fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a CRISPR-Cas effector polypeptide of the present disclosure; a nucleic acid comprising a nucleotide sequence encoding a CRISPR-Cas effector fusion polypeptide of the present disclosure; etc.), is used as a transgene to generate a transgenic plant that produces a CRISPR-Cas effector polypeptide, or a CRISPR-Cas effector fusion polypeptide, of the present disclosure. The present disclosure provides a transgenic plant comprising a nucleotide sequence encoding a CRISPR-Cas effector polypeptide, or a CRISPR-Cas effector fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and *Biotechnology*, Boca Raton, Fla.: CRC Press (1993).

Microprojectile-mediated transformation also can be used to produce a subject transgenic plant. This method, first described by Klein et al. (*Nature* 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a CRISPR-Cas effector polypeptide, or a CRISPR-Cas effector fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) *Nature* 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. *Biotechnol* 18: 333-338, 2000; O'Neill et al Plant J. 3:729-738, 1993; Knoblauch et al Nat. Biotechnol 17: 906-909; U.S. Pat. Nos. 5,451,513, 5,545, 817, 5,545,818, and 5,576,198; in Intl. Application No. WO 95/16783; and in Boynton et al., Methods in Enzymology 217: 510-536 (1993), Svab et al., *Proc. Natl. Acad. Sci.* USA 90: 913-917 (1993), and McBride et al., *Proc. Natl. Acad. Sci.* USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CRISPR-Cas effector polypeptide, or a CRISPR-Cas effector fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CRISPR-Cas effector polypeptide, or a CRISPR-Cas effector fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-121 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A composition comprising: a) a CRISPR-Cas effector polypeptide, or a nucleic acid molecule encoding the CRISPR-Cas effector polypeptide, wherein the CRISPR-Cas effector polypeptide comprises an amino acid sequence having 50% or more amino acid sequence identity to the amino acid sequence depicted in any one of FIG. 6A-6BB; and b) a CRISPR-Cas effector guide RNA, or one or more DNA molecules encoding the CRISPR-Cas effector guide RNA.

Aspect 2. The composition of aspect 1, wherein the CRISPR-Cas effector polypeptide comprises an amino acid sequence having 80% or more amino acid sequence identity to the amino acid sequence depicted in any one of FIG. 6A-6BB.

Aspect 3. The composition of aspect 1 or aspect 2, wherein the CRISPR-Cas effector guide RNA comprises a nucleotide sequence having 80%, 90%, 95%, 98%, 99%, or 100%, nucleotide sequence identity with any one of the crRNA sequences depicted in FIG. 7.

Aspect 4. The composition of aspect 1 or aspect 2, wherein the CRISPR-Cas effector polypeptide is fused to a nuclear localization signal (NLS).

Aspect 5. The composition of any one of aspects 1-4, wherein the composition comprises a lipid.

Aspect 6. The composition of any one of aspects 1-4, wherein a) and b) are within a liposome.

Aspect 7. The composition of any one of aspects 1-4, wherein a) and b) are within a particle.

Aspect 8. The composition of any one of aspects 1-7, comprising one or more of: a buffer, a nuclease inhibitor, and a protease inhibitor.

Aspect 9. The composition of any one of aspects 1-8, wherein the CRISPR-Cas effector polypeptide comprises an amino acid sequence having 85% or more identity to the amino acid sequence depicted in any one of FIG. 6A-6BB.

Aspect 10. The composition of any one of aspects 1-9, wherein the CRISPR-Cas effector polypeptide is a nickase that can cleave only one strand of a double-stranded target nucleic acid molecule.

Aspect 11. The composition of any one of aspects 1-9, wherein the CRISPR-Cas effector polypeptide is a catalytically inactive CRISPR-Cas effector polypeptide (dCRISPR-Cas effector).

Aspect 12. The composition of aspect 10 or aspect 11, wherein the CRISPR-Cas effector polypeptide comprises one or more amino acid substitutions in one or more of a RuvC-I domain, a RuvC-II domain, and a RuvC-III domain.

Aspect 13. The composition of any one of aspects 1-12, further comprising a DNA donor template.

Aspect 14. A CRISPR-Cas effector fusion polypeptide comprising: a CRISPR-Cas effector polypeptide fused to a heterologous polypeptide, wherein the CRISPR-Cas effector polypeptide comprises an amino acid sequence having 50% or more amino acid sequence identity to the amino acid sequence depicted in any one of FIG. 6A-6BB.

Aspect 15. The CRISPR-Cas effector fusion polypeptide of Aspect 14, wherein the CRISPR-Cas effector polypeptide comprises an amino acid sequence having 80% or more identity to the amino acid sequence depicted in any one of FIG. 6A-6BB.

Aspect 16. The CRISPR-Cas effector fusion polypeptide of Aspect 14, wherein the CRISPR-Cas effector polypeptide comprises an amino acid sequence having 85% or more identity to the amino acid sequence depicted in any one of FIG. 6A-6BB.

Aspect 17. The CRISPR-Cas effector fusion polypeptide of any one of aspects 14-16, wherein the CRISPR-Cas effector polypeptide is a nickase that can cleave only one strand of a double-stranded target nucleic acid molecule.

Aspect 18. The CRISPR-Cas effector fusion polypeptide of any one of aspects 14-17, wherein the CRISPR-Cas effector polypeptide is a catalytically inactive CRISPR-Cas effector polypeptide (dCRISPR-Cas effector).

Aspect 19. The CRISPR-Cas effector fusion polypeptide of aspect 17 or aspect 18, wherein the CRISPR-Cas effector polypeptide comprises one or more amino acid substitutions in one or more of a RuvC-I domain, a RuvC-II domain, and a RuvC-III domain.

Aspect 20. The CRISPR-Cas effector fusion polypeptide of any one of aspects 14-19, wherein the heterologous polypeptide is fused to the N-terminus and/or the C-terminus of the CRISPR-Cas effector polypeptide.

Aspect 21. The CRISPR-Cas effector fusion polypeptide of any one of aspects 14-20, comprising a nuclear localization signal (NLS).

Aspect 22. The CRISPR-Cas effector fusion polypeptide of any one of aspects 14-21, wherein the heterologous polypeptide is a targeting polypeptide that provides for binding to a cell surface moiety on a target cell or target cell type.

Aspect 23. The CRISPR-Cas effector fusion polypeptide of any one of aspects 14-21, wherein the heterologous polypeptide exhibits an enzymatic activity that modifies target DNA.

Aspect 24. The CRISPR-Cas effector fusion polypeptide of aspect 23, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 25. The CRISPR-Cas effector fusion polypeptide of aspect 24, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 26. The CRISPR-Cas effector fusion polypeptide of any one of aspects 14-21, wherein the heterologous polypeptide exhibits an enzymatic activity that modifies a target polypeptide associated with a target nucleic acid.

Aspect 27. The CRISPR-Cas effector fusion polypeptide of aspect 26, wherein the heterologous polypeptide exhibits histone modification activity.

Aspect 28. The CRISPR-Cas effector fusion polypeptide of aspect 26 or aspect 27, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

Aspect 29. The CRISPR-Cas effector fusion polypeptide of aspect 28, wherein the heterologous polypeptide exhibits one or more enzymatic activities selected from: methyltransferase activity, demethylase activity, acetyltransferase activity, and deacetylase activity.

Aspect 30. The CRISPR-Cas effector fusion polypeptide of any one of aspects 14-21, wherein the heterologous polypeptide is an endosomal escape polypeptide.

Aspect 31. The CRISPR-Cas effector fusion polypeptide of aspect 30, wherein the endosomal escape polypeptide comprises an amino acid sequence selected from: GLFX-ALLXLLXSLWXLLLXA (SEQ ID NO: 12), and GLF-HALLHLLHSLWHLLLHA (SEQ ID NO: 13), wherein each X is independently selected from lysine, histidine, and arginine.

Aspect 32. The CRISPR-Cas effector fusion polypeptide of any one of aspects 14-21, wherein the heterologous polypeptide is a chloroplast transit peptide.

Aspect 33. The CRISPR-Cas effector fusion polypeptide of any one of aspects 14-21, wherein the heterologous polypeptide comprises a protein transduction domain.

Aspect 34. The CRISPR-Cas effector fusion polypeptide of any one of aspects 14-21, wherein the heterologous polypeptide is a protein that increases or decreases transcription.

Aspect 35. The CRISPR-Cas effector fusion polypeptide of aspect 34, wherein the heterologous polypeptide is a transcriptional repressor domain.

Aspect 36. The CRISPR-Cas effector fusion polypeptide of aspect 34, wherein the heterologous polypeptide is a transcriptional activation domain.

Aspect 37. The CRISPR-Cas effector fusion polypeptide of any one of aspects 14-21, wherein the heterologous polypeptide is a protein binding domain.

Aspect 38. A nucleic acid comprising a nucleotide sequence encoding the CRISPR-Cas effector fusion polypeptide of any one of aspects 14-37.

Aspect 39. The nucleic acid of Aspect 38, wherein the nucleotide sequence encoding the CRISPR-Cas effector fusion polypeptide is operably linked to a promoter.

Aspect 40. The nucleic acid of Aspect 39, wherein the promoter is functional in a eukaryotic cell.

Aspect 41. The nucleic acid of Aspect 40, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

Aspect 42. The nucleic acid of any one of Aspects 39-41, wherein the promoter is one or more of: a constitutive promoter, an inducible promoter, a cell type-specific promoter, and a tissue-specific promoter.

Aspect 43. The nucleic acid of any one of Aspects 38-42, wherein the nucleic acid is a recombinant expression vector.

Aspect 44. The nucleic acid of Aspect 43, wherein the recombinant expression vector is a recombinant adenoassociated viral vector, a recombinant retroviral vector, or a recombinant lentiviral vector.

Aspect 45. The nucleic acid of Aspect 39, wherein the promoter is functional in a prokaryotic cell.

Aspect 46. The nucleic acid of Aspect 38, wherein the nucleic acid molecule is an mRNA.

Aspect 47. One or more nucleic acids comprising:
(a) a nucleotide sequence encoding a CRISPR-Cas effector guide RNA; and
(b) a nucleotide sequence encoding a CRISPR-Cas effector polypeptide, wherein the CRISPR-Cas effector polypeptide comprises an amino acid sequence having 50% or more amino acid sequence identity to the amino acid sequence depicted in any one of FIG. 6A-6BB.

Aspect 48. The one or more nucleic acids of aspect 47, wherein the CRISPR-Cas effector polypeptide comprises an amino acid sequence having 80% or more identity to the amino acid sequence depicted in any one of FIG. 6A-6BB.

Aspect 49. The one or more nucleic acids of aspect 47, wherein the CRISPR-Cas effector polypeptide comprises an amino acid sequence having 85% or more identity to the amino acid depicted in any one of FIG. 6A-6BB.

Aspect 50. The one or more nucleic acids of any one of aspects 47-49, wherein the CRISPR-Cas effector guide RNA comprises a nucleotide sequence having 80% or more identity with any one of the crRNA sequences set forth in FIG. 7.

Aspect 51. The one or more nucleic acids of any one of aspects 47-50, wherein the CRISPR-Cas effector polypeptide is fused to a nuclear localization signal (NLS).

Aspect 52. The one or more nucleic acids of any one of aspects 47-51, wherein the nucleotide sequence encoding the CRISPR-Cas effector guide RNA is operably linked to a promoter.

Aspect 53. The one or more nucleic acids of any one of aspects 47-52, wherein the nucleotide sequence encoding the CRISPR-Cas effector polypeptide is operably linked to a promoter.

Aspect 54. The one or more nucleic acids of Aspect 52 or Aspect 53, wherein the promoter operably linked to the nucleotide sequence encoding the CRISPR-Cas effector guide RNA, and/or the promoter operably linked to the nucleotide sequence encoding the CRISPR-Cas effector polypeptide, is functional in a eukaryotic cell.

Aspect 55. The one or more nucleic acids of Aspect 54, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

Aspect 56. The one or more nucleic acids of any one of Aspects 53-55, wherein the promoter is one or more of: a constitutive promoter, an inducible promoter, a cell type-specific promoter, and a tissue-specific promoter.

Aspect 57. The one or more nucleic acids of any one of Aspects 47-56, wherein the one or more nucleic acids is one or more recombinant expression vectors.

Aspect 58. The one or more nucleic acids of Aspect 57, wherein the one or more recombinant expression vectors are selected from: one or more adenoassociated viral vectors, one or more recombinant retroviral vectors, or one or more recombinant lentiviral vectors.

Aspect 59. The one or more nucleic acids of Aspect 53, wherein the promoter is functional in a prokaryotic cell.

Aspect 60. A eukaryotic cell comprising one or more of:
 a) a CRISPR-Cas effector polypeptide, or a nucleic acid comprising a nucleotide sequence encoding the CRISPR-Cas effector polypeptide, wherein the CRISPR-Cas effector polypeptide comprises an amino acid sequence having 50% or more amino acid sequence identity to the amino acid sequence depicted in any one of FIG. 6A-6BB;
 b) a CRISPR-Cas effector fusion polypeptide, or a nucleic acid comprising a nucleotide sequence encoding the CRISPR-Cas effector fusion polypeptide, wherein the CRISPR-Cas effector polypeptide present in the fusion polypeptide comprises an amino acid sequence having 50% or more amino acid sequence identity to the amino acid sequence depicted in any one of FIG. 6A-6BB; and
 c) a CRISPR-Cas effector guide RNA, or a nucleic acid comprising a nucleotide sequence encoding the CRISPR-Cas effector guide RNA.

Aspect 61. The eukaryotic cell of aspect 60, comprising the nucleic acid encoding the CRISPR-Cas effector polypeptide, wherein said nucleic acid is integrated into the genomic DNA of the cell.

Aspect 62. The eukaryotic cell of aspect 60 or aspect 61, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

Aspect 63. A cell comprising a comprising a CRISPR-Cas effector fusion polypeptide of any one of aspects 14-37, or a nucleic acid comprising a nucleotide sequence encoding the CRISPR-Cas effector fusion polypeptide.

Aspect 64. The cell of aspect 63, wherein the cell is a prokaryotic cell.

Aspect 65. The cell of aspect 63 or aspect 64, comprising the nucleic acid comprising a nucleotide sequence encoding the CRISPR-Cas effector fusion polypeptide, wherein said nucleic acid molecule is integrated into the genomic DNA of the cell.

Aspect 66. A method of modifying a target nucleic acid, the method comprising contacting the target nucleic acid with:
 a) a CRISPR-Cas effector polypeptide, wherein the CRISPR-Cas effector polypeptide comprises an amino acid sequence having 50% or more amino acid sequence identity to the amino acid sequence depicted in any one of FIG. 6A-6BB; and
 b) a CRISPR-Cas effector guide RNA comprising a guide sequence that hybridizes to a target sequence of the target nucleic acid, wherein said contacting results in modification of the target nucleic acid by the CRISPR-Cas effector polypeptide.

Aspect 67. The method of aspect 66, wherein said modification is cleavage of the target nucleic acid.

Aspect 68. The method of aspect 66 or aspect 67, wherein the target nucleic acid is selected from: double stranded DNA, single stranded DNA, RNA, genomic DNA, and extrachromosomal DNA.

Aspect 69. The method of any of aspects 66-68, wherein said contacting takes place in vitro outside of a cell.

Aspect 70. The method of any of aspects 66-68, wherein said contacting takes place inside of a cell in culture.

Aspect 71. The method of any of aspects 66-68, wherein said contacting takes place inside of a cell in vivo.

Aspect 72. The method of aspect 70 or aspect 71, wherein the cell is a eukaryotic cell.

Aspect 73. The method of aspect 72, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 74. The method of aspect 70 or aspect 71, wherein the cell is a prokaryotic cell.

Aspect 75. The method of any one of aspects 66-74, wherein said contacting results in genome editing.

Aspect 76. The method of any one of aspects 66-75, wherein said contacting comprises: introducing into a cell: (a) the CRISPR-Cas effector polypeptide, or a nucleic acid comprising a nucleotide sequence encoding the CRISPR-Cas effector polypeptide, and (b) the CRISPR-Cas effector guide RNA, or a nucleic acid comprising a nucleotide sequence encoding the CRISPR-Cas effector guide RNA.

Aspect 77. The method of aspect 76, wherein said contacting further comprises: introducing a DNA donor template into the cell.

Aspect 78. The method of any one of aspects 66-77, wherein the CRISPR-Cas effector guide RNA comprises a nucleotide sequence having 80% or more identity with any one of the crRNA sequences set forth in FIG. 7.

Aspect 79. The method of any one of aspects 66-78, wherein the CRISPR-Cas effector polypeptide is fused to a nuclear localization signal.

Aspect 80. A method of modulating transcription from a target DNA, modifying a target nucleic acid, or modifying a protein associated with a target nucleic acid, the method comprising contacting the target nucleic acid with:
 a) a CRISPR-Cas effector fusion polypeptide comprising a CRISPR-Cas effector polypeptide fused to a heterologous polypeptide, wherein the CRISPR-Cas effector polypeptide present in the fusion polypeptide comprises an amino acid sequence having 50% or more amino acid sequence identity to the amino acid sequence depicted in any one of FIG. 6A-6BB; and
 b) a CRISPR-Cas effector guide RNA comprising a guide sequence that hybridizes to a target sequence of the target nucleic acid.

Aspect 81. The method of aspect 80, wherein the CRISPR-Cas effector guide RNA comprises a nucleotide sequence having 80% or more identity with any one of the crRNA sequences set forth in FIG. 7.

Aspect 82. The method of aspect 80 or aspect 81, wherein the CRISPR-Cas effector fusion polypeptide comprises nuclear localization signal.

Aspect 83. The method of any of aspects 80-82, wherein said modification is not cleavage of the target nucleic acid.

Aspect 84. The method of any of aspects 80-83, wherein the target nucleic acid is selected from: double stranded DNA, single stranded DNA, RNA, genomic DNA, and extrachromosomal DNA.

Aspect 85. The method of any of aspects 80-84, wherein said contacting takes place in vitro outside of a cell.

Aspect 86. The method of any of aspects 80-84, wherein said contacting takes place inside of a cell in culture.

Aspect 87. The method of any of aspects 80-84, wherein said contacting takes place inside of a cell in vivo.

Aspect 88. The method of aspect 86 or aspect 87, wherein the cell is a eukaryotic cell.

Aspect 89. The method of aspect 88, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 90. The method of aspect 86 or aspect 87, wherein the cell is a prokaryotic cell.

Aspect 91. The method of any one of aspects 80-90, wherein said contacting comprises: introducing into a cell: (a) the CRISPR-Cas effector fusion polypeptide, or a nucleic acid comprising a nucleotide sequence encoding the CRISPR-Cas effector fusion polypeptide, and (b) the CRISPR-Cas effector guide RNA, or a nucleic acid comprising a nucleotide sequence encoding the CRISPR-Cas effector guide RNA.

Aspect 92. The method of any one of aspects 80-91, wherein the CRISPR-Cas effector polypeptide is a catalytically inactive CRISPR-Cas effector polypeptide (dCRISPR-Cas effector polypeptide).

Aspect 93. The method of any one of aspects 80-92, wherein the CRISPR-Cas effector polypeptide comprises one or more amino acid substitutions in one or more of a RuvC-I domain, a RuvC-II domain, and a RuvC-III domain.

Aspect 94. The method of any one of aspects 80-93, wherein the heterologous polypeptide exhibits an enzymatic activity that modifies target DNA.

Aspect 95. The method of aspect 94, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 96. The method of aspect 95, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 97. The method of any one of aspects 80-93, wherein the heterologous polypeptide exhibits an enzymatic activity that modifies a target polypeptide associated with a target nucleic acid.

Aspect 98. The method of aspect 97, wherein the heterologous polypeptide exhibits histone modification activity.

Aspect 99. The method of aspect 97 or aspect 98, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from 0-GlcNAc transferase) and deglycosylation activity.

Aspect 100. The method of aspect 99, wherein the heterologous polypeptide exhibits one or more enzymatic activities selected from: methyltransferase activity, demethylase activity, acetyltransferase activity, and deacetylase activity.

Aspect 101. The method of any one of aspects 80-93, wherein the heterologous polypeptide is protein that increases or decreases transcription.

Aspect 102. The method of aspect 101, wherein the heterologous polypeptide is a transcriptional repressor domain.

Aspect 103. The method of aspect 101, wherein the heterologous polypeptide is a transcriptional activation domain.

Aspect 104. The method of any one of aspects 80-93, wherein the heterologous polypeptide is a protein biding domain.

Aspect 105. A transgenic, multicellular, non-human organism whose genome comprises a transgene comprising a nucleotide sequence encoding one or more of:
  a) a CRISPR-Cas effector polypeptide, wherein the CRISPR-Cas effector polypeptide comprises an amino acid sequence having 50% or more amino acid sequence identity to the amino acid sequence depicted in any one of FIG. 6A-6BB;
  b) a CRISPR-Cas effector fusion polypeptide, wherein the CRISPR-Cas effector polypeptide present in the fusion polypeptide comprises an amino acid sequence having 50% or more amino acid sequence identity to the amino acid sequence depicted in any one of FIG. 6A-6BB; and
  c) a CRISPR-Cas effector guide RNA.

Aspect 106. The transgenic, multicellular, non-human organism of aspect 105, wherein the CRISPR-Cas effector polypeptide comprises an amino acid sequence having 80% or more amino acid sequence identity to the amino acid sequence set forth in any one of FIG. 6A-6BB.

Aspect 107. The transgenic, multicellular, non-human organism of aspect 105, wherein the CRISPR-Cas effector polypeptide comprises an amino acid sequence having 95% or more amino acid sequence identity to the amino acid sequence set forth in any one of FIG. 6A-6BB.

Aspect 108. The transgenic, multicellular, non-human organism of any one of aspects 105-107, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.

Aspect 109. A system comprising:
  a) a CRISPR-Cas effector polypeptide and a CRISPR-Cas effector guide RNA;
  b) a CRISPR-Cas effector polypeptide, a CRISPR-Cas effector guide RNA, and a DNA donor template;
  c) a CRISPR-Cas effector fusion polypeptide of any one of aspects 14-37 and a CRISPR-Cas effector guide RNA;
  d) a CRISPR-Cas effector fusion polypeptide of any one of aspects 14-37, a CRISPR-Cas effector guide RNA, and a DNA donor template;
  e) an mRNA encoding a CRISPR-Cas effector polypeptide, and a CRISPR-Cas effector guide RNA;
  f) an mRNA encoding a CRISPR-Cas effector polypeptide; a CRISPR-Cas effector guide RNA, and a DNA donor template;

g) an mRNA encoding a CRISPR-Cas effector fusion polypeptide of any one of aspects 14-37, and a CRISPR-Cas effector guide RNA;
h) an mRNA encoding a CRISPR-Cas effector fusion polypeptide of any one of aspects 14-37, a CRISPR-Cas effector guide RNA, and a DNA donor template;
i) one or more recombinant expression vectors comprising: i) a nucleotide sequence encoding a CRISPR-Cas effector polypeptide; and ii) a nucleotide sequence encoding a CRISPR-Cas effector guide RNA;
j) one or more recombinant expression vectors comprising: i) a nucleotide sequence encoding a CRISPR-Cas effector polypeptide; ii) a nucleotide sequence encoding a CRISPR-Cas effector guide RNA; and iii) a DNA donor template;
k) one or more recombinant expression vectors comprising: i) a nucleotide sequence encoding a CRISPR-Cas effector fusion polypeptide of any one of aspects 14-37; and ii) a nucleotide sequence encoding a CRISPR-Cas effector guide RNA; and
l) one or more recombinant expression vectors comprising: i) a nucleotide sequence encoding a CRISPR-Cas effector fusion polypeptide of any one of aspects 14-37; ii) a nucleotide sequence encoding a CRISPR-Cas effector guide RNA; and a DNA donor template.

Aspect 110. The CRISPR-Cas effector system of aspect 109, wherein the CRISPR-Cas effector polypeptide comprises an amino acid sequence having 80% or more amino acid sequence identity to the amino acid sequence depicted in any one of FIG. 6A-6BB.

Aspect 111. The CRISPR-Cas effector system of aspect 109, wherein the CRISPR-Cas effector polypeptide comprises an amino acid sequence having 95% or more amino acid sequence identity to the amino acid sequence depicted in any one of FIG. 6A-6BB.

Aspect 112. The CRISPR-Cas effector system of any of aspects 109-111, wherein the donor template nucleic acid has a length of from 8 nucleotides to 1000 nucleotides.

Aspect 113. The CRISPR-Cas effector system of any of aspects 109-111, wherein the donor template nucleic acid has a length of from 25 nucleotides to 500 nucleotides.

Aspect 114. A kit comprising the CRISPR-Cas effector system of any one of aspects 109-113.

Aspect 115. The kit of aspect 114, wherein the components of the kit are in the same container.

Aspect 116. The kit of aspect 114, wherein the components of the kit are in separate containers.

Aspect 117. A sterile container comprising the CRISPR-Cas effector system of any one of aspects 109-116.

Aspect 118. The sterile container of aspect 117, wherein the container is a syringe.

Aspect 119. An implantable device comprising the CRISPR-Cas effector system of any one of aspects 109-116.

Aspect 120. The implantable device of aspect 119, wherein the CRISPR-Cas effector system is within a matrix.

Aspect 121. The implantable device of aspect 119, wherein the CRISPR-Cas effector system is in a reservoir.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Metagenomic datasets from many diverse ecosystems were generated and hundreds of huge phage genomes, between 200 kbp and 716 kbp in length, were reconstructed. Thirty four genomes were manually curated to completion, including the largest phage genomes yet reported. Expanded genetic repertoires include diverse and new CRISPR-Cas systems, tRNAs, tRNA synthetases, tRNA modification enzymes, initiation and elongation factors and ribosomal proteins. Phage CRISPR have the capacity to silence host transcription factors and translational genes, potentially as part of a larger interaction network that intercepts translation to redirect biosynthesis to phage-encoded functions. Some phage repurpose bacterial systems for phage-defense to eliminate competing phage. Seven major clades of huge phage from human and other animal microbiomes, oceans, lakes, sediments, soils and the built environment were phylogenetically defined. It is concluded that large gene inventories reflect a conserved biological strategy, observed across a broad bacterial host range and resulting in the distribution of huge phage across Earth's ecosystems.

Hundreds of phage sequences>200 kbp in length that were reconstructed from microbiome datasets generated from a wide variety of ecosystems were presented. The three largest complete genomes for phage known to date, ranging up to 642 kbp in length, were reconstructed. A graphical abstract provides an overview of the approach and main findings. The research expands the understanding of phage biodiversity and brings to light the variety of ecosystems in which phage have genome sizes that rival those of small celled bacteria.

Ecosystem Sampling

Figure 5:
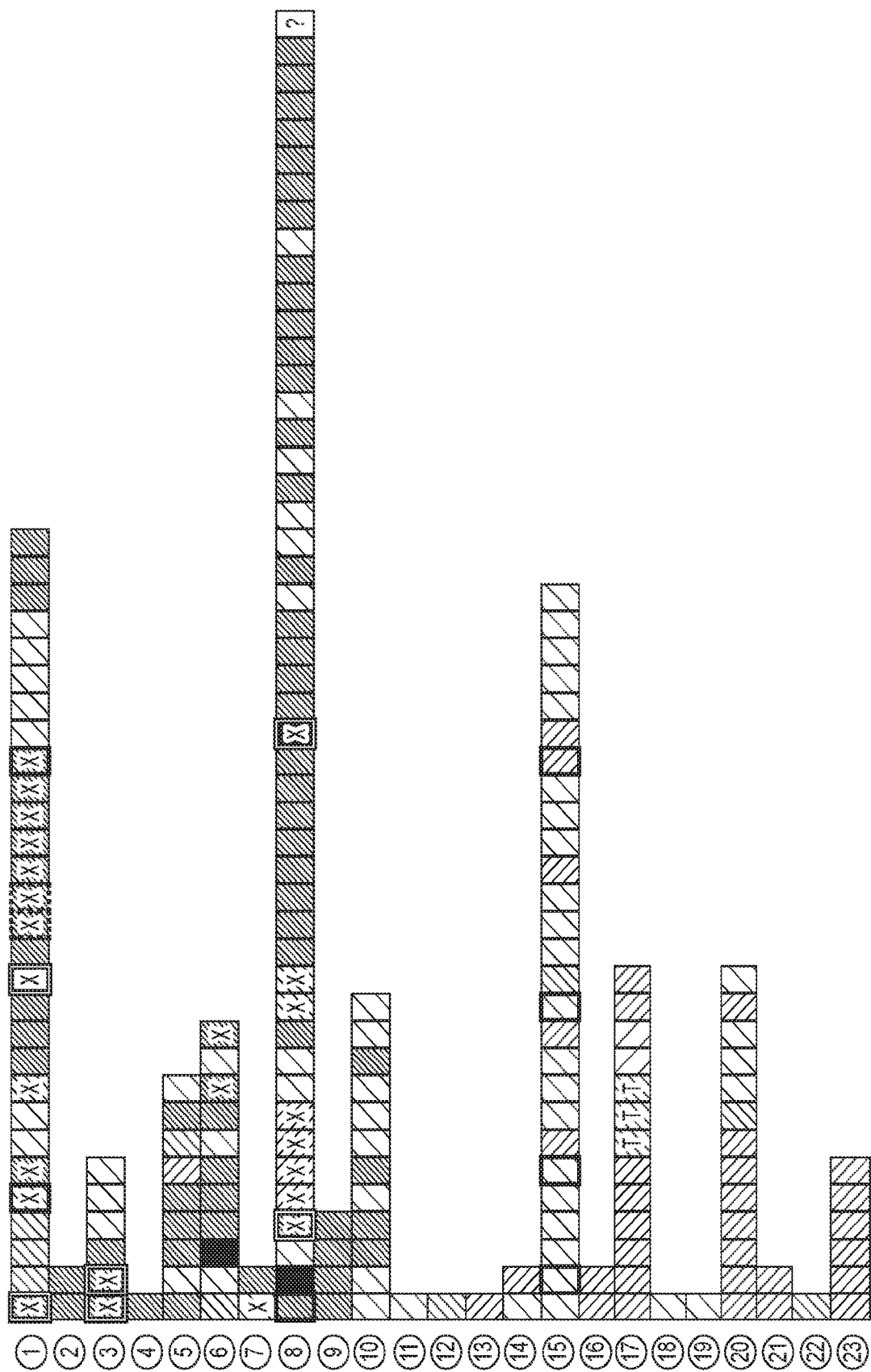
FIG. 5 shows ecosystems with phage and some plasmids with >200 kbp genomes, grouped by sampling site type. Each box represents a phage genome, and boxes are arranged in order of decreasing genome size; size range for each site type is listed to the right. Colors indicate putative host phylum based on genome phylogenetic profile, with confirmation by CRISPR targeting (X) or information system gene phylogenetic analyses (T).
Figure 5:
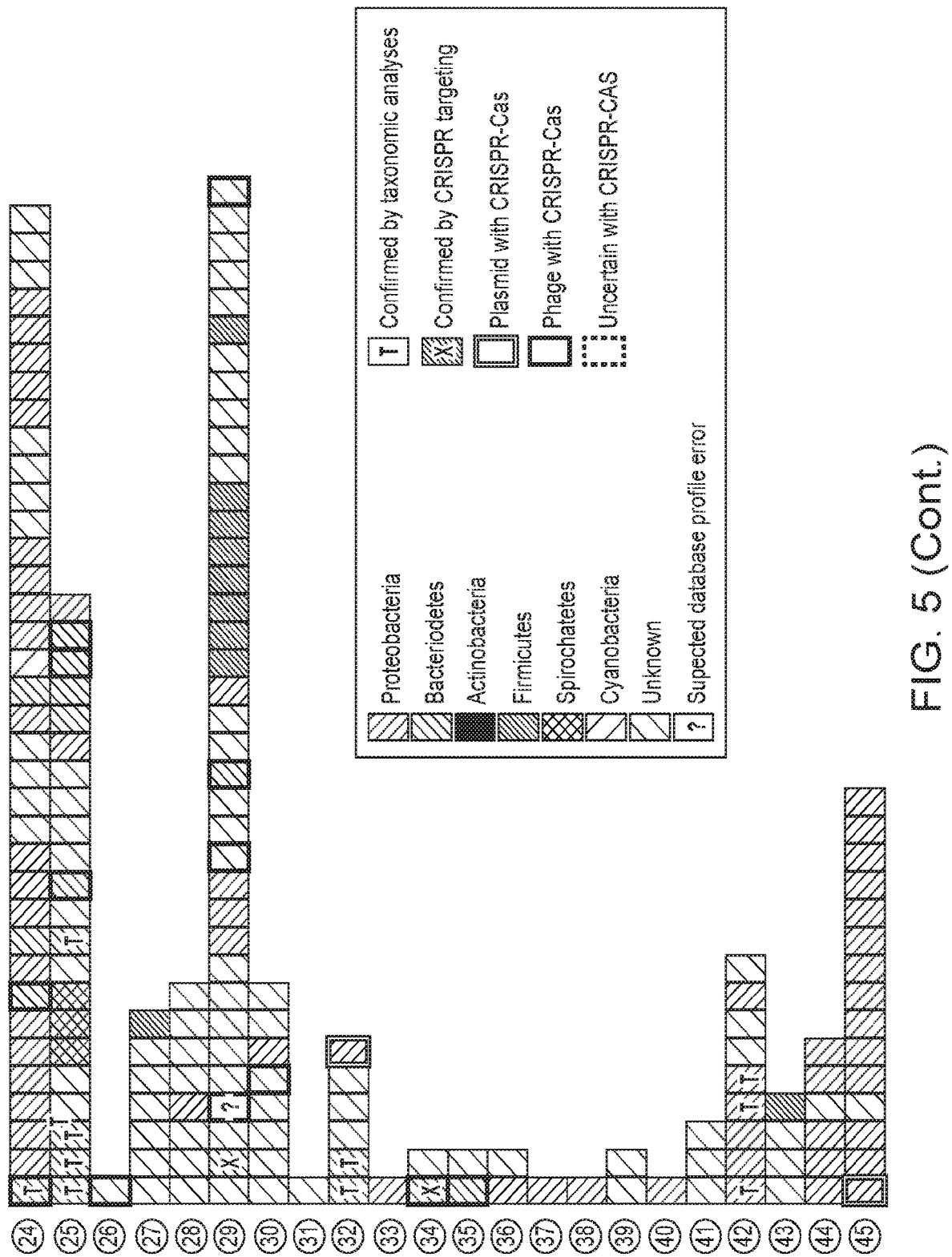
Figure 10:
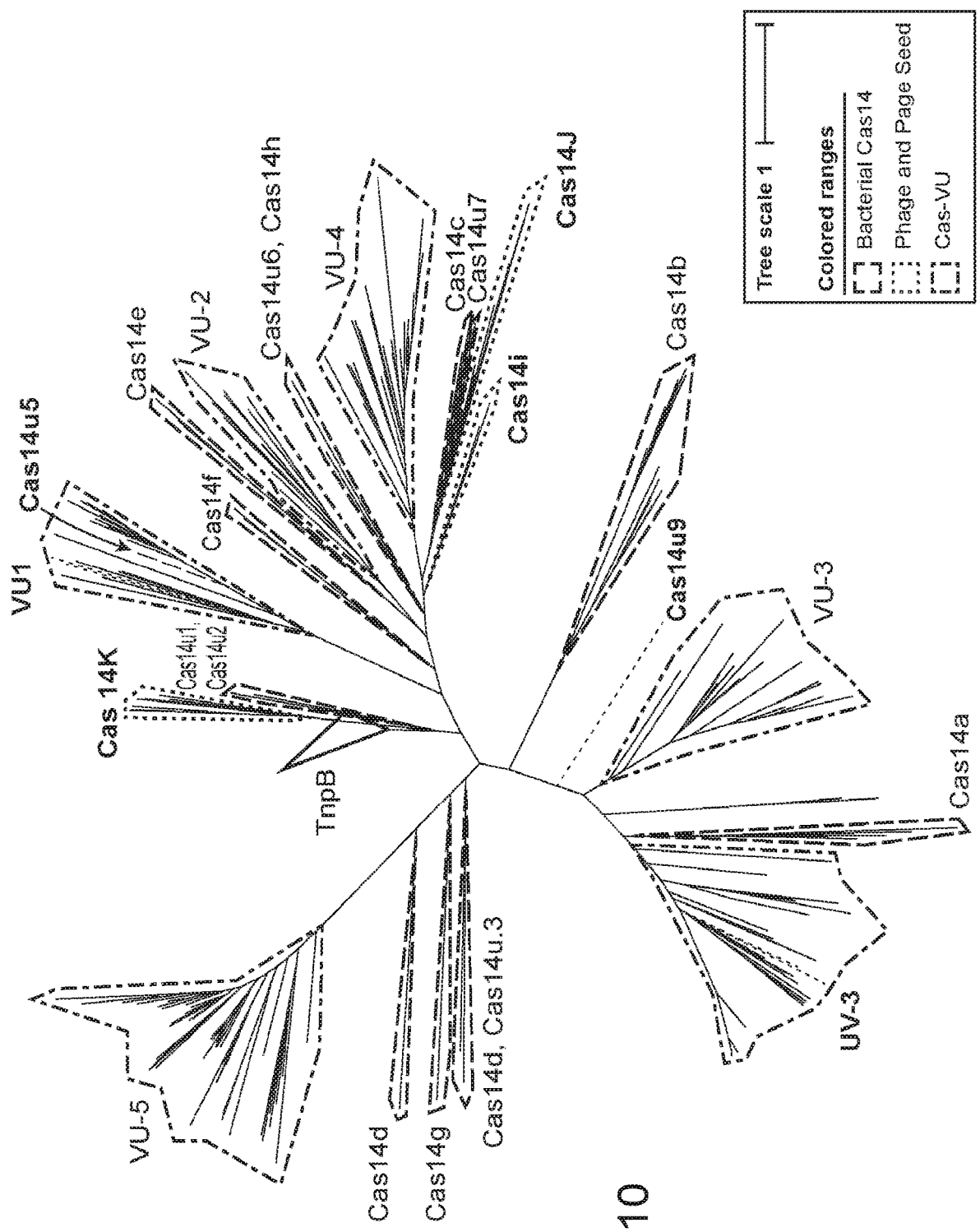
FIG. 10 provides a tree showing various CRISPR-Cas effector protein families.

Metagenomic datasets were acquired from human fecal and oral samples, fecal samples from other animals, freshwater lakes and rivers, marine ecosystems, sediments, hot springs, soils, deep subsurface habitats and the built environment (FIG. 5). For a subset of these, analyses of bacterial, archaeal and eukaryotic organisms were published previously. Genome sequences that were clearly not bacterial, archaeal, archaeal virus, eukaryotic or eukaryotic virus were classified as either phage or plasmid-like based on their gene inventories. De novo assembled fragments of close to or >200 kbp in length were tested for circularization and a subset selected for manual verification and curation to completion (see Methods).

Figure 1B:
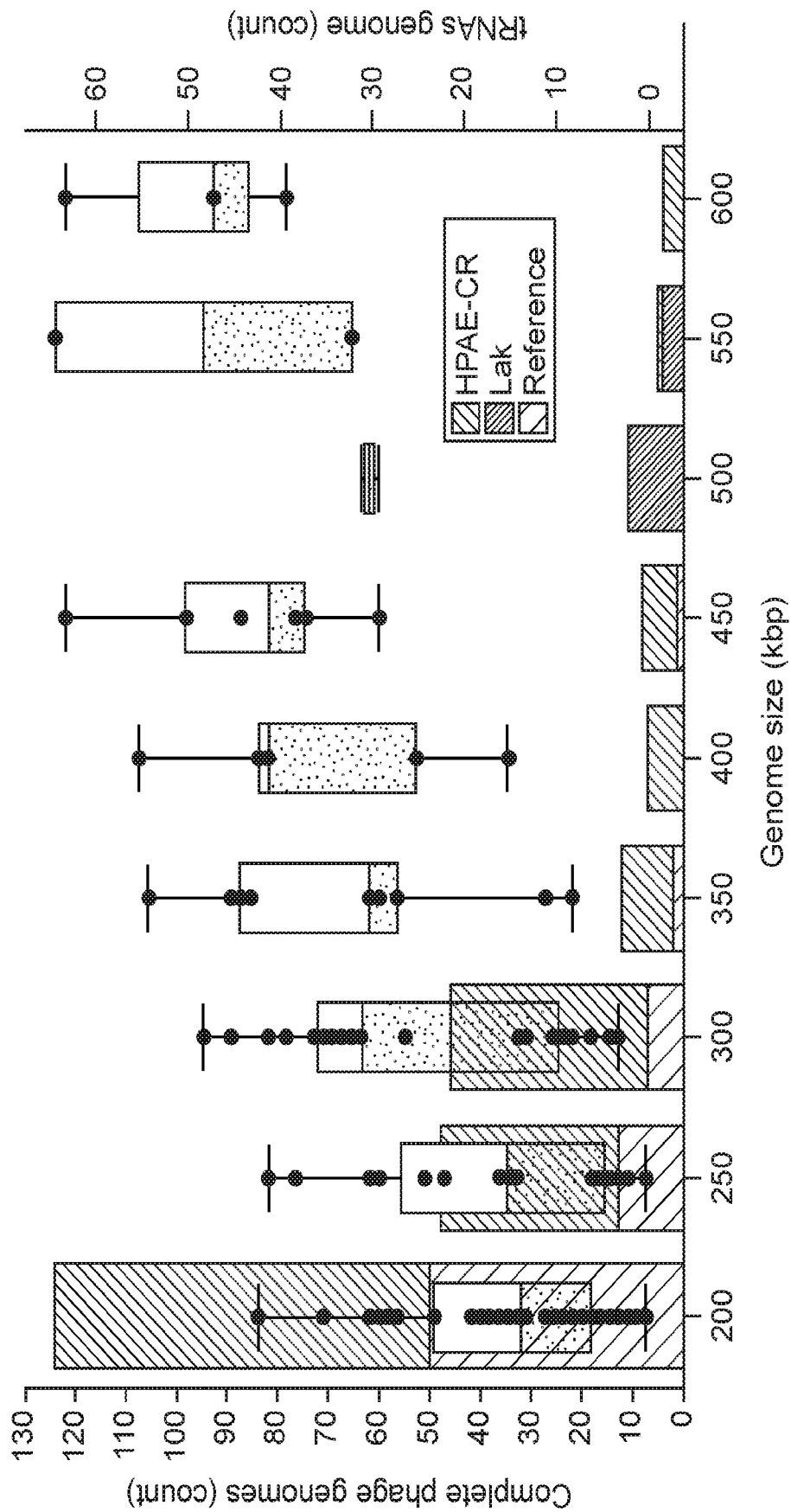
FIG. 1B shows a histogram of the genome size distribution of phage with genomes>200 kb from this study, Lak, and reference genomes. Box and whisker plots of tRNA counts per genome as a function of genome size.

Genome Sizes and Basic Features 358 phage, 3 plasmid and 4 phage-plasmid sequences were reconstructed (FIG. 5). Additional sequences inferred to be plasmids were excluded (see Methods), and only those encoding CRISPR-Cas loci were retained (see below). Consistent with classification as phage, a wide variety of phage-relevant genes were identified, including those involved in lysis and encoding structural proteins, and other expected phage genomic features were documented. Some phage predicted proteins are large, up to 7694 amino acids in length. Many of these were tentatively annotated as structural proteins. 180 phage sequences were circularized and 34 were manually curated to completion, in some cases by resolving complex repeat regions and their encoded proteins (see Methods). Some genomes show a clear GC skew signal for bi-directional replication, information that constrains their replication origin. The three largest complete, manually curated and circularized phage genomes are 634, 636 and 643 kbp in length and represent the largest phage genomes reported to date. Previously, the largest circularized phage genome was 596 kbp in length (Paez-Espino et al. (2016) supra). The same study reported a circularized genome of 630 kbp in length, but this is an artifact. The problem of concatenated sequences was sufficiently prominent in IMG-VR that these data were not included in further analyses. The complete and circularized genomes from the study, Refseq and published research were used to depict a current view of the distribution of phage genome sizes (Methods). The median genome size for complete phage is ~52 kbp (FIG. 1A), similar to the average size of ~54 kpp reported previously (Paez-Espino et al. (2016) supra). Thus, sequences reported here substantially expand the inventory of phage with unusually large genomes (FIG. 1B).

Intriguingly, two related sequences of 712 and >716 kbp in length were identified and manually curated (FIG. 5). These were classified as phage based on their overall genome content and the presence of terminase genes. The assemblies are confounded by few kb-long complex regions comprised of small repeats at both genome ends. It is anticipated that these genomes could be closed if the repeat regions could be rationalized.

Some genomes have very low coding density (nine<75%) due to use of a genetic code different from that used for gene prediction. A similar phenomenon was reported for Lak phage (Devoto et al. (2019) *Nat Microbiol*, and Ivanova et al. (2014) *Science* 344: 909-913). Distinct from prior studies, the genomes appear to use genetic code 16, in which TAG, normally a stop codon, codes for an amino acid.

In only one case, a sequence of >200 kbp that was classified as a prophage based on transition into flanking bacterial genome sequence was identified. However, around half the genomes were not circularized, so their derivation from prophage cannot be ruled out. The presence of integrases in some genomes is suggestive of a lysogenic lifestyle under some conditions.

Hosts, Diversity and Distribution

Figure 2:
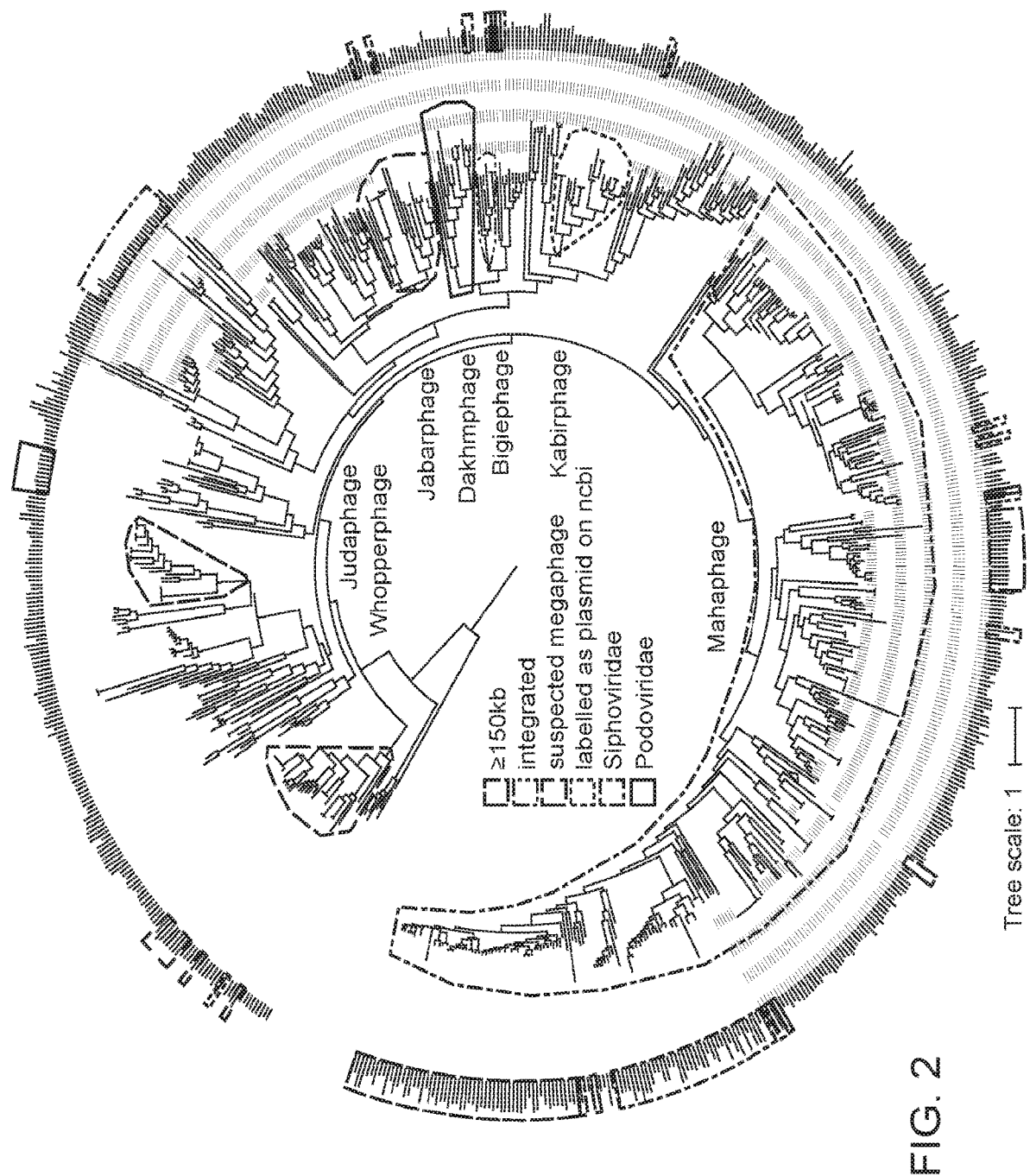
FIG. 2 shows a phylogenetic tree constructed using terminase sequences from huge phage genomes of this study and related database sequences. Colored regions of the tree indicate large clades of phage, all of which have huge genomes.

An intriguing question relates to the evolutionary history of phage with huge genomes. Are they the result of recent genome expansion within clades of normal sized phage or is a large inventory of genes an established, persistent strategy? To investigate this, phylogenetic trees for the large terminase subunit (FIG. 2) and major capsid proteins using as context sequences in public databases for phage of all sizes were constructed (Methods). Many of the sequences from the large phage genomes cluster together, defining clades. Analysis of the genome size information for database sequences shows that the public sequences that fall into these clades are from phage with genomes of at least 120 kbp in length. The largest clade, referred to here as Mahaphage (Maha being Sanskrit for huge), includes all of the present study's largest genomes as well as the Lak genomes from human and animal microbiomes (Devoto et al. (2019) supra). Six other clearly defined clusters of large phage were identified, and they were named using the word for "huge" in a variety of languages. The existence of these clades establishes that large genome size is a relatively stable trait. Within the seven clades, phage were sampled from a wide variety of environment types, indicating diversification of these large phage and their hosts across ecosystems. The environmental distribution of phage that are closely enough related that their genomes largely can be aligned was also examined. In 17 cases, these phage occur in at least two biotope types.

To determine the extent to which bacterial host phylogeny correlates with phage clades, phage hosts were identified using CRISPR spacer targeting from bacteria in the same or related samples and phylogeny of normally host-associated genes that occur on phage (see below). The predictive value of bacterial affiliations of the phage gene inventories was also tested (Methods) and it was found that in every case, CRISPR spacer targeting and phylum-level phylogenetic profiling agreed with gene inventory characterizations. Consequently, this method was used to predict the phylum-level affiliations of hosts for many phage. The results establish the importance of firmicute and proteobacterial hosts, and indicate the higher prevalence of firmicute phage in the human and animal gut compared to other environments (FIG. 5). Notably, the four largest genomes (634-716 kbp in length) are all for phage predicted to replicate in Bacteroidetes, as do Lak phage with 540-552 kbp genomes (Devoto et al. (2019) supra), and all cluster within Mahaphage. Overall, phage grouped together phylogenetically are predicted to replicate in bacteria of the same phylum.

Metabolism, Transcription, Translation

The phage genomes encode proteins predicted to localize to the bacterial membrane or cell surface. These may impact the susceptibility of the host to infection by other phage. Almost all previously reported categories of genes suggested to augment host metabolism during infection were identified. Many phage have genes involved in steps of de novo biosynthesis of purines and pyrimidines and multiple steps that interconvert nucleic and ribonucleic acids and nucleotide phosphorylation states. These gene sets are intriguingly similar to those of bacteria with very small cells and putative symbiotic lifestyles (Castelle and Banfield (2018) *Cell* 172: 1181-1197).

Figure 3:
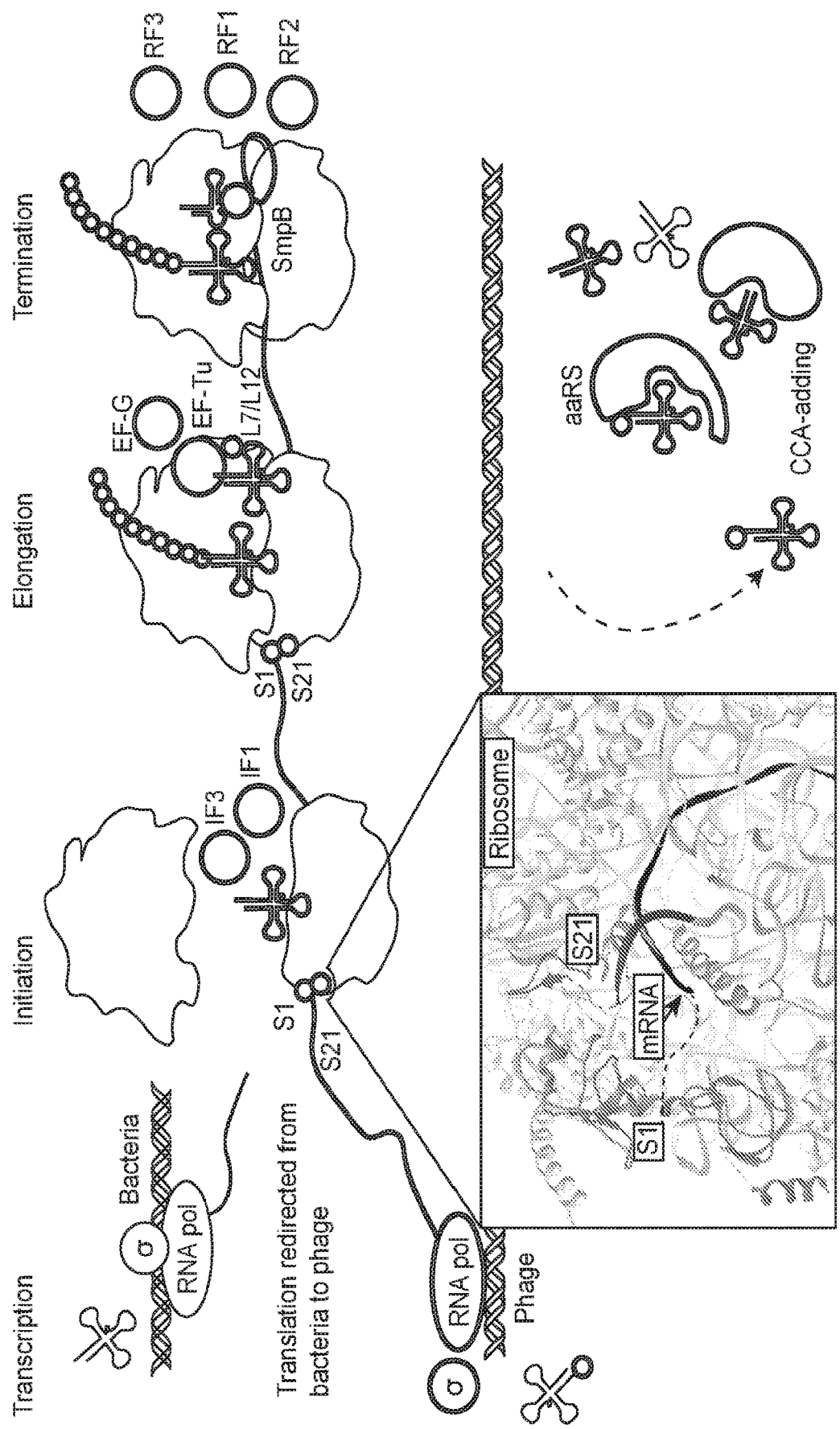
FIG. 3 shows a model for how phage-encoded capacities could function to redirect the host's translational system to produce phage proteins. No huge phage has all of these genes, but many have tRNAs (clover leaf shapes) and tRNA synthetases (aaRS). Phage proteins with up to 6 ribosomal protein S1 domains occur in a few genomes. The S1 binds mRNA to bring it into the site on the ribosome where it is decoded. Ribosomal protein S21 (S21) might selectively initiate translation of phage mRNAs, and many sequences have N-terminal extensions that may be involved in binding RNA (dashed line in ribosome insert, which is based on PDB code 6bu8 and pmid: 29247757 for ribosome and S1 structural model). Some phage have initiation factors (IF) and elongation factor G (EF G) and some have rpL7/L12, which could mediate efficient ribosome binding. Abbreviation: RNA pol, RNA polymerase.

Notably, many phage have genes whose predicted functions are in transcription and translation. Phage encode up to 64 tRNAs per genome, with sequences distinct from those of their hosts. Generally, the number of tRNAs per genome increases with genome length (FIG. 1). They often have up to 16 tRNA synthetases per genome, that are related to, but distinct from, those of their hosts. Phage may use these proteins to charge their own tRNA variants with host-derived amino acids. A subset of genomes have genes for tRNA modification and to repair tRNAs cleaved as part of host defense against phage infection. Also identified are up to three probable ribosomal proteins per genome, the most common of which is rpS21 (a phenomenon only recently reported in phage) (Mizuno et al. (2019) *Nat. Commun.* 10: 752); FIG. 3). Intriguingly, it is noted that the phage rpS21 sequences have N-terminal extensions rich in arginine, lysine, and phenylalanine: residues that bind nucleic acids. It is predicted that these phage ribosomal proteins substitute for host proteins in the ribosome (Mizuno et al. (2019) supra), and that the extensions protrude from the ribosome surface near the site of translation initiation to localize the phage mRNAs.

Some phage have genes predicted to function in other protein synthesis steps, including to ensure efficient translation. Several encode either initiation factor 1 or 3 or both, sometimes as well as elongation factors G, Tu, Ts and release factors. Also identified are genes that encode ribosome recycling factors, along with tmRNAs and small protein B (SmpB) that rescue ribosomes stalled on damaged transcripts and trigger the degradation of aberrant proteins. tmRNAs are also used by phages to sense the physiological state of host cells and can induce lysis when the number of stalled ribosomes in the host is high.

These observations suggest many ways in which some large phage can substantially intercept and redirect ribosome function. As phage mRNA sequences need to engage with the 3' end of the host 16S rRNA to initiate translation, their mRNA ribosomal binding sites were predicted. In the majority of cases, phage mRNAs have canonical Shine Dalgarno (SD) sequences, and an additional ~15% have non-standard SD binding sites. Interestingly, however, phage whose genomes encode a probable or possible rpS1 rarely have identifiable or canonical SD sequences. Thus, phage-encoded rpS1 may selectively initiate translation of phage mRNAs. Overall, phage genes appear to redirect the host's protein production capacity to favor phage genes by intercepting the earliest steps of translation. These inferences are aligned with findings for some eukaryotic viruses, which control every phase of protein synthesis (Jaafar and Kieft (2019) *Nat. Rev. Microbiol.* 17:110-123). Interestingly, some large putative plasmids also have analogous suites of translation relevant genes.

About half of the phage genomes have one to fifty sequences>25 nt in length that fold into perfect hairpins. The palindromes (sequences with dyad symmetry) are almost exclusively intergenic and each is unique within a genome. Some, but not all, are predicted to be rho-independent terminators, thus provide clues regarding genes that function as independently regulated units (Methods). However, some palindromes are up to 74 bp in length, and 34 genomes have examples of ≥40 nt in length, seemingly larger than normal terminators. These occur almost exclusively in Mahaphage and may have alternative or additional functions, such as modulation of the movement of the mRNA through the ribosome.

CRISPR-Cas Mediated Interactions

Almost all major types of CRISPR-Cas systems on phage, including Cas9, the recently described Type V-I (Yan et al. (2019) *Science* 363: 88-91), and new subtypes of Type V-F systems were identified (Harrington et al. (2018) *Science* 362: 839-842.). The Class II systems (types II and V) are reported in phage for the first time. Most effector nucleases (for interference) have conserved catalytic residues, implying that they may be functional.

Unlike the previously well described case of a phage with a CRISPR system (Seed et al. (2013) *Nature* 494: 489-491), almost all phage CRISPR systems lack spacer acquisition machinery (Cas1, Cas2, and Cas4) and many lack recognizable genes for interference. For example, two related phage have both a Type I-C variant system lacking Cas1 and Cas2 and a helicase protein in lieu of Cas3. They also harbor a second system containing a new candidate ~750 aa Type V effector protein that occurs proximal to CRISPR arrays. In some cases, phage lacking genes for interference and spacer integration have similar CRISPR repeats as their hosts, thus may use Cas proteins synthesized by their host for these functions. Alternatively the systems lacking an effector nuclease may repress transcription of the target sequences without cleavage (Luo et al. (2015) *Nucleic Acids Res.* 43:674-681; Stachler and Marchfelder (2016) *J. Biol. Chem.* 291:15226-15242).

The phage-encoded CRISPR arrays are often compact (3-55 repeats; median 6 per array. This range is substantially smaller than typically found in bacterial genomes (Toms and Barrangou (2017) *Biol. Direct* 12:20). Some phage spacers target core structural and regulatory genes of other phage. Thus, phage apparently augment their hosts' immune arsenal to prevent infection by competing phage.

Several large plasmid or plasmid-like genomes that encode a variety of types of CRISPR-Cas systems were identified. Some of these systems also lack Cas1 and Cas2. Most commonly, the spacers target the mobilization and conjugation-related genes of other plasmids, as well as nucleases and structural proteins of phage.

Some phage-encoded CRISPR loci have spacers that target bacteria in the same sample or in a sample from the same study. It is supposed that the targeted bacteria are the hosts for these phage, an inference supported by other host prediction analyses. Some loci with bacterial chromosome-targeting spacers encode Cas proteins that could cleave the host chromosome, and some do not. Targeting of host genes could disable or alter their regulation, which may be advantageous during the phage infection cycle. Some phage CRISPR spacers target bacterial intergenic regions, possibly interfering with genome regulation by blocking promoters or silencing non-coding RNAs.

Among the most interesting examples of CRISPR targeting of bacterial chromosomes are genes involved in transcription and translation. For instance, one phage targets a $\sigma^{70}$ transcription factor in its host's genome, while encoding the gene for $\sigma^{70}$. There are previous reports of $\sigma^{70}$ hijacking by phage with anti-sigma factors This may also occur with some huge phage whose genomes encode anti-sigma factors. In another example, a phage spacer targets the host Glycyl tRNA synthetase.

Figure 4A:
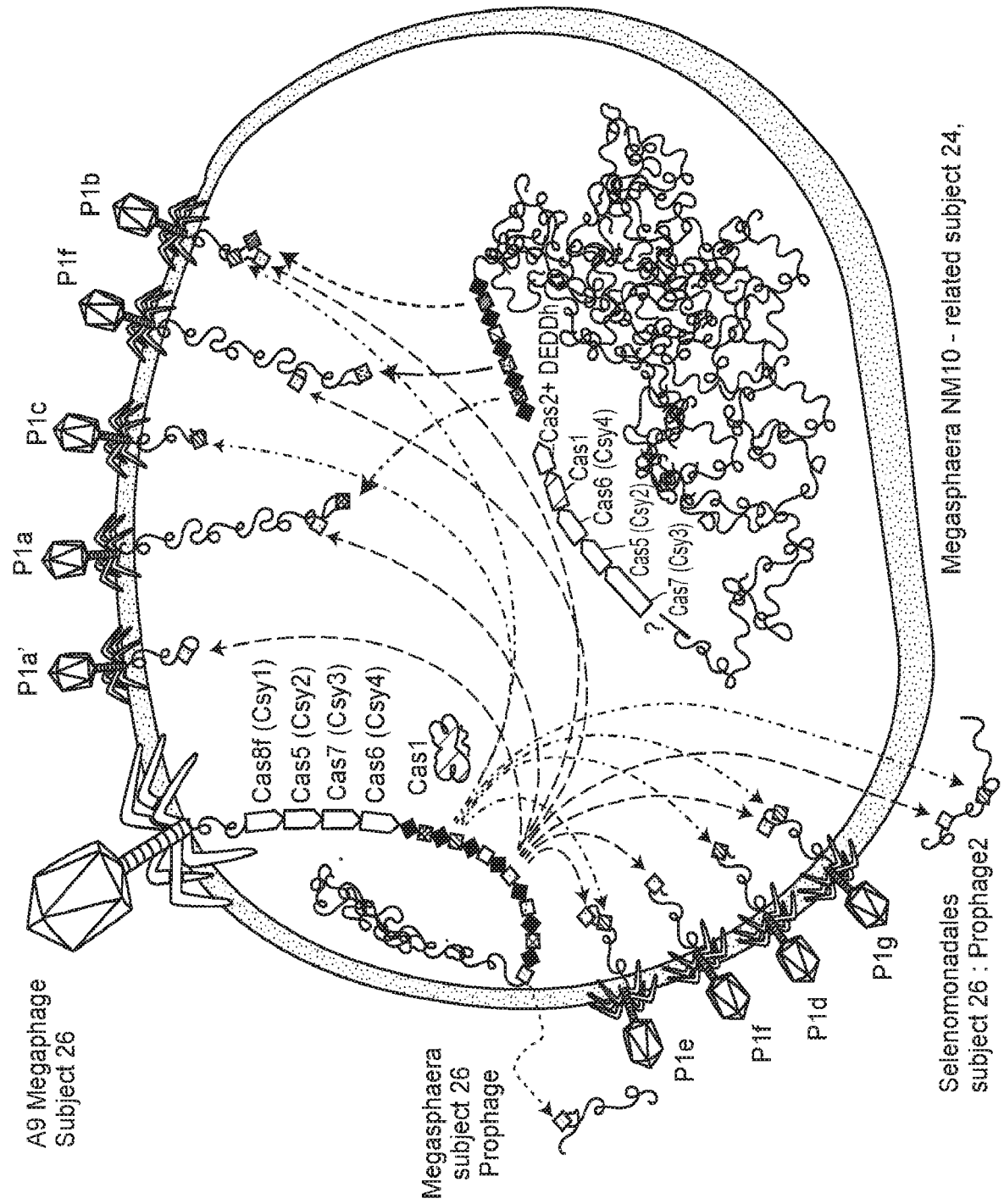
FIG. 4A shows a bacterium-phage interaction involving CRISPR targeting (cell diagram).
Figure 4B:
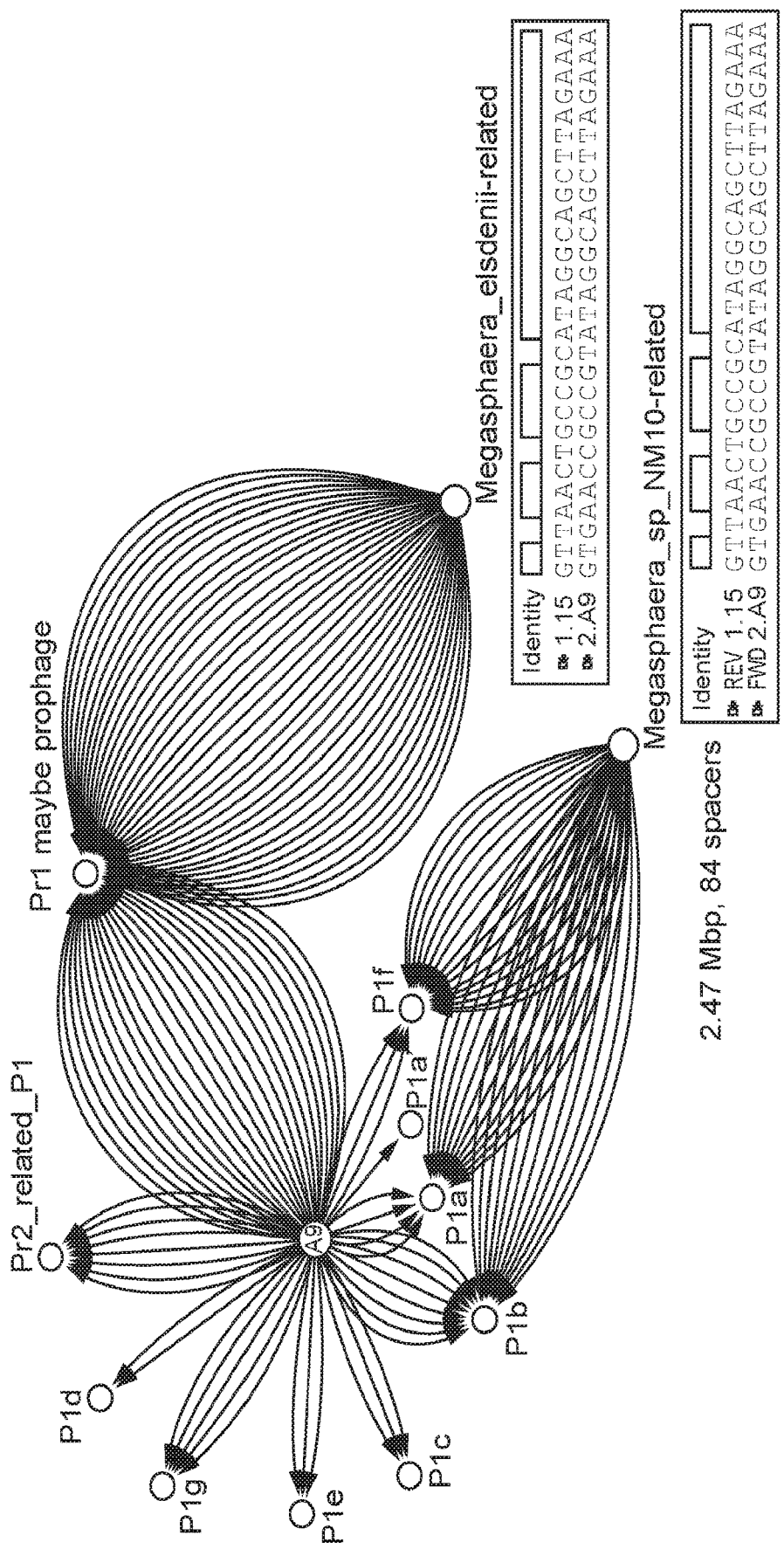
FIG. 4B shows the interaction network showing targeting of bacterial (from top to bottom: SEQ ID NOs: 49-50) and phage-encoded (from top to bottom: SEQ ID NOs: 49-50) CRISPR spacers.

Interestingly, no evidence was found of targeting of any CRISPR-bearing phage by a host-encoded spacer, hinting at yet to be revealed components in phage-host-CRISPR interactions. However, phage CRISPR targeting of other phage that are also targeted by bacterial CRISPR (FIG. 4) suggested phage-host associations that were broadly confirmed by the phage phylogenetic profile.

Some large *Pseudomonas* phage encode Anti-CRISPRs (Acr) (Bondy-Denomy et al. (2015) *Nature* 526:136-139; Pawluk et al. (2016) *Nat Microbiol* 1: 16085) and proteins that assemble a nucleus-like compartment segregating their replicating genomes from host defense and other bacterial systems. Proteins encoded in huge phage genomes that cluster with AcrVA5, AcrVA2, and AcrIIA7 that may function as Acrs were identified. Also identified were tubulin-homologs (PhuZ) that position the "phage nucleus", and proteins related to components of the proteinaceous barrier. Thus, phage 'nuclei' may be a relatively common feature in large phage.

Methods

Phage and Plasmid Genome Identification

Datasets generated in the current study, those from prior research, the Tara Oceans microbiomes (Karsenti et al. (2011) *PLoS Biol.* 9:e1001177), and the Global Oceans Virome (GOV; (Roux et al. (2016) *Nature* 537:689-693) were searched for sequence assemblies that could have derived from phage with genomes of >200 kbp in length. Read assembly, gene prediction, and initial gene annotation followed standard methods reported previously (Wrighton et al. (2014) *ISME J.* 8:1452-1463).

Phage candidates were initially found by retrieving sequences that were not assigned to a genome and had no clear taxonomic profile at the domain level. Taxonomic profiles were determined through a voting scheme, where there had to be a winner taxonomy>50% votes at each taxonomic rank based on Uniprot and ggKbase (see ggkbase at Berkeley.edu) database annotations. Phages were further narrowed down by identifying sequences with a high number of hypothetical protein annotations and/or the presence of phage structural genes, e.g. capsid, tail, holin. All candidate phage sequences were checked throughout to distinguish putative prophage from phage. Prophage were identified based on a clear transition into genome with a high fraction of confident functional predictions, often associated with core metabolic functions, and much higher similarity to bacterial genomes. Plasmids were distinguished from phage based on matches to plasmid marker genes (e.g. parA). Three sequence assemblies could not unambiguously be distinguished between phage and plasmid, and were assigned as "phage-plasmid".

Phage and Plasmid Genome Manual Curation

All scaffolds classified as phage or phage-like were tested for end overlaps using a custom script and checked manually for overlap. Assembled sequences that could be perfectly circularized were considered potentially "complete". Erroneous concatenated sequence assemblies were initially flagged by searching for direct repeats>5 kb using Vmatch (Kurtz (2003) *Ref Type: Computer Program* 412:297). Potentially concatenated sequence assemblies were manually checked for multiple large repeating sequences using the dotplot and RepeatFinder features in Geneious v9. Sequences were corrected and removed from further analysis if the corrected length was <200 kbp.

A subset of the phage sequences was selected for manual curation, with the goal of finishing (replacing all N's at scaffolding gaps or local misassemblies by the correct nucleotide sequences and circularization). Curation generally followed methods described previously (Devoto et al. (2019) supra). In brief, reads from the appropriate dataset were mapped using Bowtie2 (Langmead and Salzberg (2012) *Nat. Methods* 9:357-359) to the de novo assembled sequences. Unplaced mate pairs of mapped reads were retained with shrinksam (github.com/bcthomas/shrinksam). Mappings were manually checked throughout to identify local misassemblies using Geneious v9. N-filled gaps or misassembly corrections made use of unplaced paired reads, in some cases using reads relocated from sites where they were mis-mapped. In such cases, mis-mappings were identified based on much larger than expected paired read distances, high polymorphism densities, backwards mapping of one read pair, or any combination of the aforementioned.

Similarly, ends were extended using unplaced or incorrectly placed paired reads until circularization could be established. In some cases, extended ends were used to recruit new scaffolds that were then added to the assembly. The accuracy of all extensions and local assembly changes were verified in a subsequent phase of read mapping. In many cases, assemblies were terminated or internally corrupted by the presence of repeated sequences. In these cases, blocks of repeated sequence as well as unique flanking sequence were identified. Reads were then manually relocated, respecting paired read placement rules and unique flanking sequences. After gap closure, circularization, and verification of accuracy throughout, end overlap was eliminated, genes were predicted and throughout, and the start moved to an intergenic region, in some cases suspected to be origin based on a combination of coverage trends and GC skew (Brown et al. (2016) *Nat. Biotechnol.* 34:1256-1263). Finally, the sequences were checked to identify any repeated sequences that could have led to an incorrect path choice because the repeated regions were larger than the distance spanned by paired reads. This step also ruled out artifactual long phage sequences generated by end to end repeats of smaller phage, which occur in previously described datasets.

Structural and Functional Annotation

Following identification and curation of phage genomes, coding sequences (CDS) were predicted with prodigal (-m -c -g 11 -p single) with genetic code 11. The resulting CDS were annotated as previously described by searching against UniProt, UniRef, and KEGG (Wrighton et al. (2014) supra). Functional annotations were further assigned by searching proteins against Pfam r32 (Finn et al. (2014) *Nucleic Acids Res.* 42:D222-30), TIGRFAMS r15 (Haft et al. (2013) *Nucleic Acids Res.* 41:D387-95), and Virus Orthologous Groups r90 (vogdb.org). tRNAs were identified with tRNAscan-SE 2.0 (Lowe and Eddy, (1997) *Nucleic Acids Res.* 25: 955-964) using the bacterial model. tmRNAs were assigned using ARAGORN v1.2.38 (Laslett and Canback, (2004) *Nucleic Acids Res.* 32: 11-16) with the bacterial/plant genetic code. Clustering of the protein sequences into families was achieved using a two-step procedure. A first protein clustering was done using the fast and sensitive protein sequence searching software MMseqs (Hauser et al. (2016) *Bioinformatics* 32: 1323-1330). An all-vs-all sequences search was performed using e-value: 0.001, sensitivity: 7.5 and coverage: 0.5. A sequence similarity network was built based on the pairwise similarities and the greedy set cover algorithm from MMseqs was performed to define protein subclusters. The resulting subclusters were defined as subfamilies. In order to test for distant homology, subfamilies were grouped into protein families using an HMM-HMM comparison. The proteins of each subfamily with at least two protein members were aligned using the result2msa parameter of mmseqs2, and from the multiple sequence alignments HMM profiles were built using the HHpred suite. The subfamilies were then compared to each other using HHblits (Remmert et al. (2011) *Nat. Methods* 9: 173-175) from the HHpred suite (with parameters-v 0 -p 50 -z 4 -Z 32000 -B 0 -b 0). For subfamilies with probability scores of ≥95% and coverage ≥0.50, a similarity score (probability×coverage) was used as weights of the input network in the final clustering using the Markov Clustering algorithm, with 2.0 as the inflation parameter. These clusters were defined as the protein families. Hairpins (palindromes, based on identical overlapping repeats in the forward and reverse directions) were identified using the Geneious Repeat Finder and located dataset-wide using Vmatch (Kurtz (2003) supra). Repeats >25 bp with 100% similarity were tabulated.

Reference Genomes for Size Comparisons

RefSeq v92 genomes were recovered by using the NCBI Virus portal and selecting only complete dsDNA genomes with bacterial hosts. Genomes from (Paez-Espino et al. (2016) supra) were downloaded from IMG/VR and only sequence assemblies labeled "circular" with predicted bacterial hosts were retained. Many of the genomes were the result of erroneous concatenated repeating assemblies. Given the presence of sequences in IMG/VR that are based on erroneous concatenations, the study only considered sequences from this source that are >200 kb; a subset of these were removed as artifactual sequences.

Host Prediction

The phylum affiliations of bacterial hosts for phage were predicted by considering the Uniprot taxonomic profiles of every CDS for each phage genome. The phylum level matches for each phage genome were summed and the phylum with the most hits was considered as the potential host phylum. However, only cases where this phylum that had 3× as many counts as the next most counted phylum were assigned as the tentative phage host phylum. Phage hosts were further assigned and verified using CRISPR targeting. CRISPR arrays were predicted on sequence assemblies >1 kbp from the same environment that each phage genome was reconstructed. Spacers were extracted and searched against the genomes from the same site using BLASTN-short (Altschul et al. (1990) *J. Mol. Biol.* 215: 403-410). Sequence assemblies containing spacers with a match of length >24 bp and ≤1 mismatch or at least 90% sequence identity to a genome were considered targets. In the case of phage, the match was used to infer a phage-host relationship. In all cases, the predicted host phylum based on taxonomic profiling and CRISPR targeting were in complete agreement. Similarly, the phyla of hosts were predicted based on phylogenetic analysis of phage genes also found in host genomes (e.g., involved in translation and nucleotide reactions). Inferences based on computed taxonomic profiles and phylogenetic trees were also in complete agreement.

Alternative Genetic Codes

In cases where gene prediction using the standard bacterial code (code 11) resulted in seemingly anomalously low coding densities, potential alternative genetic codes were investigated. In addition to making a prediction using Fast and Accurate genetic Code Inference and Logo (FACIL; (Dutilh et al. (2011) *Bioinformatics* 27:1929-1933)), genes with well defined functions (e.g., polymerase, nuclease) were identified and the stop codons terminating genes that were shorter than expected were determined. Genes were then re-predicted using Glimmer and Prodigal set such that codon was not interpreted as a stop. Other combinations of repurposed stop codons were evaluated, and candidate codes (e.g., code 6, with only one stop codon) were ruled out due to unlikely gene fusion predictions.

Introns were identified in some longer than expected pseudo-tRNAs by re-predicting the tRNAs using eukaryotic settings (as tRNA scan does not expect introns in tRNA genes in bacteria and phage).

Terminase Phylogenetic Analysis

The large terminase phylogenetic tree was constructed by recovering large terminases from the aforementioned annotation pipeline. CDS that matched with >30 bitscore against PFAM, TIGRFAMS, and VOG were retained. Any CDS that had a hit to large terminase, regardless of bitscore, was searched using HHblits (Steinegger et al. *Bioinformatics* 21:951-960) against the uniclust30_2018_08 database. The resulting alignment was then further searched against the PDB70 database. Remaining CDS that clustered in protein families with a large terminase HMM were also included after manual verification. Detected large terminases were manually verified using HHPred (Steinegger et al. supra) and jPred (Cole et al. (2008) *Nucleic Acids Res.* 36:W197-201). Large terminases from the >200 kb (Paez-Espino et al. (2016) supra) phage genomes and all >200 kb complete dsDNA phage genomes from RefSeq r92 were also included by protein family clustering with the phage CDS from this study. The resulting terminases were clustered at 95% amino acid identity (AAI) to reduce redundancy using cd-hit (Huang et al. (2010) *Bioinformatics* 26:680-682). Smaller phage genomes were included by searching the resulting CDS set against the Refseq protein database and retaining the top 10 best hits. Those hits that had no large terminase match against PFAM, TIGRFAMS, or VOG were removed from further consideration and the remaining set was clustered 90% AAI. The final set of large terminase CDS were aligned MAFFT v7.407 (—localpair—maxiterate 1000) and poorly aligned sequences were removed and the resulting set was realigned. The phylogenetic tree was inferred using IQTREE v1.6.9 (Nguyen et al. (2015) *Mol. Biol. Evol.* 32:268-274).

Phage Encoded tRNA Synthetase Trees

Phylogenetic trees were constructed for phage encoded tRNA synthetase, ribosomal and initiation factor protein sequences using a set of the closest set of reference from NCBI and bacterial genomes from the current study.

CRISPR-Cas Locus Detection and Host Identification

Phage-encoded CRISPR-Cas loci were identified using the same methods as used to identify bacterial CRISPR-Cas loci, spacers extracted from between repeats of the CRISPR locus using MinCED (github.com/ctSkennerton/miinced) and CRISPRDetect (Biswas et al., 2016) were compared to sequences reconstructed from the same site and targets classified as bacterial, phage or other.

Because many phage hosts cannot be identified by CRISPR targeting (perhaps because phage had proliferated in samples containing sensitive hosts, or the targets are sufficiently mutated to avoid spacer detection) additional lines of evidence were used to propose host identities. Due to uncertainty in these methods, possible phage predictions were made only at the phylum level. In this analysis, the fraction of genes encoded on any genome with the best predicted protein match to each phylum was computed. Only in cases where the most highly represented phylum exceeded in frequency the next most common phylum by ≥3× was a tentative bacterial host proposed. This threshold was verified as conservative, based on confirmed host phylum information from CRISPR targeting or phylogenetic analysis.

Data Availability

Supplementary document "Genbank" includes the Genbank format files for the genome sequences reported in this study. All reads are being deposited in the short read archive (if not already lodged there) and genome sequences in NCBI.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising:
   a) a CRISPR-Cas effector polypeptide, or a nucleic acid molecule encoding the CRISPR-Cas effector polypeptide, wherein the CRISPR-Cas effector polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96; and
   b) a CRISPR-Cas effector guide RNA, or one or more DNA molecules encoding the CRISPR-Cas effector guide RNA, wherein the CRISPR-Cas effector guide RNA comprises:
   i) a first region that binds to the CRISPR-Cas effector polypeptide; and
   ii) a second region that hybridizes to a target nucleic acid, wherein the first region is heterologous to the second region.

2. The composition of claim 1, wherein the first region of the CRISPR-Cas effector guide RNA comprises the nucleotide sequence set forth in any one of SEQ ID NOs:98-116 with T(s) substituted with U(s).

3. The composition of claim 1, wherein the CRISPR-Cas effector polypeptide is fused to a nuclear localization signal (NLS).

4. The composition of claim 1:
   a) wherein the composition comprises a lipid;
   b) wherein a) and b) are within a liposome;
   c) wherein a) and b) are within a particle; or
   d) wherein the composition comprises one or more of a buffer, a nuclease inhibitor, and a protease inhibitor.

5. The composition of claim 1, further comprising a DNA donor template.

6. A CRISPR-Cas effector fusion polypeptide comprising: a CRISPR-Cas effector polypeptide fused to a heterologous polypeptide, wherein the CRISPR-Cas effector polypeptide comprises an amino acid sequence having the amino acid sequence set forth in any one of SEQ ID NOs: 51, 53, 55, 57, 59-62, 64, 66, 68, 70, 72-78, 80, 82, 84, 86, 88, 90, 92, 94, and 96.

7. A nucleic acid comprising a nucleotide sequence encoding the CRISPR-Cas effector fusion polypeptide of claim 6.

8. One or more nucleic acids comprising:
   (a) a nucleotide sequence encoding a CRISPR-Cas effector guide RNA, wherein the CRISPR-Cas effector guide RNA comprises:
   i) a first region that binds to the CRISPR-Cas effector polypeptide; and
   ii) a second region that hybridizes to a target nucleic acid, wherein first region is heterologous to the second region; and
   (b) a nucleotide sequence encoding a CRISPR-Cas effector polypeptide, wherein the CRISPR-Cas effector polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96.

9. A eukaryotic cell comprising one or more of:
   a) a CRISPR-Cas effector polypeptide, or a nucleic acid comprising a nucleotide sequence encoding the CRISPR-Cas effector polypeptide, wherein the CRISPR-Cas effector polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96;
b) a CRISPR-Cas effector fusion polypeptide, or a nucleic acid comprising a nucleotide sequence encoding the CRISPR-Cas effector fusion polypeptide, wherein the CRISPR-Cas effector polypeptide present in the fusion polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96; and
c) a CRISPR-Cas effector guide RNA, or a nucleic acid comprising a nucleotide sequence encoding the CRISPR-Cas effector guide RNA.

10. A method of modifying a target nucleic acid, the method comprising contacting the target nucleic acid with:
a) a CRISPR-Cas effector polypeptide, wherein the CRISPR-Cas effector polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96; and
b) a CRISPR-Cas effector guide RNA comprising a guide sequence that hybridizes to a target sequence of the target nucleic acid,
wherein said contacting results in modification of the target nucleic acid by the CRISPR-Cas effector polypeptide.

11. A method of modulating transcription from a target DNA, modifying a target nucleic acid, or modifying a protein associated with a target nucleic acid, the method comprising contacting the target nucleic acid with:
a) a CRISPR-Cas effector fusion polypeptide comprising a CRISPR-Cas effector polypeptide fused to a heterologous polypeptide, wherein the CRISPR-Cas effector polypeptide present in the fusion polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96; and
b) a CRISPR-Cas effector guide RNA comprising a guide sequence that hybridizes to a target sequence of the target nucleic acid.

12. A transgenic, multicellular, non-human organism whose genome comprises a transgene comprising a nucleotide sequence encoding one or more of:
a) a CRISPR-Cas effector polypeptide, wherein the CRISPR-Cas effector polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96;
b) a CRISPR-Cas effector fusion polypeptide, wherein the CRISPR-Cas effector polypeptide present in the fusion polypeptide comprises the amino acid sequence set forth in any one of SEQ ID NOs: 51, 53, 55, 57, 59-62, 64, 66, 68, 70, 72-78, 80, 82, 84, 86, 88, 90, 92, 94, and 96; and
c) a CRISPR-Cas effector guide RNA.

13. A system comprising one or more of:
a) a CRISPR-Cas effector polypeptide and a CRISPR-Cas effector guide RNA;
b) a CRISPR-Cas effector polypeptide, a CRISPR-Cas effector guide RNA, and a DNA donor template;
c) a CRISPR-Cas effector fusion polypeptide and a CRISPR-Cas effector guide RNA;
d) a CRISPR-Cas effector fusion polypeptide, a CRISPR-Cas effector guide RNA, and a DNA donor template;
e) an mRNA encoding a CRISPR-Cas effector polypeptide, and a CRISPR-Cas effector guide RNA;
f) an mRNA encoding a CRISPR-Cas effector polypeptide; a CRISPR-Cas effector guide RNA, and a DNA donor template;
g) an mRNA encoding a CRISPR-Cas effector fusion polypeptide, and a CRISPR-Cas effector guide RNA;
h) an mRNA encoding a CRISPR-Cas effector fusion polypeptide, a CRISPR-Cas effector guide RNA, and a DNA donor template;
i) one or more recombinant expression vectors comprising: i) a nucleotide sequence encoding a CRISPR-Cas effector polypeptide; and ii) a nucleotide sequence encoding a CRISPR-Cas effector guide RNA;
j) one or more recombinant expression vectors comprising: i) a nucleotide sequence encoding a CRISPR-Cas effector polypeptide; ii) a nucleotide sequence encoding a CRISPR-Cas effector guide RNA; and iii) a DNA donor template;
k) one or more recombinant expression vectors comprising: i) a nucleotide sequence encoding a CRISPR-Cas effector fusion polypeptide; and ii) a nucleotide sequence encoding a CRISPR-Cas effector guide RNA; and
l) one or more recombinant expression vectors comprising: i) a nucleotide sequence encoding a CRISPR-Cas effector fusion polypeptide; ii) a nucleotide sequence encoding a CRISPR-Cas effector guide RNA; and a DNA donor template,
wherein, in any of (a)-(I), the CRISPR-Cas effector polypeptide, or the CRISPR-Cas effector polypeptide present in the fusion polypeptide, comprises an amino acid sequence the amino acid sequence set forth in any one of SEQ ID NOs: 51, 53, 55, 57, 59-62, 64, 66, 68, 70, 72-78, 80, 82, 84, 86, 88, 90, 92, 94, and 96.

14. A sterile container comprising the CRISPR-Cas effector system of claim 13.

15. The sterile container of claim 14, wherein the container is a syringe.

16. An implantable device comprising the CRISPR-Cas effector system of claim 13.

* * * * *